United States Patent
Boussie et al.

(10) Patent No.: US 7,060,848 B2
(45) Date of Patent: *Jun. 13, 2006

(54) BRIDGED BI-AROMATIC CATALYSTS, COMPLEXES, AND METHODS OF USING THE SAME

(75) Inventors: Thomas Boussie, Menlo Park, CA (US); Gary M. Diamond, San Jose, CA (US); Anne M. LaPointe, Sunnyvale, CA (US); Margarete K. Leclerc, Mountain View, CA (US); Cynthia Micklatcher, Hayward, CA (US); Pu Sun, Mountain View, CA (US); Xiaohong Bei, Sunnyvale, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/117,006

(22) Filed: Apr. 28, 2005

(65) Prior Publication Data

US 2006/0052554 A1    Mar. 9, 2006

Related U.S. Application Data

(63) Continuation-in-part of application No. 10/421,235, filed on Apr. 23, 2003, now Pat. No. 6,897,276.

(60) Provisional application No. 60/566,527, filed on Apr. 29, 2004, provisional application No. 60/375,363, filed on Apr. 24, 2002.

(51) Int. Cl.
  *C07F 7/28* (2006.01)
  *C08F 7/00* (2006.01)

(52) U.S. Cl. .................. 556/54; 556/21; 556/22; 556/56; 556/51

(58) Field of Classification Search .......... 556/21, 556/22, 54, 56, 51
  See application file for complete search history.

(56) References Cited

U.S. PATENT DOCUMENTS

| | | | |
|---|---|---|---|
| 4,297,465 A | 10/1981 | Smith | 526/141 |
| 4,971,936 A | 11/1990 | Wilson et al. | 502/124 |
| 5,064,802 A | 11/1991 | Stevens et al. | 502/155 |
| 5,093,415 A | 3/1992 | Brady, III et al. | 525/53 |
| 5,153,157 A | 10/1992 | Hlatky et al. | 502/117 |
| 5,318,935 A | 6/1994 | Canich et al. | 502/117 |
| 5,385,993 A | 1/1995 | Fujita | 526/119 |
| 5,453,410 A | 9/1995 | Kolthammer et al. | 502/155 |
| 5,599,761 A | 2/1997 | Turner | 502/152 |
| 5,616,664 A | 4/1997 | Timmers et al. | 526/127 |
| 5,985,356 A | 11/1999 | Schultz et al. | 427/8 |
| 6,030,917 A | 2/2000 | Weinberg et al. | 502/104 |
| 6,175,409 B1 | 1/2001 | Nielsen et al. | 356/337 |
| 6,214,939 B1 | 4/2001 | Shinozaki et al. | 525/270 |
| 6,239,236 B1 | 5/2001 | Morini et al. | 526/124.9 |
| 6,260,407 B1 | 7/2001 | Petro et al. | 73/61.52 |
| 6,262,199 B1 | 7/2001 | Ewen et al. | 526/127 |
| 6,294,388 B1 | 9/2001 | Petro | 436/8 |
| 6,306,658 B1 | 10/2001 | Turner et al. | 436/37 |
| 6,406,632 B1 | 6/2002 | Safir et al. | 210/656 |
| 6,436,292 B1 | 8/2002 | Petro | 210/656 |
| 6,454,947 B1 | 9/2002 | Safir et al. | 210/656 |
| 6,455,316 B1 | 9/2002 | Turner et al. | 436/37 |
| 6,461,515 B1 | 10/2002 | Safir et al. | 210/656 |
| 6,475,391 B1 | 11/2002 | Safir et al. | 210/656 |
| 6,489,168 B1 | 12/2002 | Wang et al. | 436/37 |
| 6,491,816 B1 | 12/2002 | Petro | 210/198.2 |
| 6,491,823 B1 | 12/2002 | Safir et al. | 210/656 |
| 6,508,984 B1 | 1/2003 | Turner | 422/65 |
| 6,548,026 B1 | 4/2003 | Dales et al. | 422/138 |
| 6,713,577 B1 | 3/2004 | Boussie | 526/161 |
| 6,759,014 B1 | 7/2004 | Dales et al. | 422/130 |
| 6,841,502 B1 | 1/2005 | Boussie et al. | |
| 6,869,904 B1 | 3/2005 | Boussie et al. | |
| 6,897,276 B1 | 5/2005 | Boussie et al. | |
| 2002/0002256 A1 | 1/2002 | Peterson | 526/133 |

FOREIGN PATENT DOCUMENTS

| | | |
|---|---|---|
| EP | 0 277 004 | 8/1988 |
| EP | 0 292 134 | 11/1988 |
| EP | 0 534 405 | 3/1993 |
| EP | 0 582 194 | 2/1994 |
| EP | 0 622 380 | 11/1994 |
| EP | 0 922 712 | 6/1999 |
| EP | 1 110 930 | 6/2001 |
| JP | 8-134064 | 5/1996 |
| JP | 08134064 | 5/1996 |
| JP | 8-217775 | 8/1996 |
| JP | 08217775 | 8/1996 |
| JP | 2002280179 | 9/2002 |
| WO | WO 94/07926 | 4/1994 |
| WO | WO 94/11409 | 5/1994 |

(Continued)

OTHER PUBLICATIONS

Jordan, 1991, vol.: 32, pp.: 325–387, Adv. Organometallic Chem., Chemistry Of Cationic Dicyclopentadienyl Group 4 Metal-Alkyl Complexes.

(Continued)

*Primary Examiner*—Caixia Lu

(57) ABSTRACT

Ligands, compositions, metal-ligand complexes and arrays with substituted bridged bis-biaromatic ligands, and methods of making and using the same, are disclosed that are useful in the catalysis of transformations such as the polymerization of monomers into polymers, The catalysts have high performance characteristics, including higher comonomer incorporation into ethylene/olefin copolymers, where such olefins are for example, 1-octene, propylene or styrene. The catalysts also polymerize propylene into isotactic polypropylene.

25 Claims, No Drawings

FOREIGN PATENT DOCUMENTS

| | | |
|---|---|---|
| WO | WO 98/03521 | 1/1998 |
| WO | WO 99/05186 | 2/1999 |
| WO | WO 99/06413 | 2/1999 |
| WO | WO 99/42467 | 8/1999 |
| WO | WO 00/09255 | 2/2000 |
| WO | WO 01/00581 | 1/2001 |
| WO | WO 01/48028 | 7/2001 |
| WO | WO 01/98371 | 12/2001 |
| WO | WO 02/02576 | 1/2002 |
| WO | WO 02/36638 | 5/2002 |
| WO | WO 02/083306 | 10/2002 |
| WO | WO 02/085820 | 10/2002 |

OTHER PUBLICATIONS

Negishi, 2001, vol.: 73, pp.: 239-242, Pure & Appl. Chem., Some Newer Aspects of Organizirconium Chemistry of Relevance to Organic Synthesis; Zr-Ca'alyzed enantioselective carbometallation.

Barron, 2000, vol.: 1, pp.: 33-67, Metallocene-Based Polylefins; Prep, Prop, & Tech., Alkylalumoxanes: Synthesis, Structure, and Reactivity.

Maruoka, 1993, volume: pp. 413-440, Book, Asymmetric Reactions with Chiral Lewis Acid Catalysts.

Hoveyda, 2002, Volume: pp.: 180-229, Book, Chiral Zirconium Catalysts for Enantioselective Synthesis.

Kuber, 1996, vol.: 2 pp.: 893-902, Applied Homogeneous Catalysts, Metallocenes as a Source of Fine Chemicals.

Blaser et al., 2002, Vol.: 3 pp.: 1131-1149, Applied Homogeneous Catalysts, Enantioselective Synthesis.

LoCoco et al., Sep. 22, 2003, vol.: 22, pp.: 5498-5503, Organometallics, Chelate-Controlled Synthesis of rac- and meso-Me2Si(3-tBu-C5H3)2ZrCl2.

Forni et al., 1973, vol.: 23, pp.: 455-459, Ind. Eng. Chem. Process Des. Develop., Kinetics and Mechanism of Propylene to 4-Methyl-1-pentene Catalytic Dimerization.

Diamond, Feb. 14, 1996 vol.: 118, pp.: 8024-8033, J. Am. Chem. Soc., Efficient Synthesis of Chiral ansa-Metallocenes by Amine Elimination.

Deckers, Sep. 13, 2002, vol.: 21, pp.: 5122-5135, Organometallics, Catalytic Trimerization of Ethene with Highly Active Cyclopentadienyl-Arene Titanium Catalysts.

Chen, Dec. 9, 2003, 2004, vol.: 126, pp.: 42-43, J. Am. Chem. Soc., Divalent ansa-Zirconoces: Stereoselective Synthesis and High Activity for Propylene Polymerization.

Carter, 2002, Volume: pp.: 858-859, Chem. Commun., High Activity ethylene timerisation catalysts based on hiphosphine ligands.

Balsells et al., Sep. 25, 2001, 2002, vol.: 124, pp.: 10336-10348, 10th Intl Conference on Adaptive Structures and Technologies.

Insight into the Mechanism of the Asymmetric Addition of Alkyl Groups to Aldehydes Catalyzed by Titanium-BINOLate Species.

Zhang et al., Mar. 21, 2000, vol.: 22, pp.: 8093-8094, J. Am. Chem. Soc., General Synthesis of Racemic Me2Si-Bridged Bis(indenyl) Zirconocene Complexes.

Agapie et al., Jan. 15, 2004, vol.: 126, pp.: 1304-1305, J. Am. Chem. Soc., Mechanistic Studies of the Ethylene Trimerization Reaction with Xhromium-Diphosphine Catalysts: Experimental Evidence for a Mechanism Involving Metalacyclic Intermediates.

Marks et al., Mar. 28, 2000 vol.: 100 pp.: 1391-1434, Chem Rev., Cocatalysts for Metal-Catalyzed Olefin Polymerization: Activators, Activation Processes, and Structure- Activity Relationships.

McGuinness et al., Jan. 2, 2003, Volume: pp.: 334-335, Chem. Commun., Novel Cr-PNP Complexes as Catalysts for the Trimerisation of Ethylene.

Scott et al., Mar. 5, 2004, Volume: pp.: 894-895, Chem. Commun., Zirconium Catalysed Enantioselective Hydramination/Cyclisation.

McGuinness et al., Apr. 15, 2003, vol.: 125, pp.: 5272-5273, J. Am. Chem. Soc., First Cr(III)-SNS Complexes and Their Use as Highly Efficient Catalysts for the Trimerization of Ethylene to 1-Hexene.

Ringwald, Feb. 5, 1999, vol.: 121, pp.: 1524-1527, J. Am. Chem. Soc., Asymmetric Thermal Transformation, a New Way to Eantiopure Biphenyl-Bridged Titanocene and Zirconocene Complexes.

Svejda and Bookhart, Dec. 15, 1998, vol.: 18, pp.: 65-74, Organometallics, Ethylene Oligomerization and Propylene Dimerization Using Cationic (a-Diimine)nickel(II) Catalysts.

Walsh, Jul. 31, 2003, vol.: 36, pp.: 739-749, ACC. Chem. Res., Titanium-Catalyzed Enantioselective Additions of Alkyl groups to Aldehydes: Mechanistic Studies and New Concepts in Asymmetric Catalysis.

Wulff et al., 2001, vol.: 40, pp.: 2271-2274, Angew. Chem. Int. Ed., Active Site Design in a Chemzyme: Development of a Highly Asymmetric and Remarkably Temperature-Independent Catalyst for the Imino Aldol Reaction.

Yamashita et al., Mar. 8, 2003, vol.: 125, pp.: 3793-3798, J. Am. Chem. Soc., Chiral Hetero Diels-Alder Products by Enantioselective and Diasteroselective Zirconium Catalysts. Scope, Limitation, Mechanism, and Application to the Concise Synthesis of (+)-Prelactone C and (+)-9-De.

Neugebauer, 1972, vol.: 105, pp.: 2686-2693, Chem Ber., tert.-Butyl-Substituierte Carbazole (German).

Brintzinger et al., 1995, vol.: 34, pp.: 1143-1170, Angew. Chem. Int. Ed. Engl., Stereospecific Olefin Polymerization With Chiral Metallocene Catalysts.

LaPointe, 2000, vol.: 22, pp.: 9560-9561, J. Am. Chem. Soc., New Family Of Weakly Coordinating Anions.

Piers et al., 1999, vol.: 121, pp.: 3244-3245, J. Am. Chem. Soc., New Bifunctional Perfluoroaryl Boranes: Synthesis And Reactivity Of The Ortho-Phenylene-Bridged Diboranes . . . .

Cram et al., 1981, vol.: 103, pp.: 6228-6232, J. Am. Chem. Soc., Augmented And Diminished Spherands And Scales Of Binding.

Cram et al., 1985, vol.: 107, pp.: 3657-3668, J. Am. Chem. Soc., Host-Guest Complexation. 36. Spherand And Lithium And Sodium Ion Complexation Rates And Equilibria.

Cram et al., 1985, vol.: 107, pp.: 3645-3657, J. Am. Chem. Soc., Host-Guest Complexation. 35. Spherands The First Completely Preorganized Ligand SYstems.

Helgeson et al., 2000, vol.: 56, pp.: 795-797, Acta Cryst., The Lithium Chloride Complex Of The Anti Isomer Of The Bridged Sherand C50H4806.

Knobler et al., 1992, vol.: 12, pp.: 341-360, J. Incl. Phen. & Molec. Recog. In Chem, The Crystal And Molecular Structures Of Bridged Spherands.

Ueda et al., 1995, Volume: pp.: 935-936, J.Chem Soc, Doubly Helical, Chiral Crown Thioether Fully Preorganized For Planner Coordination.

Cram et al., 1979, Volume: pp.: 948-950, J.C.S. Chemm Commun, A Spherand Containing An Enforced Cavity That Selectively Binds Lithium And Sodium Ions.

Schrock et al., Aug. 12, 1999, vol.: 18, pp.: 3649-3670, Organometallics, Synthesis of Titanium, Zirconium, and Hafnium Complexes that Contain Diamido Donor Ligands of the Type [(t-BuN-o-C6H4)20]2.

Coates, 2000, vol.: 100, pp.: 1223-1252, Chem Rev., Precise Control of Polyolefin Stereochemistry Using Single-Site Metal Catalysts.

Deng et al., 1996, vol.: 29, pp.: 6371-6376, Macromolecules, Synthesis of High-Melting, Isotactic Polypropylene with C2- and C1-Symmetrical Zirconocenes.

Resconi et al., 2000, vol.: 100, pp.: 1253-1345, Chem Rev., Selectivity in Propene Polymerization with Metallocene Catalysts.

Cornils et al., 2002, vol.: 2 pp.: 740-747, Journal: Applied Homogeneous Catalysts Title: Applied Homogeneous Catalysts.

Cornils et al., 2002, vol.: 1, pp.: 213-273 Journal: Applied Homogeneous Catalysts Title: Applied Homogeneous Catalysts.

Arrowsmith et al., 2001, vol.: 202, pp.: 2161-2167, Macromol. Chem. Phys., Comparison of the Polymerization of Propene by Homogeneous and Heterogeneous Metallocene/MAO-Catalysts Under Different Polymerization Conditions.

Bennett et al., 1999, vol.: 1, pp.: 3127-3132.

J. Chem. Soc., Perkins Trans., Catalytic Conjugate Addition Promoted by the Copper(sup)1(sup)-monothiobinaphthol System. Part 3. (sup)1(sup) Comparison of Three Thiolate-based Catalytic Systems.

Bochmann et al., 1993, vol.: 12, pp.: 633-640, Organometallics, Base-Free Cationic Zirconium Benzyl Complexes as Highly Active Polymerization Catalysts.

Britovsek et al., 1999, vol.: 38, pp.: 428-447, Angew. Chem. Int. Ed. Engl., The Search for New-Generation Olefin Polymerization Catalysts: Life Beyond Metallocenes.

Chang et al., 1998, vol.: 9 (6) pp.: 842-845, J. Korean Ind. & Eng. Chemistry, Syntheses of New Lactones Containing Phenyl or Methyl Groups.

Publish Date: Publish Year: 2000, vol.: 100 (4) Pages: Entire Issue, Chem. Rev., Frontiers in Metal-Catalyzed Polymerization.

Chen et al., 2000, vol.: 100 pp.: 1391-1434, Chem Rev., Cocatalysts for Metal-Catalyzed Olefin Polymerization: Activators, Activation Processes, and Structure-Activity Relationships.

Ewen, 1998, vol.: 19, pp.: 71-73, Macromol. Rapid Commun., Evaluation of the Dimethylsilyl-Bis(2-Methyl-4-Phenyl-1-Indenyl) Ligand with Group 4 Triad Metals in Propene Polymerizations with Methylaluminoxane.

Fink, 2000, vol.: 100, pp.: 1377-1390, Chem. Rev., Propene Polymerization with Silica-Supported Metallocene/MAO Catalysts.

Gibson et al., 2003, vol.: 103, pp.: 283-315, Chem Rev., Advances in Non-Metallocene Olefin Polymerization Catalysis.

Hlatky, 2000, vol.: 100 pp.: 1347-1376, Chem Rev., Heterogeneous Single-Site Catalysts for Olefin Polymerization.

Klapars et al., 2001, vol.: 123 (31) pp.: 7727-7729, J. Am. Chem. Soc., A General and Efficient Copper Catalyst for the Amidation of Aryl Halides on the N-Arylation of Nitrogen Heterocycles.

Kaminsky et al., 2001, vol.: 24 (11) pp.: 1124-1128, Chem. Eng. Technol., The Influence of the Polymerization Process on the Product Properties of Metallocene-Polypropene.

Kol et al., 2000, vol.: 122 (43) pp.: 10706-10707, J. Am. Chem. Soc., Isospecific Living Polymerization of 1-Hexene by a Readily Available Nonmetallocene C(sub)2(sub)-Symmetrical Zirconium Catalyst.

Luongo, 1960, vol.: 3, pp.: 302-309, J. Applied Polymer Science, Infrared Study of Polypropylene.

Pellecchia et al., 1994, vol.: 13, pp.: 298-302, Organometallics, Single Insertion of a-Olefins into the Cationic Complex [Zr(CH(sub)2(sub)Ph)(sub)3(sub)]+ Affording Isolable [Zr(CH(sub)2(sub)Ph)(sub)2(sub)(CH(sub)2(sub)CHRCH (sub)2(sub)Ph)]+ Adducts.

Pellecchia et al., 1993, vol.: 115, pp.: 1160-1162, J. Am. Chem. Soc., Synthesis, Crystal Structure, and Olefin Polymerization of a Zwitterionic n(sup)6(sup)-Arene Zirconium Tris (hydrocarbyl).

Pellecchia et al., 1994, vol.: 13, pp.: 3773-3775, Organometallics, A Novel n(sup)7(sup) Coordination Mode of a Benzyl Ligand in a Cationic Zirconium Complex.

Stanforth, 1998, vol.: 54, pp.: 263-303, Tetrahedron, Catalytic Cross-Coupling Reactions in Biaryl Synthesis.

Sundell, 1996, vol.: 37, pp.: 3227-3231, Polymer, Isotacticity Determination of Polypropylene Using FT-Raman Spectroscopy.

Takahashi et al., 1997, vol.: 8 (18) pp.: 3125-3130, Tetrahedron Asymmetry, An Expedient Route to Some Monoalkyl Ethers of Enantiomerically Pure Bi-Beta-Napthol.

Vathauer et al., 2001, vol.: 42, pp.: 4017-4024, Polymer, Extremely Active Polymerizations of Propene by Bisindenzylzirconocenes and Tera(pentafluorophenyl)-borate.

Walter et al., 1999, vol.: A36 (11) pp.: 1613-1639, Pure & Appl. Chem., Novel Polypropylene Materials.

Cram et al., 1989, vol.: 54, pp.: 5460-5482, J. Org. Chem., Host-Guest Complexation. 52. Bridged and Chiral Hemispherands.

Cram et al., 1982, vol.: 5, pp.: 301-304, Chem. Commun. Spherand Complexation and Decomplexation Rates with Sodium and Lithium Picrates, and Activation Parameters for Decomplexation.

BRIDGED BI-AROMATIC CATALYSTS, COMPLEXES, AND METHODS OF USING THE SAME

CROSS-REFERENCE TO RELATED APPLICATIONS

This application claims the benefit of U.S. Provisional Application No. 60/566,527, filed on Apr. 29, 2004. This application also is a continuation-in-part of and claims the benefit of U.S. application Ser. No. 10/421,235, filed on Apr. 23, 2003 now U.S. Pat. No. 6,897,276, which claims the benefit of U.S. Provisional Application No. 60/375,363, filed on Apr. 24, 2002. Also, this application is related to U.S. application Ser. No. 10/421,212, now U.S. Pat. No. 6,841,502; U.S. application Ser. No. 10/421,219, now U.S. Pat. No. 6,869,904; U.S. application Ser. No. 10/957,036, filed Sep. 30, 2004; and U.S. application Ser. No. 11/034,410, filed Jan. 12, 2005. All of these applications are incorporated herein by reference for all purposes.

TECHNICAL FIELD

The present invention relates to ligands, complexes, compositions and/or catalysts, as well as to methods of polymerization that employ such catalysts and to the resulting polymers.

BACKGROUND

Ancillary (or spectator) ligand-metal coordination complexes (e.g., organometallic complexes) and compositions are useful as catalysts, additives, stoichiometric reagents, solid-state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, *Adv. Organometallic Chem.*, 1991, Vol. 32, pp. 325–153 and the references therein, all of which is incorporated herein by reference.

One application for metallocene catalysts is producing isotactic polypropylene. An extensive body of scientific literature examines catalyst structures, mechanism and polymers prepared by metallocene catalysts. See, e.g., Resconi et al., "Selectivity in Propene Polymerization with Metallocene Catalysts," *Chem. Rev.* 2000, 100, 1253–1345 and G. W. Coates, "Precise Control of Polyolefin Stereochemistry Using Single-Site Metal Catalysts," *Chem. Rev.* 2000, 100, 1223–1252 and the references cited in these review articles. Isotactic polypropylene has historically been produced with heterogeneous catalysts that may be described as a catalyst on a solid support (e.g., titanium tetrachloride and aluminum alkyls on magnesium dichloride). This process typically uses hydrogen to control the molecular weight and electron-donor compounds to control the isotacticity. See also EP 0 622 380, EP 0 292 134 and U.S. Pat. Nos. 4,971,936, 5,093,415, 4,297,465, 5,385,993 and 6,239,236.

Given the extensive research activities with respect to metallocene catalysts, there is continued interested in the next generation of non-cyclopentadienyl ligands for olefin polymerization catalysts providing attractive alternatives. See, e.g., "The Search for New-Generation Olefin Polymerization Catalysts: Life beyond Metallocenes", Gibson, et al., *Angew. Chem. Int. Ed.,* 1999, vol. 38, pp. 428–447; *Organometallics* 1999, 18, pp. 3649–3670 and "Advances in Non-Metallocene Olefin polymerization Catalysts", Gibson, et al., *Chem Rev.* 2003, 103, 283–315. Recently, for isotactic polypropylene, bis-amide catalysts have been disclosed in U.S. Pat. No. 5,318,935 and amidinate catalysts have been disclosed in WO 99/05186. See also U.S. Pat. Nos. 6,214,939 and 6,713,577 for non-metallocene isotactic polypropylene catalysts.

Isotactic polypropylene and its production has been extensively studied. See, e.g., U.S. Pat. No. 6,262,199 for isotactic polypropylene produced with metallocene catalysts. In general, those of skill in the art have concentrated on $C_2$ symmetrical metal complexes based on the theory that such symmetry allows for tacticity control. See, e.g., "Stereospecific Olefin Polymerization with Chiral Metallocene Catalysts", Brintzinger, et al., *Angew. Chem. Int. Ed. Engl.,* 1995, Vol. 34, pp. 1143–1170. For example, Kol et al., *J. Am. Chem. Soc.* 2000, 122, 10706–10707 and WO 02/36638 disclose a $C_2$-symmetrical structure that may induce tacticity control. However, the art still fails to provide a higher molecular-weight, narrow polydispersity, isotactic polypropylene with a high melting point, in part provided by an isotactic polypropylene having few, if any, regio-errors (or regio-irregularities), produced at high temperatures (e.g., greater than 100° C.) that is commercially desirable.

Therefore, a need exists for the discovery and optimization of non-cyclopentadienyl based catalysts for olefin polymerization, and in particular for certain polymers, such as isotactic polypropylene and ethylene-alpha-olefin copolymers. Furthermore, a need still exists for new catalysts to produce high molecular weight isotactic polypropylene with a high melting point, particularly in a solution process and at higher polymerization temperatures.

SUMMARY

The invention features ligands, compositions and metal complexes that are useful in catalysts for olefin polymerization and other transformations, as well as methods for preparing the ligands and for using the compositions or complexes in catalytic transformations such as olefin polymerization. In general, the ligands are dianionic chelating ligands that can occupy up to four coordination sites of a metal atom and more specifically have a substituted bridged bis-bi-aromatic structure—that is, a bis-bi-aromatic structure in which the bi-aromatic groups are joined by a substituted bridge, as will be discussed in more detail below. Catalysts according to the invention can be provided by compositions including a ligand, a metal precursor, and optionally an activator, combination of activators, or an activator package. Alternatively, catalysts can be provided by metal-ligand complexes and optionally may additionally include an activator, combination of activators or activator package. For example, metal-ligand complexes according to the invention can be characterized by the general formula:

$$(4,2,O,S)ML_{n'} \qquad (VI)$$

where (4,2,O,S) is a dianionic ligand having at least 4 atoms that are oxygen or sulfur and chelating to the metal M at at least 2, more specifically 4, coordination sites through oxygen and/or sulfur atoms; M is a metal selected from the group consisting of groups 3–6 and Lanthanide elements of the Periodic Table of Elements, more specifically, from group 4 (Hf, Zr and Ti); each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof; and optionally two or more L groups may be linked together in a ring structure; n' is 1, 2, 3, or 4.

In general, in one aspect, the invention features compositions of matter, including ligands, compositions and metal-ligand complexes, that include a compound characterized by the general formula:

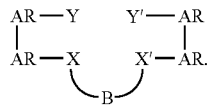

The compound has at least two hydrogen atoms capable of removal in a binding reaction with a metal atom or metal precursor or base. Each AR is independently selected from the group consisting of optionally substituted aryl or heteroaryl. B is a bridging group having from two to 50 atoms not counting hydrogen atoms and is selected from the group consisting of substituted divalent hydrocarbyl and divalent heteroatom-containing hydrocarbyl. X and X' are independently selected from the group consisting of oxygen, sulfur, —$NR^{30}$—, —$PR^{30}$—, where $R^{30}$ is selected from the group consisting of hydrogen, halogen, and optionally substituted hydrocarbyl, heteroatom-containing hydrocarbyl, silyl, boryl, alkoxy, aryloxy and combinations thereof. Y and Y' are independently selected from the group consisting of hydroxy, mercapto, and optionally substituted amino, phosphino, alkoxy, aryloxy, alkylthio, and arylthio.

Particular embodiments can include one or more of the following features. The bridging group B can be selected from the group consisting of substituted divalent alkyl, alkenyl, alkynyl, heteroalkyl, heteroalkenyl, heteroalkynyl, aryl, heteroaryl and silyl. The bridging group B can be substituted with one or more optionally substituted hydrocarbyl or heteroatom-containing hydrocarbyl groups, not counting AR—X and ARX'. The bridging group B can be substituted with two or more hydrocarbyl or heteroatom-containing hydrocarbyl groups, not counting AR—X and AR—X', wherein two or more of the hydrocarbyl or heteroatom-containing hydrocarbyl groups are optionally joined into a ring structure having from 3 to 50 atoms in the ring structure not counting hydrogen atoms.

The bridging group B can include a bridge of one or more atoms extending from X to X', the bridge including one or more atoms adjacent to the X and/or the X', and one or more of the bridge atoms adjacent to the X and/or the X' can be bonded to one or more substituents, not counting bonds to X and/or X' or neighboring atoms along the bridge, where the one or more substituents are independently selected from the group consisting of optionally substituted alkyl, heteroalkyl, aryl and heteroaryl. The bridging group B can be substituted with a plurality of substitutents independently selected from the group consisting of optionally substituted alkyl, heteroalkyl, aryl and heteroaryl, where each of the bridge atoms adjacent to the X and/or the X' is bonded to at least one of the plurality of substituents, not counting bonds to X and/or X' or neighboring atoms along the bridge, and where two or more of the substituents are optionally joined into a ring structure having from 3 to 50 atoms in the ring structure not counting hydrogen atoms. Each of the bridge atoms adjacent to the X and/or the X' can be bonded to two of the plurality of substituents. The group X—B—X' can be selected from the group consisting of

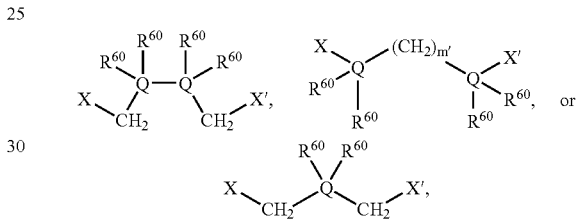

wherein each Q is independently selected from the group consisting of carbon and silicon, each $R^{60}$ is independently selected from the group consisting of hydrogen and optionally substituted hydrocarbyl and heteroatom containing hydrocarbyl, provided that at least one $R^{60}$ substituent is not hydrogen, wherein the $R^{60}$ substituents are optionally joined into a ring structure having from 3 to 50 atoms in the ring structure not counting hydrogen atoms, and m' is 0, 1, or 2.

The bridging group B can be represented by the general formula—$(Q''R^{40}_{2-z''})_{z'}$—wherein each Q'' is independently either carbon or silicon and wherein each $R^{40}$ substituent is independently selected from the group consisting of hydrogen and optionally substituted hydrocarbyl and heteroatom containing hydrocarbyl, provided that at least one $R^{40}$ substituent is not hydrogen, and wherein two or more $R^{40}$ substituents can optionally be joined into a ring structure having from 3 to 50 atoms in the ring structure not counting hydrogen atoms; z' is an integer from 1 to 10; and z'' is 0, 1 or 2. z' can be an integer greater than 1, and two or more $R^{40}$ substituents can be independently selected from the group consisting of optionally substituted hydrocarbyl or heteroatom-containing hydrocarbyl. Similarly, z' can be an integer greater than 1, and the bridging group B can be substituted such that one or more of the $R^{40}$ substituents bonded to a Q'' adjacent to one or more of X and X' is independently selected from the group consisting of optionally substituted alkyl, heteroalkyl, aryl and heteroaryl. The bridging group B can be substituted such that a plurality of $R^{40}$ substitutents are independently selected from the group consisting of optionally substituted alkyl, heteroalkyl, aryl and heteroaryl, each Q'' adjacent to the X and/or the X' being bonded to at least one of the plurality of $R^{40}$ substituents. Each Q" adjacent to the X and/or the X' can be bonded to two of the plurality of $R^{40}$ substituents.

The compound can be characterized by the general formula:

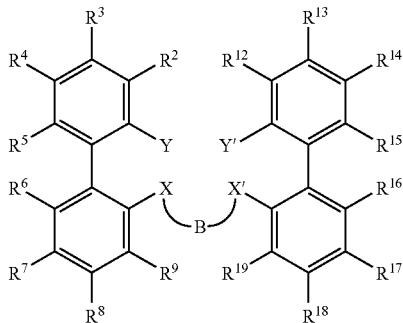

wherein each of $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$ and $R^{19}$ is independently selected from the group consisting of hydrogen, halogen, nitro, and optionally substituted hydrocarbyl, heteroatom-containing hydrocarbyl, alkoxy, aryloxy, silyl, boryl, phosphino, amino, alkylthio, arylthio, and combinations thereof; and optionally two or more R groups can combine together into ring structures, with such ring structures having from 3 to 100 atoms in the ring not counting hydrogen atoms. The compound can be characterized by the formula:

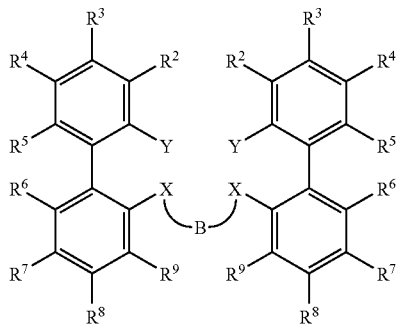

wherein each of $R^2$, $R^3$, $R^4$, $R^5$, $R^6$, $R^7$, $R^8$ and $R^9$ is independently selected from the group consisting of hydrogen, halogen, nitro, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, and combinations thereof The $R^2$ and/or $R^{12}$ substituents can be independently selected from the group consisting of optionally substituted aryl and heteroaryl. The $R^7$ and/or $R^{17}$ substituents can be independently selected from the group consisting of hydrogen and optionally substituted alkyl, heteroalkyl, aryl, heteroaryl, alkoxyl, and aryloxyl.

X and X' can be independently selected from the group consisting of oxygen and sulfur, and Y and Y' can be hydroxy. At least one AR group, or two or more AR groups, can be heteroaryl. The bridging group B can include one or more chiral centers.

In general, in another aspect, the invention features catalyst compositions that include any of the compositions identified above; a metal precursor compound characterized by the general formula $M(L)_n$ where M is a metal selected from groups 3–6 and lanthanide elements of the periodic table of elements, each L is a moiety that forms a covalent, dative or ionic bond with M, and n is 1, 2, 3, 4, 5, or 6; and, optionally, at least one activator.

Particular embodiments can include one or more of the following features. The metal M can be a Group 4 element. Each L can be independently selected from the group consisting of hydrogen, halogen, optionally substituted alkyl, heteroalkyl, alkenyl, heteroalkenyl, aryl, heteroaryl, alkoxy, aryloxy, boryl, silyl, amino, phosphino, carboxylate, alkylthio, arylthio, 1,3-dionate, oxalate, carbonate, nitrate, sulphate, and combinations thereof. At least one L can be an anion. The metal precursor can be an activated metal precursor, such as $[Zr(CH_2Ph)_3^+][B(C_6F_5)_4^-]$, $[Zr(CH_2Ph)_3^+][PhCH_2B(C_6F_5)_3^-]$, $[Hf(CH_2Ph)_3^+][B(C_6F_5)_4^-]$, and $[Hf(CH_2Ph)_3^+][PhCH_2B(C_6F_5)_3^{13}]$.

In general, in another aspect, the invention features metal-ligand complexes characterized by the formula:

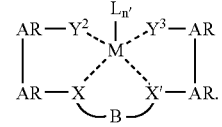

At least two of the bonds from $Y^2$, $Y^3$, X' and X' to M are covalent, with the other bonds being dative. AR is an aromatic group that can be the same or different from the other AR groups, and each AR is independently selected from the group consisting of optionally substituted aryl or heteroaryl. B is a bridging group having from two to 50 atoms not counting hydrogen atoms and is selected from the group consisting of substituted divalent hydrocarbyl and divalent heteroatom-containing hydrocarbyl. X, X', $Y^2$, and Y are independently selected from the group consisting of oxygen, sulfur, —N($R^{30})_r$—, and —P($R^{30})_r$—, and optionally substituted alkoxy, aryloxy, alkylthio, and arylthio, where $R^{30}$ is selected from the group consisting of hydrogen, halogen, and optionally substituted hydrocarbyl, heteroatom-containing hydrocarbyl, silyl, boryl, alkoxy, aryloxy and combinations thereof, and r is 0 or 1. Each L is independently a moiety that forms a covalent, dative or ionic bond with M. n' is 1, 2, 3 or 4.

Particular embodiments include one or more of the following features. X and X' can be independently selected from oxygen and sulfur, while $Y^2$ and $Y^3$ are independently selected from oxygen, sulfur, —$NR^{30}$—, and —$PR^{30}$. X and X' can be independently selected from the group consisting of nitrogen and phosphorus, while $Y^2$ and $Y^3$ are independently selected from the group consisting of optionally substituted amino, phosphino, alkoxy, aryloxy, alkylthio and arylthio.

The complex can be characterized by the general formula:

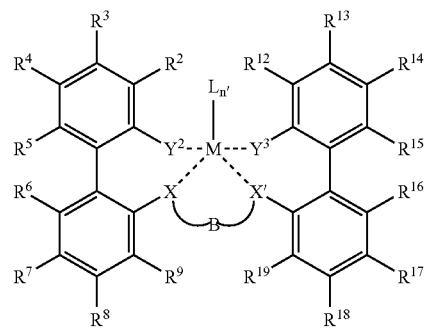

wherein each of $R^2$, $R^3$, $R^4$, $R^5$, $R^6$, $R^7$, $R^8$, $R^9$, $R^{12}$ $R^{13}$, $R^{14}$, $R^{15}$, $R^{16}$, $R^{17}$, $R^{18}$, and $R^{19}$ is independently selected from the group consisting of hydrogen, halogen, nitro, and optionally substituted hydrocarbyl, heteroatom-containing hydrocarbyl, alkoxy, aryloxy, silyl, boryl, phosphino, amino, alkylthio, arylthio, and combinations thereof; optionally two or more R groups can combine together into ring structures, with such ring structures having from 3 to 100 atoms in the ring not counting hydrogen atoms The bridging group B can be selected from the group consisting of substituted divalent alkyl, alkenyl, alkynyl, heteroalkyl, heteroalkenyl, heteroalkynyl, aryl, heteroaryl and silyl. The bridging group B can be substituted with one or more optionally substituted hydrocarbyl or heteroatom-containing hydrocarbyl groups, not counting AR—X and AR—X'. The bridging group B can be substituted with two or more hydrocarbyl or heteroatom-containing hydrocarbyl groups, not counting AR—X and ARX', wherein two or more of the hydrocarbyl or heteroatom-containing hydrocarbyl groups are optionally joined into a ring structure having from 3 to 50 atoms in the ring structure not counting hydrogen atoms.

The bridging group B can include a bridge of one or more atoms extending from X to X', where the bridge includes one or more atoms adjacent to the X and/or the X', and one or more of the bridge atoms adjacent to one or more of the X and/or the X' can be bonded to one or more substituents, not counting bonds to X and/or X' or neighboring atoms along the bridge, where the one or more substituents are independently selected from the group consisting of optionally substituted alkyl, heteroalkyl, aryl and heteroaryl. The bridging group B can be substituted with a plurality of substitutents independently selected from the group consisting of optionally substituted alkyl, heteroalkyl, aryl and heteroaryl, where each of the bridge atoms adjacent to the X and/or the X' is bonded to at least one of the plurality of substituents, not counting bonds to X and/or X' or neighboring atoms along the bridge, and where two or more of the substituents can optionally be joined into a ring structure having from 3 to 50 atoms in the ring structure not counting hydrogen atoms. Each of the bridge atoms adjacent to the X and/or the X' can be bonded to two of the plurality of substituents. The group X—B—X' can be selected from the group consisting of

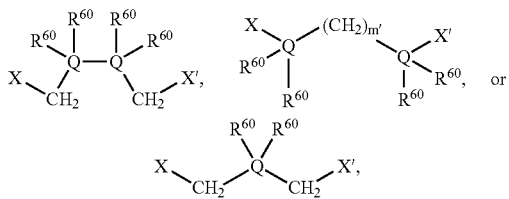

wherein each Q is independently selected from the group consisting of carbon and silicon, each $R^{60}$ is independently selected from the group consisting of hydrogen and optionally substituted hydrocarbyl and heteroatom containing hydrocarbyl, provided that at least one $R^{60}$ substituent is not hydrogen, and where the $R^{60}$ substituents can optionally be joined into a ring structure having from 3 to 50 atoms in the ring structure not counting hydrogen atoms, and where m' is 0, 1, or 2.

The bridging group B can be represented by the general formula—$(Q''R^{40}_{2-z''})_{z'}$—where each Q" is independently either carbon or silicon and wherein each $R^{40}$ substituent is independently selected from the group consisting of hydrogen and optionally substituted hydrocarbyl and heteroatom containing hydrocarbyl, provided that at least one $R^{40}$ substituent is not hydrogen, and where two or more $R^{40}$ substituents can optionally be joined into a ring structure having from 3 to 50 atoms in the ring structure not counting hydrogen atoms; and where z' is an integer from 1 to 10; and z" is 0, 1 or 2. z' can be an integer greater than 1, and two or more $R^{40}$ substituents can be independently selected from the group consisting of optionally substituted hydrocarbyl or heteroatom-containing hydrocarbyl. Similarly, z' can be an integer greater than 1, and the bridging group B can be substituted such that one or more of the $R^{40}$ substituents bonded to a Q" adjacent to one or more of X and X' is independently selected from the group consisting of optionally substituted alkyl, heteroalkyl, aryl and heteroaryl. The bridging group B can be substituted such that a plurality of $R^{40}$ substitutents are independently selected from the group consisting of optionally substituted alkyl, heteroalkyl, aryl and heteroaryl, and each Q" adjacent to the X and/or the X' is bonded to at least one of the plurality of $R^{40}$ substituents. Each Q" adjacent to the X and/or the X' can be bonded to two of the plurality of $R^{40}$ substituents.

The complex can be characterized by the general formula

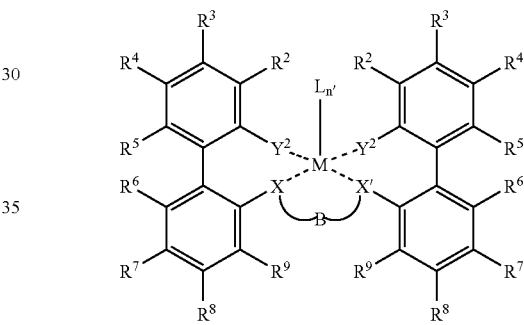

wherein each of $R^2$, $R^3$, $R^4$, $R^5$, $R^6$, $R^7$, $R^8$ and $R^9$ is independently selected from the group consisting of hydrogen, halogen, nitro, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, and combinations thereof.

At least one of the $R^2$ and/or $R^{12}$ substituents can be a substituent other than hydrogen. The $R^2$ and/or $R^{12}$ substituents can be independently selected from the group consisting of optionally substituted aryl and heteroaryl. The $R^2$ and/or $R^{12}$ substituents can be carbazolyl, anthracenyl, or octahydro-anthracenyl. The $R^7$ and/or $R^{17}$ substituents can be independently selected from the group consisting of hydrogen and optionally substituted alkyl, heteroalkyl, aryl, heteroaryl, alkoxyl, and aryloxyl.

X and X' can be independently selected from the group consisting of oxygen and sulfur, and $Y^2$ and $Y^3$ can be oxygen. At least one AR group, or two or more AR groups, can be a heteroaryl.

Each L can be independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. At least one L can be an anion. The metal M can be a Group 4 element. The bridging group B can include one or more chiral centers.

In general, in another aspect, the invention provides methods of preparing metal-ligand complexes. The methods include reacting the above-described compositions with a metal precursor and, optionally, at least one activator.

In general, in another aspect, the invention provides methods of catalyzing a transformation. The methods include reacting one or more reagents in the presence of a catalyst incorporating a composition or complex according to the invention as described above, under conditions sufficient to yield one or more reaction products.

Particular embodiments can include one or more of the following features. The selectivity, including the stereoselectivity, diastereoselectivity or enantioselectivity, of the reaction can be influenced by the catalyst. The composition or the complex can be substantially enantiomerically or diastereomerically pure. The reaction product can be substantially enantiomerically or diastereomerically pure.

In general, in another aspect, the invention provides polymerization processes employing the compositions of the invention as described above. The processes optionally employ at least one activator, which can be an ion forming activator and optional group 13 reagent, or an alumoxane.

In general, in another aspect, the invention provides polymerization processes for olefinic monomers. The processes involve subjecting one or more monomers to the catalyst compositions or complexes according to the invention under polymerization conditions. The polymerization processes can be continuous, batch or semi-batch and can be homogeneous, supported homogeneous or heterogeneous, and can be carried out in solution, slurry or the gas phase.

In general, in another aspect, the invention provides processes for the polymerization of an alpha-olefin. The processes include polymerizing at least one alpha-olefin in the presence of a catalyst formed from composition or complex according to the invention, as described above, optionally in the presence of one or more activators, under polymerization conditions sufficient to form a substantially stereoregular polymer.

Particular embodiments can include one or more of the following features. The at least one alpha-olefin can include propylene. The substantially steroregular polymer can be isotactic polypropylene. The process can be a solution process operated under polymerization conditions that comprise a temperature of at least 100° C. The process can be a solution process operated under polymerization conditions that comprise a temperature of at least 125° C. The stereoregular polymer can contain substantially no regioerrors detectable by standard carbon 13 nuclear magnetic resonance spectroscopy. The metal M can be Hf or Zr.

In general, in another aspect, the invention provides processes for polymerizing ethylene and at least one alpha-olefin. The processes include polymerizing ethylene in the presence of at least one alpha-olefin in the presence of a catalyst formed from a composition or complex according to the invention, as described above, optionally in the presence of one or more activators.

Particular embodiments can include one or more of the following features. The at least one alpha-olefin can be propylene, hexene, octene or styrene. The process can be a solution process. The solution process can be operated under polymerization conditions that comprise a temperature of at least 125° C.

In general, in another aspect, the invention provides processes for polymerizing at least one monomer. The processes include providing a reactor with reactor contents including at least one polymerizable monomer and a composition or complex according to the invention, as described above, and subjecting the reactor contents to polymerization conditions. In particular embodiments, the at least one polymerizable monomer can be ethylene and propylene, ethylene and hexene, ethylene and octene, or ethylene and styrene.

In general, in another aspect, the invention provides methods for preparing a bridged bis biaryl compound. The methods include providing a compound characterized by the formula AR—Y; providing a compound characterized by the formula AR'—X; and reacting the AR—Y compound or the AR'—X compound to substitute the aryl or heteroaryl ring to form a functionalized aryl compound, the aryl or heteroaryl ring being substituted in a position alpha to the corresponding Y or X substituent with a substituent suitable for subsequent cross-coupling. If the functionalized aryl compound was formed by reacting the AR—Y compound, the methods continue by reacting the functionalized aryl compound with the AR'—X compound under cross-coupling conditions to form a biaryl compound characterized by the formula Y—AR—AR'—X; alternatively, if the functionalized aryl compound was formed by reacting the AR'—X compound, the method reacts the functionalized aryl compound with the AR—Y compound under cross-coupling conditions to form a biaryl compound characterized by the formula Y—AR—AR'—X. The biaryl compound is then reacted with a second biaryl compound characterized by the formula Y'—AR'—AR'''—X' and a compound characterized by the formula LG—B—LG to form a bridged bis biaryl compound characterized by the formula:

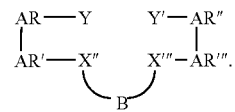

AR is selected from the group consisting of optionally substituted aryl or heteroaryl. AR' is different from AR and is also selected from the group consisting of optionally substituted aryl or heteroaryl. Y is selected from the group consisting of optionally protected hydroxyl, mercapto, and optionally substituted amino, phosphino, alkoxy, aryloxy, alkylthio, and arylthio. X is selected from the group consisting of optionally protected hydroxy, mercapto, and optionally substituted amino and phosphino. B is a bridging group having from two to 50 atoms not counting hydrogen atoms and is selected from the group consisting of optionally substituted divalent hydrocarbyl and divalent heteroatom-containing hydrocarbyl. Each LG is a leaving group for a nucleophilic substitution reaction, and can be the same or different. X' is selected from the group consisting of optionally protected hydroxy, mercapto, and optionally substituted amino and phosphino, and can be the same as or different from X. X'' and X''' are derived from X and X', respectively, and are independently selected from the group consisting of oxygen, sulfur, —NR$^{30}$—, —PR$^{30}$—, where R$^{30}$ is selected from the group consisting of hydrogen, halogen, and optionally substituted hydrocarbyl, heteroatom-containing hydrocarbyl, silyl, boryl, alkoxy, aryloxy and combinations thereof. Y' is selected from the group consisting of optionally protected hydroxy, mercapto, and optionally substituted amino, phosphino, alkoxy, aryloxy, alkylthio, and arylthio and can be the same as or different from Y. AR" and AR'" are independently selected from the group consisting of optionally substituted aryl or heteroaryl and can be the same as or different from AR and AR'.

Particular embodiments can include one or more of the following features. Reacting the AR—Y compound or the AR'—X compound to form the functionalized aryl compound can include reacting the AR—Y compound or the AR'—X compound with a metallating agent, or, more specifically, a lithiating agent. The AR—Y compound can be a compound characterized by the formula

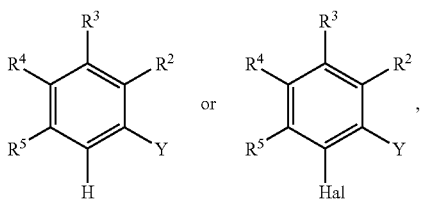

the AR'—X compound can be a compound characterized by the formula

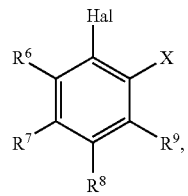

and the AR—Y compound can reacted to form the functionalized aryl compound, wherein $R^2$, $R^3$, $R^4$, $R^5$, $R^6$, $R^7$, $R^8$ and $R^9$ are independently selected from the group consisting of hydrogen, halogen, nitro, and optionally substituted hydrocarbyl, heteroatom-containing hydrocarbyl, alkoxy, aryloxy, silyl, boryl, phosphino, amino, alkylthio, arylthio, and combinations thereof; optionally two or more R groups can combine together into ring structures, with such ring structures having from 3 to 100 atoms in the ring not counting hydrogen atoms; Hal is Cl, Br, I, or OTf; and X and Y are optionally protected by a protecting group for amino, phosphino, hydroxy or mercapto moieties.

The AR—Y compound can be a compound characterized by the formula:

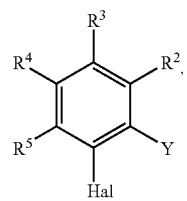

the AR'—X compound can be a compound characterized by the formula:

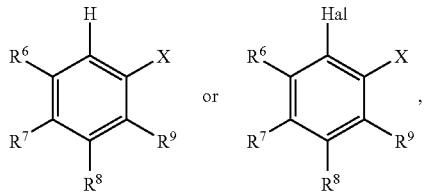

and the AR'—X compound is reacted to form the functionalized aryl compound, wherein $R^2$, $R^3$, $R^4$, $R^5$, $R^6$, $R^7$, $R^8$ and $R^9$ are independently selected from the group consisting of hydrogen, halogen, nitro, and optionally substituted hydrocarbyl, heteroatom-containing hydrocarbyl, alkoxy, aryloxy, silyl, boryl, phosphino, amino, alkylthio, arylthio, and combinations thereof; optionally two or more R groups can combine together into ring structures, with such ring structures having from 3 to 100 atoms in the ring not counting hydrogen atoms; Hal is Cl, Br, I, or OTf; and X and Y are optionally protected by a protecting group for amino, phosphino, hydroxy or mercapto moieties.

In general, in another aspect, the invention provides an alternative method for preparing a bridged bis biaryl compound. The method includes providing a bridged bis aryl compound characterized by the formula AR—X—B—X'—AR', providing compounds characterized by the formula AR"—Y and AR'"—Y', and reacting the bridged bis aryl compound or the AR"—Y and AR'"—Y' compounds to substitute each of the corresponding aryl or heteroaryl rings to form a functionalized bridged bis aryl compound or a pair of functionalized aryl compounds, each of corresponding the aryl or heteroaryl rings being substituted in a position alpha to the corresponding X and X' or Y and Y' substituents with a substituent suitable for subsequent cross-coupling. The functionalized bridged bis aryl compound is reacted with the AR"—Y and AR'"—Y' compounds, or the functionalized aryl compounds are reacted with the bridged bis aryl compound, under cross-coupling conditions to form a bridged bis biaryl compound characterized by the formula:

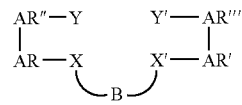

AR, AR', AR" and AR'" are independently selected from the group consisting of optionally substituted aryl or heteroaryl. At least one of AR" and AR'" is different from at least one of AR and AR'. B is a bridging group having from two to 50 atoms not counting hydrogen atoms and is selected from the group consisting of optionally substituted divalent hydrocarbyl and divalent heteroatom-containing hydrocarbyl. X and X' are independently selected from the group consisting of oxygen, sulfur, —NR$^{30}$—, —PR$^{30}$—, where R$^{30}$ is selected from the group consisting of hydrogen, halogen, and optionally substituted hydrocarbyl, heteroatom-containing hydrocarbyl, silyl, boryl, alkoxy, aryloxy and combinations thereof. Y and Y' are independently selected from the group consisting of optionally protected hydroxyl, mercapto, and optionally substituted amino, phosphino, alkoxy, aryloxy, alkylthio, and arylthio.

Particular embodiments can include one or more of the following features. Reacting the bridged bis aryl compound or the AR''—Y and AR'''—Y' compounds to form the functionalized bridged bis aryl compound or the functionalized aryl compounds can include reacting the bridged bis aryl compound or the AR''—Y and AR'''—Y' compounds with a metallating agent, or more specifically a lithiating agent. The bridged bis aryl compound can be characterized by the formula

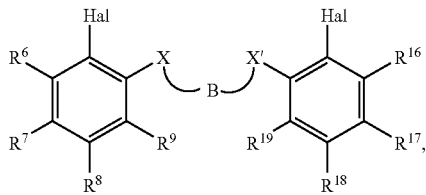

the AR''—Y and AR'''—Y' compounds can be independently characterized by the formulae

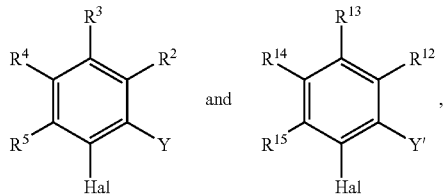

and the bridged bis biaryl compound is characterized by the formula

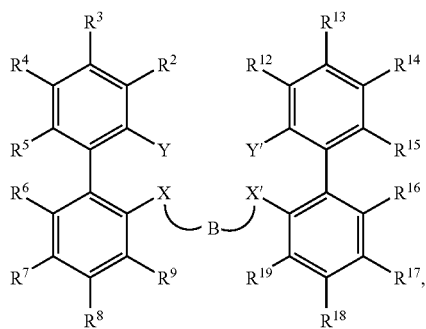

where $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently selected from the group consisting of hydrogen, halogen, nitro, and optionally substituted hydrocarbyl, heteroatom-containing hydrocarbyl, alkoxy, aryloxy, silyl, boryl, phosphino, amino, alkylthio, arylthio, and combinations thereof; optionally two or more of $R^2$, $R^3$, $R^4$, and $R^5$, $R^6$, $R^7$, $R^8$, and $R^9$, $R^{12}$, $R^{13}$, $R^{14}$ and $R^{15}$, or $R^{16}$, $R^{17}$, $R^{18}$ and $R^{19}$ can combine together into ring structures, with such ring structures having from 3 to 100 atoms in the ring not counting hydrogen atoms; and where Y and Y' are optionally protected by a protecting group for amino, phosphino, hydroxy or mercapto moieties, where Y and Y' are optionally protected by a protecting group as defined above.

The functionalized aryl compounds can be independently characterized by the formulae:

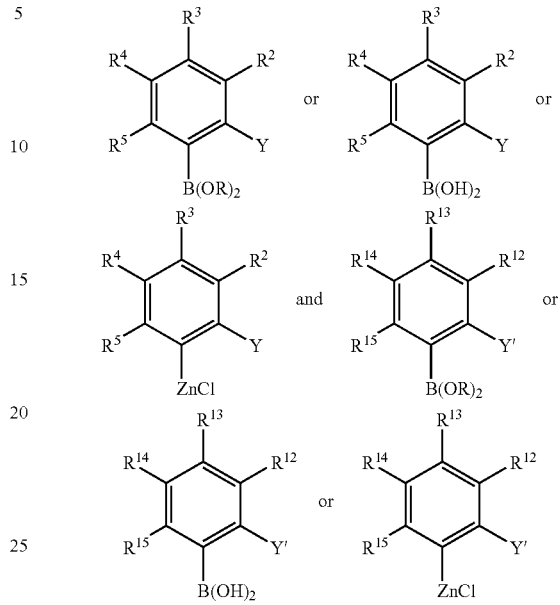

respectively, wherein each R is independently selected from the group consisting of optionally substituted hydrocarbyl, heteroatom-containing hydrocarbyl, silyl, and combinations thereof, wherein the R groups are optionally joined to form a ring structure containing from 3 to 50 atoms, not counting hydrogen, and where Y and Y' are optionally protected by a protecting group for amino, phosphino, hydroxy or mercapto moieties.

The functionalized bis aryl compound can be characterized by the formula:

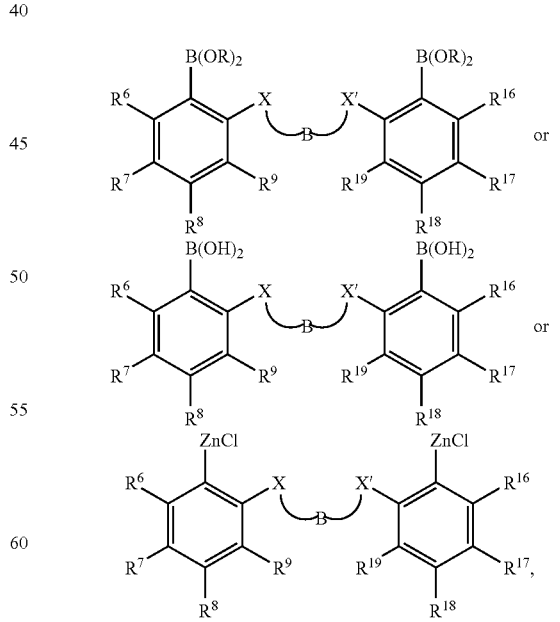

respectively, wherein each R is independently selected from the group consisting of optionally substituted hydrocarbyl, heteroatom-containing hydrocarbyl, silyl, and combinations thereof, wherein the R groups are optionally joined to form a ring structure containing from 3 to 50 atoms, not counting hydrogen.

Providing the bridged bis aryl compound can include reacting a compound characterized by the formula LG—B—LG' with compounds characterized by the formulae AR—X and AR'—X' to form the bridged bis aryl compound, wherein LG and LG' are leaving groups for nucleophilic displacement reactions and can be the same or different. Providing the bridged bis aryl compound can include reacting a compound characterized by the formula HX—B—X'H with compounds characterized by the formulae AR—Hal and AR'—Hal, or AR—F and AR'—F, to form the bridged bis aryl compound in a cross-coupling or nucleophilic displacement reaction, respectively. The bridging group B can be selected from the group consisting of divalent alkyl, alkenyl, alkynyl, heteroalkyl, heteroalkenyl, heteroalkynyl, aryl, heteroaryl and silyl, substituted with one or more optionally substituted hydrocarbyl or heteroatom-containing hydrocarbyl groups, not counting AR—X and AR'—X'. The bridging group B can be substituted with two or more hydrocarbyl or heteroatom-containing hydrocarbyl groups, not counting AR—X and AR'—X', wherein two or more of the hydrocarbyl or heteroatom-containing hydrocarbyl groups are optionally joined into a ring structure having from 3 to 50 atoms in the ring structure not counting hydrogen atoms. The bridging group B can include a bridge of one or more atoms extending from X to X', the bridge including one or more atoms adjacent to the X and/or the X', and one or more of the bridge atoms adjacent to the X and/or the X' can be bonded to one or more substituents, not counting bonds to X and/or X' or neighboring atoms along the bridge, the one or more substituents being independently selected from the group consisting of optionally substituted alkyl, heteroalkyl, aryl and heteroaryl. The bridging group B can be substituted with a plurality of substitutents independently selected from the group consisting of optionally substituted alkyl, heteroalkyl, aryl and heteroaryl, where each of the bridge atoms adjacent to the X and/or the X' is bonded to at least one of the plurality of substituents, not counting bonds to X and/or X' or neighboring atoms along the bridge, and where two or more of the substituents are optionally joined into a ring structure having from 3 to 50 atoms in the ring structure not counting hydrogen atoms. Each of the bridge atoms adjacent to the X and/or the X' can be bonded to two of the plurality of substituents.

In general, in still another aspect, the invention provides arrays of ligands, metal precursors and/or metal-ligand complexes. These arrays can be useful for the high speed or combinatorial materials science discovery or optimization of the catalyst compositions or complexes disclosed herein.

The invention can be implemented to provide one or more of the following advantages. The ligands, compositions, complexes and polymerization methods of the invention can be used to provide catalysts exhibiting enhanced activity. Catalysts incorporating the ligands, compositions and/or complexes can be used to catalyze olefin polymerizations, or to catalyze other transformations, including stereo-, enantio-, or diastereoselective transformations. By selecting an appropriate ligand, compositions and/or complexes can be obtained to provide for desired properties in the resulting product. Thus, polymers produced using the ligands, compositions, complexes, and methods of the invention can exhibit higher (or lower) melting points, higher (or lower) molecular weights, and/or higher (or lower) polydispersities, than polymers produced using prior known catalysts. Catalysts incorporating the ligands, compositions and/or complexes can be used according to the polymerization methods of the invention to produce polymers under commercially desirable polymerization conditions. Chiral compositions and/or complexes according to the inveniton can be used to catalyze stereoselective, enantioselective or diastereoselective transformations. In some embodiments, such chiral compositions and/or complexes can be used to produce polymers exhibiting broad (e.g., bimodal) polydispersities. Catalysts incorporating the ligands, compositions and complexes of the invention can exhibit catalytic activity at higher temperatures than prior known catalysts. Copolymerization processes (e.g., ethylene/α-olefin copolymerizations) using the ligands, compositions and complexes of the invention can exhibit higher (or lower) comonomer incorporation than processes involving prior known catalysts.

The synthetic methods of the invention require fewer steps than previous methods, and employ a convergent approach that provides for higher yields and readily incorporates diversity into the resulting ligands. As a result, the ligand synthesis chemistry is now amenable to a wider range of commercially-available starting materials, and can be used to generate a larger number of ligands, and therefore compositions and complexes, for high throughput screening applications. These techniques make it possible to use a broad range of compounds as starting materials, thereby offering a greater number of structural options for the resulting ligands, and potentially lower operating costs.

The details of one or more embodiments of the invention are set forth in the description below. Other features, objects and advantages of the invention will be apparent from the description and from the claims.

DETAILED DESCRIPTION

As used herein, the phrase "characterized by the formula" is not intended to be limiting and is used in the same way that "comprising" is commonly used. The term "independently selected" is used herein to indicate that the groups in question—e.g., $R^1$, $R^2$, $R^3$, $R^4$, and $R^5$—can be identical or different (e.g., $R^1$, $R^2$, $R^3$, $R^4$, and $R^5$ may all be substituted alkyls, or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, tbutyl, octyl, decyl, and the like, as well as cycloalkyl groups such as cyclopentyl, cyclohexyl and the like. Generally, although again not necessarily, alkyl groups herein may contain 1 to about 12 carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., —CH$_2$OCH$_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 12 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O—alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In particular embodiments, aryl substituents have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, pyrazine, isoxazole, pyrazole, pyrrole, furan, thiazole, oxazole, imidazole, isothiazole, oxadiazole, triazole, etc. or benzo-fused analogues of these rings, such as indole, carbazole, benzofuran, benzothiophene, etc., are included in the term "heteroaryl"). In some embodiments herein, multi-ring moieties are substituents and in such an embodiment the multi-ring moiety can be attached at an appropriate atom. For example, "naphthyl" can be 1 naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The terms "halo" and "halogen" are used in the conventional sense to refer to a chloro, bromo, fluoro or iodo substituent.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," and the like, as alluded to in some of the aforementioned definitions, is meant that in the hydrocarbyl, alkyl, aryl or other moiety, at least one hydrogen atom bound to a carbon atom is replaced with one or more substituent groups such as hydroxy, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multple bonds, such as around a ring.

As used herein the term "silyl" refers to the —SiZ$^1$Z$^2$Z$^3$ radical, where each of Z$^1$, Z$^2$, and Z$^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above. As used herein, the term "phosphino" refers to the group—PZ$^1$Z$^2$, where each of Z$^1$ and Z$^2$ is as defined above. As used herein, the term "phosphine" refers to the group :PZ$^1$Z$^2$Z$^3$, where each of Z$^1$, Z$^3$ and Z$^2$ is as defined above. The term "amino" is used herein to refer to the group —NZ$^1$Z$^2$, where each of Z$^1$ and Z$^2$ is as defined above. The term "amine" is used herein to refer to the group :NZ$^1$Z$^2$Z$^3$, where each of Z$^1$, Z$^2$ and Z$^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like.

Other abbreviations used herein include: "$^i$Pr" to refer to isopropyl; "$^t$Bu" to refer to tertbutyl; "Me" to refer to methyl; "Et" to refer to ethyl; "Ph" refers to phenyl; "Np" refers to napthyl; "Cbz" refers to carbazolyl; "Ant" refers to anthracenyl; and "H$_8$-Ant" refers to 1,2,3,4,5,6,7,8-octahydroanthracenyl.

The ligands of the present invention can be described in a number of different ways. Thus, the ligands can be described as dianionic, chelating ligands that may occupy up to four coordination sites of a single metal atom. The ligands can also be described as diaionic ligands that, when chelated to a metal atom, form at least one or two seven member metalocycles (counting the metal atom as one member of the seven member ring). Alternatively, the ligands can be described as dianionic, chelating ligands that use either oxygen or sulfur as binding atoms to the metal atom. In still other alternatives, the ligands can be described as non-metallocene ligands that can coordinate in an approximate C$_2$-symmetrical complex with a metal atom. These descriptions are not mutually exclusive, and can be used together or separately.

For example, suitable ligands according to the invention may be characterized by the following general formula:

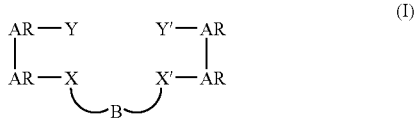

(I)

wherein each ligand has at least two hydrogen atoms capable of removal in a binding reaction with a metal atom or metal precursor or base; AR is an aromatic group that can be the same as or different from the other AR groups with, generally, each AR being independently selected from the group consisting of optionally substituted aryl or heteroaryl; B is a bridging group having from two to 50 atoms (not counting hydrogen atoms); X and X' are the same or different and are independently selected from the group consisting of oxygen, sulfur, —NR —, —PR$^{30}$—, where R$^{30}$ is selected from the group consisting of hydrogen, halogen, and optionally substituted hydrocarbyl, heteroatom-containing hydrocarbyl, silyl, boryl, alkoxy, aryloxy and combinations thereof; and Y and Y' are the same or different and are independently selected from the group consisting of hydroxy, mercapto, and optionally substituted amino, phosphino, alkoxy, aryloxy, alkylthio and arylthio.

In formula I, it is required that there be at least 2 hydrogen atoms associated with each ligand that are capable of being removed in a complexation reaction with a metal atom or metal precursor or in a reaction with base. In some embodiments, prior to such a complexation reaction, a base may be reacted with the ligand to form a salt, the product of which may then be reacted with a metal precursor (as described herein). In some embodiments at least two of X, X', Y and Y' have at least one labile hydrogen atom (e.g., an —OH, —SH, —NH, or the like). In some more particular embodiments, X and X' are independently selected from the group consisting of oxygen, sulfur and —NR$^{30}$—; and in still other embodiments X and X' are independently selected from the group consisting of oxygen and sulfur. In some embodiments, Y and Y' are selected from the group consisting of hydroxy, mercapto, and optionally substituted amino, alkoxy, aryloxy, alkylthio and arylthio; and in more particular embodiments Y and Y' are independently selected from the group consisting of hydroxy and mercapto.

Generally, the "upper aromatic ring" is the ring to which a Y group (such as Y, Y') is bonded or part of. Similarly, the "lower aromatic ring" is the ring to which an X group (such as X, X') is bonded or part of. In some embodiments, AR—AR (that is, the structure formed from one upper aromatic ring and its corresponding lower aromatic ring) is a biaryl species, more specifically a biphenyl. In other embodiments, at least one AR is a heteroaryl group. More specifically, in some embodiments, at least one upper aromatic ring and/or at least one lower aromatic ring is a heteroaryl.

In some embodiments, the bridging group B is selected from the group consisting of substituted divalent hydrocarbyl and divalent heteroatom containing hydrocarbyl. In more particular embodiments, B is selected from the group consisting of substituted divalent alkyl, alkenyl, alkynyl, heteroalkyl, heteroalkenyl, heteroalkynyl, aryl, heteroaryl and silyl. In any of these embodiments, the bridging group can be substituted with one or more optionally substituted hydrocarbyl or heteroatom-containing hydrocarbyl groups, such as optionally substituted alkyl, alkenyl, alkynyl, heteroalkyl, heteroalkenyl, heteroalkynyl, aryl, or heteroaryl. It should be noted that these substitutions are in addition to the bonds between the bridging group B and the X and X' components of the AR—X and AR—X' groups in formula I. Two or more of the hydrocarbyl or heteroatom-containing hydrocarbyl groups can be joined into a ring structure having from 3 to 50 atoms in the ring structure (not counting hydrogen atoms). In some embodiments in which the bridging group includes one or more ring structures, it may be possible to identify more than one chain of bridge atoms extending from X to X', and in such cases it can be convenient to define the "bridge" as the shortest path of connectivity between X and X', and the "substitutents" as the groups bonded to atoms in the bridge. Where there are two alternative, equally short paths of connectivity, the bridge can be defined along either path.

In still other embodiments, B can be represented by the general formula —(Q"R$^{40}_{2-z"}$)$_{z'}$—wherein each Q" is independently either carbon or silicon and where each R$^{40}$ is independently selected from the group consisting of hydrogen and optionally substituted hydrocarbyl or heteroatom-containing hydrocarbyl. Two or more R$^{40}$ groups may be joined into a ring structure having from 3 to 50 atoms in the ring structure (not counting hydrogen atoms). In these embodiments, z' is an integer from 1 to 10, more specifically from 1 to 5 and even more specifically from 2–5, and z" is 0, 1 or 2. For example, when z" is 2, there is no R$^{40}$ group associated with Q", which allows for those cases where one Q" is multiply bonded to a second Q". In more specific embodiments, R$^{40}$ is selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, alkylthio, arylthio, and combinations thereof, where at least one R$^{40}$ group in B is not hydrogen. In any of the embodiments mentioned above, the B group can include one or more chiral centers. Thus, for example, B can be represented by the formula —CHR$^{50}$—(CH$_2$)$_m$—CHR$^{51}$—, where R$^{50}$ and R$^{51}$ are independently selected from the group consisting of optionally substituted alkyl, heteroalkyl, aryl or heteroaryl, R$^{50}$ and R$^{51}$ can be arranged in any relative configuration (e.g., syn/anti, threo/erythro, or the like), and where the ligand can be generated as a racemic mixture or in an enantiomerically pure form.

In particular embodiments, the bridging group B includes a chain of one or more bridge atoms extending from X to X', and one or more of the bridge atoms situated adjacent to the X and/or the X' is bonded to one or more substituents (not counting bonds to X and/or X' or neighboring bridge atoms along the chain, as noted above), where the substituents are independently selected from the group consisting of optionally substituted alkyl, heteroalkyl, aryl and heteroaryl. In more particular embodiments, the bridging group B is substituted with a plurality of substitutents that are independently selected from the group consisting of optionally substituted alkyl, heteroalkyl, aryl and heteroaryl, such that each of the bridge atoms that is adjacent to the X and/or the X' is bonded to at least one substituent, again not counting bonds to X and/or X' or neighboring bridge atoms. In such embodiments, two or more of the substituents can be joined into a ring structure having from 3 to 50 atoms in the ring structure (not counting hydrogen atoms).

Thus, in some embodiments, the X—B—X' fragment can be characterized by one of the following formulae

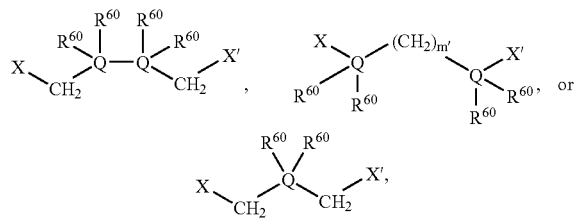

where each Q is independently selected from the group consisting of carbon and silicon, each R$^{60}$ is independently selected from the group consisting of hydrogen and optionally substituted hydrocarbyl and heteroatom containing hydrocarbyl, provided that at least one R$^{60}$ substituent is not hydrogen, wherein the R$^{60}$ substituents are optionally joined into a ring structure having from 3 to 50 atoms in the ring structure not counting hydrogen atoms, and m' is 0, 1, 2 or 3. Specific X—B—X' fragments within these embodiments include, for example, X—CH(CH$_3$)—(CH(CH$_3$)—X', X—CH$_2$—CH(CH$_3$)—CH$_2$—X', X—CH$_2$—C(CH$_3$)$_2$—CH$_2$—X', X—CH$_2$—CH(C$_6$H$_5$)—CH$_2$—X', X—CH(CH$_3$)—CH$_2$—CH(CH$_3$)—X', X—CH(C$_2$H$_5$)—CH$_2$—CH(C$_2$H$_5$)—X', X—CH(CH$_3$)CH$_2$CH$_2$CH(CH$_3$)X', X—CH(C$_6$H$_5$)CH$_2$CH(C$_6$H$_5$)—X',

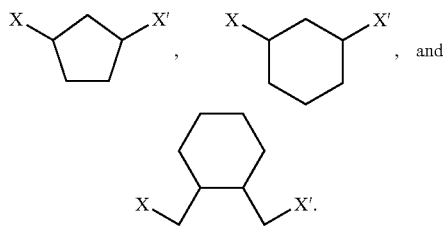

Other specific bridging moieties are set forth in the example ligands and complexes herein.

In particular embodiments, the ligands can be characterized by the general formula:

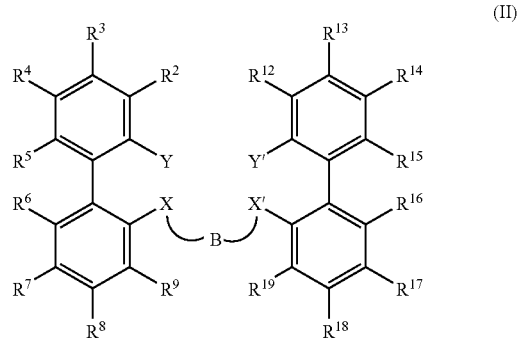

wherein each of R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, and R$^{19}$ is independently selected from the group consisting of hydrogen, halogen, and optionally substituted hydrocarbyl, heteroatom-containing hydrocarbyl, alkoxy, aryloxy, silyl, boryl, phosphino, amino, alkylthio, arylthio, nitro, and combinations thereof; optionally two or more R groups can combine together into ring structures (for example, single ring or multiple ring structures), with such ring structures having from 3 to 12 atoms in the ring (not counting hydrogen atoms); B is a bridging group as defined above; X and X' and Y and Y' are as defined above, provided that each of Y and Y' includes a labile hydrogen. In particular embodiments Y and Y' are OH or SH.

In more specific embodiments, each of R$^2$, R$^3$, R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, and R$^{19}$ is independently selected from the group consisting of hydrogen, halogen, and optionally substituted alkyl, heteroalkyl, aryl, heteroaryl, alkoxyl, aryloxyl, silyl, boryl, phosphino, amino, alkylthio, arylthio, nitro, and combinations thereof. In even more specific embodiments, each of R$^2$, R$^3$, R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, and R$^{19}$ is independently selected from the group consisting of hydrogen, halogen, and optionally substituted alkyl, heteroalkyl, aryl, heteroaryl, alkoxyl, aryloxyl, silyl, amino, alkylthio and arylthio. In some embodiments, at least one of R$^2$ and R$^{12}$ is not hydrogen and in still other embodiments both R$^2$ and R$^{12}$ are not hydrogen.

In more specific embodiments, the ligands can be characterized by the formula:

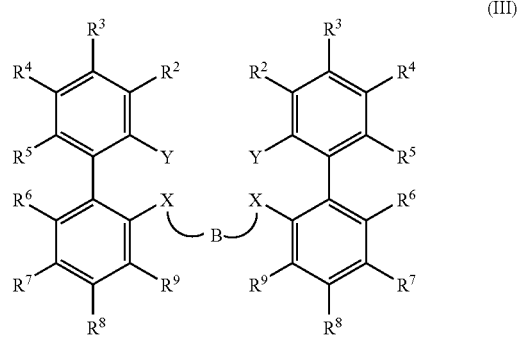

In formula III, each of R$^2$, R$^3$, R$^4$, R$^5$, R$^6$, R$^7$, R$^8$ and R$^9$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio and arylthio, nitro, and combinations thereof. The remaining substitutents B, X and Y are defined as above.

Examples of specific ligands within the scope of this invention include those set out in Table 1.

TABLE 1

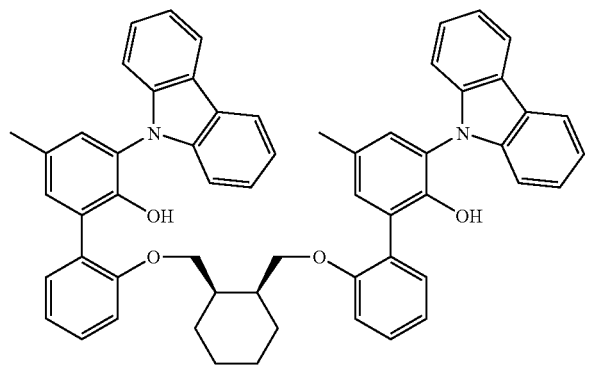

LL117

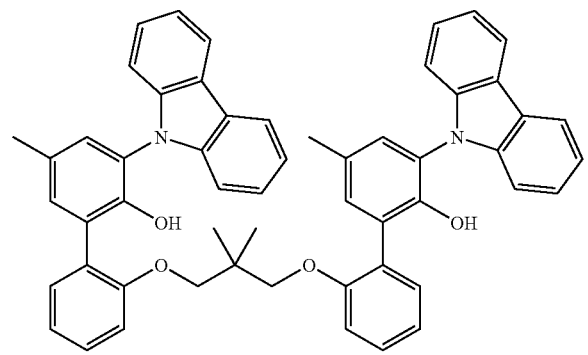

LL118

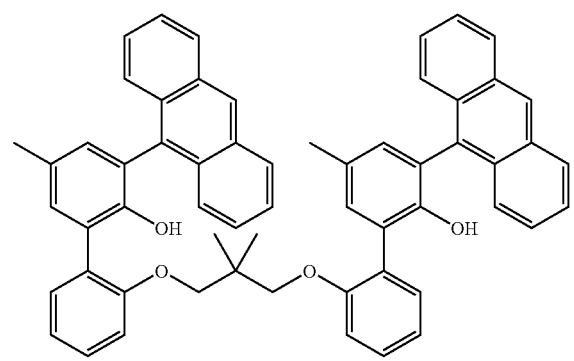

LL119

TABLE 1-continued
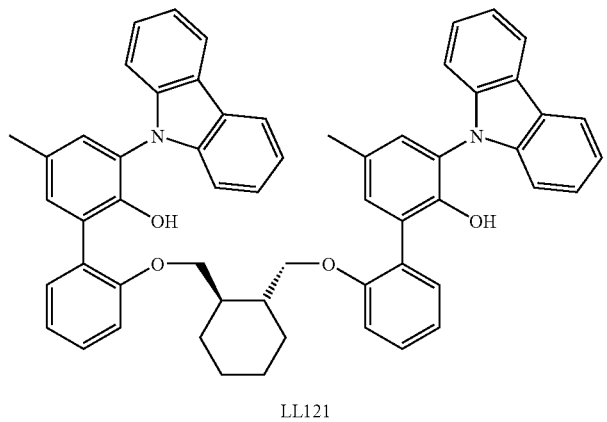
LL121
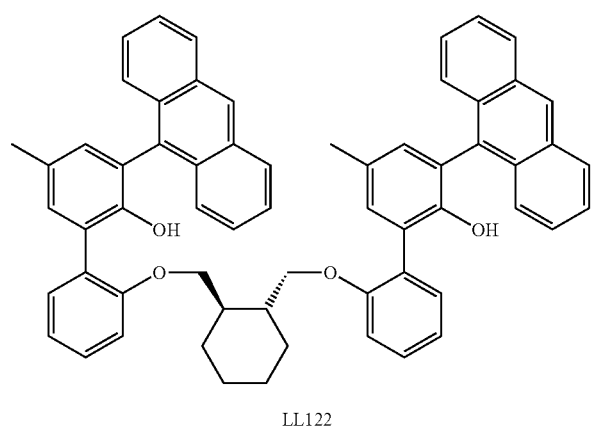
LL122
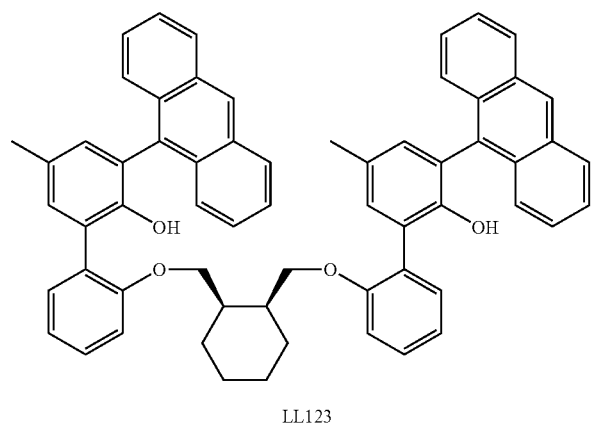
LL123

TABLE 1-continued
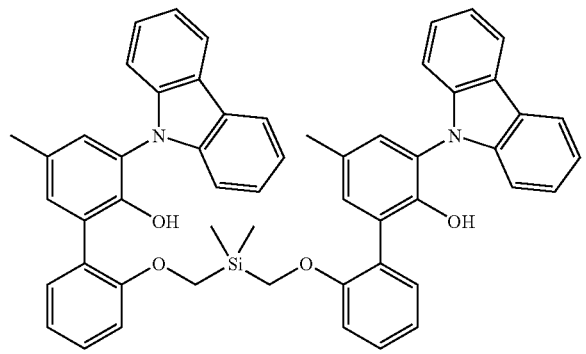
LL124
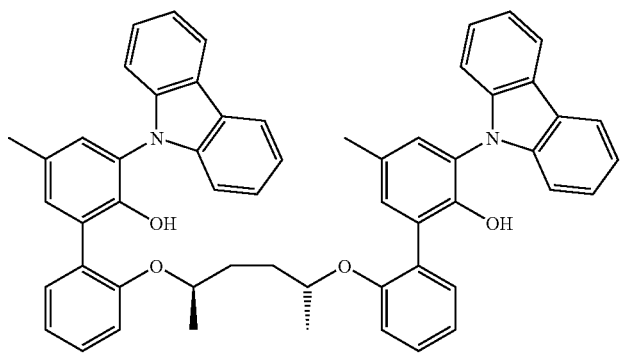
LL125
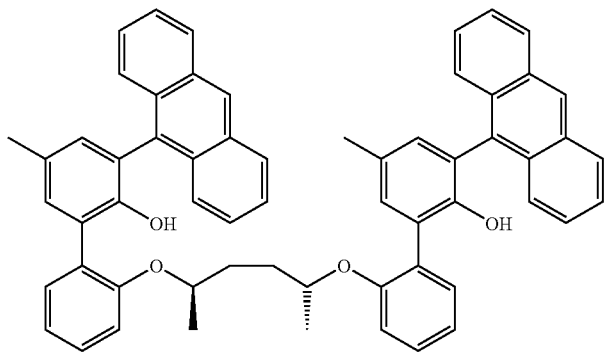
LL127
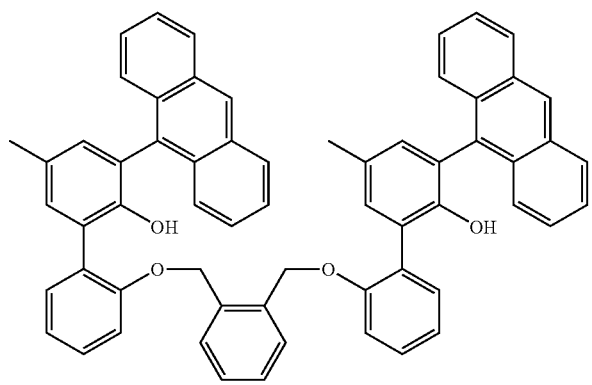
LL128

TABLE 1-continued
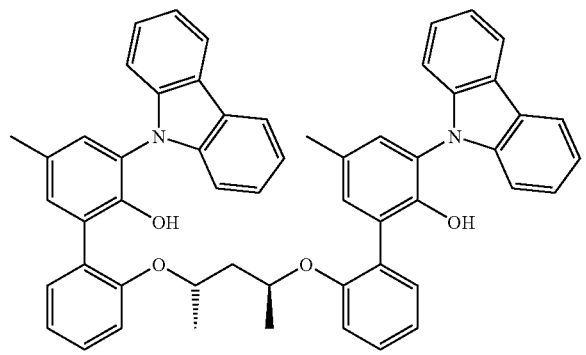
LL129
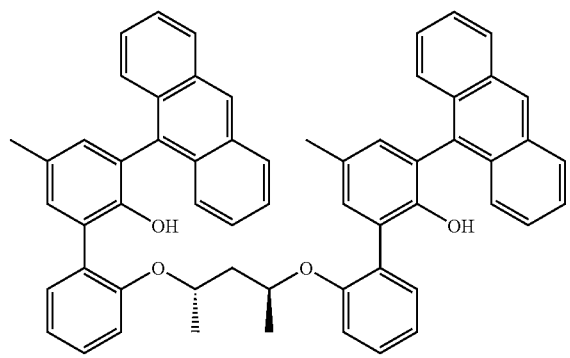
LL130
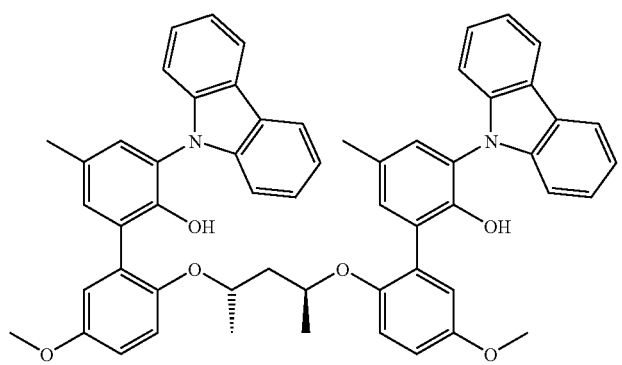
LL132

TABLE 1-continued
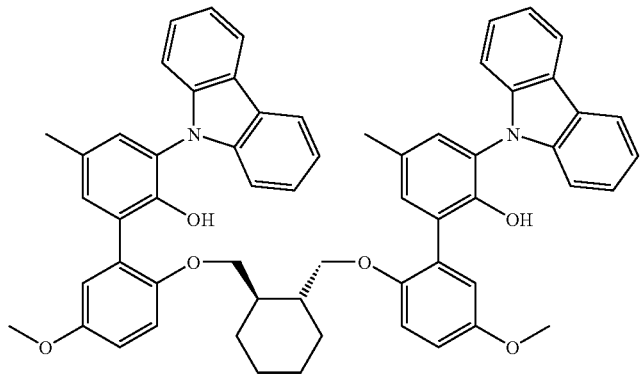
LL134
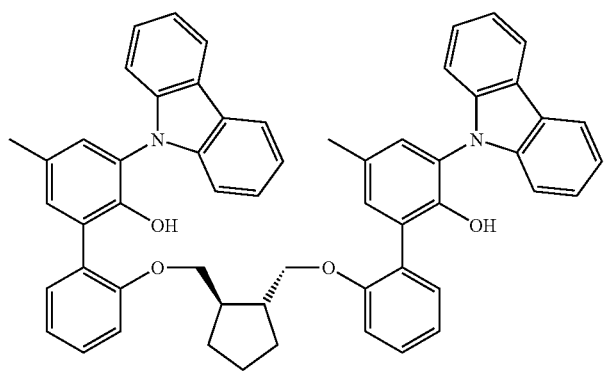
LL136
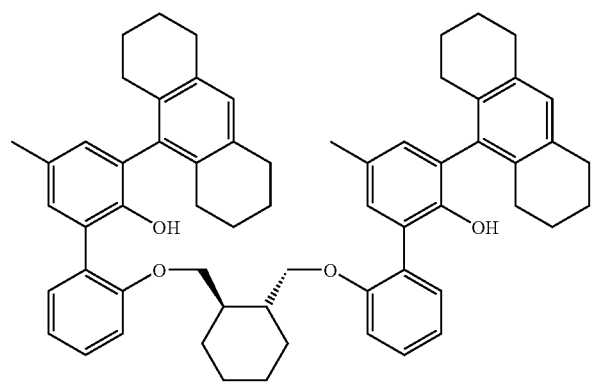
LL137

TABLE 1-continued
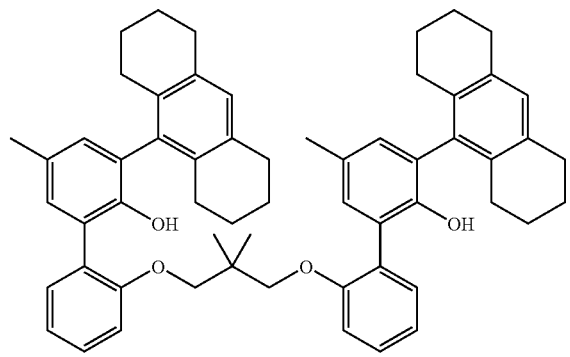
LL138
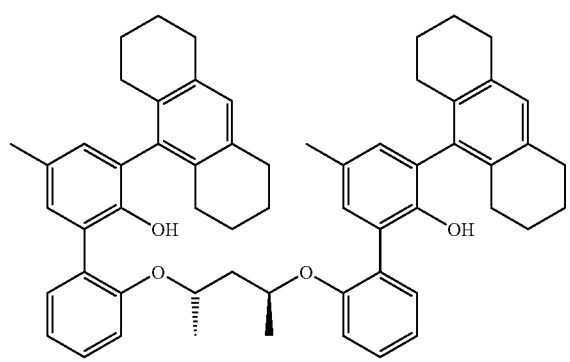
LL139
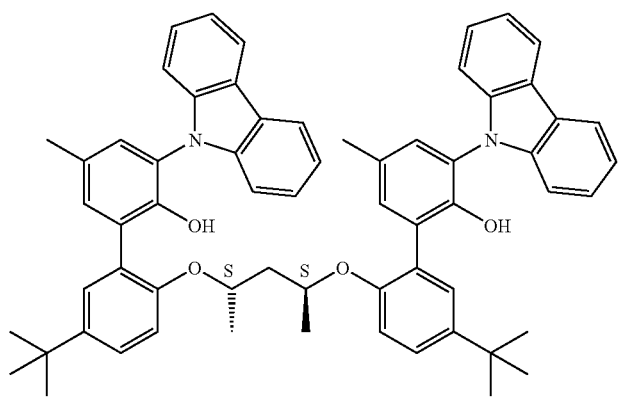
LL140
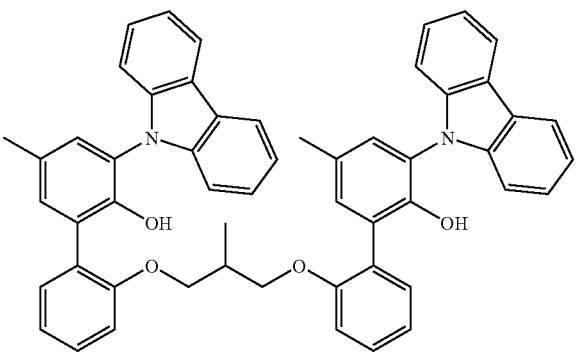
LL145

TABLE 1-continued
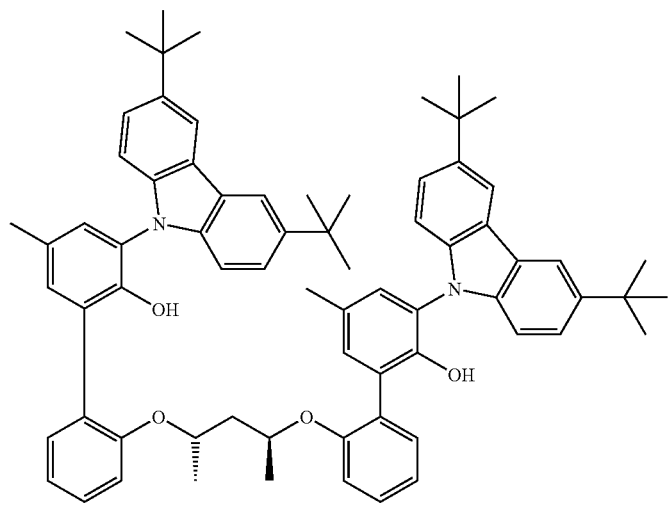
LL146
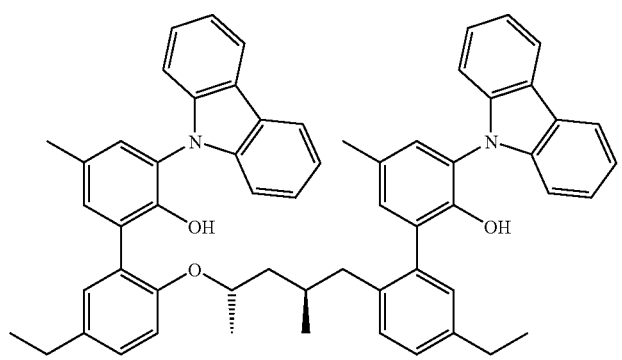
LL147
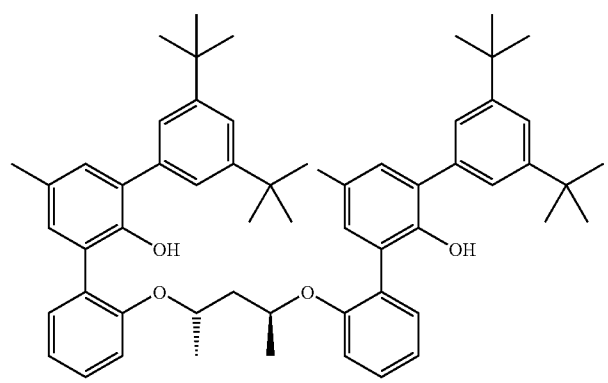
LL148

TABLE 1-continued
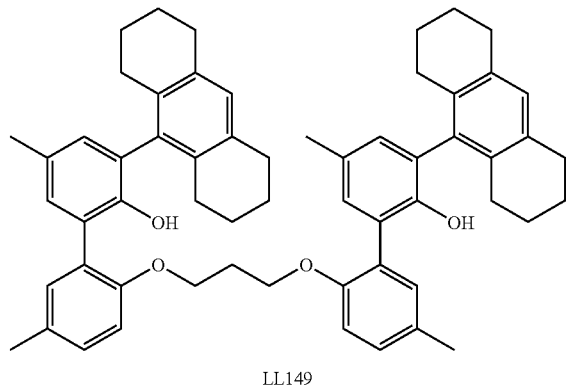
LL149
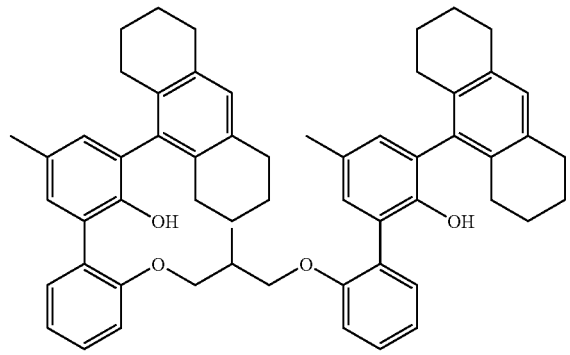
LL150
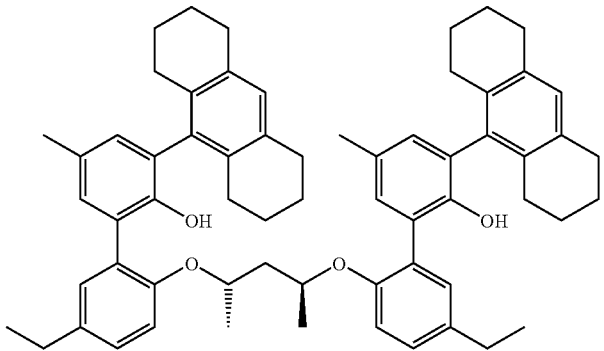
LL151
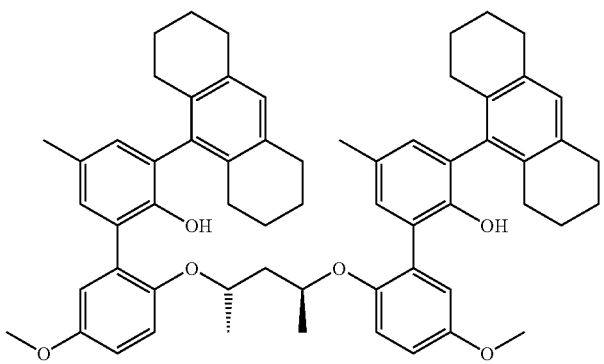
LL152

TABLE 1-continued
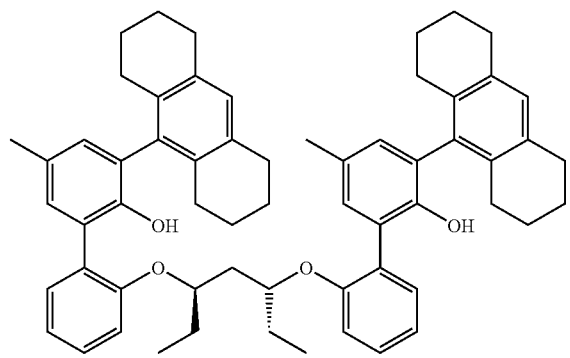
LL153
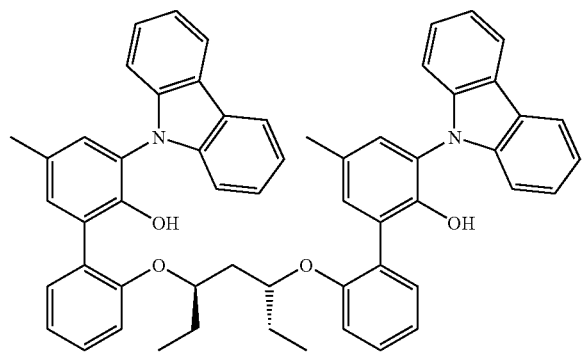
LL154
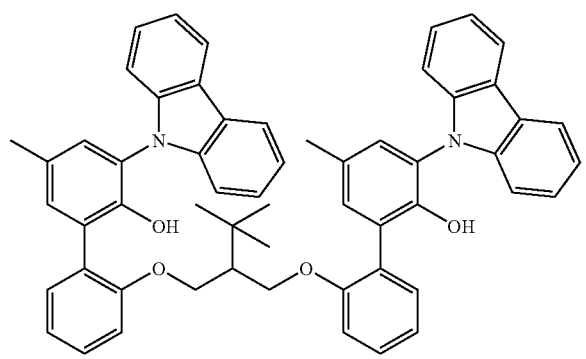
LL155

TABLE 1-continued
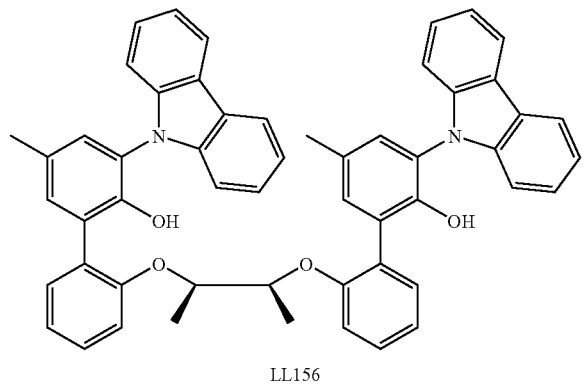
LL156
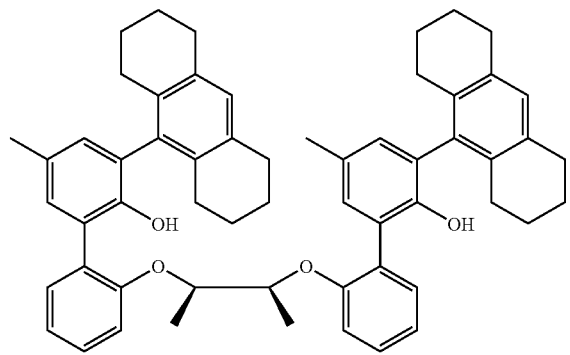
LL157
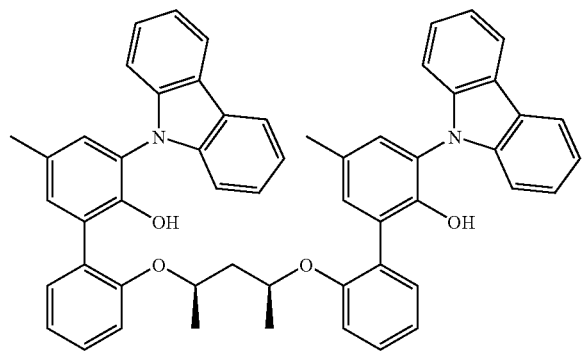
LL158
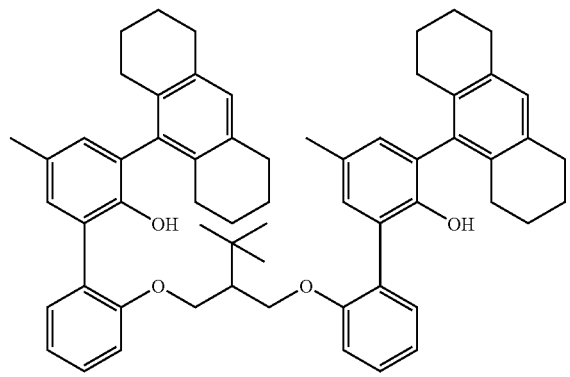
LL159

TABLE 1-continued
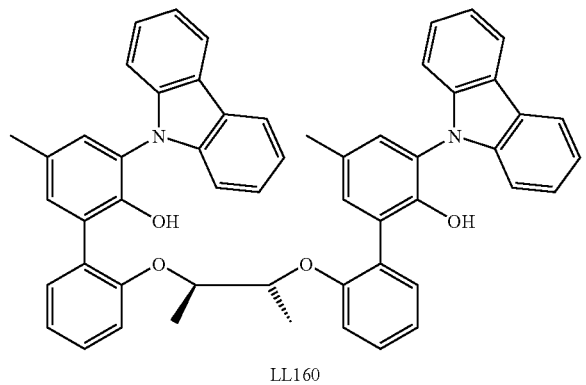
LL160
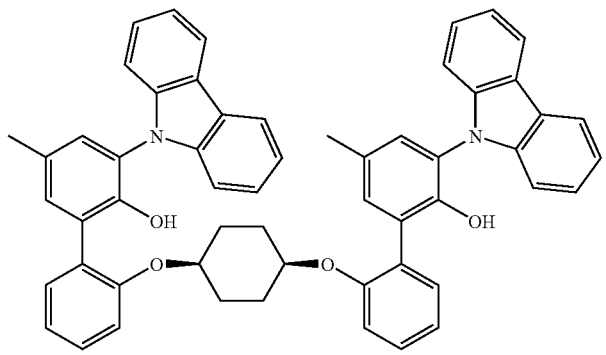
LL161
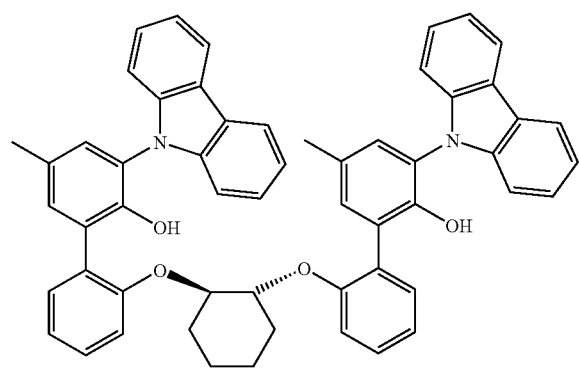
LL162
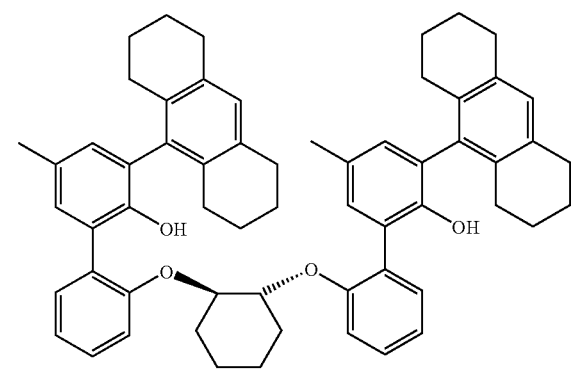
LL163

TABLE 1-continued
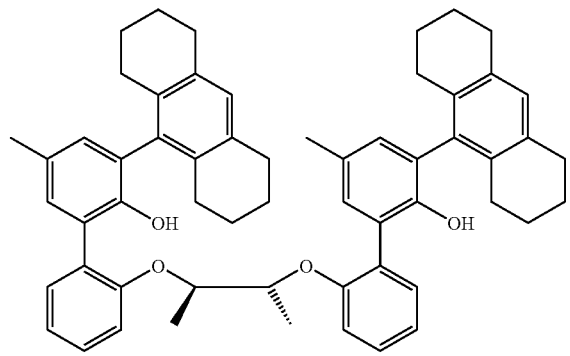
LL164
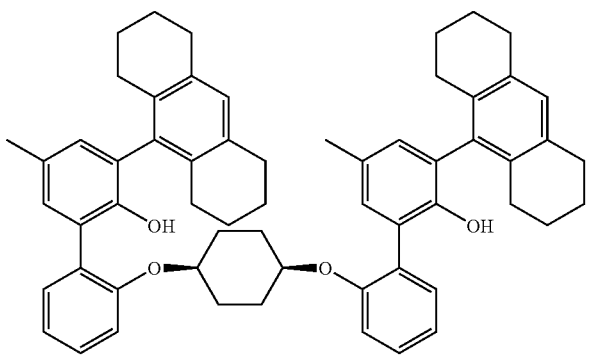
LL165
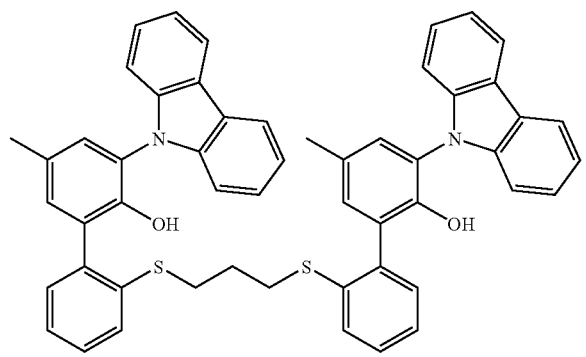
LL166
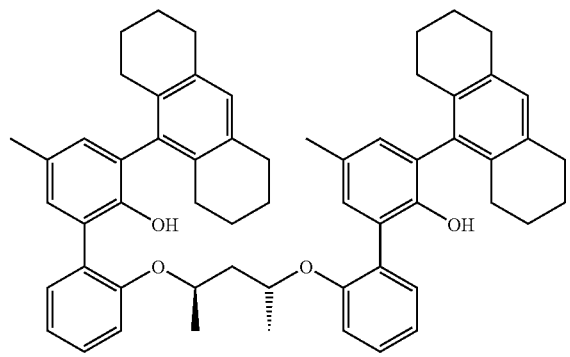
LL167

TABLE 1-continued
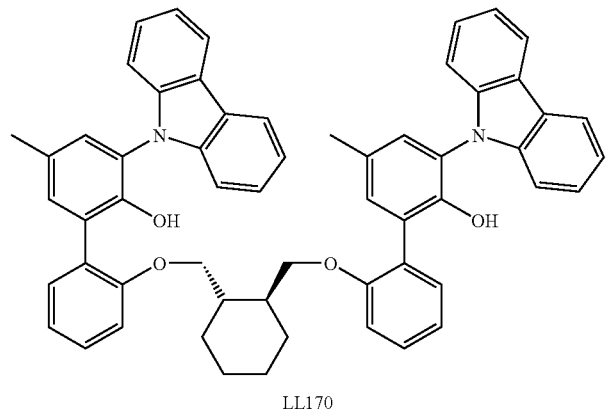
LL170
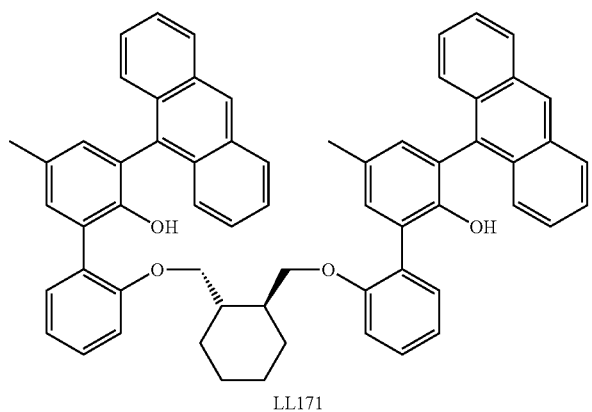
LL171
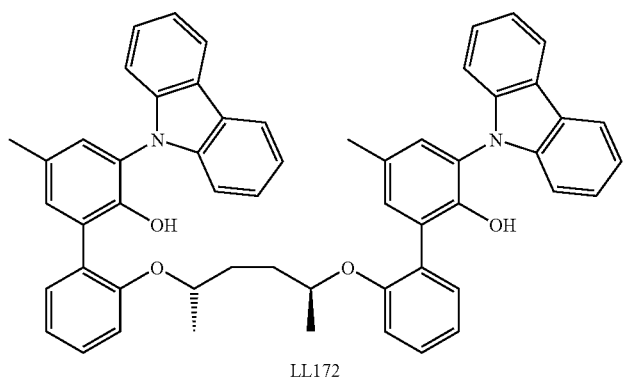
LL172
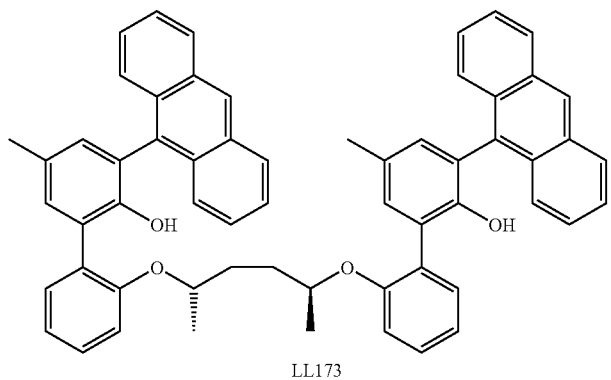
LL173

TABLE 1-continued
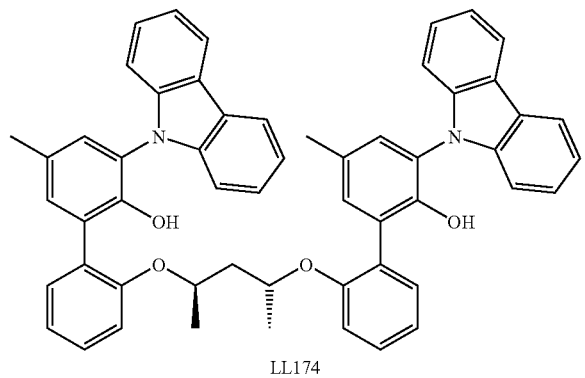
LL174
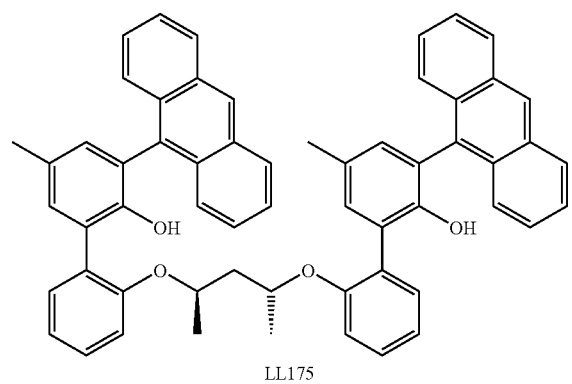
LL175
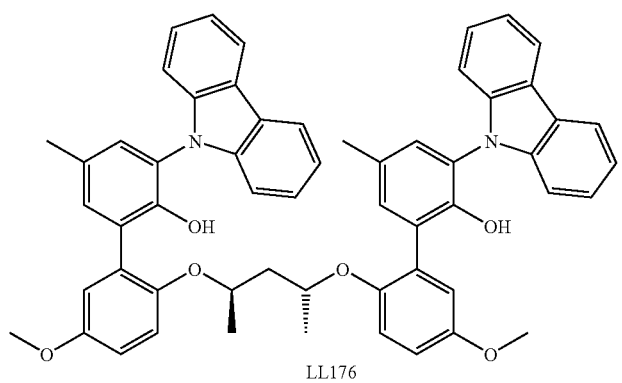
LL176
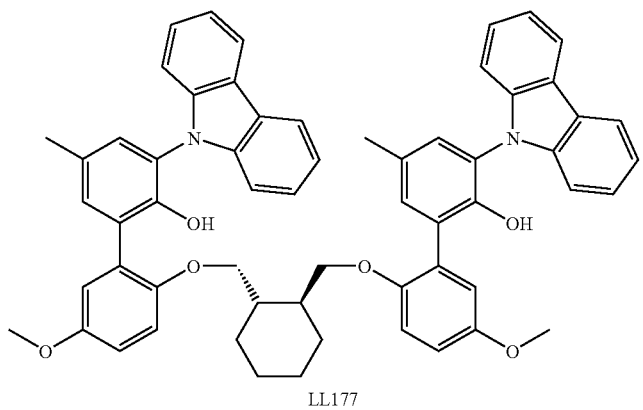
LL177

TABLE 1-continued
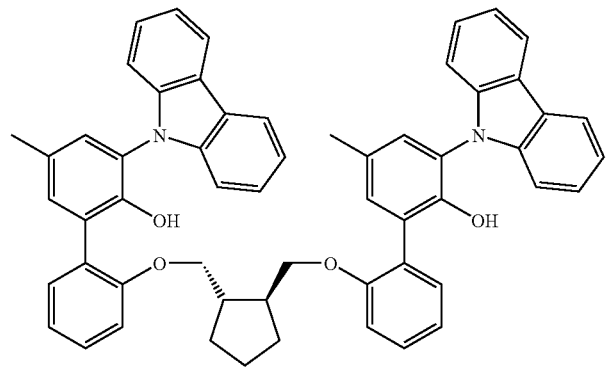
LL178
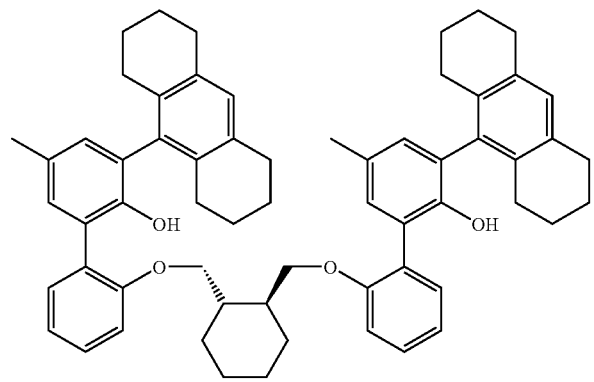
LL179
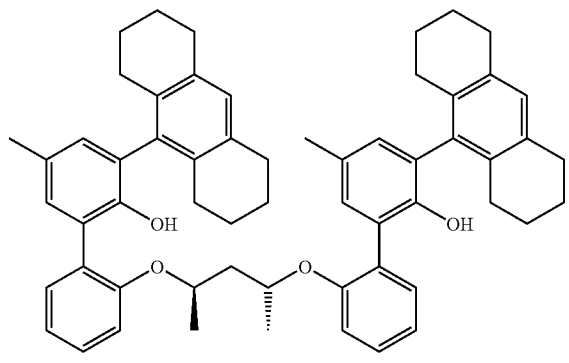
LL180
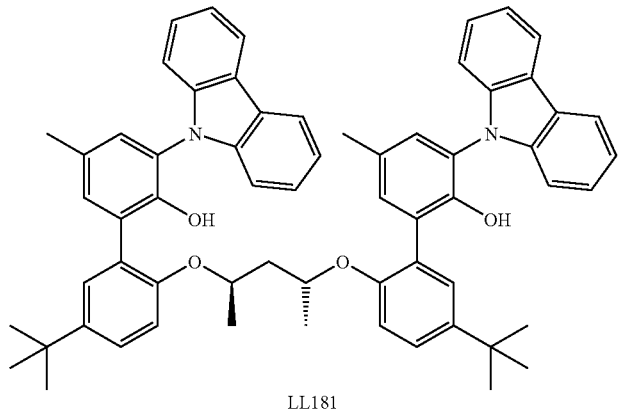
LL181

TABLE 1-continued
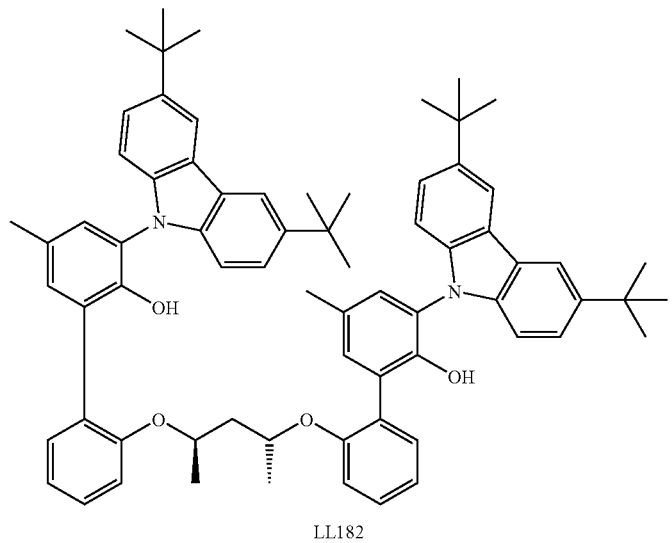
LL182
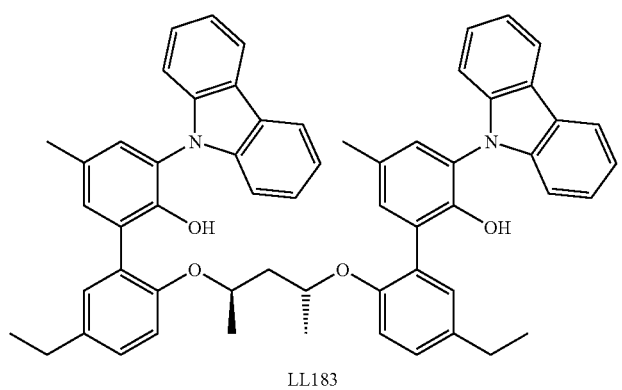
LL183
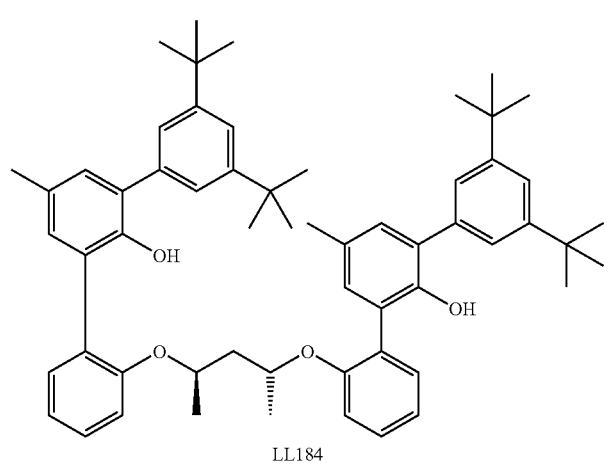
LL184

TABLE 1-continued
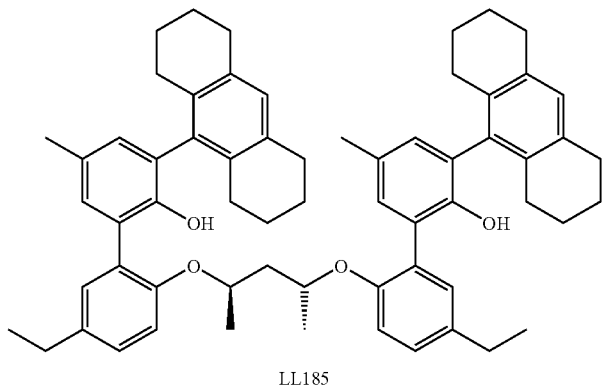
LL185
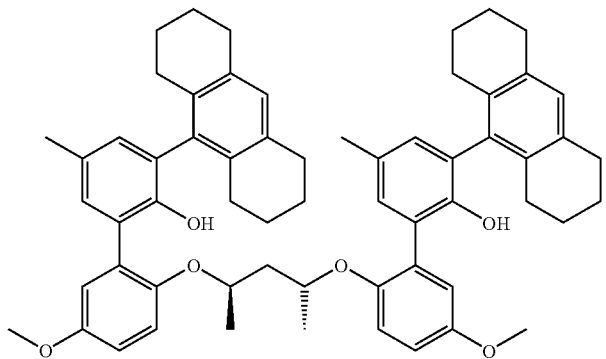
LL186
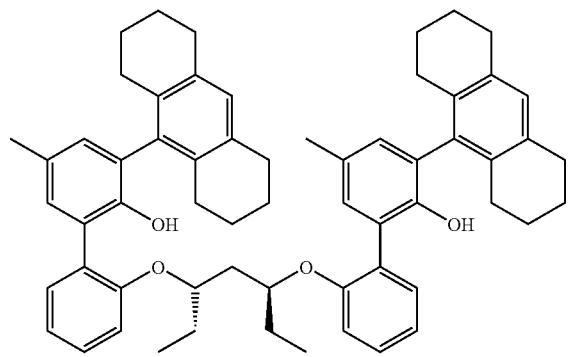
LL187
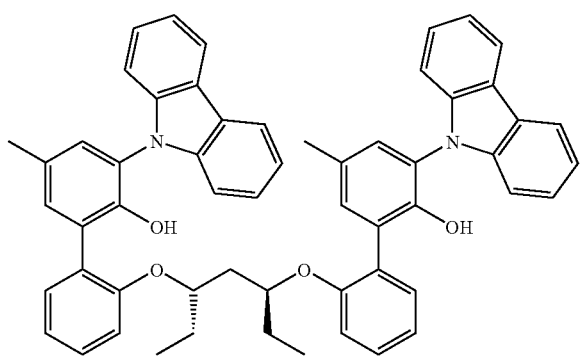
LL188

TABLE 1-continued
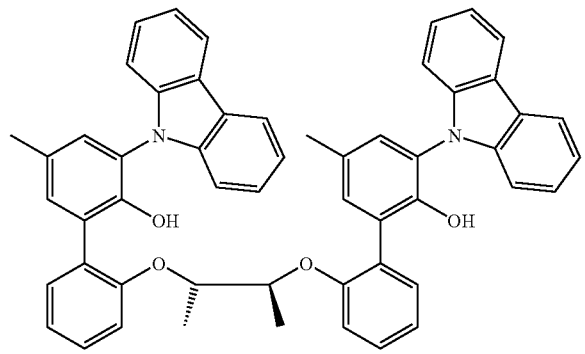
LL189
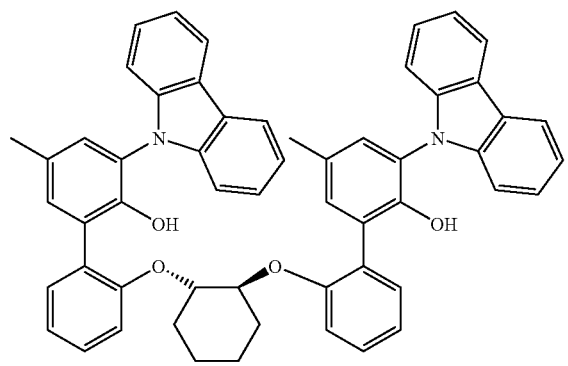
LL190
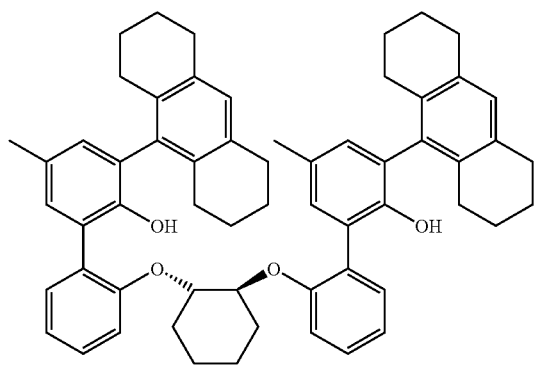
LL191
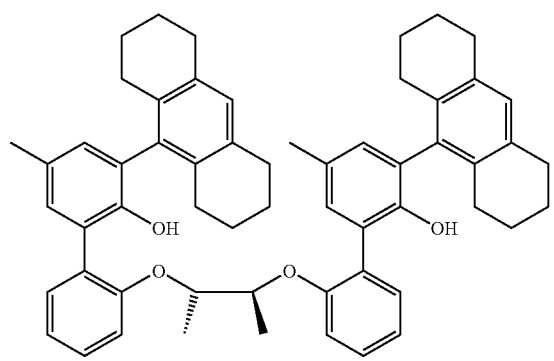
LL192

TABLE 1-continued
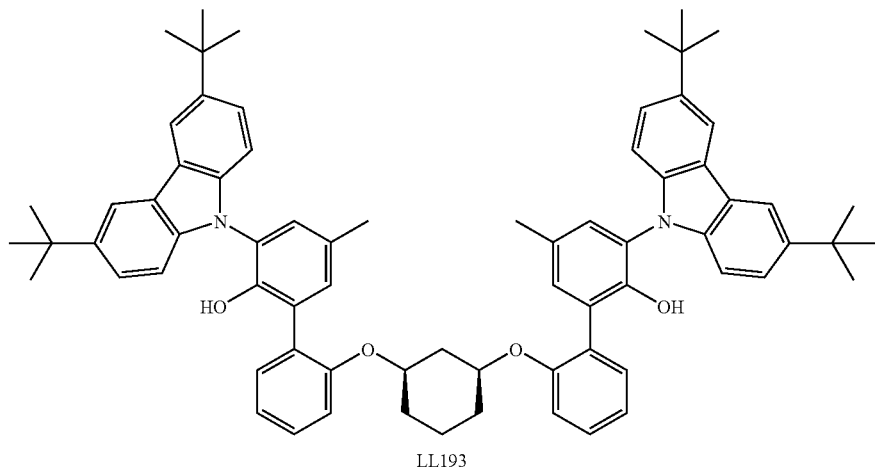
LL193
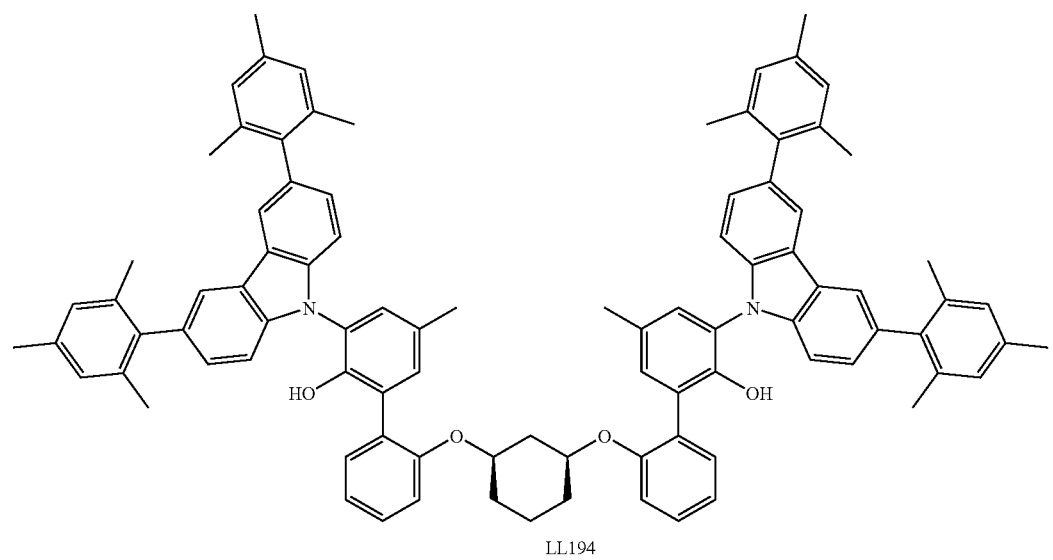
LL194
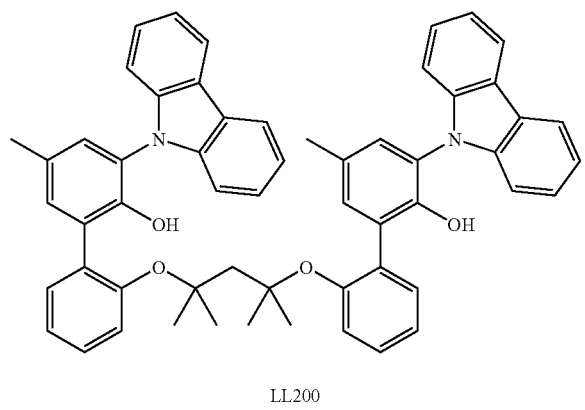
LL200

TABLE 1-continued
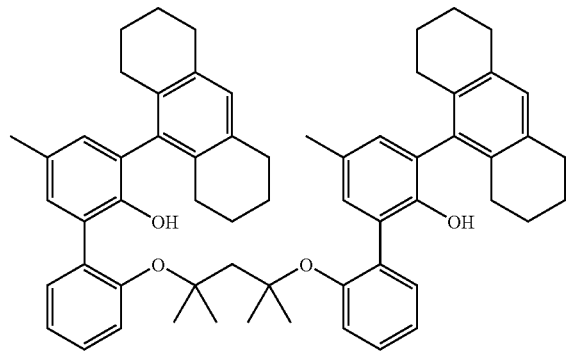
LL201
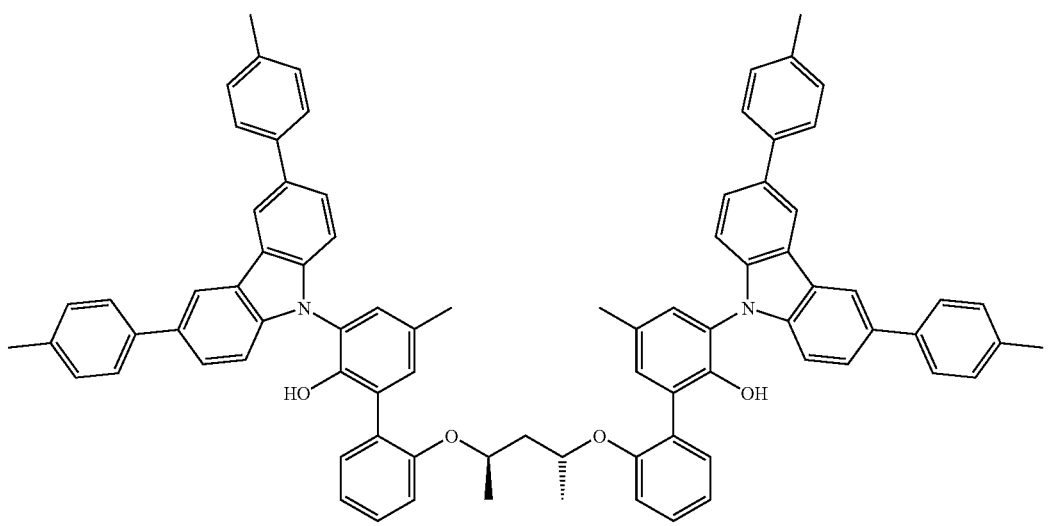
LL202
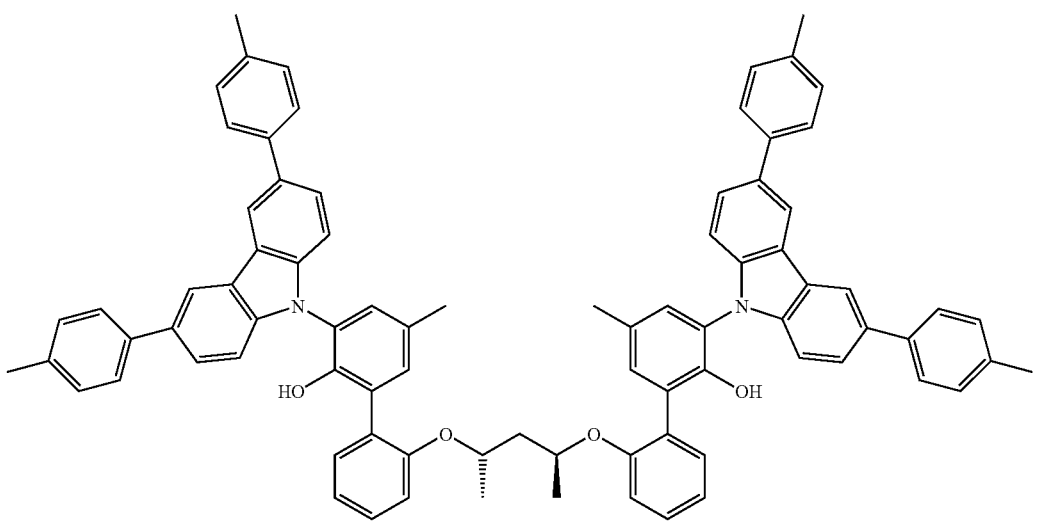
LL203

TABLE 1-continued
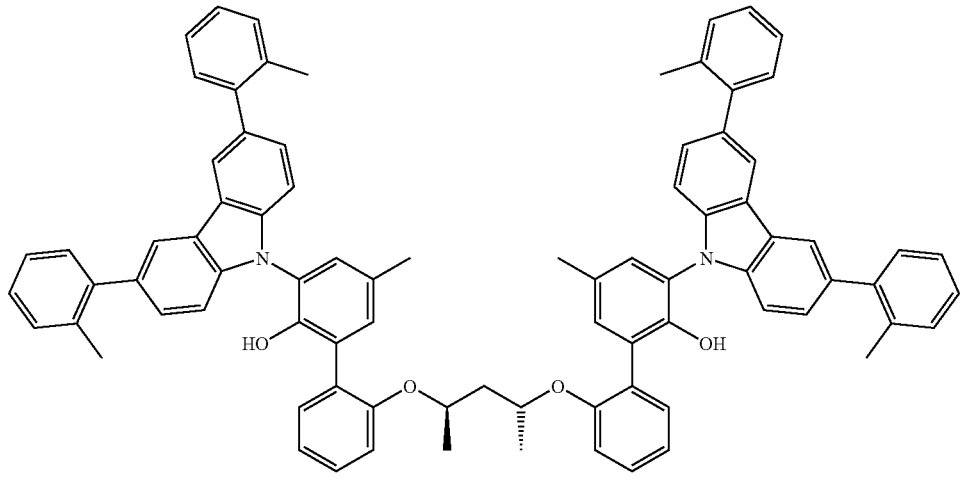
LL204
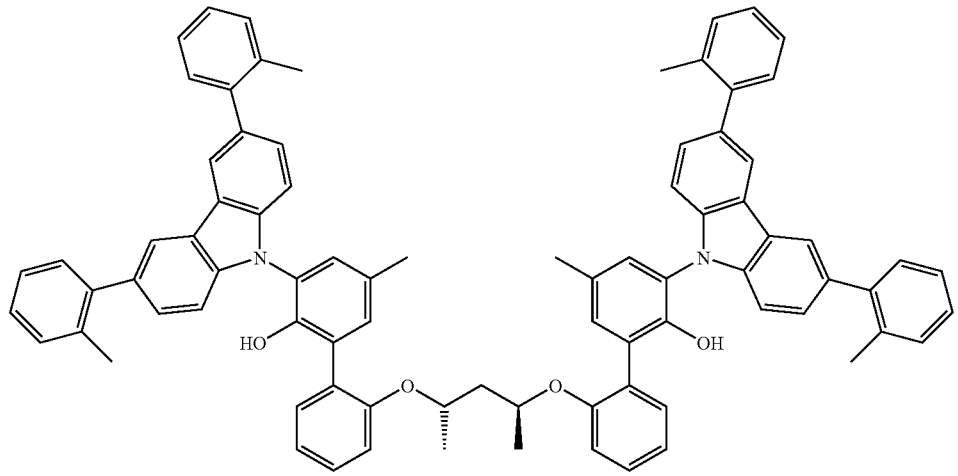
LL205
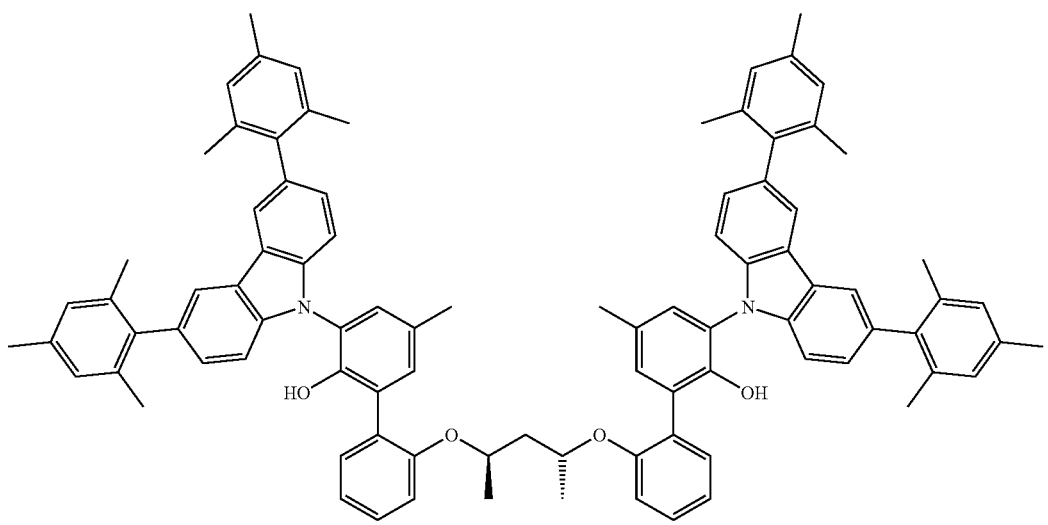
LL206

TABLE 1-continued
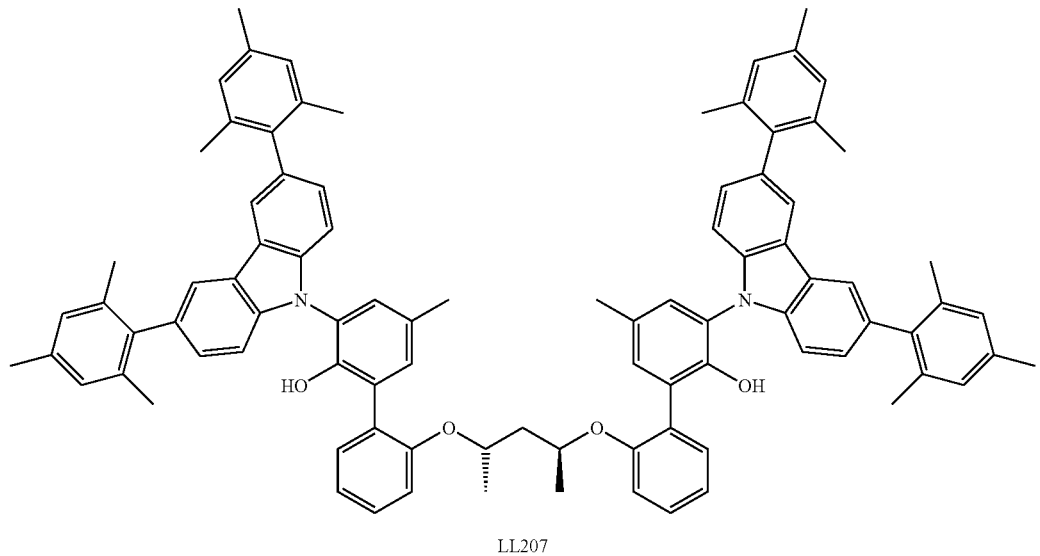
LL207
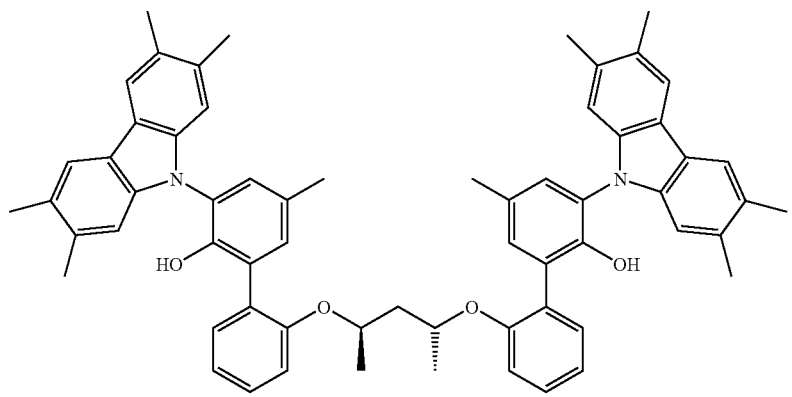
LL208
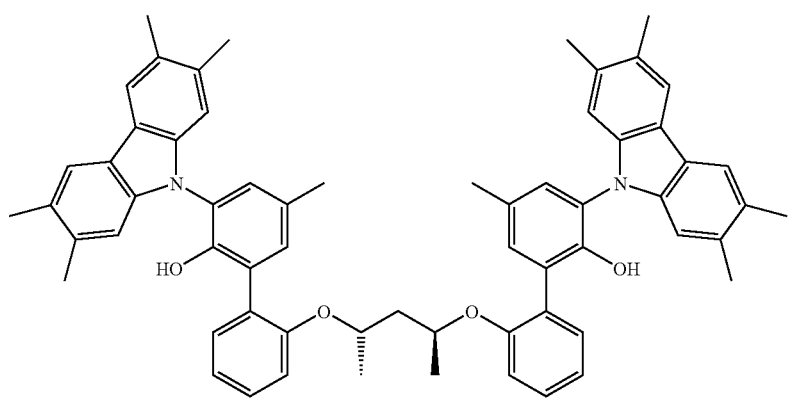
LL209

TABLE 1-continued
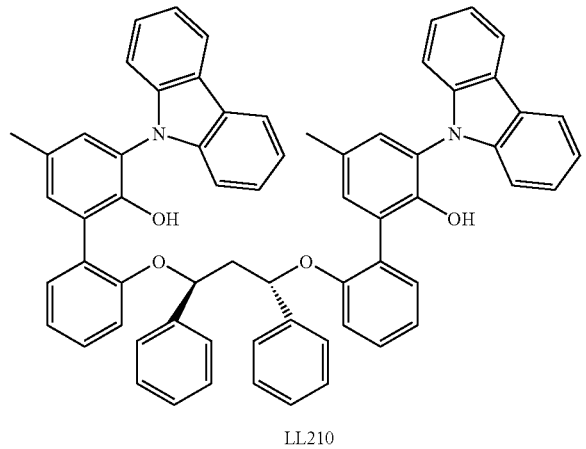
LL210
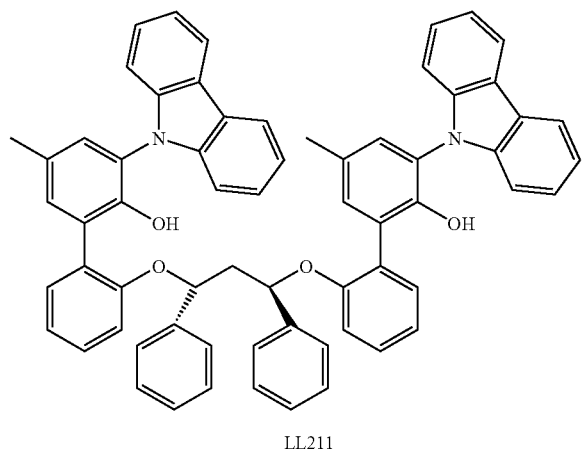
LL211
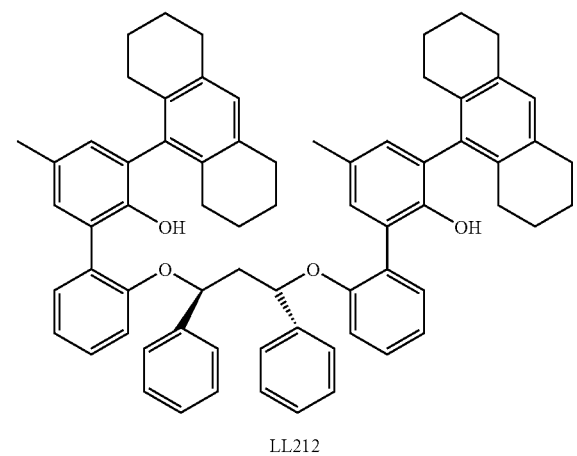
LL212

TABLE 1-continued
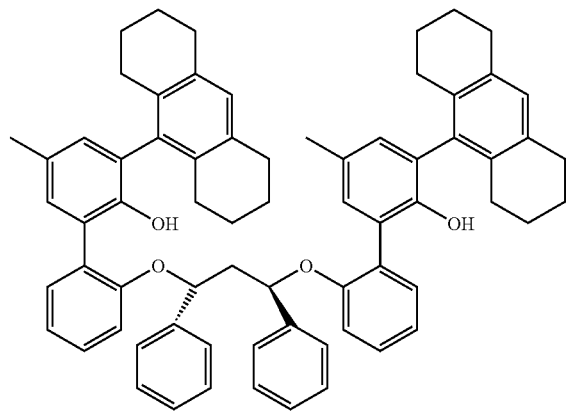
LL213
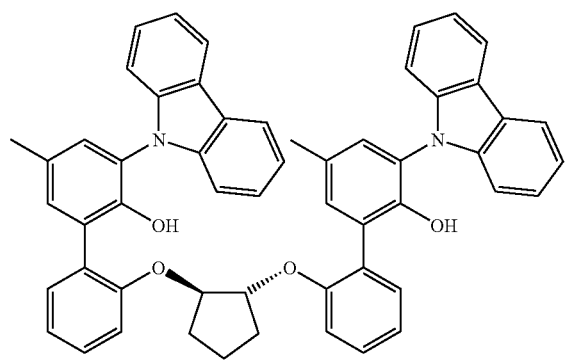
LL214
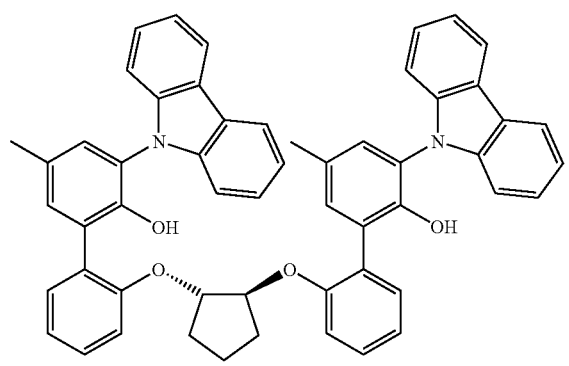
LL215

TABLE 1-continued
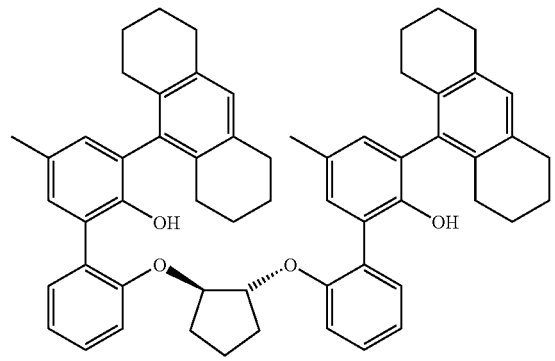
LL216
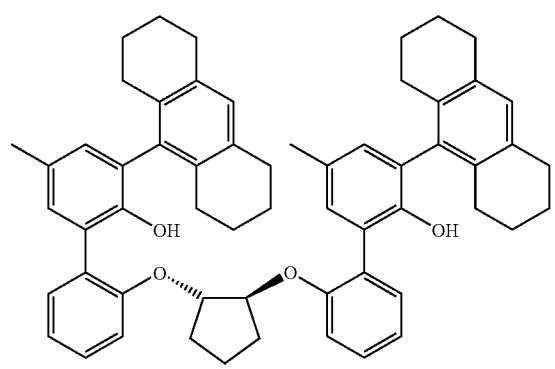
LL217
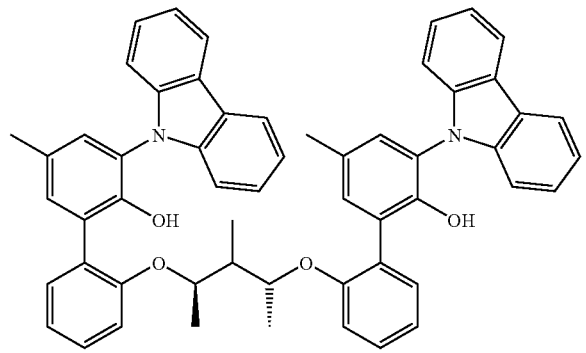
LL218
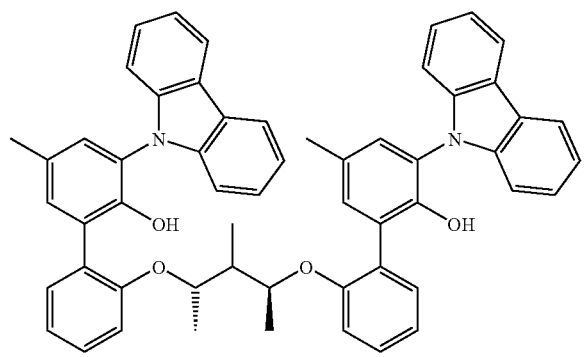
LL219

TABLE 1-continued
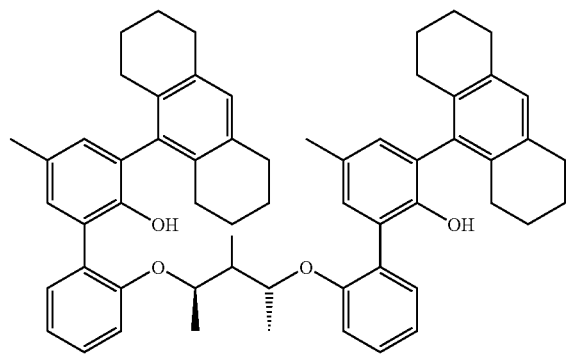
LL220
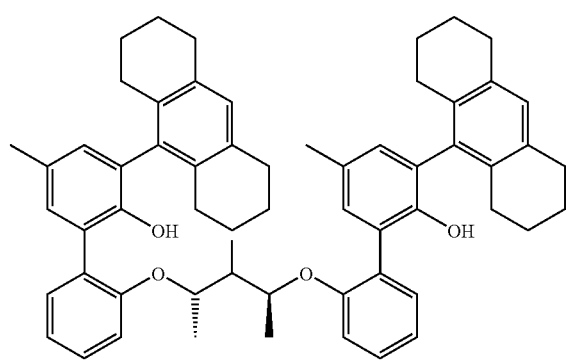
LL221
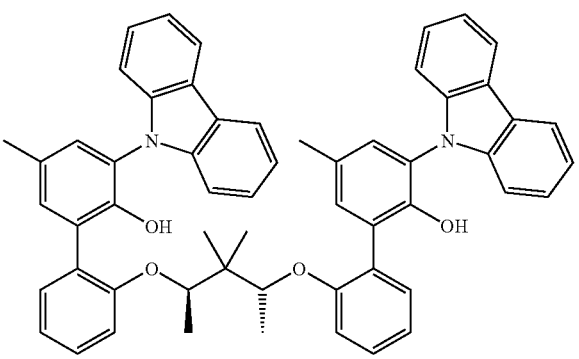
LL222
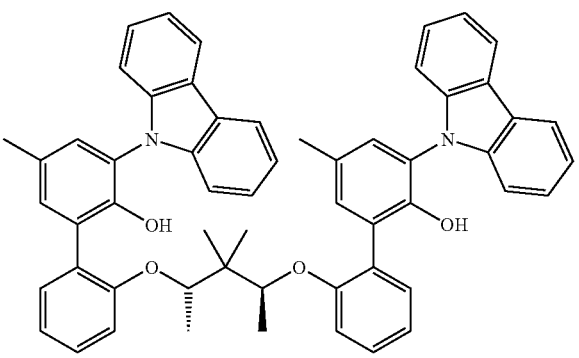
LL223

TABLE 1-continued
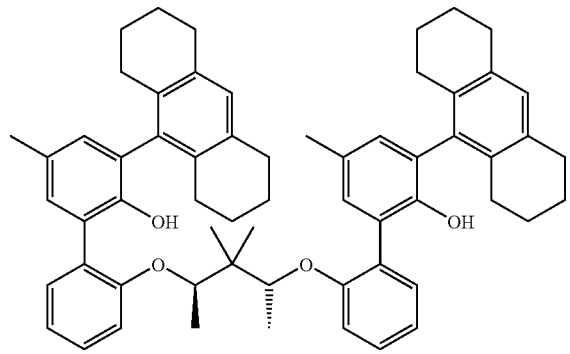
LL224
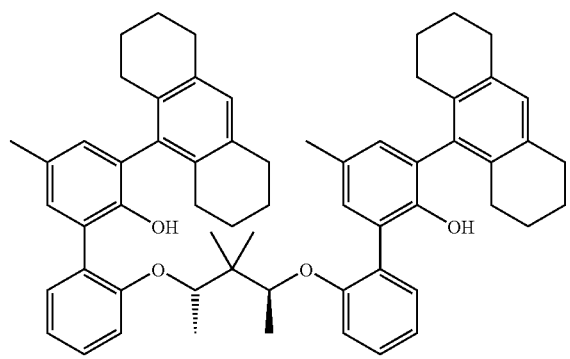
LL225
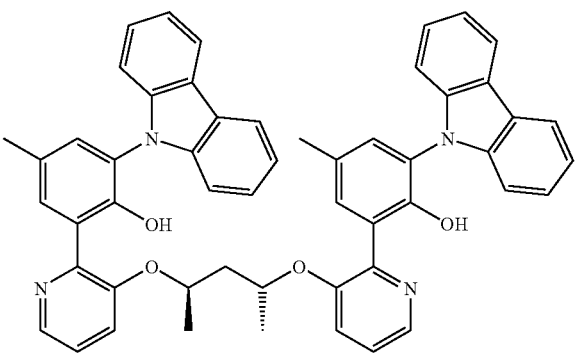
LL226
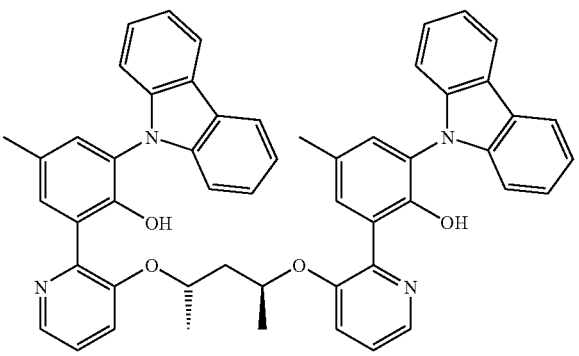
LL227

TABLE 1-continued
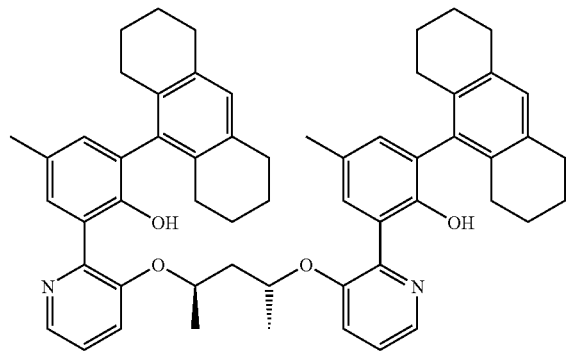
LL228
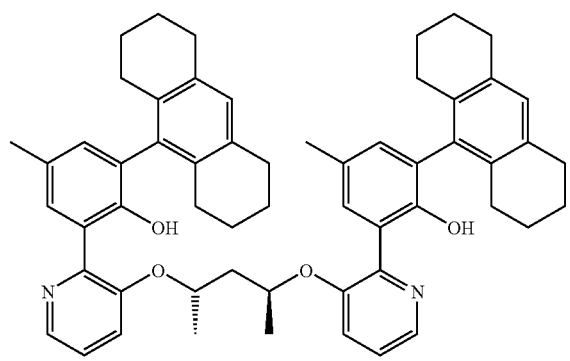
LL229
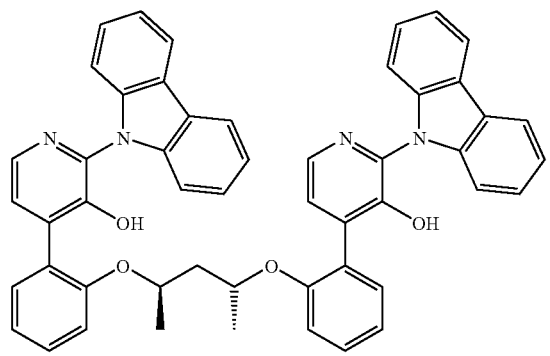
LL230
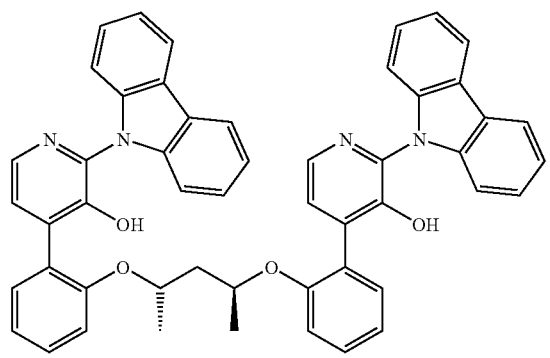
LL231

TABLE 1-continued
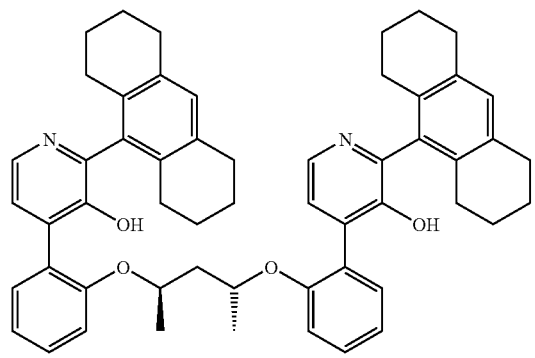
LL232
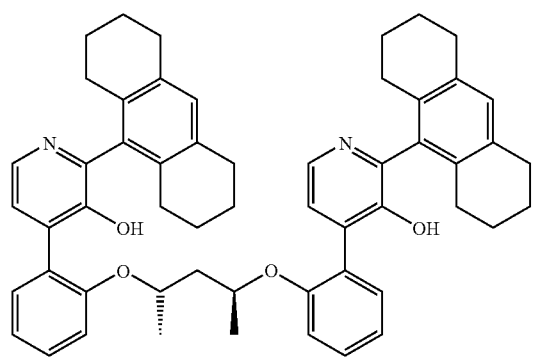
LL233
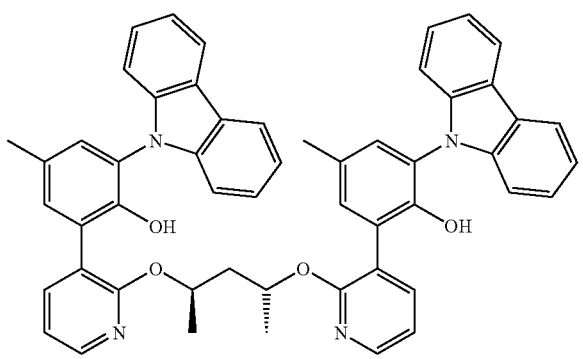
LL234
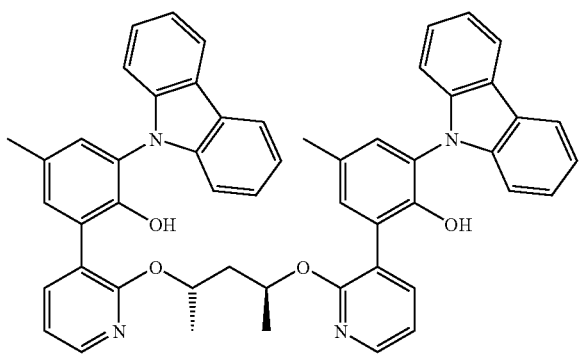
LL235

TABLE 1-continued
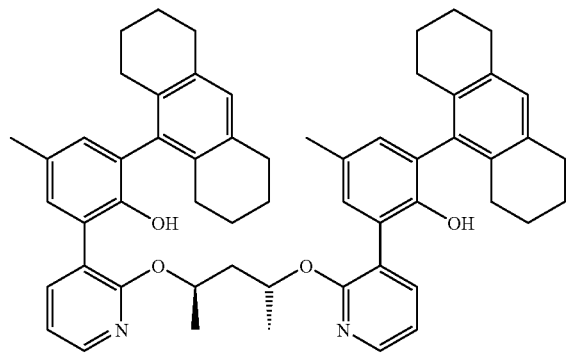
LL236
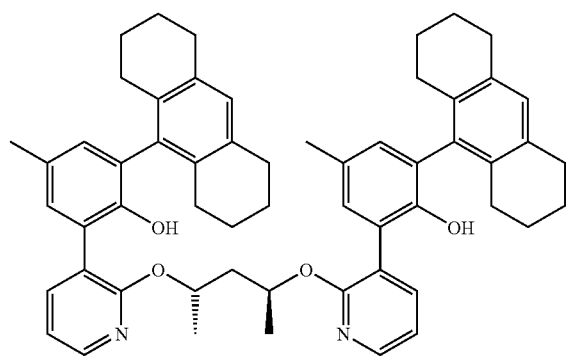
LL237
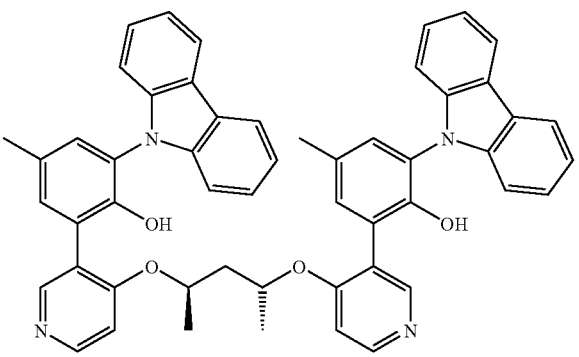
LL238
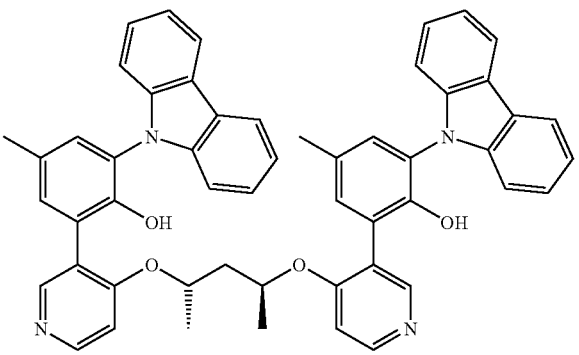
LL239

TABLE 1-continued
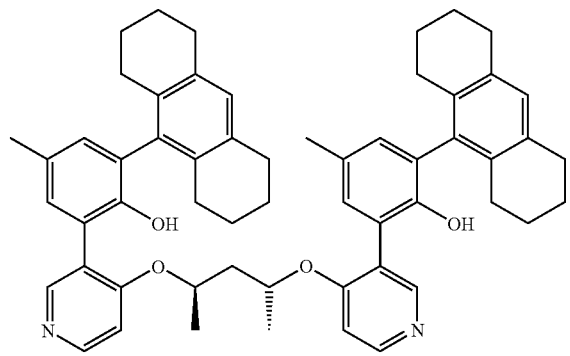
LL240
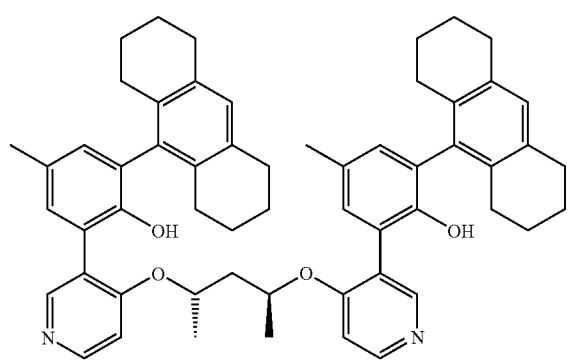
LL241
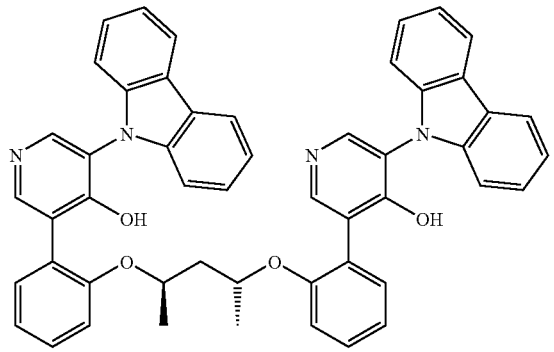
LL242
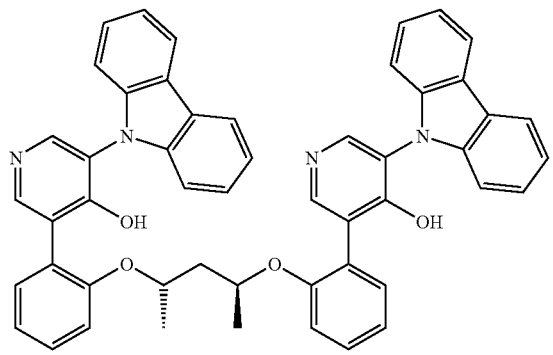
LL243

TABLE 1-continued
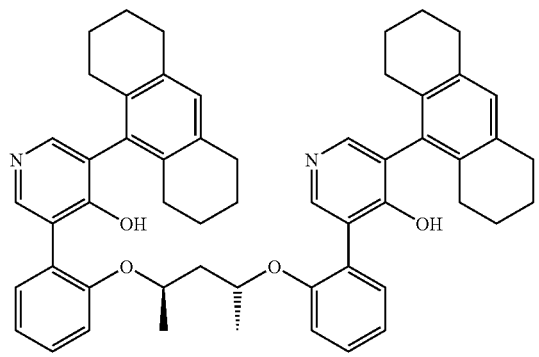
LL244
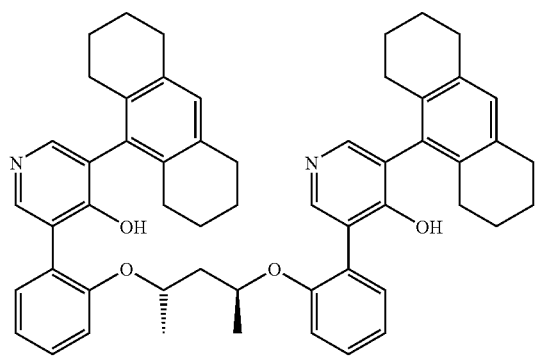
LL245
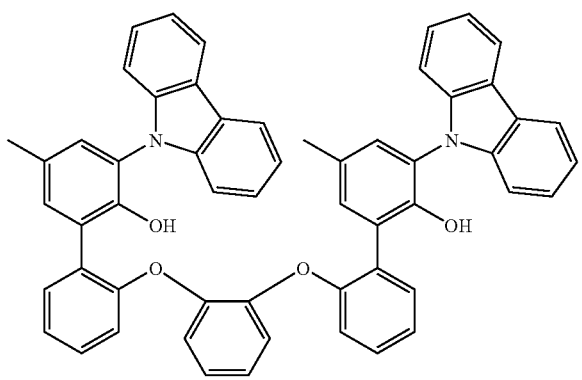
LL246

TABLE 1-continued
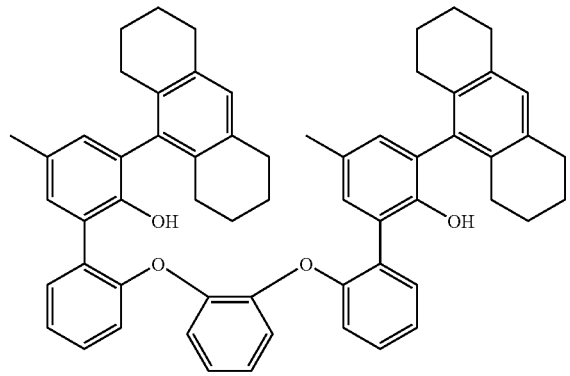
LL247
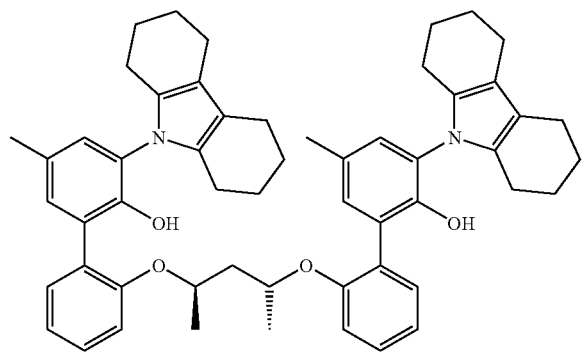
LL248
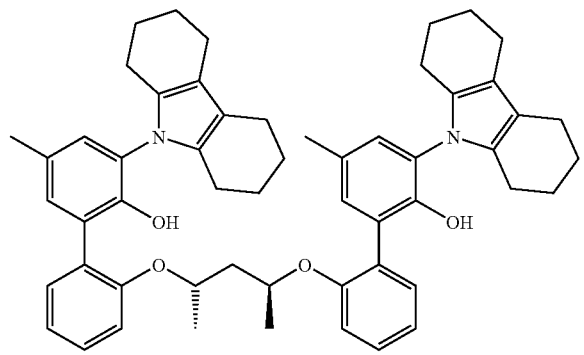
LL249
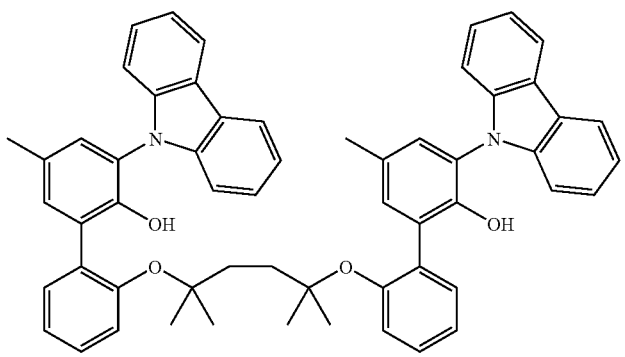
LL250

TABLE 1-continued
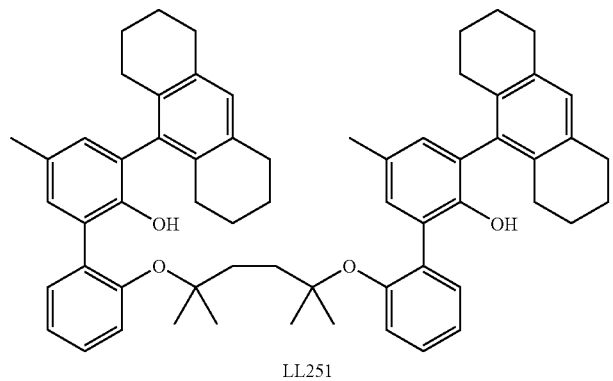
LL251
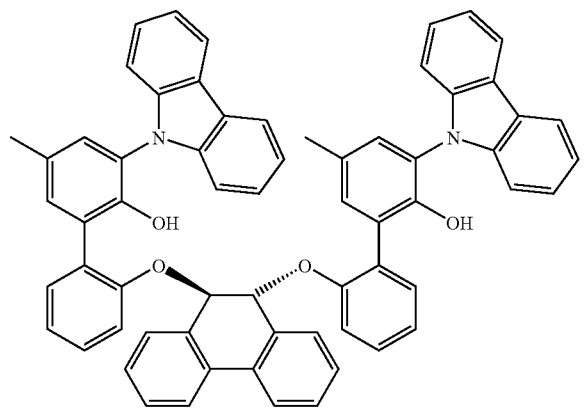
LL252
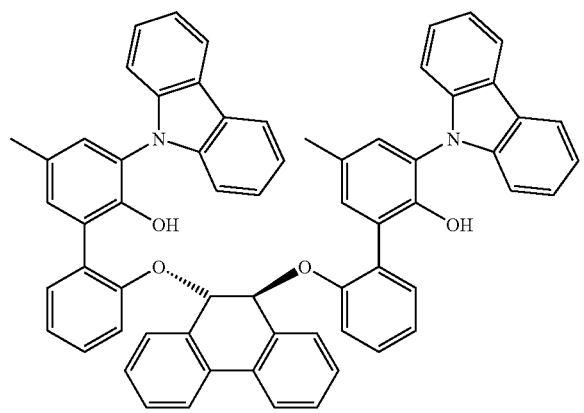
LL253

TABLE 1-continued
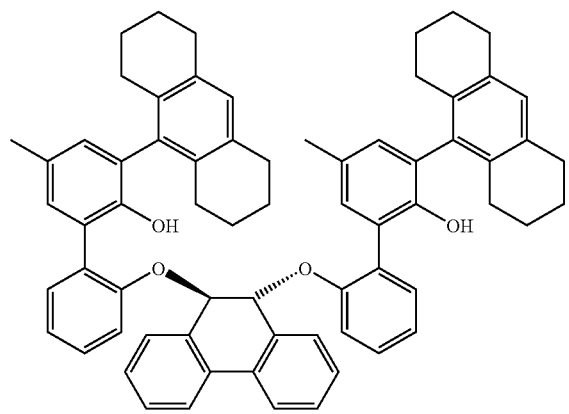
LL254
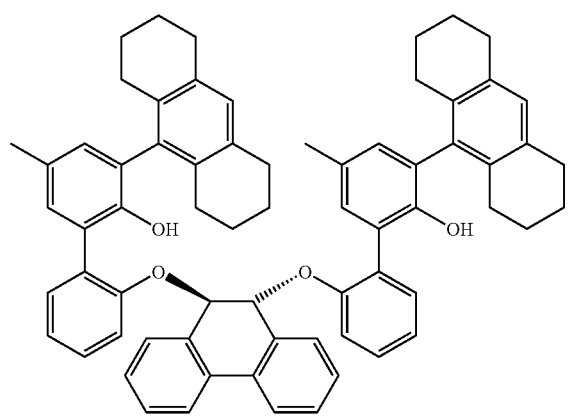
LL255
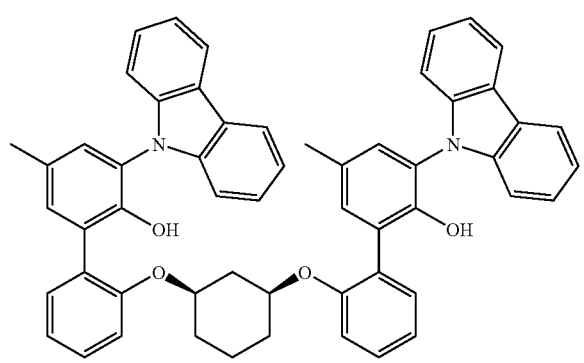
LL256

TABLE 1-continued
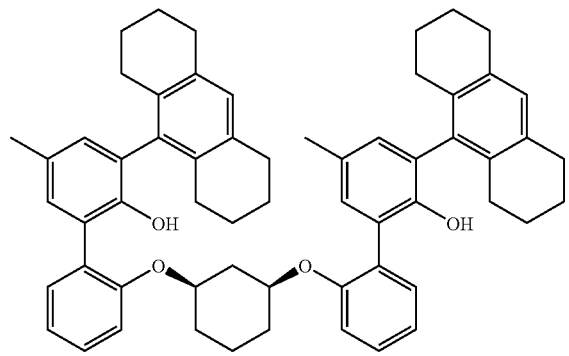
LL257
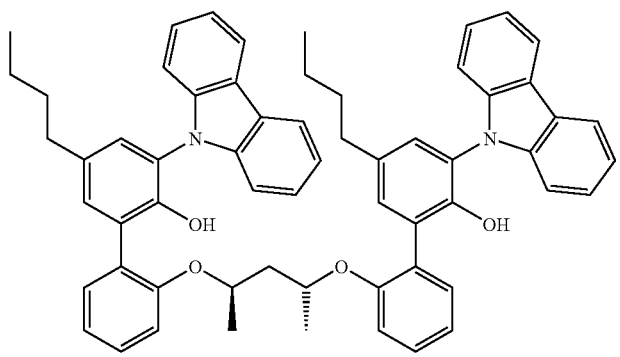
LL258
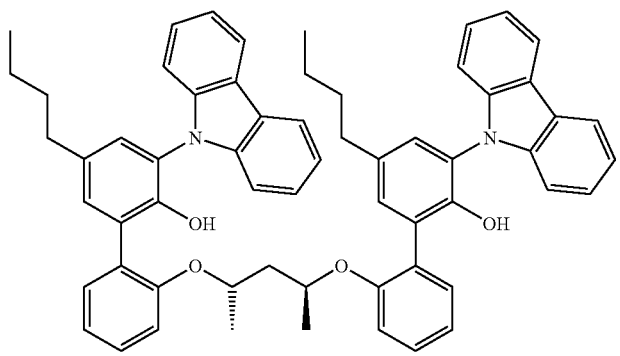
LL259
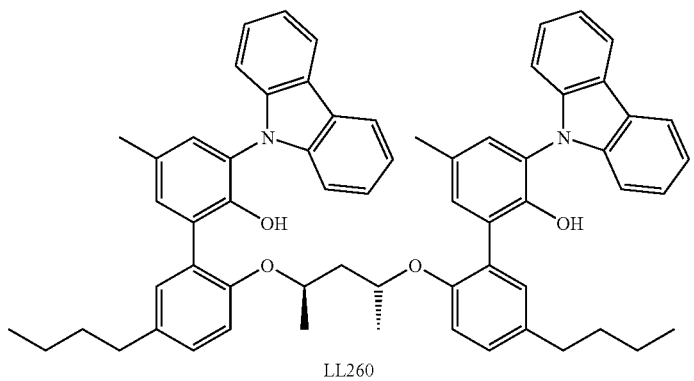
LL260

TABLE 1-continued
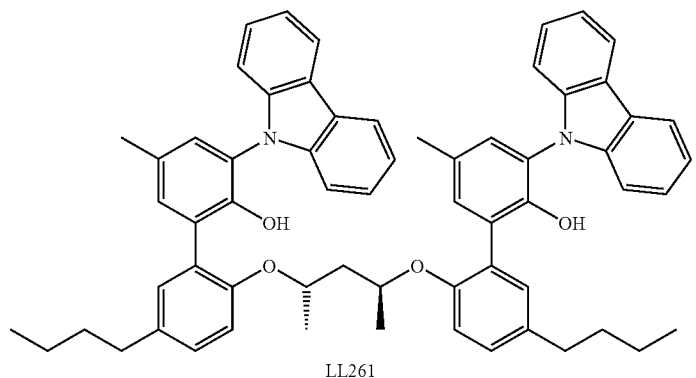
LL261
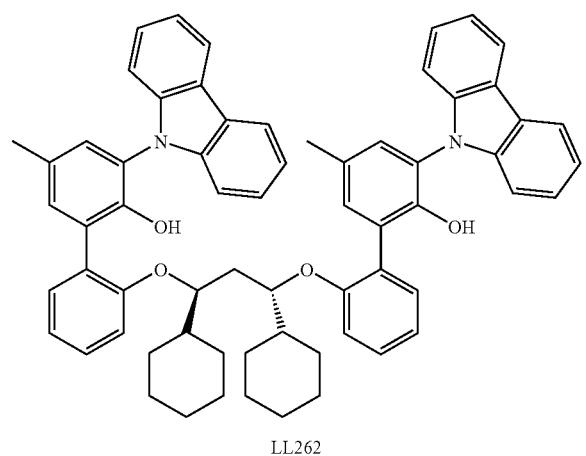
LL262
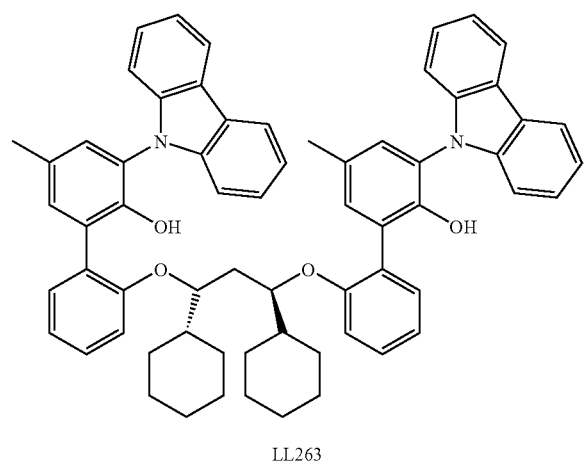
LL263

TABLE 1-continued

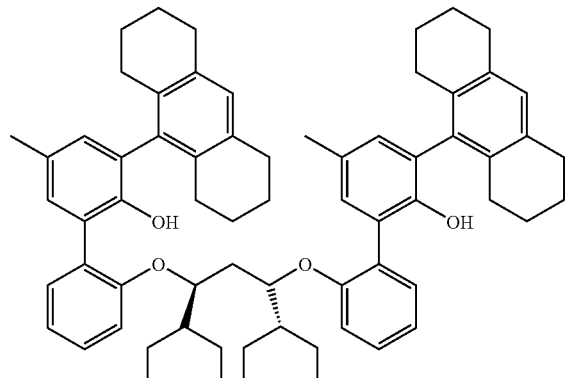

LL264

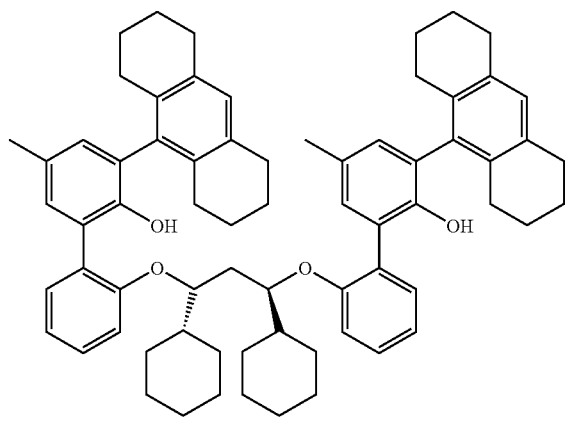

LL265 as well as the thioether analogs of the ether compounds in the above list.

The choice of particular X, Y, R, and B groups can have a strong influence on the polymerization of olefins. Thus, the choice of substitutent can affect catalyst activity, thermal stability, the molecular weight of the product polymer, the degree and/or kind of stereo- or regioerrors, as well as other factors known to be significant in the production of various polymers.

Thus, in some embodiments, the choice of X, X', Y, Y', $R^2$, $R^{12}$ and B has an influence on the production of isotactic polypropylene in a solution process. More particularly, in some embodiments the size and identity of the substituents on the AR—Y and AR—Y', such as the $R^2$ and/or $R^1$ groups in the ligands of formula II or formula III, has an influence on the production of isotactic polypropylene in a solution process, allowing for a range of isotactic polypropylene polymers to be prepared with desired properties. In some such embodiments, R and R are independently selected from the group consisting of optionally substituted aryl and heteroaryl. Specific $R^2$ and/or $R^{12}$ groups include carbazolyl, 3,6-bis-tert-butyl carbazolyl, 2,7-bis-tert-butyl carbazolyl, 3,5-bis-tert-butyl-phenyl, 9-anthracenyl, 1,2,3,4,5,6,7,8-octahydroanthacenyl and 2,4,6-trimethylphenyl. Similarly, in some embodiments $R^4$ and/or $R^{14}$ may be independently selected from the group consisting of halo and optionally substituted hydrocarbyl, alkoxy, aryloxy, dialkyl- or diarylamino, alkyl- or arylthio.

Likewise, in some embodiments, the size and identity of the substituents on the lower aromatic ring (e.g., AR—X and AR—X'), such as the $R^7$ and/or $R^{17}$ groups in the ligands of formula II and formula III has an influence on the production of isotactic polypropylene in a solution process, allowing for a range of isotactic polypropylene polymers to be prepared with desired properties. Thus, in such embodiments, $R^7$ and $R^{17}$ may be independently selected from the group consisting of halo and optionally substituted hydrocarbyl, alkoxy, aryloxy, amino, alkyl- or arylthio. In more specific embodiments, the $R^7$ and/or $R^{17}$ groups can be methyl, ethyl, t-butyl, or methoxy.

In some such embodiments, substituents can be selected to affect solubility of the resulting ligand, complex or catalyst. For example, in some such embodiments $R^4$ and/or $R^{14}$ can be selected from alkyl groups having 4 or more carbons, 6 or more carbons, or 10 or more carbons.

Certain of these ligands are preferred for the polymerization of certain monomers in a catalytic composition and/or in a metal complex. These certain embodiments are discussed further below.

In some embodiments, the ligands of the invention can be prepared using known procedures, such as those described, for example, in March, *Advanced Organic Chemistry*, Wiley, New York 1992 (4th Ed.). Specifically, the ligands of the invention can be prepared using a variety of synthetic routes, depending on the variation desired in the ligand. In general, the ligands are prepared in a convergent approach by preparing building blocks that are then linked together either directly or with a bridging group. Variations in the R group substituents can be introduced in the synthesis of the building blocks. Variations in the bridge can be introduced with the synthesis of the bridging group.

Specific ligands within the scope of the invention can be prepared according to the general schemes shown below, where building blocks (designated BB) are first prepared and are then coupled together. There are several different ways to use these building blocks. In one general approach, each of the optionally substituted aryl rings is prepared as a separate building block (Schemes 1 (a–d), 2 (a and b), and 3 (a and b)). The desired optionally substituted aryls are then combined into bi-aryl building blocks (Schemes 4 (a and b) and 5), which are then bridged together (Schemes 8 (a and b) and 9 (a and b)). In another approach, two optionally substituted aryl building blocks are bridged together (Schemes 6 (a–h) and 7 (a–b)) and then additional optionally substituted aryl building blocks are added to form the bridged bis (bi-aryl) structures (Schemes 10 (ac), and 11 (a–c)). In addition, schemes to effect certain substitutions on the aryl groups are included (Scheme 12 (a–d)). In many of these schemes, cross coupling reactions are used (e.g., Suzuki, Negishi or Buchwald-Hartwig cross coupling). These cross coupling reactions are generally known in the art; for example, see *Tetrahedron*, 1998, 54 (3/4), 263–303 and *J. Am. Chem. Soc.* 2001, 123(31), 7727–7729. The starting materials or reagents used in these schemes are generally commercially available, or are prepared via routine synthetic means.

In one embodiment, described in more detail below, hydroxy-, mercapto-, or amine-protected heteroatom-substituted aryl or heteroaryl building blocks are functionalized by introducing a substituent that supports subsequent cross-coupling (e.g., Suzuki or Negishi cross-coupling, as will be described in more detail below) at a ring position a to the protected hydroxy, mercapto, or amine substituent (e.g., the ortho carbon where aryl=phenyl). In particular embodiments, this is done by means of an ortho-directedh metallation reaction, in which the protected heteroatom-substituted aryl or heteroaryl building blocks is reacted with a metallating agent, such as a lithiating agent, to introduce the desired substitutent in the alpha position. The functionalized aryl or heteroaryl building blocks are then coupled with additional hydroxy-, mercapto-, or amine-substituted aryl or heteroaryl building blocks under cross-coupling conditions to form functionalized bi-aryl building blocks. Two bi-aryl building blocks, which may be the same or different, are then reacted with a bridging compound LG-B-LG in a double-displacement reaction to provide a bridged bis (bi-aryl) compound, which can undergo further manipulations (e.g., deprotection or further functionalization) to produce a bridged bis (bi-aryl) ligand.

In another embodiment, also discussed in more detail below, the bridged bis (bi-aryl) compound is provided by first forming a bridged aryl species by reacting two functionalized aryl or heteroaryl compounds with a bridging compound of the formula HX—B—XH under cross-coupling conditions. After further manipulation to introduce appropriate functionality into the aryl or heteroaryl rings, the bridged building block is then substituted with additional substituted aryl building blocks in an additional double cross-coupling reaction to provide the bridged bis (bi-aryl) species, which can then be further substituted and/or deprotected to provide the desired ligand.

In the following description and reaction schemes, the following abbreviations are used: "Hal"=Cl, Br, I or OTf (trifluoromethanesulfonyl); "X" and "Y"=oxygen or sulfur; "PG" and "PG'" protecting group (e.g., phenol or thiophenol protecting groups including, but not limited to methyl (Me), benzyl (Bz), substituted benzyl (2-methoxyphenylmethyl: MPM, etc.), alkoxymethyl (methoxymethyl: MOM, methoxyethyl: MEM, etc.), tetrahydropyranyl (THP), silyl (trimethylsilyl:TMS, tert-butyldimethylsilyl:TBDMS, etc.) and allyl (Allyl); "LG"=leaving group (e.g., leaving groups for nucleophilic displacement reactions including, but not limited to: chloro, bromo, iodo, para-toluenesulfonyl, methanesulfonyl and trifluoromethanesulfonyl. "Protection" and "cleavage" refers to introduction of and removal of protecting groups, respectively. The symbol ⌐B⌐ depicts a bridging moiety as defined elsewhere in this specification. The terms "upper aryl ring" and "upper phenyl ring" are used consistently with the term "upper aromatic ring", described above. The terms "lower aryl ring" and "lower phenyl ring" are used consistently with the term "lower aromatic ring", described above. While the reactions are illustrated with phenyl compounds in the reaction schemes, those skilled in the art will recognize that similar techniques can be used with other aryl and heteroaryl rings.

Scheme 1a below is a general building block synthesis scheme, specifically depicting the synthesis of Y-protected, ortho-H substituted, upper ring building block BB(1), Y-unprotected, ortho-Hal substituted, upper ring building block BB(2), and Y-protected, ortho-Hal substituted, upper ring building block BB(3):

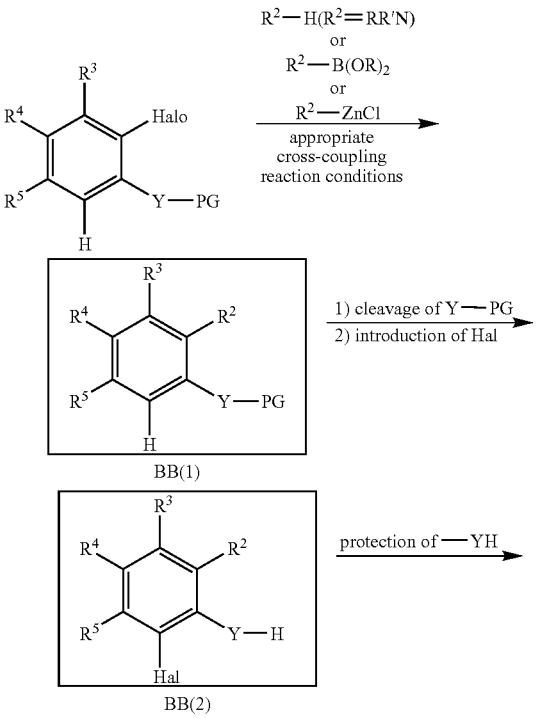

-continued

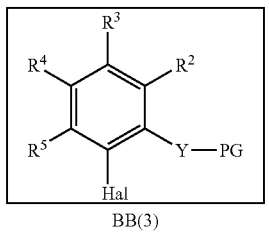
BB(3)

As shown in Scheme 1a, protecting groups (PG) are used to prepare these building blocks (BB(1), BB(2) and BB (3)). The substituents on the building blocks are as defined above. The variables R and R' are generally selected from the same group as $R^2$, and may be optionally substituted alkyl, aryl, amino and the like; optionally R and R' may be linked or fused. "Appropriate cross-coupling reaction conditions" are generally known to those of skill in the art, and may be found in the above-cited references. "Introduction of Hal" refers to known reactions for the introduction of Hal substituents such as bromination, iodination, etc. Other reaction conditions will be known to those of skill in the art, with reference to the examples herein.

As an alternative, Scheme 1b shows a general synthesis scheme for Y-protected, ortho-H substituted, upper aryl ring building blocks:

Scheme 1b

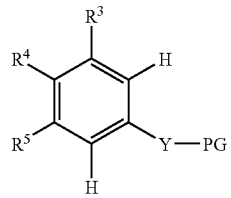

1) R—Li
2) B(OR) or ZnCl$_2$
3) $R^2$—Br, appopriate cross-coupling conditions

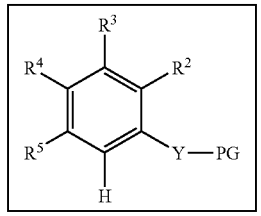
BB(1)

In scheme 1b, the variables are defined as discussed above.

Scheme 1c shows an alternative general synthesis for Y-protected, ortho-Hal substituted, upper aryl ring building blocks:

Scheme 1c

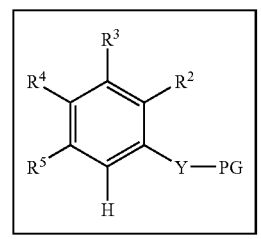
BB(1)

introduction of Hal

-continued

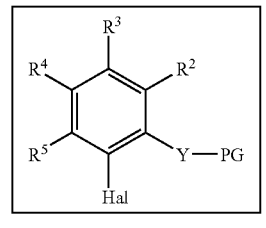
BB(3)

Again, in Scheme 1c, the variables are defined as discussed above.

Scheme 1d shows an alternative general synthesis of Y-unprotected, ortho-Hal substituted, upper ring building block BB(2), and Y-protected, ortho-Hal substituted, upper ring building block BB(3):

Scheme 1d

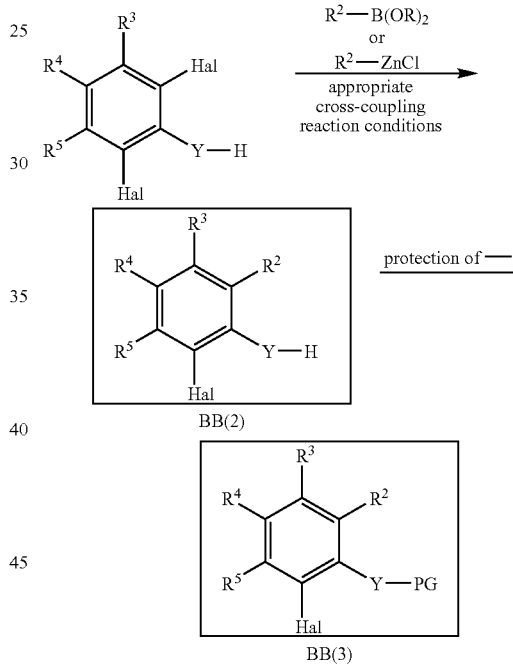

Again, in Scheme 1d, the variables are defined as discussed above.

Scheme 1e shows still another alternative general synthesis of Y-protected, ortho-Hal substituted, upper ring building block BB(3) and Y-unprotected, ortho-Hal substituted, upper ring building block BB(2):

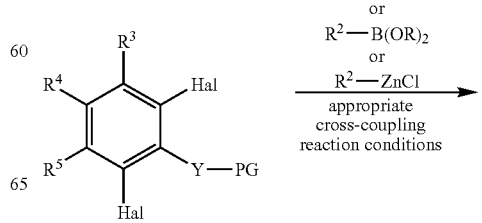

$R^2$—H($R^2$=RR'N)
or
$R^2$—B(OR)$_2$
or
$R^2$—ZnCl
appropriate cross-coupling reaction conditions -continued

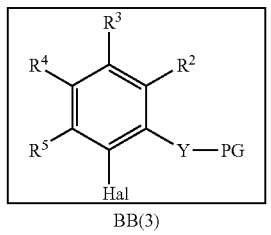
BB(3)

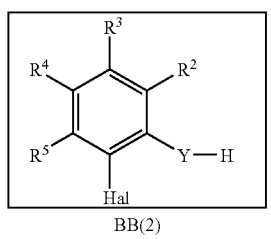
BB(2)

Scheme 2a below is a general scheme for the synthesis of Y-protected ortho-boronic ester substituted upper-ring building block BB(4), Y-unprotected ortho-boronic acid substituted upper-ring building block BB(5) and Y-protected ortho-ZnCl substituted upper-ring building blocks BB(6):

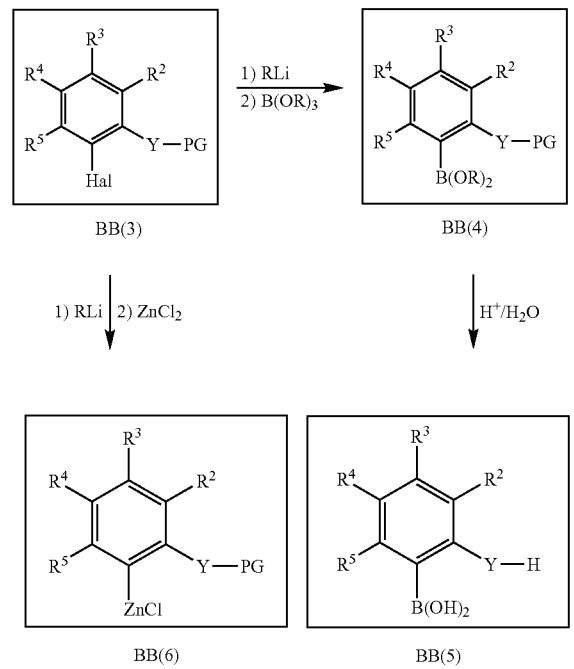

Scheme 2a

In scheme 2a, the variables are defined as discussed above.

Scheme 2b, below, shows an alternative general synthesis of Y-protected ortho-boronic ester substituted upper-ring building block BB(4), Y-unprotected ortho-boronic acid substituted upper-ring building block BB(5) and Y-protected ortho-ZnCl substituted upper-ring building blocks BB(6) via directed ortho-metallation, as described in more detail below:

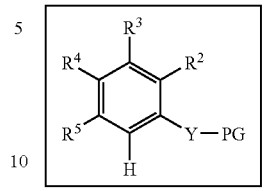

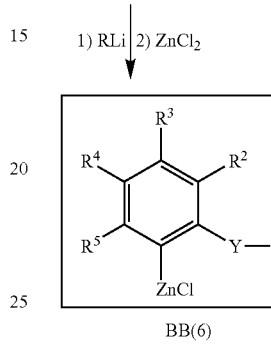
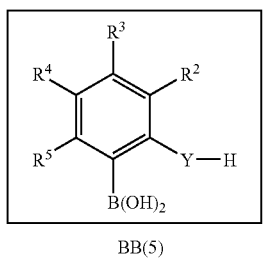

Scheme 2b

In Scheme 2b, the variables are defined as discussed above. In Scheme 2b, the ortho-metallation is depicted as proceding with an alkyl lithium reagent. This is an example of a general class of reactions in which a functional group on a molecule (typically containing a coordinating group such as an ether, thioether or amine) selectively directs metallation (transmetallation or deprotonation) to a specific site on the molecule. In this case directed ortho-deprotonation/metallation is mediated by the —Y—PG substitution on the ring. The use of directed ortho-deprotonation/metallation allows generation of the ortho-functionalized building blocks BB(4), BB(5), and BB(6) (Scheme 2b above) in a facile manner from the unfunctionalized building block BB(1). This precludes the need to synthesize the ortho-Hal functionalized building block BB(3) (scheme 2a above) and provides a shorter, higher-yielding synthesis of building blocks BB(4), BB(5), and BB(6).

Scheme 3a below is a general scheme for the synthesis of X-protected ortho-Hal substituted lower-ring building block BB(8), X-protected ortho-boronic ester substituted lower-ring building block BB(9), X-protected ortho-ZnCl substituted lower-ring building block BB(10) and X-unprotected ortho-boronic acid substituted lower-ring building block BB(11):

Scheme 3a

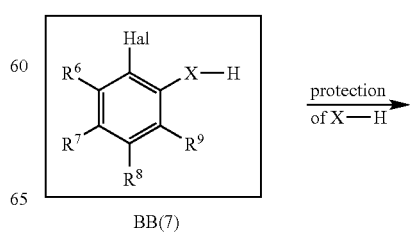
BB(7)

-continued

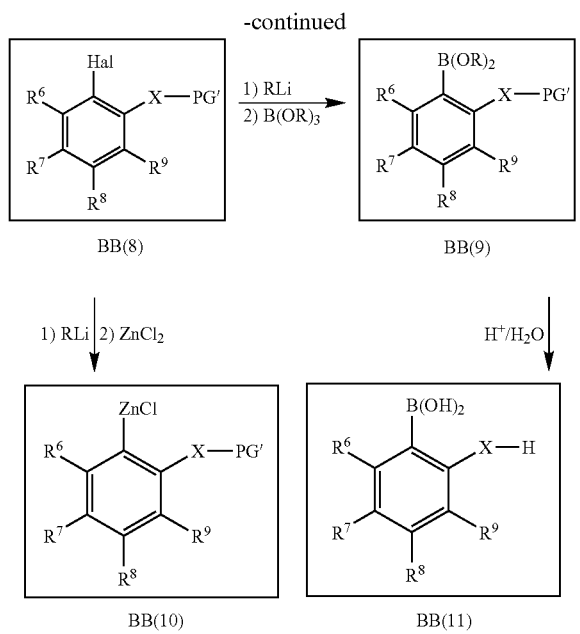

In scheme 3a, the variables are defined as discussed above. In addition the phrase "protection of X—H" refers to a protection step for the AR—XH (e.g, phenolic or thiophenolic group), such as reaction with dihydropyran under acidic conditions to provide a tetrahydropyranyl protecting group (i.e., PG' =THP) for the aryl-X substituent.

Scheme 3b below shows an alternative general synthesis of X-protected ortho-boronic ester substituted lower-ring building block BB(9), X-protected ortho-ZnCl substituted lower-ring building block BB(10) and X-unprotected ortho-boronic acid substituted lower-ring building block BB(11) via directed ortho-metallation:

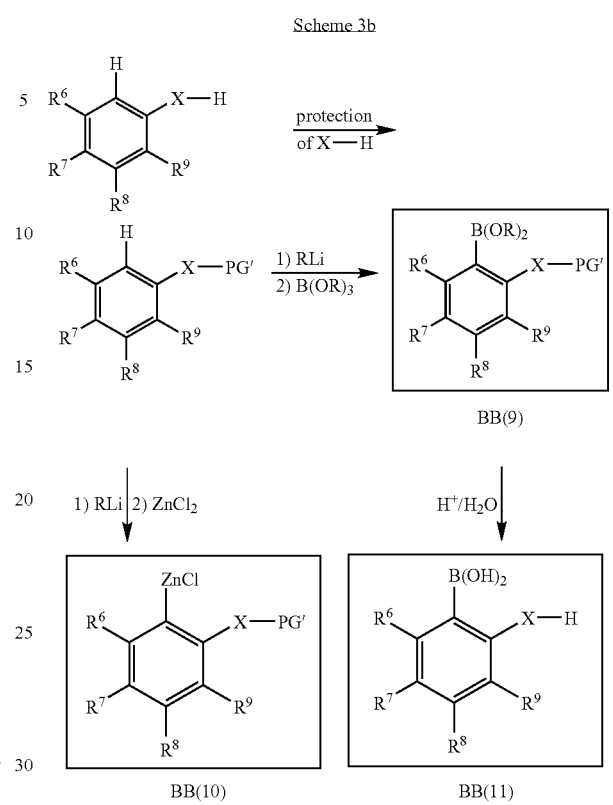

In Scheme 3b, the variables, protection and advantages of advantages of employing an ortho-metallation approach are as discussed above.

Scheme 4a below is a general scheme for the synthesis of Y-protected upper-ring, X-unprotected lower-ring building block BB(12):

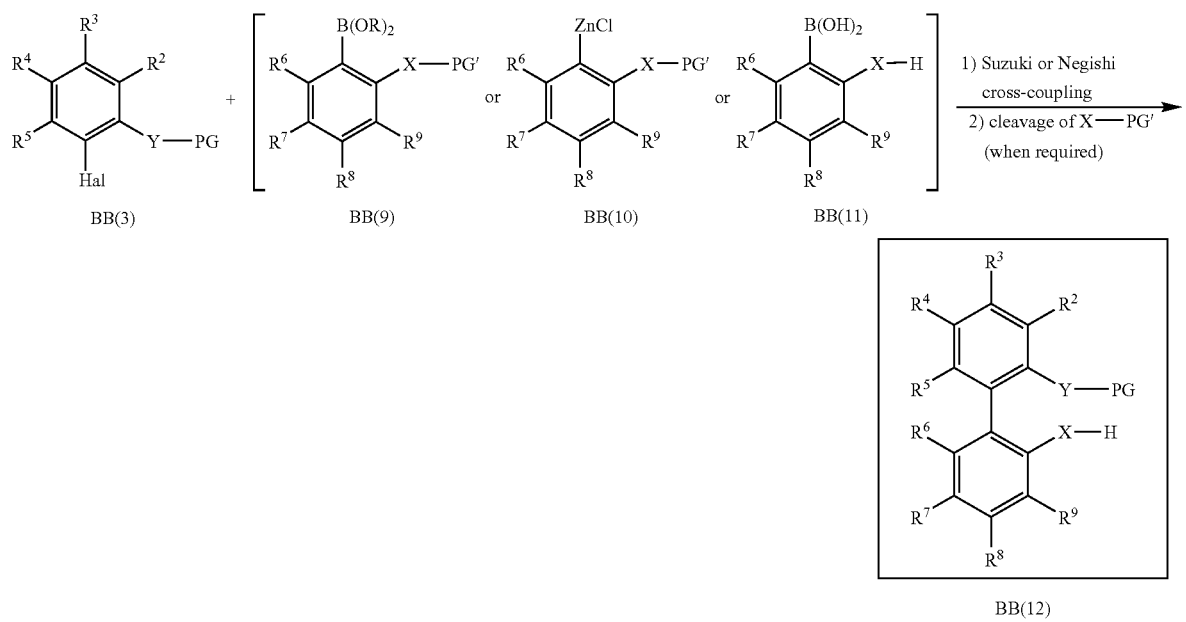

In scheme 4a, the variables are defined as discussed above.

Scheme 4b below shows an alternative synthesis of Y-protected upper-ring, X-unprotected lower-ring building block BB(12):
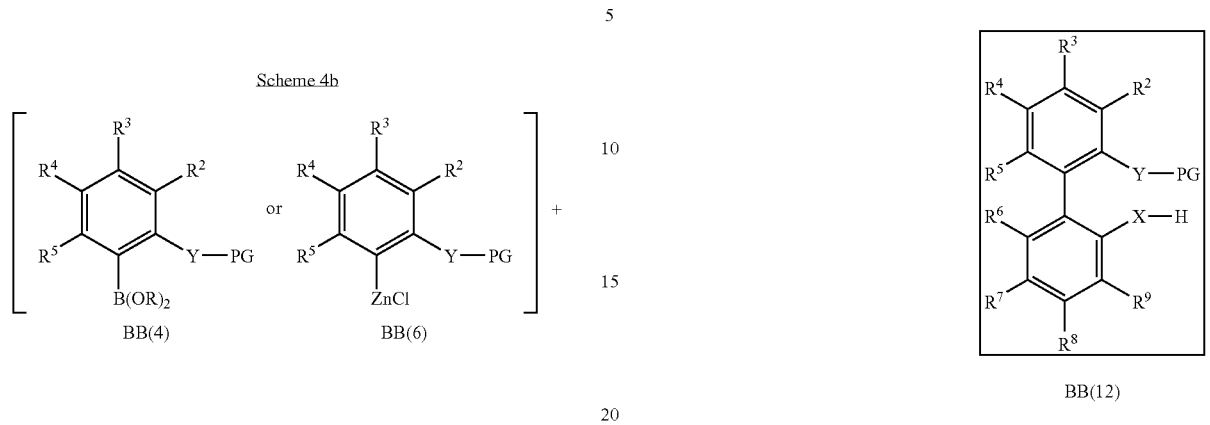
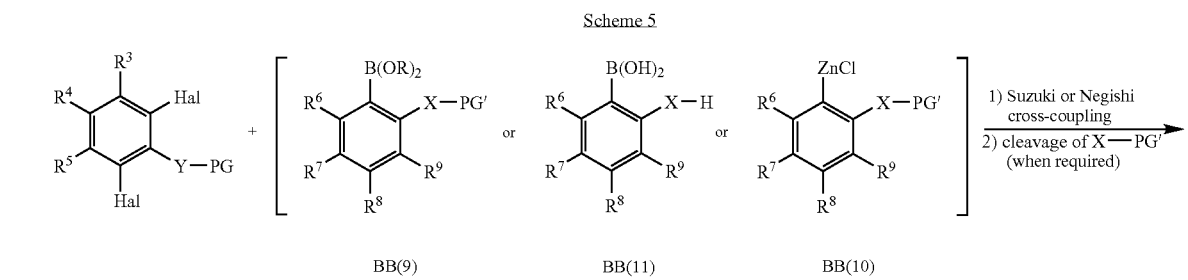
In Scheme 4b, the variables are defined as discussed above.
Scheme 5 below is a general scheme for the synthesis of ortho-Hal, Y-protected upper-ring, X-unprotected lower-ring building block BB(13):
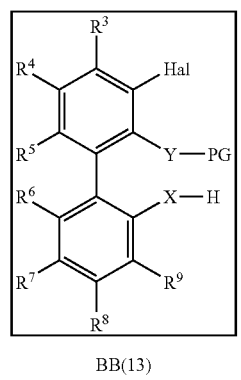
In scheme 5, the variables are defined as discussed above.

Scheme 6a below is a general scheme for the synthesis of symmetric ortho-Hal substituted bridged lower-ring building block BB(14):

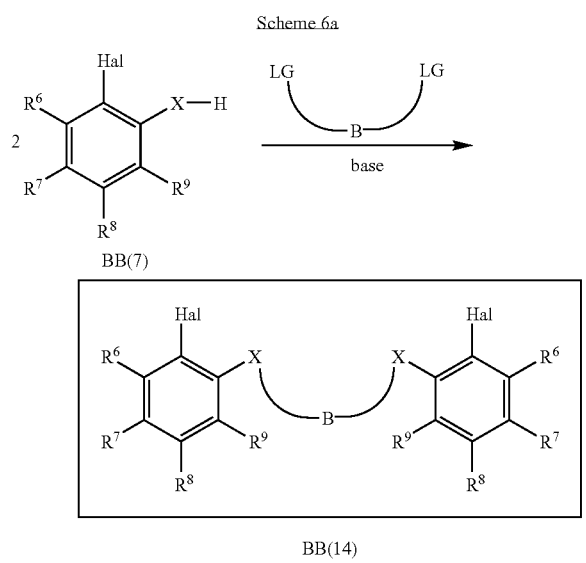

In scheme 6a, the variables are defined as discussed above. In addition the phrase "base" refers to bases in general (such as cesium carbonate or potassium tert-butoxide, triethylamine, etc.).

Scheme 6b below is a general scheme for the synthesis of asymmetric ortho-Hal substituted bridged lower-ring building block BB(15):

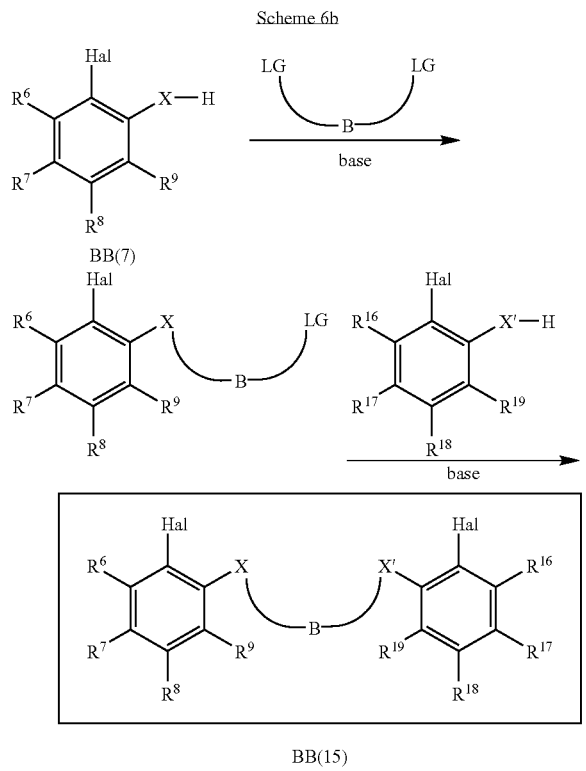

In scheme 6b, the variables are defined as discussed above.

Scheme 6c below shows an alternative synthesis of symmetric ortho-Hal substituted bridged lower-ring building block BB(14):

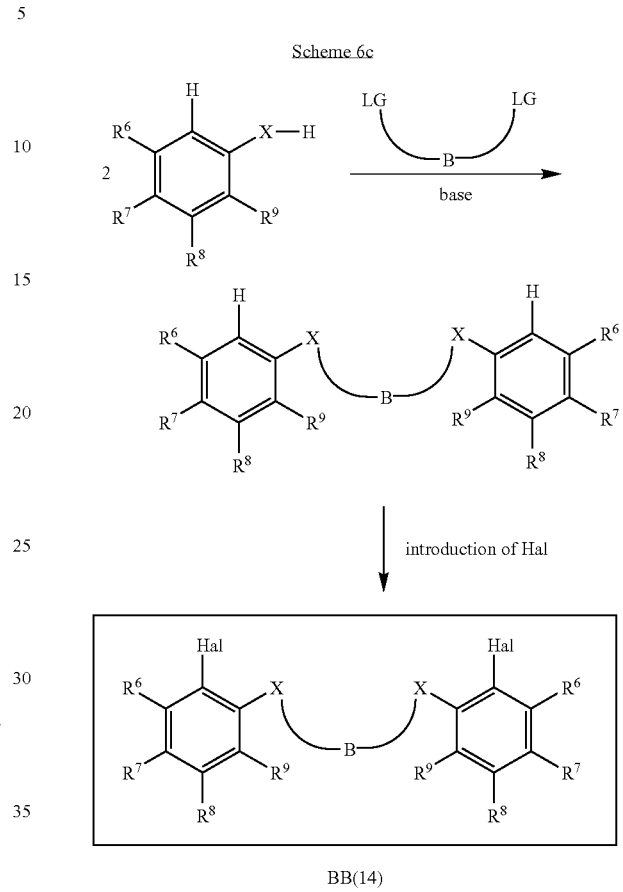

In Scheme 6c, the variables are defined as discussed above.

Similarly, Scheme 6d below shows an analogous alternative synthesis of asymmetric ortho-Hal substituted bridged lower-ring building block BB(15):

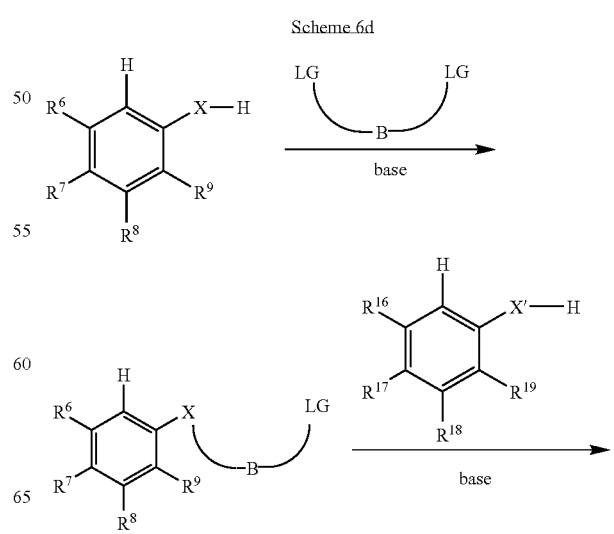

-continued

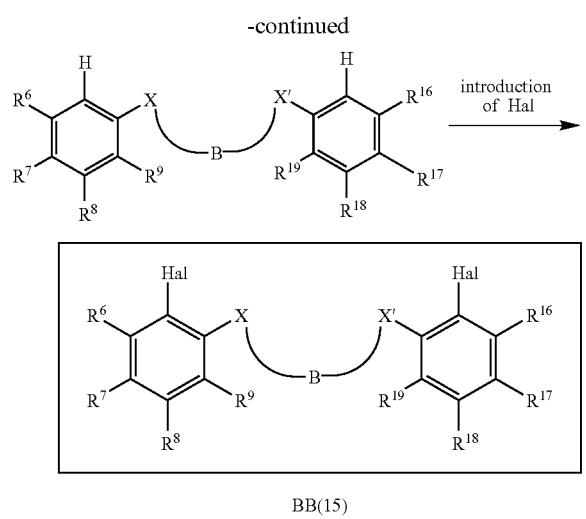

BB(15)

In Scheme 6d, the variables are defined as discussed above.

Scheme 6e illustrates an alternative approach to the synthesis of symmetric ortho-Hal substituted bridged lower-ring building block BB(14), in which the bridging group is coupled to a pair of Hal-functionalized aryl building blocks under cross-coupling conditions:

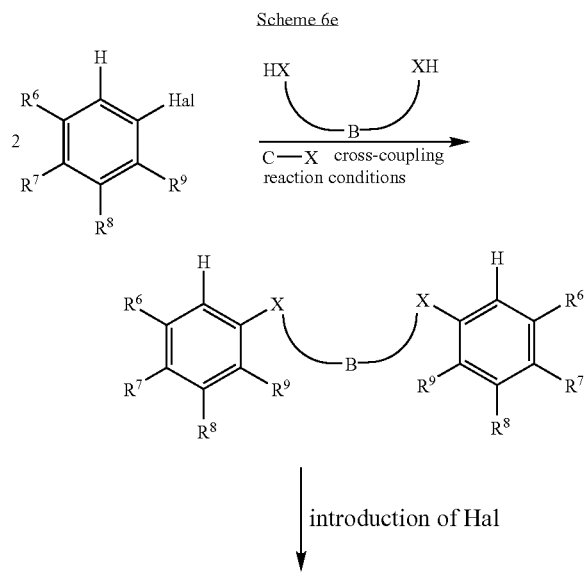

BB(14)

In Scheme 6e, the variables are defined as discussed above.

An analogous synthesis of asymmetric ortho-Hal substituted bridged lower-ring building block BB(15) is shown in Scheme 6f, with variables again defined as disccused above.

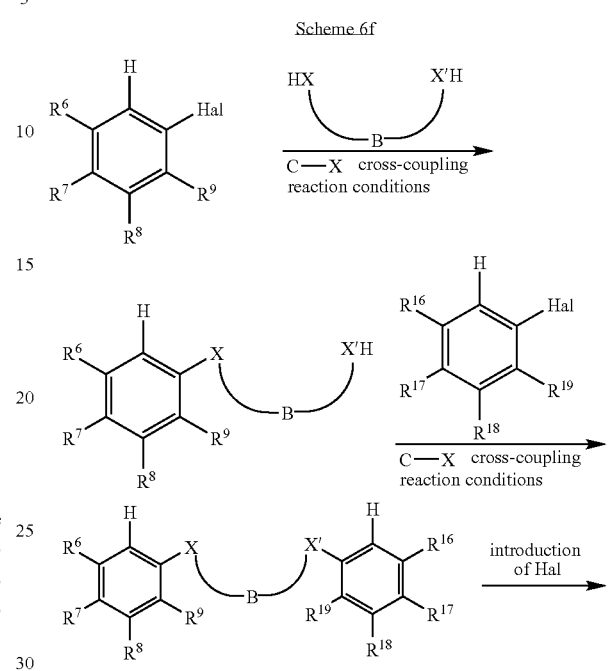

BB(15)

Scheme 6g shows an alternative synthesis of symmetric ortho-Hal substituted bridged lower-ring building block BB(14):

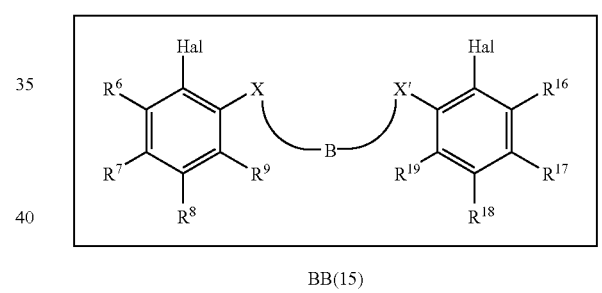

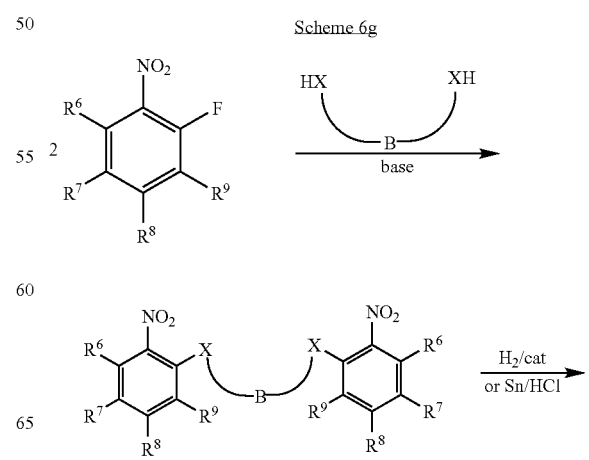

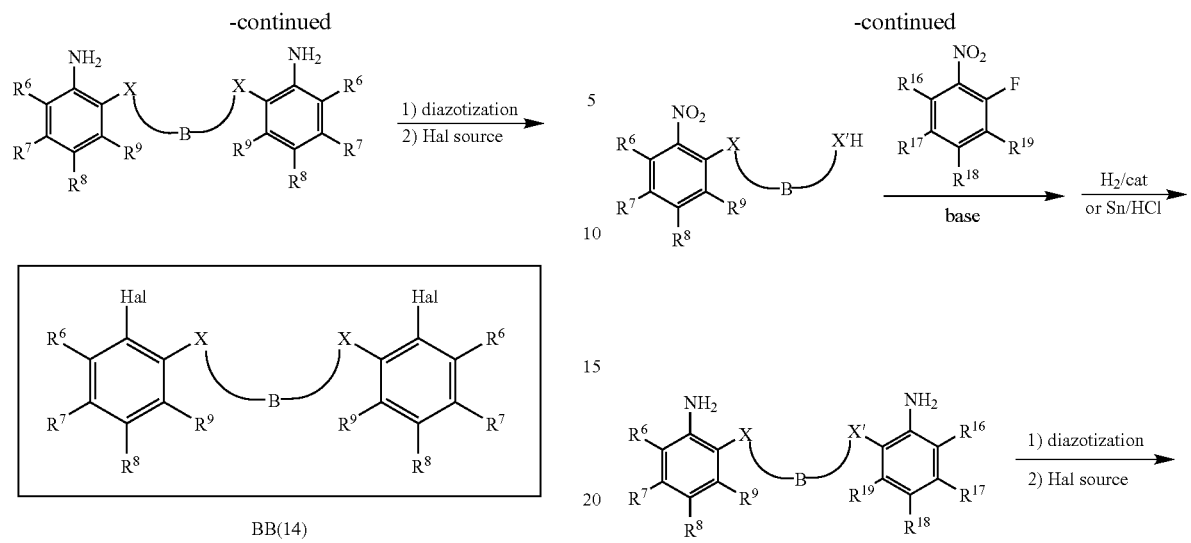

"Diazotization" is the conversion of an amine into a diazonium salt by methods known to those skilled in the art. "Halide source" is a reaction medium to provide reactive Hal anions. In Scheme 6g, the variables are defined as discussed above.

Scheme 6h shows an analogous alternative synthesis of asymmetric ortho-Hal substituted bridged lower-ring building block BB(15), with variables defined as discussed above:

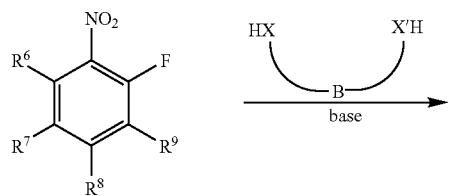

Scheme 7a shows a general scheme for synthesis of symmetric ortho-boronic ester substituted bridged lower-ring building block BB(16), symmetric ortho-boronic acid substituted bridged lower-ring building block BB(17), and symmetric ortho-ZnCl substituted bridged lower-ring building block BB(18):

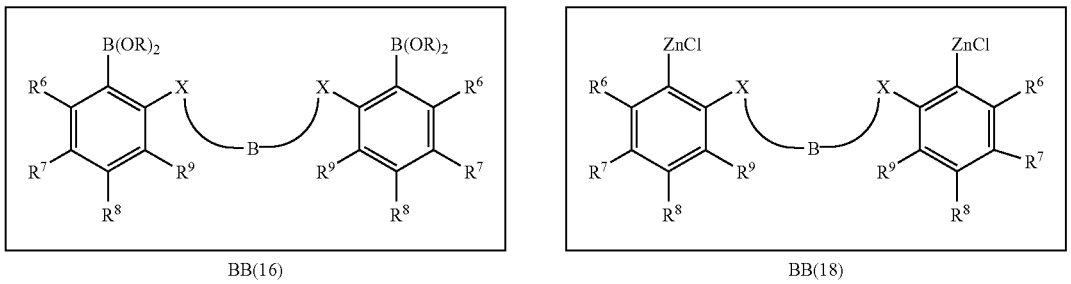

BB(16)                            BB(18)

↓ H⁺/H₂O

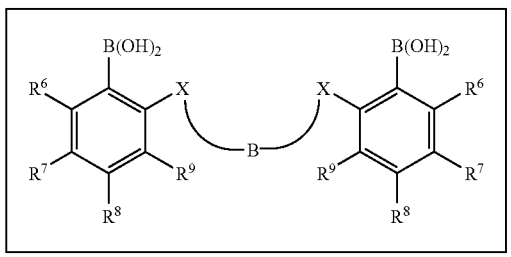

BB(17)

In scheme 7a, the variables are defined as discussed above. The phrase "cat. Pd(0)" refers to a catalyst that uses a ligand-stabilized Pd⁰ complex, known to those of skill in the art.

Scheme 7b shows an analogous synthesis of asymmetric ortho-boronic ester substituted bridged lower-ring building block BB(19), asymmetric ortho-boronic acid substituted bridged lower-ring building block BB(20), and asymmetric ortho-ZnCl substituted bridged lower-ring building block BB(21), with variables defined as discussed above:

Scheme 7b

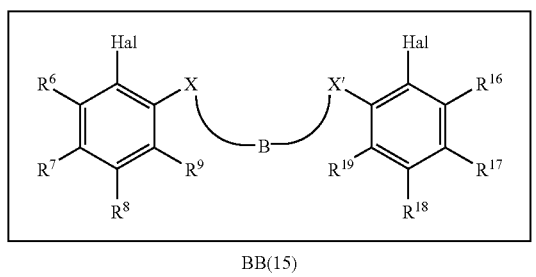

BB(15)

-continued

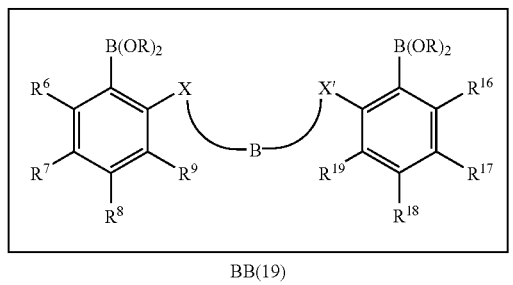

BB(19)

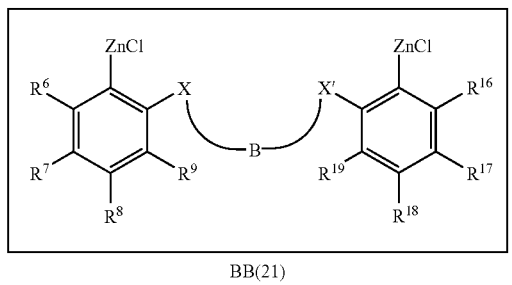

BB(21)

H⁺/H₂O

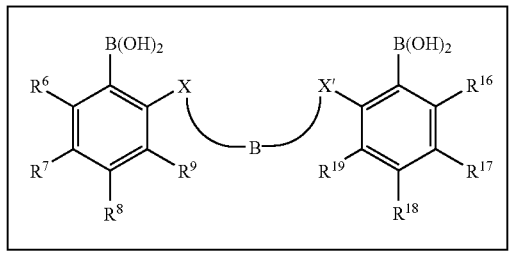

BB(20)

Scheme 8a below is a general scheme for the synthesis of symmetric Y-protected, upper-ring ortho-Hal-substituted, lower-ring bridged building block BB(22):

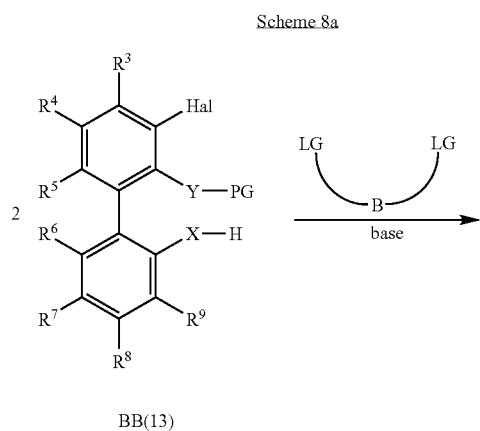

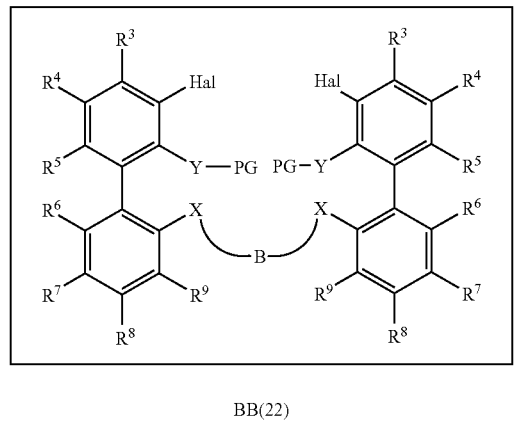

BB(22)

In scheme 8a, the variables are defined as discussed above.

Scheme 8b is a general scheme for the synthesis of asymmetric Y-protected, upper-ring ortho-Hal-substituted, lower-ring bridged building block BB(23), with variables defined as discussed above:

Scheme 8b

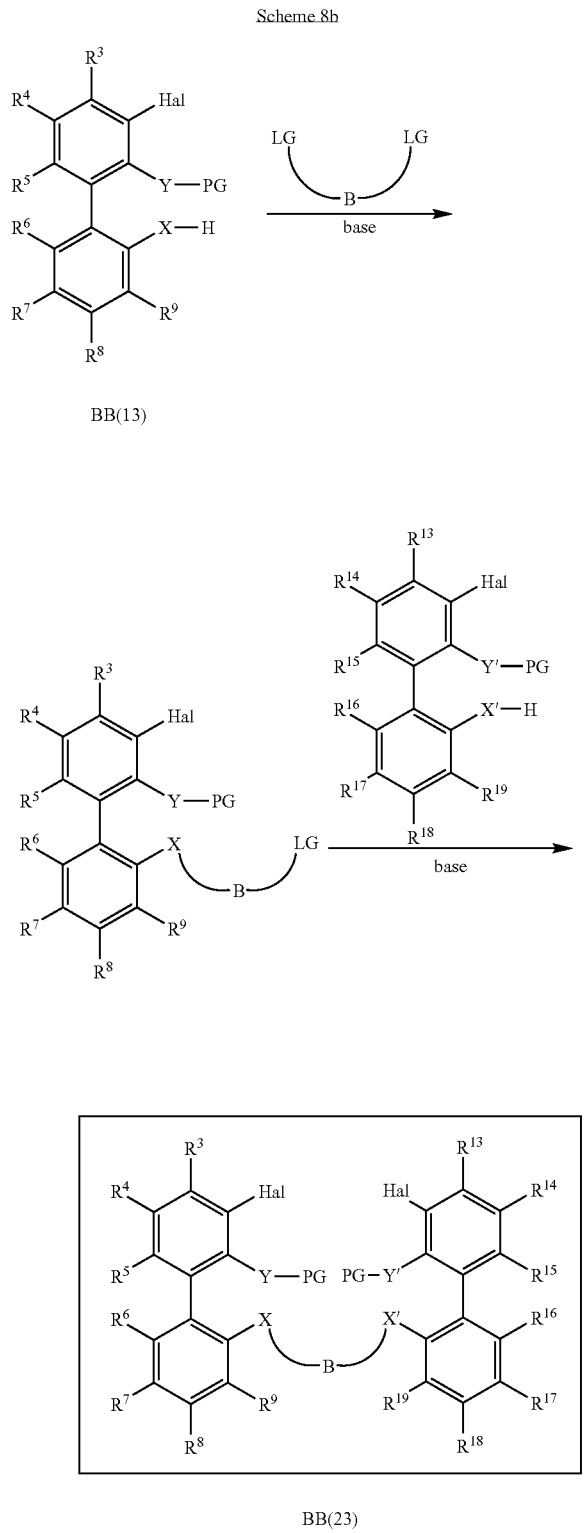

BB(13)

BB(23)

These building blocks can be combined in various ways to obtain bridged bis (bi-aryl) ligands according to the invention. Thus, Scheme 9a is a general scheme for the synthesis of a symmetric bridged bis (bi-aryl) ligand by the double reaction of building block BB(12) with bridge, followed by deprotection of Y—PG:

Scheme 9a

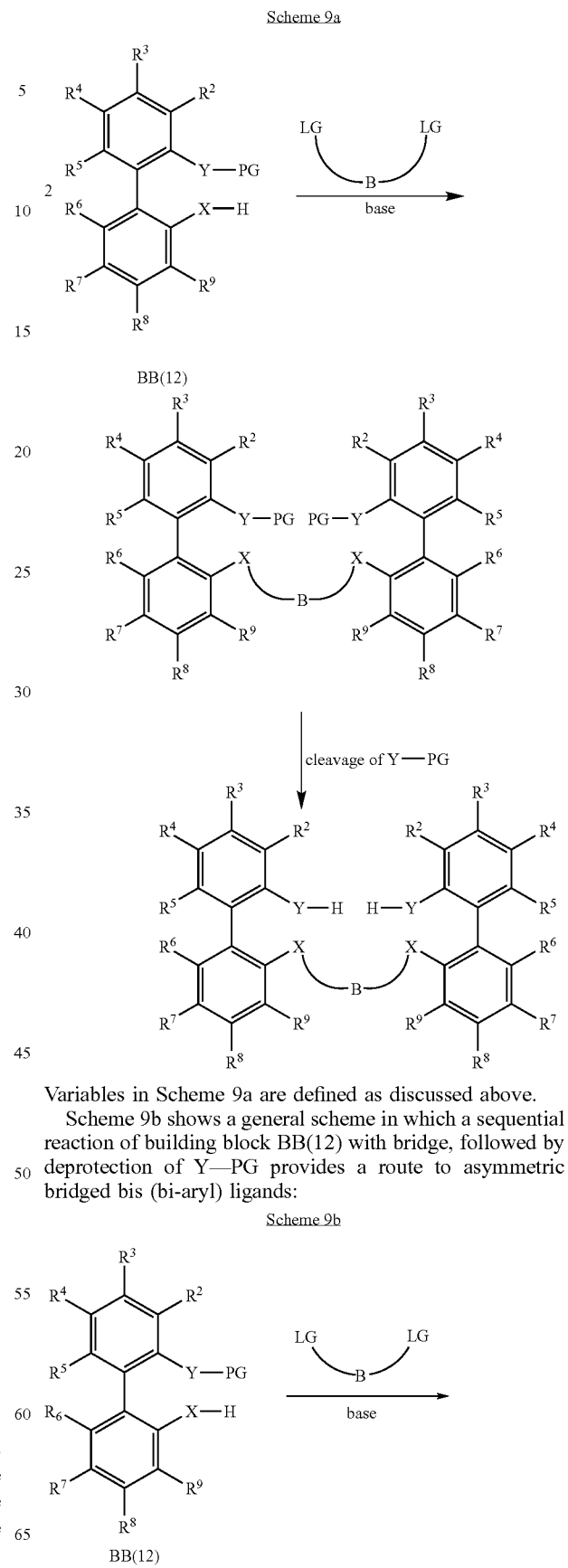

BB(12)

Variables in Scheme 9a are defined as discussed above.

Scheme 9b shows a general scheme in which a sequential reaction of building block BB(12) with bridge, followed by deprotection of Y—PG provides a route to asymmetric bridged bis (bi-aryl) ligands:

Scheme 9b

BB(12)

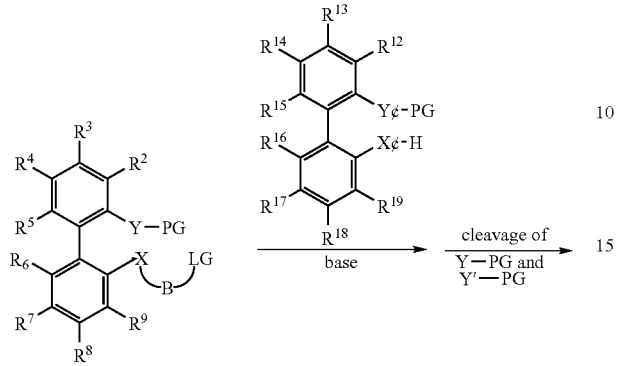
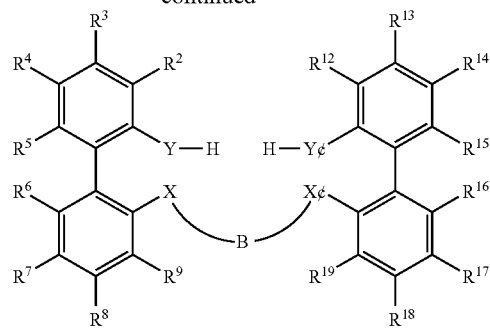
In scheme 9b, the variables are defined as discussed above.
Scheme 10a below is a general scheme that features a double cross-coupling of BB(4), BB(5) or BB(6) with BB(14) followed by deprotection of Y—PG, again providing a route to symmetric bridged bis (bi-aryl) ligands:
Scheme 10a
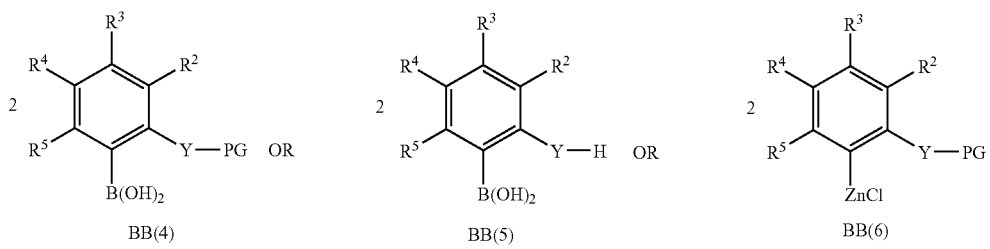
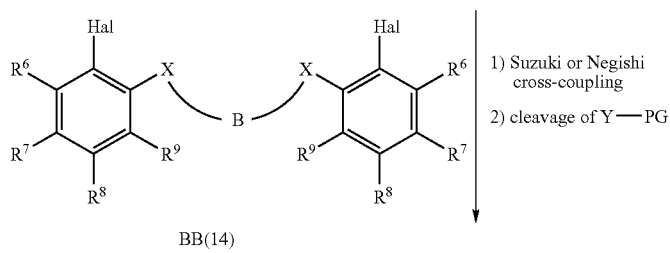
1) Suzuki or Negishi cross-coupling
2) cleavage of Y—PG
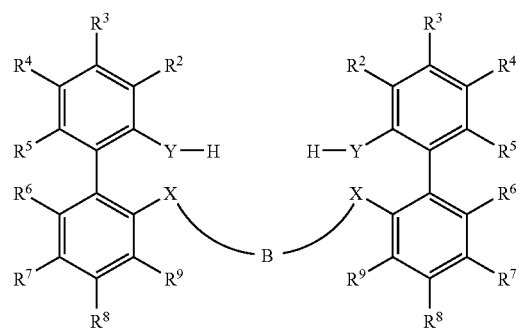
In Scheme 10a, the variables are defined as discussed above.

Scheme 10b below shows an analogous general scheme featuring a double cross-coupling of BB(4), BB(5) or BB(6) with BB(15) followed by deprotection of Y—PG, providing a route to different asymmetric ligand species:

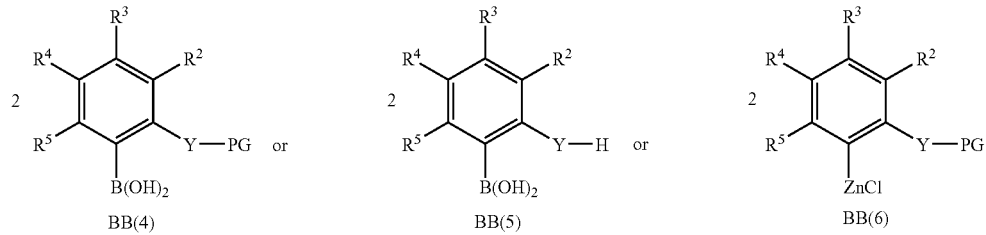

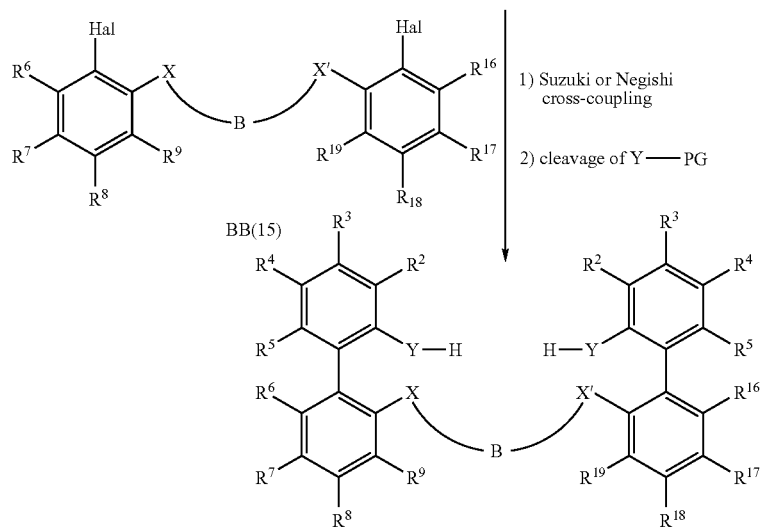

In Scheme 10b, the variables are defined as discussed above.

Scheme 10c is a general scheme for the synthesis of still another type of asymmetric ligand by the sequential cross-coupling of BB(4), BB(5) or BB(6) with BB(14) followed by deprotection of Y—PG:

Scheme 10c

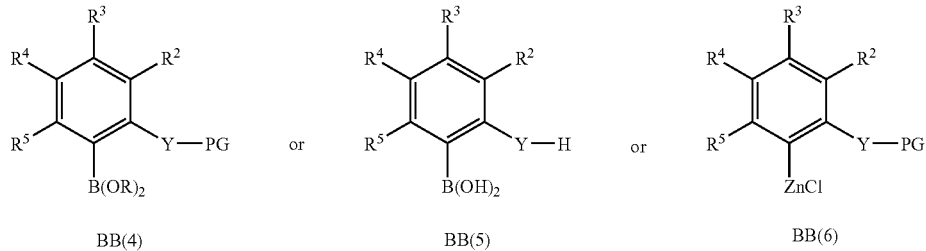

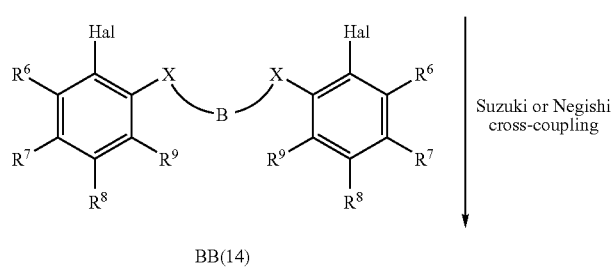

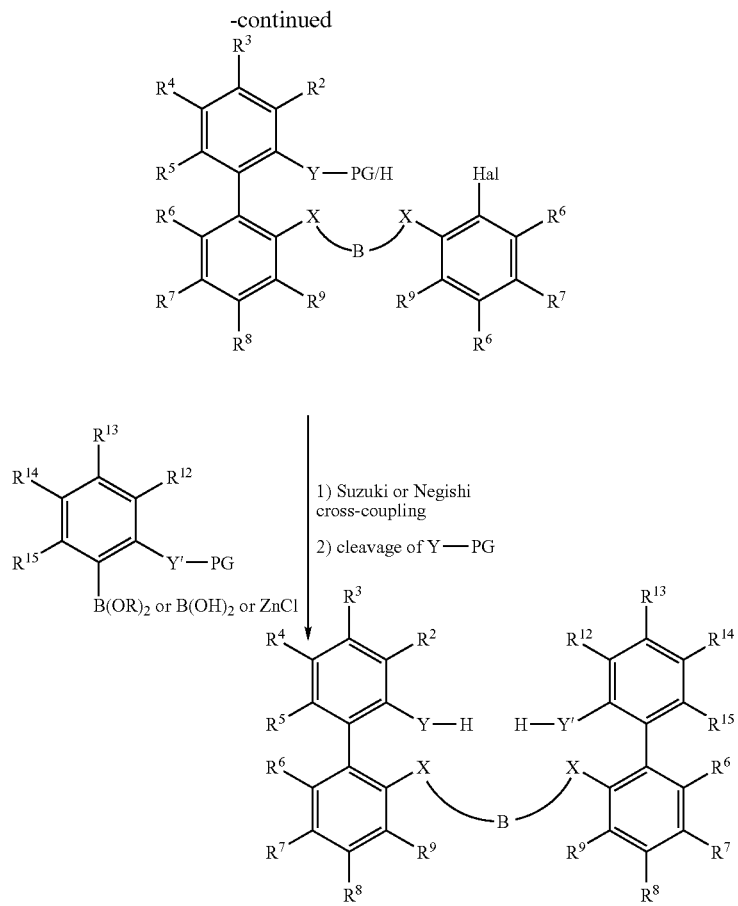
In Scheme 10c, the variables are defined as discussed above.
Scheme 11 below is a general scheme for the double cross-coupling of building blocks BB(2) or BB(3) with building blocks BB(6), BB(7) or BB(8), followed by deprotection of Y—PG:
Scheme 11a
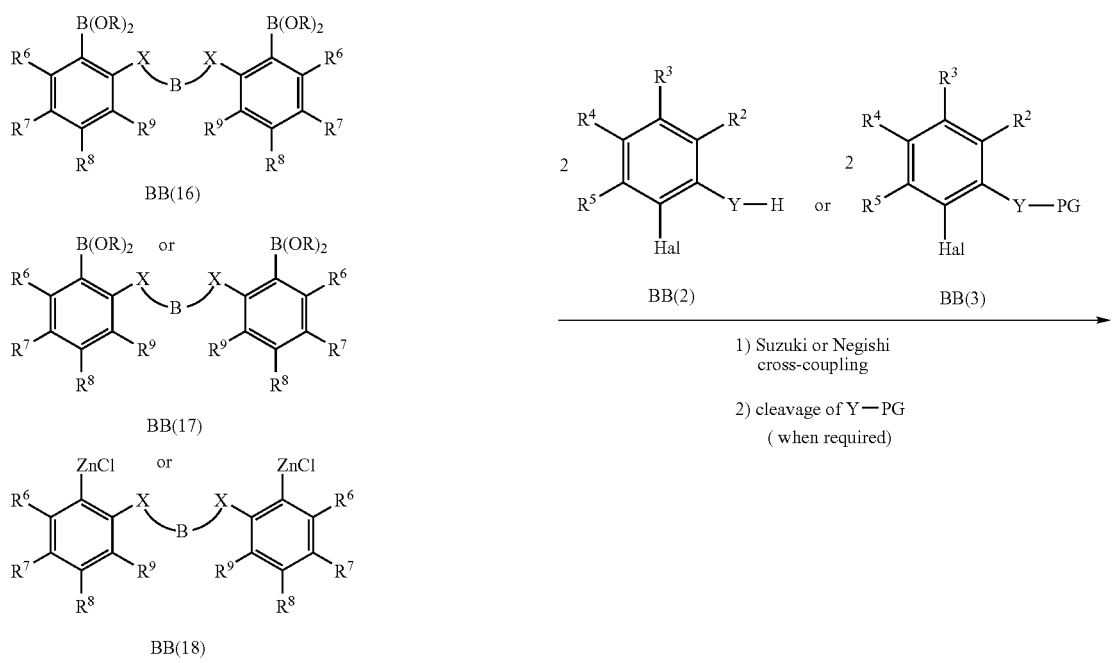

-continued
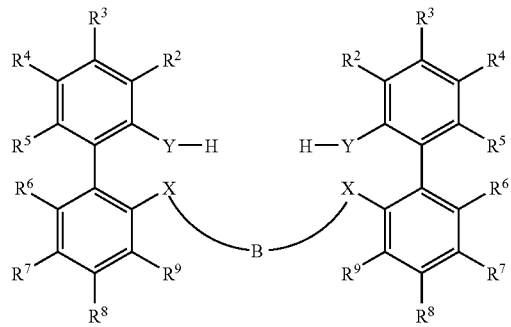
In Scheme 11a, the variables are defined as discussed above.
Scheme 11b below shows a similar scheme for the double cross-coupling of building blocks BB(2) or BB(3) with building blocks BB(19), BB(20) or BB(21), followed by deprotection of Y—PG:
Scheme 11b
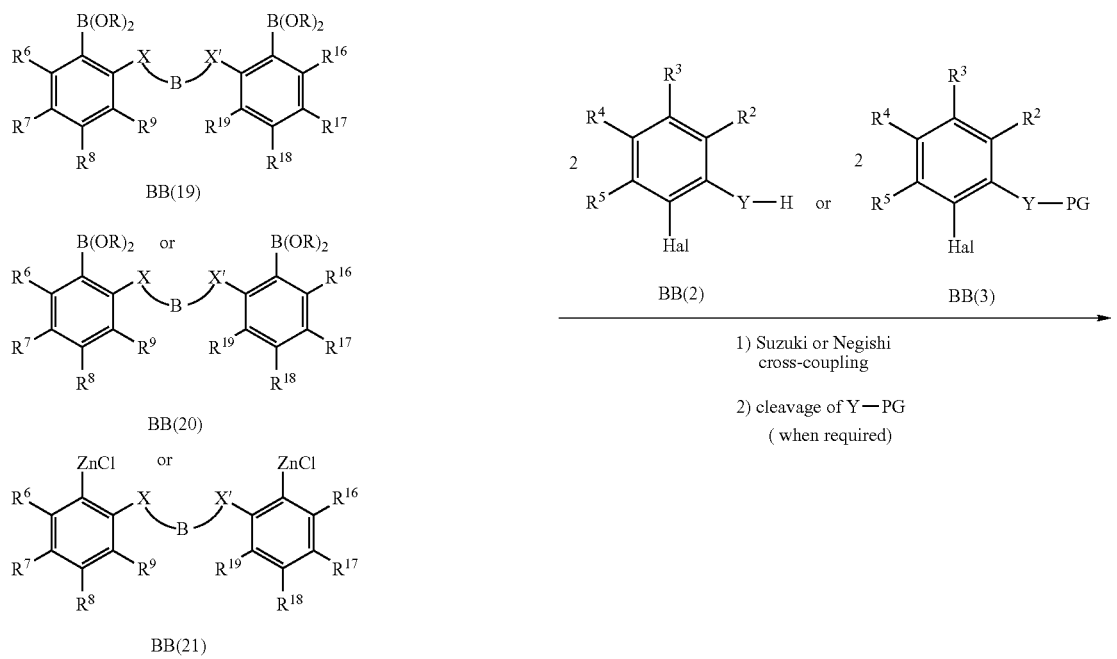
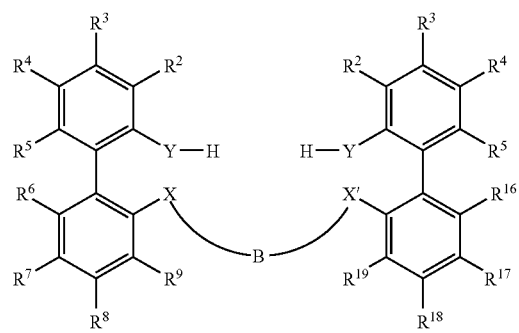
In Scheme 11b, the variables are defined as discussed above.

Scheme 11c below shows a general scheme for the sequential cross-coupling of building blocks BB(2) or BB(3) with building blocks BB(16), BB(17) or BB(18), followed by deprotection of Y—PG to produce an asymmetric ligand:
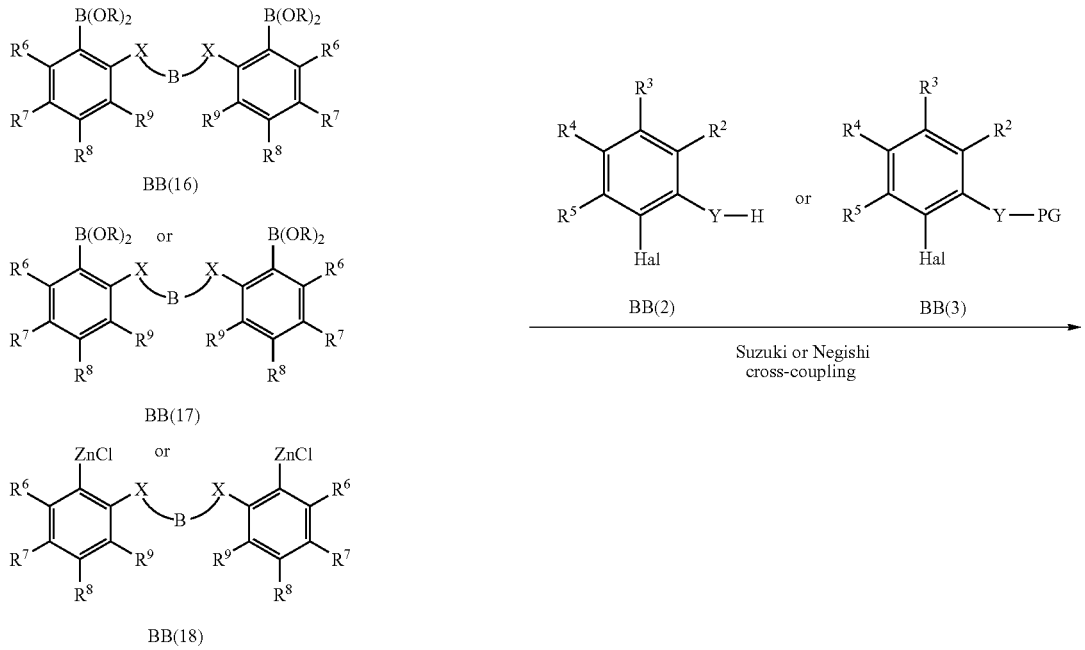
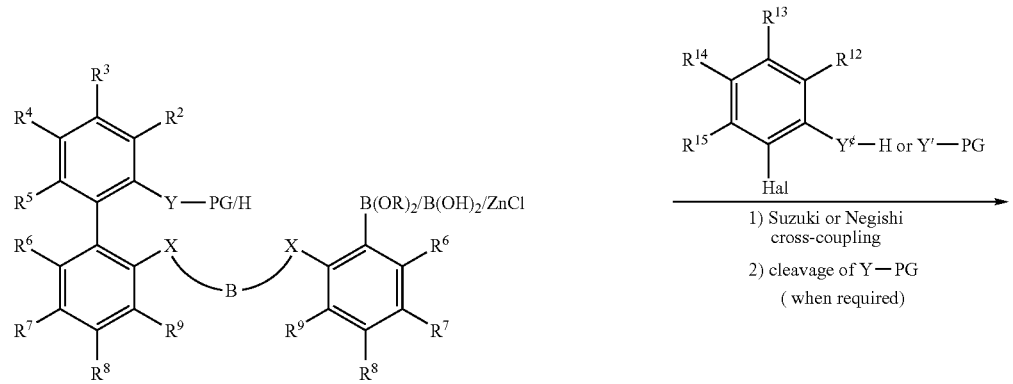
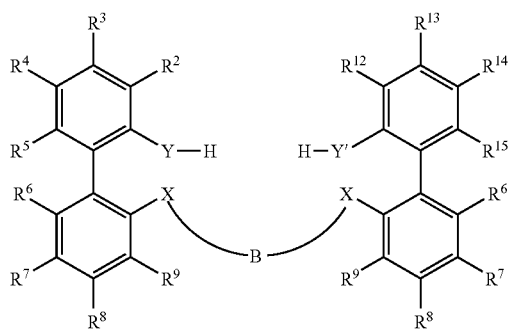
In Scheme 11c, the variables are defined as discussed above.

Scheme 12a is a general scheme for the double cross-coupling of building block BB(22), followed by deprotection of Y—PG:
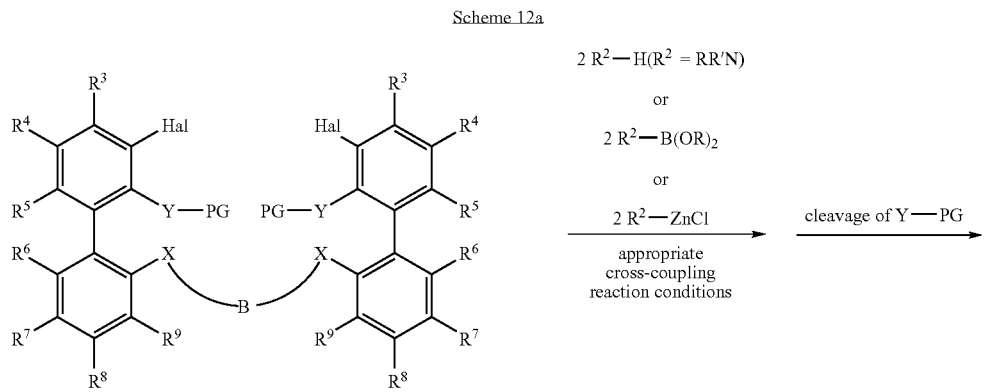
BB(22)
In Scheme 12a, the variables are defined as discussed above.
Scheme 12b below shows an analogous scheme for the double cross-coupling of building block BB(23), followed by deprotection of Y—PG:
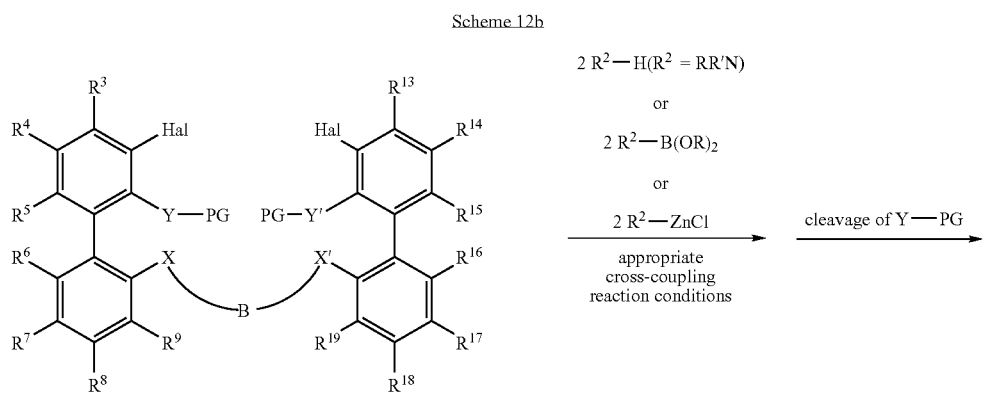
BB(23)

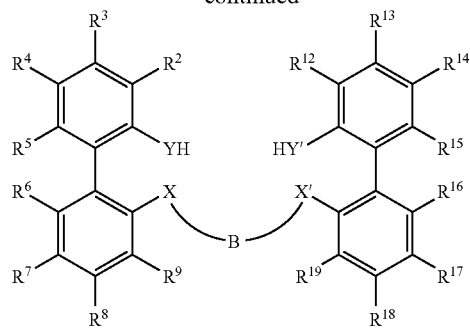

In Scheme 12b, the variables are defined as discussed above.

Scheme 12c below is a general scheme for conversion of BB(22) to double boronic ester or ZnCl, followed by double cross-coupling of building block and deprotection of Y—PG:

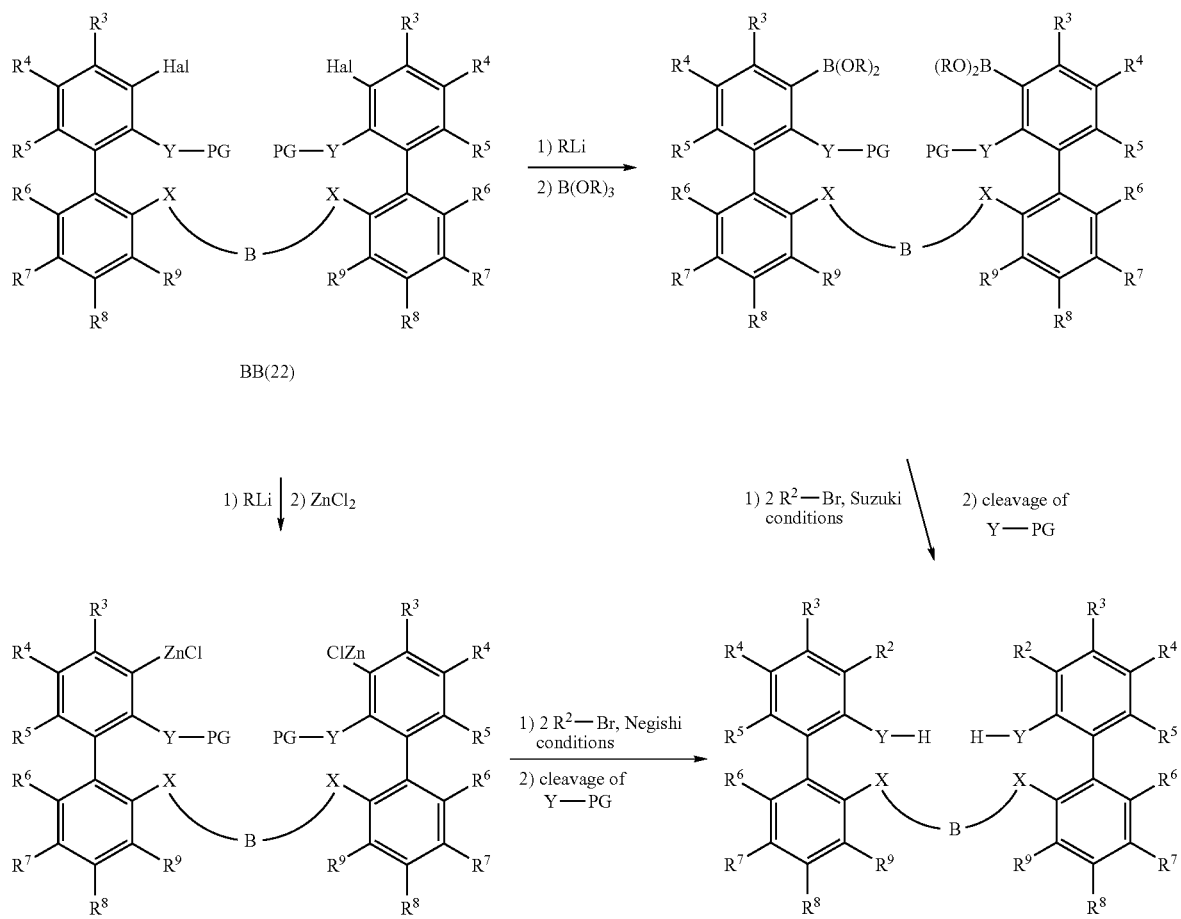

In Scheme 12c, the variables are defined as discussed above.

Scheme 12d is a general scheme for the conversion of BB(23) to double boronic ester or ZnCl derivatives, followed by double cross-coupling of building block and deprotection of Y—PG:

Scheme 12d
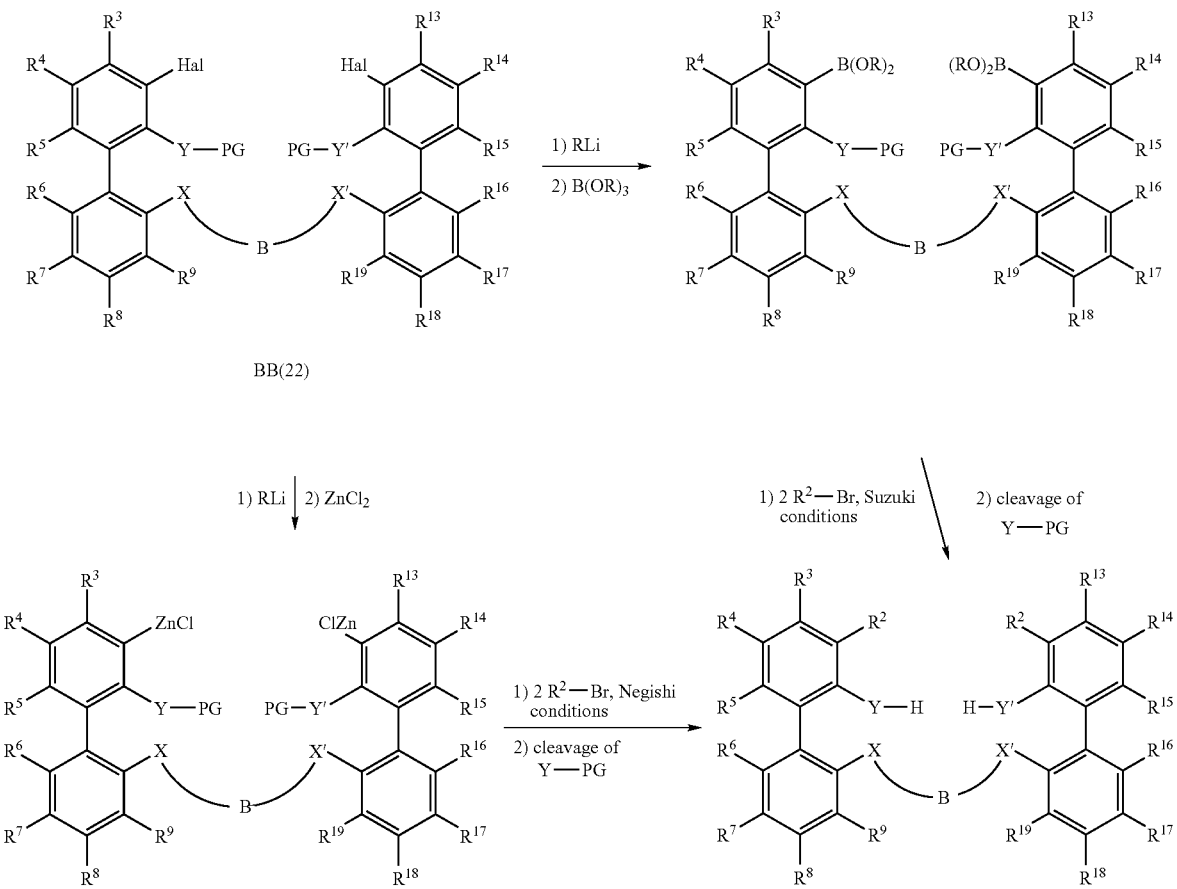
In Scheme 12d, the variables are defined as discussed above.
Ligands that can be prepared using these techniques and that are within the scope of this invention include those set out in Table 1, above, as well as the ligands set out in Table 2, below.
TABLE 2
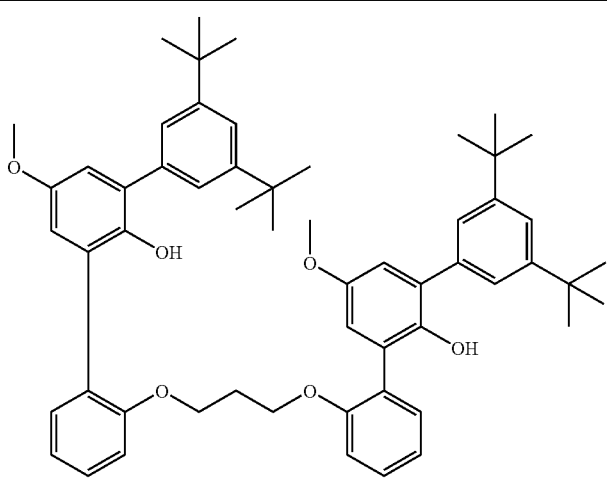
LL100

TABLE 2-continued
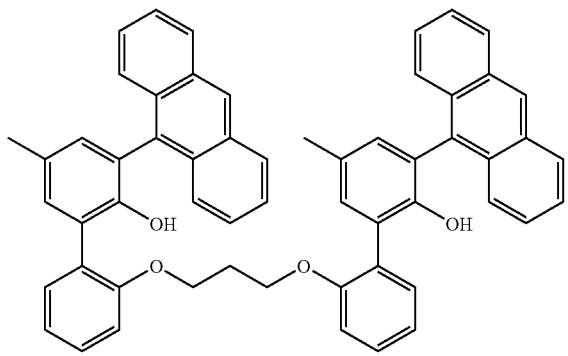
LL101
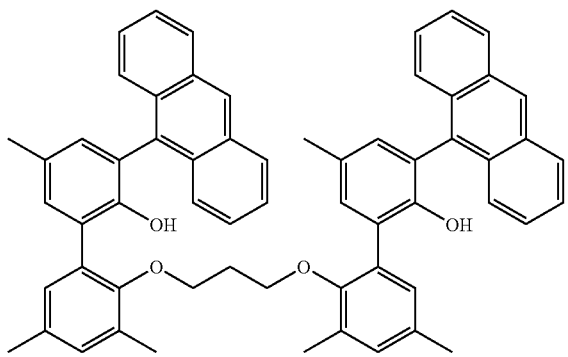
LL102
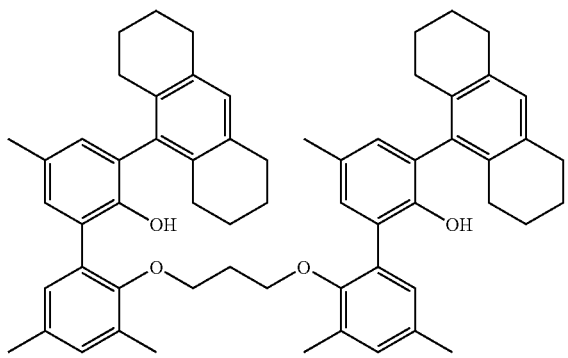
LL103
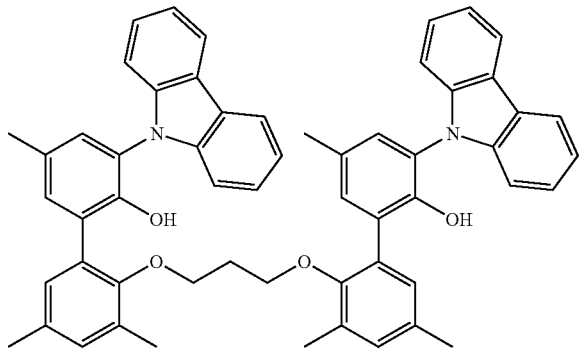
LL104

TABLE 2-continued
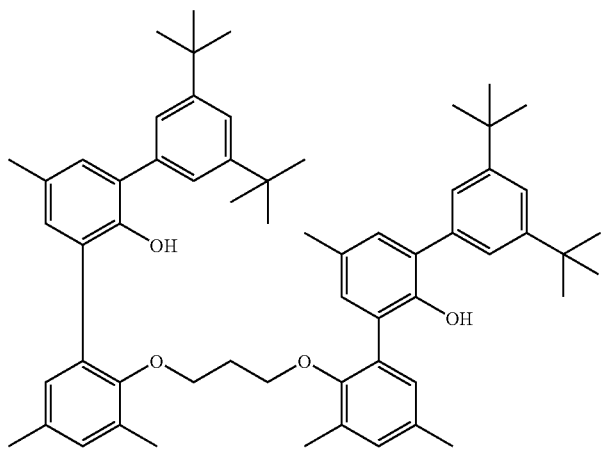
LL105
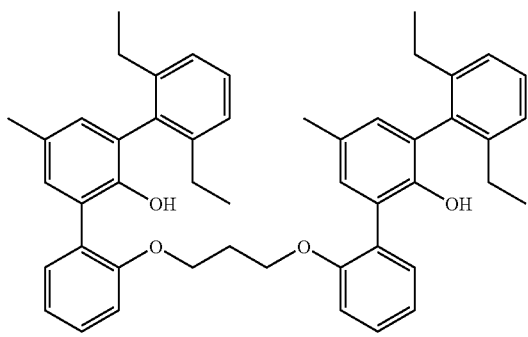
LL106
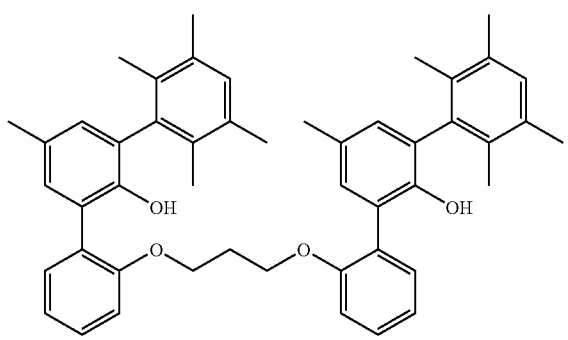
LL107

TABLE 2-continued
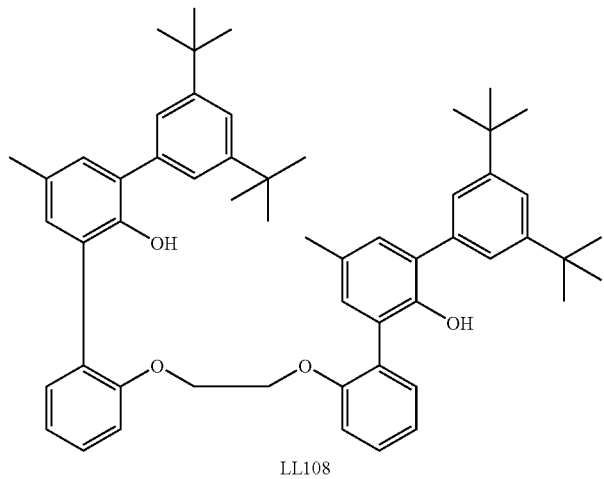
LL108
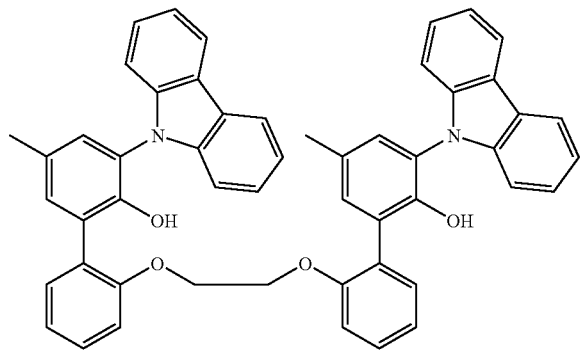
LL109
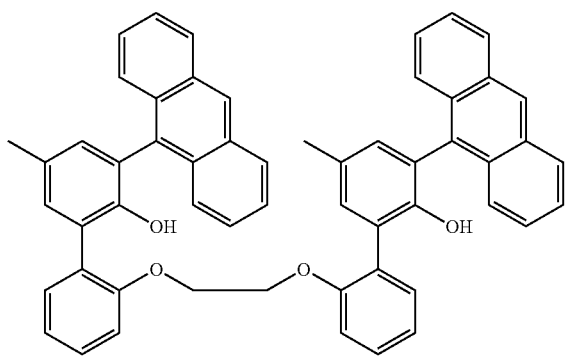
LL110
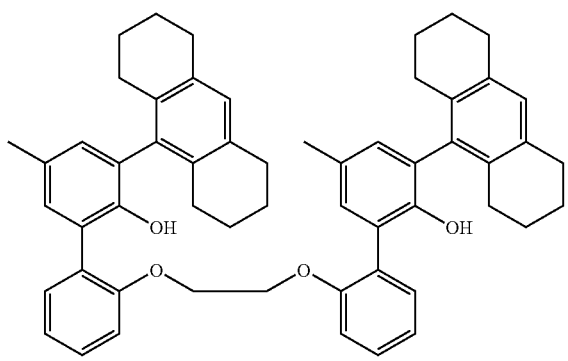
LL111

TABLE 2-continued
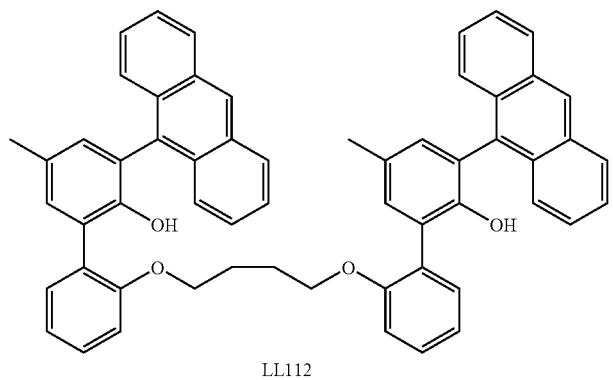
LL112
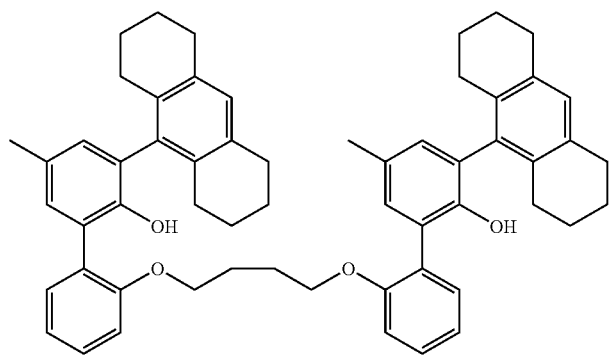
LL113
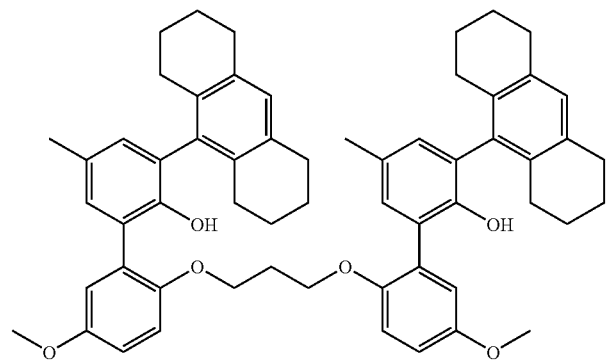
LL114
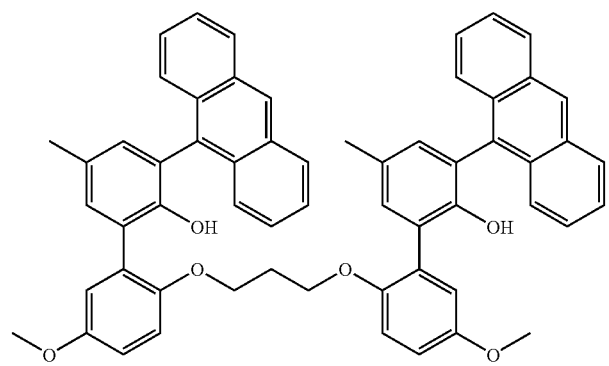
LL115

TABLE 2-continued
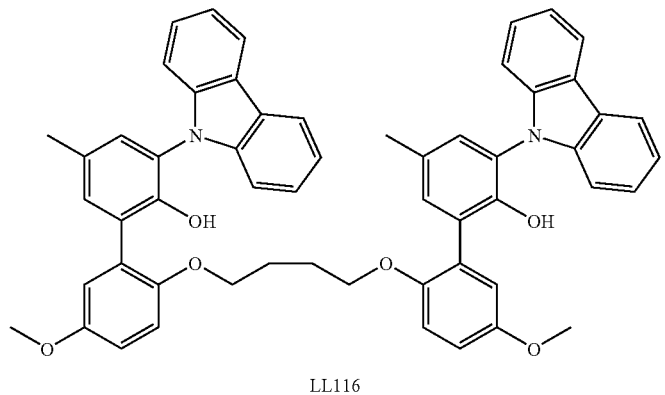
LL116
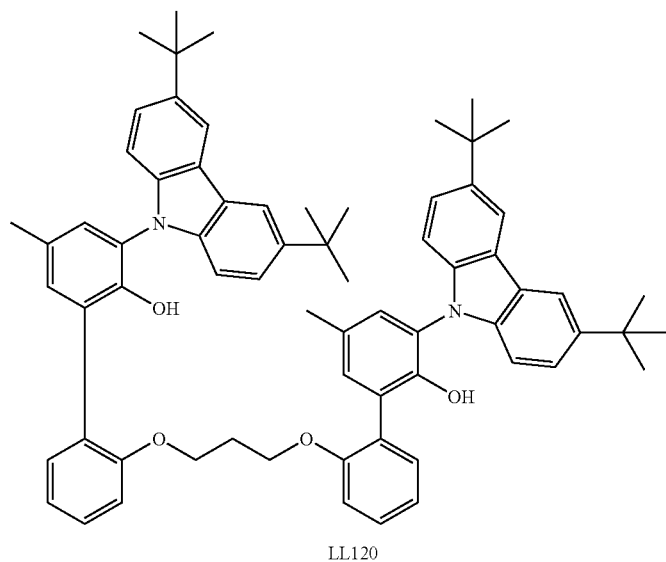
LL120
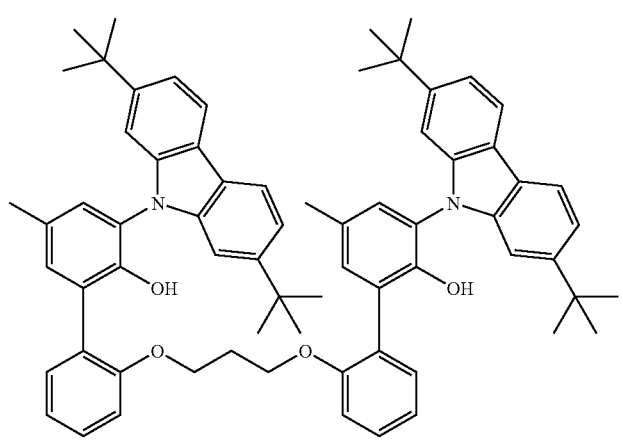
LL126

TABLE 2-continued
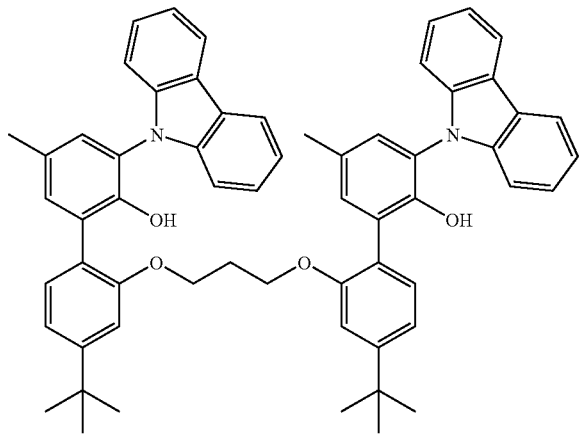
LL133
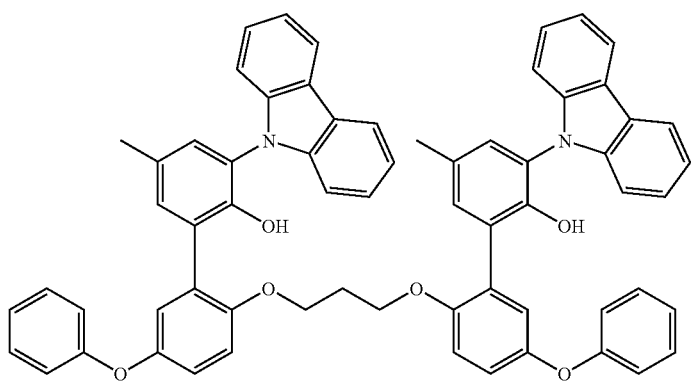
LL135
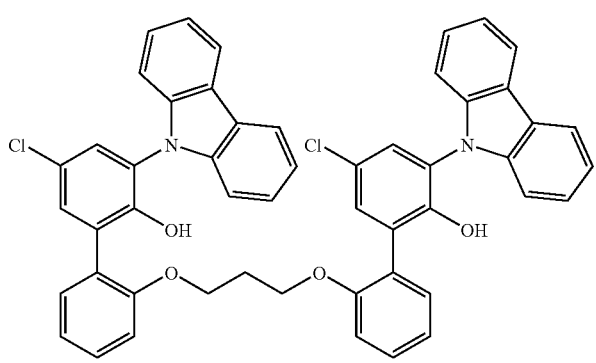
LL141

TABLE 2-continued
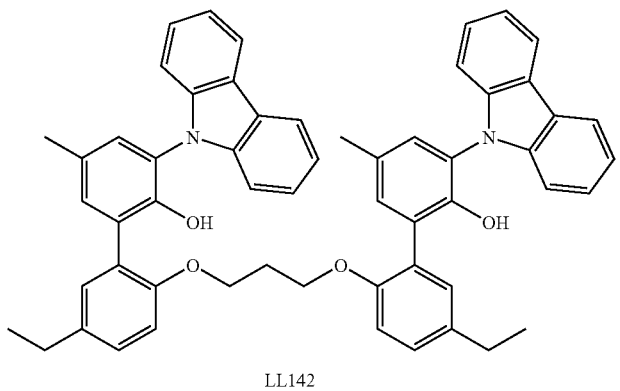
LL142
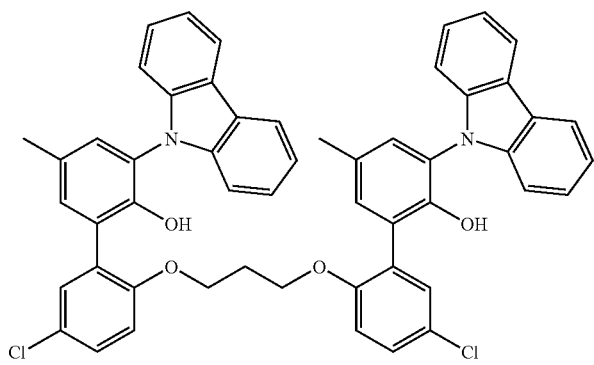
LL143
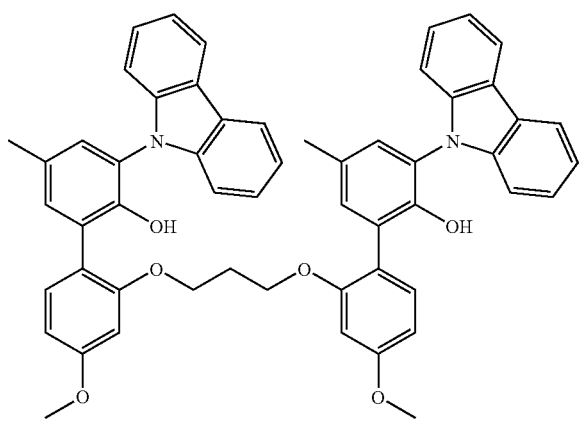
LL144

TABLE 2-continued

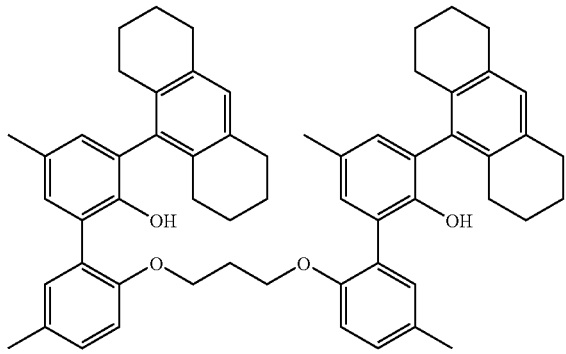

LL149

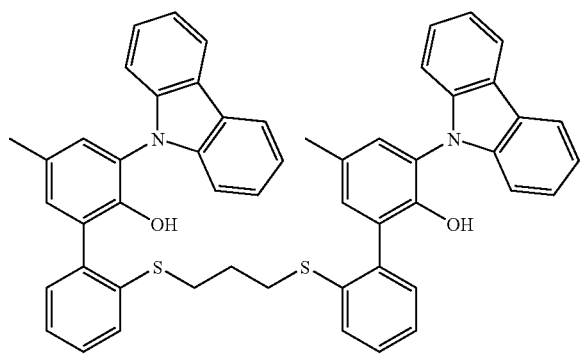

LL166

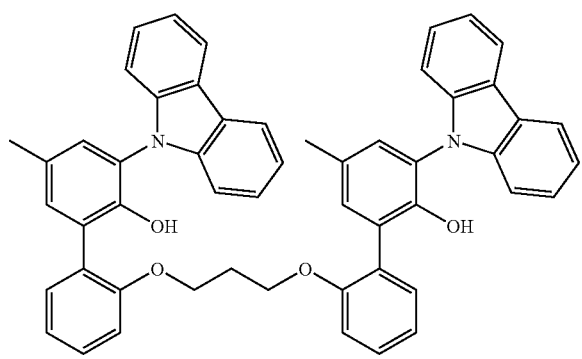

LL5

Once the desired ligand is formed, it may be combined with a metal atom, ion, compound or other metal precursor compound. For example, in some embodiments, the metal precursors are activated metal precursors, which refers to a metal precursor (described below) that has been combined or reacted with an activator (described below) prior to combination or reaction with the ancillary ligand. As noted above, in one aspect the invention relates to compositions that include such combinations of ligand and metal atom, ion, compound or precursor. In some applications, the ligands are combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

For ligands of formulas I, II, and III, the metal precursor compounds may be characterized by the general formula $M(L)_n$ where M is a metal selected from the group consisting of groups 3–6 and lanthanide elements of the periodic table of elements, more specifically, from group 4 (Hf, Zr and Ti); each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof; L may also be ionically bonded to the metal M and for example, L may be a non-coordinated or loosely coordinated or weakly coordinated anion (e.g., L may be selected from the group consisting of those anions described below in the conjunction with the activators), see Marks et al., Chem. Rev. 2000, 100, 1391–1434 for a detailed discussion of these weak interactions; and optionally two or more L groups may be linked together in a ring structure. n is 1, 2, 3, 4, 5, or 6. The metal precursors may be monomeric, dimeric or higher orders thereof. Specific examples of suitable titanium, hafnium and zirconium precursors include, but are not limited to $TiCl_4$, $Ti(CH_2Ph)_4$, $Ti(CH_2CMe_3)_4$, $Ti(CH_2SiMe_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiMe_3)_2Cl_2$, $Ti(NMe_2)_4$, $Ti(NEt_2)_4$, $Ti(O\text{-isopropyl})_4$, and $Ti(N(SiMe_3)_2)_2Cl_2$; $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$, $Hf(N(SiMe_3)CH_2CH_2CH_2N(SiMe_3))Cl_2$, $Hf(N(Ph)CH_2CH_2CH_2N(Ph))Cl_2$, $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Zr(N(SiMe_3)CH_2CH_2CH_2N(SiMe_3))Cl_2$, and $Zr(N(Ph)CH_2CH_2CH_2N(Ph))Cl_2$. Lewis base adducts of these examples are also suitable as metal precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$. Activated metal precursors may be ionic or zwitterionic compounds, such as $[M(CH_2Ph)_3^+][B(C_6F_5)_4^-]$ or $[M(CH_2Ph)_3^+][PhCH_2B(C_6F_5)_3^-]$ where M is Zr or Hf. Activated metal precursors or such ionic compounds can be prepared in the manner shown in Pellecchia et al., Organometallics, 1994, 13, 298–302; Pellecchia et al., J Am. Chem. Soc., 1993, 115, 1160–1162; Pellecchia et al., Organometallics, 1993, 13, 3773–3775 and Bochmann et al., Organometallics, 1993, 12, 633–640, each of which is incorporated herein by reference.

The ligand to metal precursor compound ratio is typically in the range of about 0.01:1 to about 100:1, more specifically in the range of about 0.1:1 to about 10:1 and even more specifically about 1:1.

As also noted above, in another aspect the invention relates to metal-ligand complexes. Generally, the ligand (or optionally a modified ligand as discussed above) is mixed with a suitable metal precursor (and optionally other components, such as activators) prior to or simultaneously with allowing the mixture to be contacted with the reactants (e.g., monomers). When the ligand is mixed with the metal precursor compound, a metal-ligand complex may be formed, which may be a catalyst or may need to be activated to be a catalyst.

The metal-ligand complexes according to the invention can in general be described in a number of overlapping or alternative ways. Thus, the metal-ligand complexes can be described as complexes having dianionic, chelating ligands that may occupy up to four coordination sites of the metal atom. The metal-ligand complexes can also be described as having dianionic ligands that form two seven-member metallocycles with the metal atom (counting the metal atom as one member of the seven member ring). Also, in some embodiments, the metal-ligand complexes can be described as having dianionic, chelating ligands that use oxygen and/or sulfur as binding atoms to the metal atom.

Also, in some embodiments, the metal-ligand complexes can be described as having ligands that can coordinate in at least two approximate $C_2$ symmetric complex isomers. By approximate $C_2$ symmetry it is meant that the ligand coordinates with a metal such that the ligand parts occupy four quadrants around the metal center extending towards the ligands L in an approximate $C_2$ symmetric fashion, and approximate means that true symmetry may not exist due to several factors that effect symmetry, including, for example, the effect of the bridge. In these embodiments, the conformation of the ligand around the metal can be described as lambda or delta. At least two isomeric complexes can be formed which may be enatiomeric or diastereomeric to each other. For ligands containing one or more chiral centers (e.g., substituted bridges with chiral centers), diastereomeric metal-ligand complexes can be formed. The diastereomeric complexes formed by a particular ligand-metal precursor combination can be used as mixtures of diastereomers, or can be separated and used as diastereomerically-pure complexes.

These isomeric structures may be separately formed by employing suitable metal precursors containing appropriately substituted ligands (such as chelating bis-amide, bisphenol, or diene ligands, as described below), which may strongly influence the stereochemistry of complexation reactions. It is known that group 4 metal complexes containing chelating ligands can be used as metal precursors in complexation reactions with the bridged bis-cyclopentadienyl ligands to control the stereochemistry of the resulting bridged metallocene complex, as is described in Zhang et al., J. Am. Chem. Soc., 2000; 122, 8093–8094, LoCoco et al., Organometallics, 2003, 22, 5498–5503, and Chen et al., J. Am. Chem. Soc., 2004, 126, 42–43. The use of analogous Group 4 metal precursors containing appropriately substituted chelating ligands in complexation reactions with the bridged bis (bi-aryl) ligands described herein may provide a mechanism to influence the stereochemistry of the resulting chiral approximately $C_2$ symmetric metal-ligand complexes. The use of analogous chiral Group 4 metal precursors containing appropriately substituted chelating ligands that possess one or more chiral centers may provide a mechanism to influence the absolute stereochemistry of the resulting chiral approximately $C_2$-symmetric metal-ligand complexes. The use of substantially enantiomerically pure chiral Group 4 metal precursors containing appropriately substituted chelating ligands that possess one or more chiral centers may provide a mechanism to prepare substantially enantiomerically or diastereomerically pure approximately $C_2$-symmetric metal-ligand complexes of this invention. Such chiral complexes may be useful as catalysts for a range of steroselective, enantioselective or asymmetric reactions, as will be discussed in more detail below.

In some cases, it may also be possible to separate mixtures of enantiomers or diastereomers by means of diastereomeric/enantiomeric resolution using a chiral reagent. See, for example, Ringwald et al., *J. Am. Chem. Soc.*, 1999, 121, pp1524–1527.

The various diastereomeric complexes may have different polymerization performance when used as catalysts for polymerizations, resulting, for example, in the formation of polymer products having bimodal molecular weight and/or composition distribution.

In some instances, substantially diastereomerically pure or substantially enantiomerically pure complexes can be envisioned to be of use for stereoselective, asymmetric, enantioselective, or diastereoselective reactions or transformations. Thus, in some embodiments substantially enantiomerically- or diastereomerically-pure complexes, ligand-metal compositions, and catalysts according to the invention can be used as asymmetric catalysts for a range of reactions, including polymerization reactions and other (non-polymerization) reactions, including many reactions useful in organic synthesis. In some embodiments, catalysts incorporating the compositions and complexes of the invention can be used to catalyze the asymmetric production of reaction products with enantiomeric excess (ee) or diastereomeric excess (de) of greater than 90% or greater than 99%. The asymmetric synthesis of chiral organic molecules is an important field, and is critical in the synthesis of many pharmaceuticals and other products. Single enantiomers of a chiral product can be prepared by a variety of techniques, including the resolution of racemates, or the use of substantially enantiomerically pure starting materials from the chiral pool of natural products, but for large scale synthesis the use of enantioselective catalysis is often the most attractive, and most economical, choice. See, e.g., Blaser et al, "Enantioselective Synthesis", pp1131–1149, in "Applied Homogeneous Catalysis with Organometallic Compounds", Vol 3, Ed. By Cornils, B., & Herrmann, W., 2nd Edition, Wiley-VCH, Weinheim, Germany (2002), and Ojima (Ed.), "Catalytic Asymmetric Synthesis", VCH Publishers, Inc., New York, (1993), and the references cited therein.

In recent years there have been many reports in the literature of the use of chiral Group 4 (titanium, zirconium or hafnium) ligand-metal compositions and complexes as stereoselective catalysts for a range of non-polymerization reactions, including many enantioselective (or asymmetric) reactions useful in organic synthesis. See, e.g., Maruoka, "Asymmetric Reactions with Chiral Lewis Acid Catalysts", pp413–440, in Ojima (Ed.), "Catalytic Asymmetric Synthesis", VCH Publishers, Inc., New York, (1993), see also Marek (Ed.), "Titanium and Zirconium in Organic Synthesis" (2002), Wiley-VCH Verlag GmbH & Co. KGaA, Weinheim, Germany, and in particular Hoveyda, "Chiral zirconium catalysts for enantioselective synthesis", included therein at pp180–229; see also Negishi, "Some newer aspects of organozirconium chemistry of relevance to organic synthesis. Zr-catalyzed enantioselective carbometallation", *Pure Appl. Chem.* 73, 239–242 (2001), and Scott et al., *Chemical Comm.*, 2004, pp 894–895, and the references cited therein. Examples of asymmetric or enantioselective reactions catalyzed by chiral Group 4 catalysts include olefin hydrogenation, olefin epoxidation, olefin isomerization, olefin-pyridine coupling, imine hydrogenation, aldol reactions, imino aldol reactions, epoxidation of allylic alcohols, alkylation of aldehydes, alkylation of imines, Diels-Alder reactions, Baeyer-Villiger reactions, hydroamination/cyclization of amino-alkenes, pinacol coupling of aldehydes, and hydrosilation of imines, ketones, and olefins. In some embodiments catalysts incorporating the ligands, compositions and complexes of the invention may be useful in catalyzing such reactions.

Chiral group 4 metallocene complexes, especially $C_2$-symmetric ansa-bridged metallocene complexes, have been used as asymmetric or enantioselective catalysts. See, e.g., Kuber, "Metallocenes as a Source of Fine Chemicals", pp893–902, in "Applied Homogeneous Catalysis with Organometallic Compounds", Vol 2, Ed. By Cornils, B., & Herrmann, W., VCH, Weinheim, Germany, 1996, and Diamond et al., *J. Am. Chem. Soc.* 118, 8024–8033 (1996), and the references cited therein. Some of the disadvantages of $C_2$-symmetric group 4 metallocene based catalysts are described in WO 02/085820 A2 (2002), including difficulty of synthesis and lack of thermal robustness. Group 4 complexes of the $C_2$-symmetric axially chiral 1,1-bi-2-naphthol (BINOL) ligands, and related ligands, have been used as enantioselective (or asymmetric) catalysts for several years. See, e.g., Walsh et al., *Acc. Chem. Res.* 36, 739–749. (2003); Balsells, et al., *J. Am. Chem. Soc.* 124, 10336–10348 (2002); Yamashita et al., *J. Am. Chem. Soc.* 125, 3793–3798 (2003); and Wulff et al., *Angewandte Chemie, Intl Edition* 40, 2271–2274 (2001), and the references cited therein. In common with the chiral group 4 metallocene and binaphthol systems described above, ligand-metal complexes, compositions, and catalysts of this invention possess Lewis-acidic metal centers in a chiral environment. However, in some embodiments the ligand-metal complexes, compositions, and catalysts of this invention show high thermal robustness and maintain high activity and high stereoselectivity at high temperatures, and may thus offer advantages over chiral Group 4 metallocenes for asymmetric or enantioselective catalysis. Also, the modular synthesis of the ligands of this invention, from diverse building blocks with a wide range of readily accessible substitutional variation, may offer significant advantages as compared to the binaphthol and related ligand systems, for the optimization of catalyst performance for a wide range of enantioselective or asymmetric reactions.

In some embodiments, metal-ligand complexes according to an aspect of the invention can be characterized by the general formula:

$$(4,2,O,S)ML_{n'} \qquad (IV)$$

where (4,2,O,S) is a dianionic ligand having at least 4 atoms that are each independently oxygen or sulfur and chelating to the metal M at 4 coordination sites through oxygen and/or sulfur atoms with two of the bonds between the oxygen or sulfur atoms and the metal being covalent in nature and two of the bonds being dative in nature (i.e., oxygen or sulfur atoms acting as Lewis bases and the metal center acting as a Lewis acid); M is a metal selected from the group consisting of groups 3–6 and lanthanide elements of the periodic table of elements, more specifically, from group 4 (Hf, Zr and Ti); each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof; and optionally two or more L groups may be linked together in a ring structure; n' is 1, 2, 3, or 4.

In other embodiments, metal-ligand complexes according to the invention comprise two seven-member metallocycles formed with bonds from the metal atom to at least 2 heteroatoms (e.g., O, S, N, P and the like). In more specific forms, these metal-ligand complexes comprise two seven-member metallocycles and even more specifically, there are at least two seven-member metallocycles that are joined together by at least one bridging group. In still other embodiments, two, bridged seven-member metallocycles form a symmetrical complex, as shown in the example below:

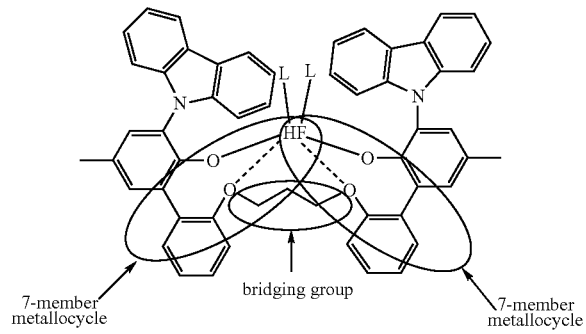

where the complex includes two metallocycles bound by a single bridging group.

In still other embodiments, metal-ligand complexes according to the invention may be characterized by the general formula:

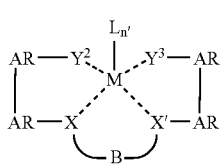

(V)

wherein each of AR, M, L, B, and n', are as defined above; and the dotted lines indicate possible binding to the metal atom, provided that at least two of the dotted lines are covalent bonds. X, X', $Y^2$ and $Y^3$ are derived from the definitions detailed above in that at least two hydrogen atoms are removed from X, X', Y and Y', in a manner known to those of skill in the art, to form the at least two covalent bonds between the X and/or Y moieties and the metal. Depending on the number of covalent bonds, as those of skill in the art can determine, in some embodiments, X, X', $Y^2$, and $Y^3$ are independently selected from the group consisting of oxygen, sulfur, —N($R^{30}$)$_r$—, and —P($R^{30}$)$_r$—, and optionally substituted alkoxy, aryloxy, alkylthio, and arylthio, where $R^{30}$ is selected from the group consisting of hydrogen, halogen, and optionally substituted hydrocarbyl, heteroatom-containing hydrocarbyl, silyl, boryl, alkoxy, aryloxy and combinations thereof, and where r is 0 or 1. In more particular embodiments, X and X' are independently selected from oxygen and sulfur, and $Y^2$ and $Y^3$ are independently selected from oxygen, sulfur, —N$R^{30}$—, and —P$R^{30}$. In other embodiments, X and X' are independently selected from the group consisting of nitrogen and phosphorous, while $Y^2$ and $Y^3$ are independently selected from the group consisting of optionally substituted amino, phosphino, alkoxy, aryloxy, alkylthio and arylthio. Note also that $L_{n'}$ indicates that the metal M is bonded to a number n' groups of L, as defined above.

In still other embodiments, metal-ligand complexes according to the invention can be characterized by the general formula:

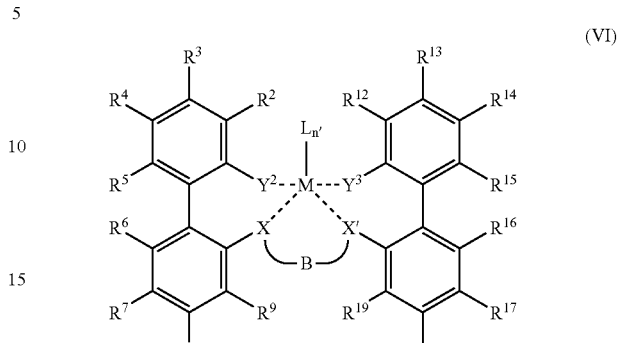

(VI)

wherein each of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are as defined above for structure (II), and M, L, n', B, X, X', $Y^2$ and $Y^3$ are as defined above and as further explained in connection with structure (V). The dotted lines indicate possible binding to the metal atom, provided that at least two of the dotted lines are covalent bonds.

In more specific embodiments, the metal-ligand complexes of this invention may be characterized by the general formula:

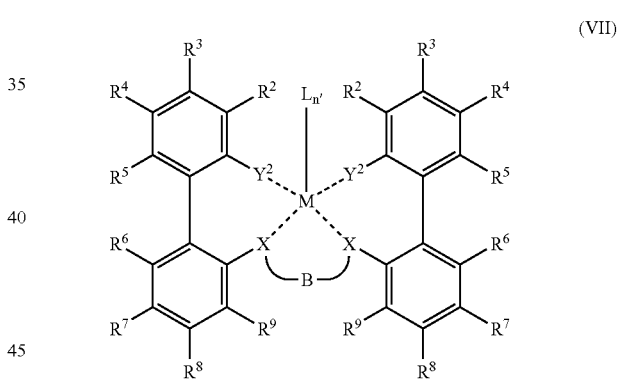

(VII)

wherein $R^2$, $R^3$, $R^4$, $R^5$, $R^6$, $R^7$, $R^8$, $R^9$, M, L, n', B, X, and $Y^2$ are as defined above are as defined above and as further explained in connection with structure V. The dotted lines indicate possible binding to the metal atom, provided that at least two of the dotted lines are covalent bonds. In formula VII, the metal-ligand complex may also have approximate $C_2$ symmetry that may provide control of stereoselectivity in a reaction catalyzed by the ligand-metal complex or a derivative thereof—for example, control of tacticity in the polymerization of propylene to isotactic polypropylene, when combined with appropriate activator(s).

In addition, specifics for the substituents on the ligands for production of the particular polymers discussed above (e.g., isotactic polypropylene) apply to the metal-ligand complexes. In addition, Lewis base adducts of the metal-ligand complexes in the above formulas may be suitable, for example, ethers, amines, thioethers, phosphines and the like are suitable as Lewis bases. The metal-ligand complexes can be formed by techniques known to those of skill in the art, such as combinations of metal precursors and ligands under conditions to afford complexation. For example, the complexes of this invention can be prepared according to the general scheme shown below:

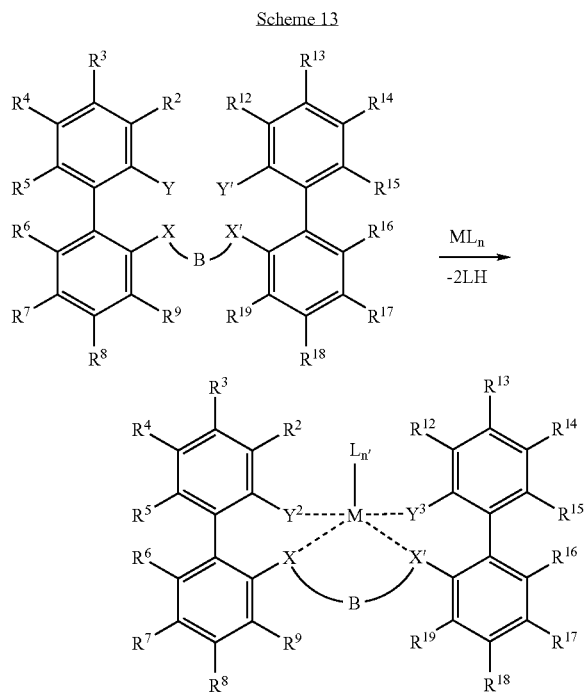

As shown in Scheme 13, a ligand according to formula II is combined with the metal precursor M(L)$_n$ under conditions to cause the removal of at least 2 leaving group ligands L, which are shown in the scheme as combining with a hydrogen (H). Other schemes where the leaving group ligand combines with other moieties (e.g., Li, Na, etc.) employing other known routes for complexation can be used, including for example, reactions where the ligand L reacts with other moieties (e.g., where the alkali metal salt of the ligand is used and the complexation reaction proceeds by salt elimation).

Specific metal-ligand complexes within the scope of the invention include Group 4 metal complexes formed from any of ligands set out in Table 1 or Table 2, above.

The ligands, complexes or catalysts may be supported on organic or inorganic supports. Suitable supports include silicas, aluminas, clays, zeolites, magnesium chloride, polystyrenes, substituted polystyrenes and the like. Polymeric supports may be cross-linked or not. Similarly, the ligands, complexes or catalysts may be supported on supports known to those of skill in the art. See for example, Hlatky, Chem. Rev. 2000, 100, 1347–1376 and Fink et al., Chem. Rev. 2000, 100, 1377–1390, both of which are incorporated herein by reference. The compositions, complexes and/or catalysts may be contacted with an activator (described below) before or after contact with the support; alternatively, the support may be contacted with the activator prior to contact with the composition, complex or catalyst. In addition, the catalysts of this invention may be combined with other catalysts in a single reactor and/or employed in a series of reactors (parallel or serial) in order to form blends of polymer products.

The metal-ligand complexes and compositions are active catalysts typically in combination with a suitable activator, combination of activators, activating technique or activating package, although some of the ligand-metal complexes may be active without an activator or activating technique depending on the ligand-metal complex and on the process being catalyzed. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453,410, 5,153,157, 5,064,802, EP-A-277,004 and Marks et al., Chem. Rev. 2000, 100, 1391–1434. In some embodiments, ionic or ion forming activators are preferred. In other embodiments, alumoxane activators are preferred.

Suitable ion forming compounds useful as an activator in one embodiment comprise a cation that is a Bronsted acid capable of donating a proton, and an inert, compatible, non-interfering, anion, A$^-$. Suitable anions include, but are not limited to, those containing a single coordination complex comprising a charge-bearing metal or metalloid core. Mechanistically, the anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are, of course, well known and many, particularly such compounds containing a single boron atom in the anion portion, are available commercially.

Specifically, such activators may be represented by the following general formula:

$$(L^*—H)_d^+(A^{d-})$$

wherein L* is a neutral Lewis base; (L*—H)+is a Bronsted acid; A$^{d-}$ is a non-interfering, compatible anion having a charge of d–, and d is an integer from 1 to 3. More specifically A$^{d-}$ corresponds to the formula: $(M^{1+3}+Q_h)^{d-}$ wherein h is an integer from 4 to 6; h–3=d; M' is an element selected from group 13 of the periodic table; and Q is independently selected from the group consisting of hydrogen, dialkylamido, halogen, alkoxy, aryloxy, hydrocarbyl, and substituted-hydrocarbyl radicals (including halogen substituted hydrocarbyl, such as perhalogenated hydrocarbyl radicals), said Q having up to 20 carbons. In a more specific embodiment, d is one, i.e., the counter ion has a single negative charge and corresponds to the formula A$^-$.

Activators comprising boron or aluminum can be represented by the following general formula:

$$(L^*—H)^+(JQ_4)^-$$

wherein: L* is as previously defined; J is boron or aluminum; and Q is a fluorinated C$_{1-20}$ hydrocarbyl group. Most specifically, Q is independently selected from the group consisting of fluorinated aryl group, such as a pentafluorophenyl group (i.e., a C$_6$F$_5$ group) or a 3,5-bis(CF$_3$)$_2$C$_6$H$_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tbutyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(secbutyl)ammonium tetrakis(pentafluorophenyl) borate, N,N-dimethylanilinium tetrakis(pentafluorophenyl) borate, N,N diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenyl)borate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphospnonium tetrakis(pentafluorophenyl) borate, tri(o-tolyl)phosphonium tetrakis(pentafluorophenyl) borate, and tri(2,6-dimethylphenyl)phosphonium tetrakis (pentafluorophenyl) borate; N,N-dimethylanilinium tetrakis (3,5-bis(trifluoromethyl)phenyl)borate; $HNMe(C_{18}H_{37})_2$+B $(C_6F_5)_4$—; $HNPh(C_{18}H_{37})_2{}^+B(C_6F_5)_4{}^-$ and $((4\text{-nBu-Ph})NH(n\text{-hexyl})_2)^+B(C_6F_5)_4{}^-$ and $((4\text{-nBu-Ph})NH(n\text{-decyl})_2)^+B(C_6F_5)_4{}^-$. Specific (L*—H)+cations are N,N-dialkylanilinium cations, such as $HNMe_2Ph+$, substituted N,N-dialkylanilinium cations, such as $(4\text{—nBu-}C_6H_4)NH(n\text{—}C_6H_{13})_2{}^+$ and $(4\text{-nBu-}C_6H_4)NH(n\text{-}C_{10}H_{21})_2{}^+$ and $HNMe(C_{18}H_{37})_2{}^+$. Specific examples of anions are tetrakis (3,5-bis(trifluoromethyl)phenyl)borate and tetrakis(pentafluorophenyl)borate. In some embodiments, the specific activator is $PhNMe_2H^+B(C_6F_5)_4{}^-$.

Other suitable ion forming activators comprise a salt of a cationic oxidizing agent and a non-interfering, compatible anion represented by the formula:

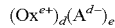

$$(Ox^{e+})_d(A^{d-})_e$$

wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, $Ag^+$, or $Pb^{+2}$. Specific embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound that is a salt of a carbenium ion or silyl cation and a non-interfering, compatible anion represented by the formula:

$$\copyright^+A^-$$

wherein: $\copyright^+$ is a $C_{1\text{-}100}$ carbenium ion or silyl cation; and $A^-$ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio, arylthio, and combinations thereof. In some embodiments, a specified activator is $Ph_3C^+B(C_6F_5)_4{}^-$.

Other suitable activating cocatalysts comprise a compound that is a salt, which is represented by the formula $(A^{*+a})_b(Z^*J^*_j)^{-c}{}_d$ wherein A* is a cation of charge +a; Z* is an anion group of from 1 to 50, specifically 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. See, WO 99/42467, which is incorporated herein by reference. In other embodiments, the anion portion of these activating cocatalysts may be characterized by the formula $((C_6F_5)_3M''''\text{—LN—}M''''(C_6F_5)_3)^-$ where M'''' is boron or aluminum and LN is a linking group, which is specifically selected from the group consisting of cyanide, azide, dicyanamide and imidazolide. The cation portion is specifically a quaternary amine. See, e.g., LaPointe, et al., *J. Am. Chem. Soc.* 2000, 122, 9560–9561, which is incorporated herein by reference.

In addition, suitable activators include Lewis acids, such as those selected from the group consisting of tris(aryl) boranes, tris(substituted aryl)boranes, tris(aryl)alanes, tris (substituted aryl)alanes, including activators such as tris (pentafluorophenyl)borane. Other useful ion forming Lewis acids include those having two or more Lewis acidic sites, such as those described in WO 99/06413 or Piers, et al. "New Bifunctional Perfluoroaryl Boranes: Synthesis and Reactivity of the ortho-Phenylene-Bridged Diboranes 1,2-$(B(C_6F_5)_2)_2C_6X_4$ (X=H, F)", *J. Am. Chem. Soc.*, 1999, 121, 3244–3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula $G^{13}R^{50}{}_{3-p}D_p$ where $G^{13}$ is selected from the group consisting of B, Al, Ga, In and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof. In other embodiments, the group 13 activator is an oligomeric or polymeric alumoxane compound, such as methylalumoxane and the known modifications thereof. See, for example, Barron, "*Alkylalumoxanes, Synthesis, Structure and Reactivity*", pp33–67 in "*Metallocene-Based Polyolefins: Preparation, Properties and Technology*", Edited by J. Schiers and W. Kaminsky, Wiley Series in Polymer Science, John Wiley & Sons Ltd., Chichester, England, 2000, and references cited therein. In other embodiments, a divalent metal reagent may be used that is defined by the general formula $M'R^{50}{}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula $M''R^{50}$ and in this embodiment $R^{50}$ is as defined above. M" is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that there is at least one D that is a hydrogen.

The molar ratio of metal:activator (whether a composition or complex is employed as a catalyst) employed specifically ranges from 1:10,000 to 100:1, more specifically from 1:5000 to 10:1, most specifically from 1:10 to 1:1. In one embodiment of the invention mixtures of the above compounds are used, particularly a combination of a group 13 reagent and an ion-forming activator. The molar ratio of group 13 reagent to ion-forming activator is specifically from 1:10,000 to 1000:1, more specifically from 1:5000 to 100:1, most specifically from 1:100 to 100:1. In another embodiment, the ion forming activators are combined with a group 13 reagent. Another embodiment is a combination of the above compounds having about 1 equivalent of an optionally substituted N,N-dialkylanilinium tetrakis(pentafluorophenyl) borate, and 5–30 equivalents of a group 13 reagent. In some embodiments from about 30 to 2000 equivalents of an oligomeric or polymeric alumoxane activator, such as a modified alumoxane (e.g., alkylalumoxane), can be used.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

Some compositions, complexes and/or catalysts according to the invention are particularly effective at polymerizing α-olefins (such as propylene, 1-butene, 1-pentene, 1-hexene, 1-heptene, 1-octene, and styrene), copolymerizing ethylene with α-olefins (such as propylene, 1-butene, 1-pentene, 1-hexene, 1-heptene, 1-octene, and styrene), and copolymerizing ethylene with 1,1-disubstituted olefins (such as isobutylene). These compositions may also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized.

In some embodiments, catalysts incorporating the ligands, compositions and/or complexes of the present invention exhibit high catalytic activity in the polymerization of such α-olefins, including at high temperatures.

In general monomers useful herein may be olefinically or unsaturated monomers having from 2 to 20 carbon atoms either alone or in combination. Generally, monomers may include olefins, diolefins and unsaturated monomers including ethylene and $C_3$ to $C_{20}$ α-olefins such as propylene, 1-butene, 1-hexene, 1-octene, 4-methyl-1 pentene, 1-norbornene, styrene and mixtures thereof; additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, α-methyl-styrene, either alone or with other monomers such as ethylene or $C_3$ to $C_{20}$ α-olefins and/or diolefins; additionally 1,2-substituted olefins, such as 2-butene. The α-olefins listed above may be polymerized in a stereospecific manner—for example, as in the generation of isotactic or syndiotactic or hemiisotactic polypropylene. Additionally the α-olefins may be polymerized to produce a polymer with differing tacticity sequences within the polymer chain, such as polypropylene containing atactic and isotactic sequences within the same polymer chain. These definitions are intended to include cyclic olefins. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprise 1,5-dienes and other non-conjugated dienes. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

More specifically, it has been found that the catalysts of the present invention are particularly active for certain monomers, particularly α-olefins. Thus, the catalysts of the present invention may provide higher comonomer incorporation for copolymers of ethylene and co-monomers having three or more carbon atoms than is currently known from other catalysts. It has been found that particular catalysts of the present invention co-polymerize ethylene and styrene (or substituted styrenes), forming ethylene-styrene copolymers. Polymers that can be prepared according to the present invention include ethylene copolymers with at least one $C_3$–$C_{20}$ α-olefin, particularly propylene, 1-butene, 1-hexene, 4-methyl-1-pentene and 1-octene. The copolymers of ethylene with at least one $C_3$–$C_{20}$ α-olefin comprise from about 0.1 mol.% α-olefin to about 50 mol.% α-olefin, more specifically from about 0.2 mol.% α-olefin to about 50 mol.% α-olefin and still more specifically from about 2 mol.% α-olefin to about 30 mol.% higher olefin. For certain embodiments of this invention, copolymers include those of ethylene and a comonomer selected from the group consisting of propylene, 1-butene, 1-hexene, and 1-octene comprise from about 0.2 to about 30 mol.% comonomer, more specifically from about 1 to about 20 mol. % comonomer. In particular, in some embodiments ethylene copolymers with at least one C3–C20 α-olefin can be produced having a high molecular weight (e.g., greater than about 50,000, more specifically greater than about 150,000, and even more specifically greater than about 500,000) in a solution process at a temperature of greater than about 100° C., more specifically greater than about 130° C., and even more specifically greater than about 160° C. In certain embodiments, ethylene copolymers with at least one C3–C20 α-olefin can be produced with a low molecular weight (e.g., less than about 30,000, more specifically, less than about 15,000, and even more specifically less than about 5,000).

Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

The α-olefins listed above may be polymerized in a stereoselective manner to produce a substantially stereoregular polymer product (that is, a polymer product that is detectably enriched in m or r dyads (as determined, e.g., by $^{13}C$ NMR) as compared to a corresponding atactic material), as in the generation of isotactic, syndiotactic or hemiisotactic poly-α-olefins. For example, 1-butene may be polymerized into isotactic poly-1-butene. Additionally the α-olefins may be polymerized to produce a polymer with differing tacticity sequences within the polymer chain, such as polypropylene containing atactic and isotactic sequences within the same polymer chain. The stereoregularity may be interrupted by stereoerrors, in particular isolated stereoerrors, which is an indication of enantiomorphic side control. Also regioerrors might be present in the isotactic polypropylene polymer as it is described in the literature (see, e.g., Resconi et al., "Selectivity in Propene Polymerization with Metallocene Catalysts," Chem. Rev. 2000, 100, 1253–1345).

More specifically, it has been found that particular catalysts of the present invention polymerize propylene to isotactic or crystalline polypropylene, forming polymers with novel properties. The combination of isotactic polypropylene properties that are obtained at higher polymerization temperatures is surprising. In particular, in some embodiments isotactic polypropylene can be produced having a narrow polydispersity (e.g., less than about 3.0 and more specifically less than 2.5) combined with a high molecular weight (e.g., greater than about 50,000, more specifically greater than about 100,000, even more specifically greater than about 150,000, and even more specifically greater than about 500,000) in a solution polymerization process at a temperature of greater than about 100° C., more specifically greater than 110° C. and even more specifically greather than 130° C. In certain embodiments, isotactic polypropylene can be produced with a low molecular weight (e.g., less than about 30,000, more specifically less than about 15,000, and even more specifically less than about 5,000). In some embodiments, broader polydispersities can be obtained for the isotactic polypropylene or other polymers (e.g., copolymers of ethylene and α-olefins as discussed in more detail below) produced according to the invention. In addition the isotactic polypropylene produced by certain embodiments of this invention can be prepared with few or no detectible using $^{13}$C NMR regio-errors (also known as regio-irregularities).

The isotactic polypropylene polymers formed from these catalysts in a solution polymerization process can be produced at a higher temperature than has been previously described, such as at a temperature of greater than about 100° C., more specifically greater than 110° C. and even more specifically greather than 130° C. The polymerization conditions are described herein, producing isotactic polypropylene with a crystallinity index of between about 0.35 and about 0.95, more specifically between about 0.65 and 0.95 and in some embodiments specifically above about 0.8, under the polymerization conditions employed. The crystallinity index is determined using FTIR as is known to those of skill in the art and calibrated based on a relative scale. In one embodiment, the crystallinity index value can be determined using commercially available FTIR equipment (such as a Bruker Equinox 55 with an IR Scope II in reflection mode using Pike MappIR software). The crystallinity index is obtained from the ratio of band heights at 995 cm$^{-1}$ and 972 cm$^{-1}$. Atactic polypropylene has a ratio of band heights or crystallinity index of 0.2. Greater than 98% isotactic polypropylene has a crystallinity index ratio of greater than 0.95. Generally, the amount of error in crystallinity index measurements is ±0.05. Polymer blends of various compositions show a linear relationship between % isotacticity and crystallinity index. See, for example, J. P. Luongo, *J. Appl. Polym. Sci.*, 3 (1960) 302–309 and T. Sundell, H. Fagerholm, H. Crozier, *Polymer* 37 (1996) 3227–3231, each of which is incorporated herein by reference.

As those of skill in the art will recognize, isotacticity can also be represented by percent pentads (%mmmm) as determined by $^{13}$C NMR spectroscopy. Proton decoupled $^{13}$C NMR spectroscopy can be performed using commercially available equipment (such as a Bruker 300 MHz at 100° C. probe temperature) to determine the degree of tacticity as %mmmm pentads (for assignment of $^{13}$C signals see the review Brintzinger H. H. et al., *Angew. Chem. Int. Ed. Eng.* 1995, 34, 1143, which is incorporated herein by reference; and Resconi, *Chem. Rev.* 2000, 100, 1253–1345 and Gibson, et al., *Chem Rev.* 2003, 103, 283–315). For example, a 15–30 mg polymer sample is dissolved in a 1:1 mixture of $C_2D_2Cl_4$ and $C_2Cl_4$ by heating the sample to ca. 100° C. The %mmmm is determined by the ratio of peak integral from 23.5 to 21.5 ppm and peak integral 23.5 to 19 ppm (in the absence of significant chain end regio-irregularity signals in this region). Proton decoupled $^{13}$C NMR spectroscopy can be also performed to determine the frequency of and nature of stereoerrors and regioerrors.

In addition, the melting point of the crystalline polypropylene is generally in the range of from about 115° C. to about 165° C., more specifically between about 120° C. and 155° C., and in some embodiments specifically above about 150° C. Melting points are determined by differential scanning calorimetry, as is known in the art (see also the example section, herein).

Novel polymers, copolymers or interpolymers may be formed having unique physical and/or melt flow properties. Polymers that can be prepared according to the present invention include copolymers of ethylene and one or more α-olefins, such as copolymers of ethylene with at least one $C_4$–$C_{20}$ α-olefin, such as 1-butene, 1-hexene, 4-methyl-1-pentene, 1-octene or styrene. Similarly, the techniques described herein can be used to prepare propylene copolymers with at least one $C_4$–$C_{20}$ α-olefin. In some embodiments, the copolymers of ethylene or propylene with at least one $C_4$–$C_{20}$ α-olefin comprise from about 0.1 wt.% higher olefin to about 60 wt.% higher olefin, more specifically from about 0.2 wt.% higher olefin to about 50 wt.% higher olefin and still more specifically from about 2 wt.% higher olefin to about 30 wt.% higher olefin. For certain embodiments of this invention, crystalline copolymers include those of ethylene or propylene and a comonomer selected from the group consisting of ethylene, 1-butene, 1-hexene, 1-octene and styrene comprise from about 0.2 to about 50 wt.% comonomer, more specifically from about 1 to about 20 wt.% comonomer, even more specifically from about 2 to about 15 wt. % comonomer and most specifically from about 5 to about 12 wt. % comonomer.

The novel polymers disclosed herein can be employed alone or with other natural or synthetic polymers in a blend. Such other natural or synthetic polymers can be polyethylene (including linear low density polyethylene, low density polyethylene, high density polyethylene, etc.), atactic polypropylene, nylon, EPDM, ethylene-propylene elastomer copolymers, polystyrene (including syndiotactic polystryene), ethylene-styrene copolymers and terpolymers of ethylene-styrene and other $C_3$–$C_{20}$ olefins (such as propylene).

Melt flow rate (MRF) for polypropylene and copolymers of propylene and one or more $C_4$–$C_{20}$ α-olefins is measured according to ASTM D-1238, condition L (2.16 kg, 230° C.). In some embodiments of this invention, the MFR is in the range of 0.005–1,000, more specifically 0.01–500 and even more specifically 0.1–100. Flex modulus for polypropylene and copolymer of propylene and one or more $C_4$–$C_{20}$ α-olefins is measured according to ASTM D-790. In some embodiments of this invention, the flex modulus ranges from 20,000–400,000 psi, more specifically from 20,000–300,000 psi and even more specifically from 100,000–200,000 psi. Notch izod impact for polypropylene and copolymer of propylene and one or more $C_4$–$C_{20}$ α-olefins is measured according to ASTM D-256A. In some embodiments of this invention, the notch izod impact ranges from 0.1 to no break in ft-lbs/in.

The novel polypropylene and copolymers of propylene and one or more $C_4$–$C_{20}$ α-olefins disclosed in the present invention are useful for a wide variety of applications, including films (such as blown and cast film, clarity film and multi-layer films), thermoforming (such as cups, plates, trays and containers), injection moulding, blow-moulding, foams (such as structural foams), pipe (such as potable water pipe and high pressure pipe), automotive parts, and other applications that will be evident to those of skill in the art.

Melt strength (measured in cN) and melt drawability (measured in mm/s) tests are conducted by pulling ("taking-up") strands of the molten polymers or blends at constant acceleration until breakage occurs. An experimental set-up comprises a capillary rheometer and a Rheotens apparatus as a take-up device. The molten strands are drawn uniaxially to a set of accelerating nips located 100 mm below the die. The force required to uniaxially extend the strands is recorded as a function of the take-up velocity or the nip rolls. In the case of polymer melts exhibiting draw resonance (indicated by the onset of a periodic oscillation of increasing amplitude in the measured force profile), the maximum force and wheel velocity before the onset of draw resonance are taken as the melt strength and melt drawability, respectively. In the absence of draw resonance, the maximum force attained during testing is defined as the melt strength and the velocity at which breakage occurs is defined as the melt drawability. These tests are typically run under the following conditions:

| | |
|---|---|
| Mass flow rate | 1.35 grams/min |
| Temperature | 190° C. |
| Equilibration time at 190° C. | 10 minutes |
| Die | 20:1 (with entrance angle of approximately 45 degrees) |
| Capillary length | 41.9 mm |
| Capillary diameter | 2.1 mm |
| Piston diameter | 9.54 mm |
| Piston velocity | 0.423 mm/s |
| Shear rate | 33.0 s$^{-1}$ |
| Draw-down distance (die exit to take-up sheels) | 100 mm |
| Cooling conditions | Ambient air |
| Acceleration | 2.4 mm/s$^2$ |

For some aspects of the present invention the novel polymers are useful to produce foams having improved properties. For foams and other applications requiring melt strength, the MFR is typically in the range of 0.1–10, more specifically in the range of 0.3–3 and most specifically in the range of 0.5–2. The melt strength is typically greater than 5 cN, more specifically greater than 9 cN and most specifically greater than 12 cN. The drawability is typically greater than 15 mm/sec, more specifically greater than 25 mm/sec and most specifically greater than 35 mm/sec.

In some aspects of the present invention, the novel polymers disclosed herein are useful for a wide variety of applications where certain optical properties are beneficial. Gloss is measured according to ASTM D-1746. Haze is measured according to ASTM D-1003 and clarity is measured according to ASTM D-2457. The novel polymers disclosed herein in some aspects are films having haze of less than 10%. In addition films having clarity of greater than 91% may be beneficially obtained.

Polymerization is carried out under polymerization conditions, including temperatures of from −100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, gas phase and high-pressure processes as known to those skilled in the art may also be used with supported catalysts of the invention.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity. The examples provide data for these comparisons.

Another measure of catalyst polymerization performance is co-monomer incorporation. As is well known in the art, many ethylene copolymers are prepared using ethylene and at least one other monomer. These copolymers or higher order polymers in some applications require higher amounts of additional co-monomer(s) than have been practical with known catalysts. Since ethylene tends to be the most reactive monomer, obtaining higher co-monomer incorporations is a benefit that is examined for polymerization catalysts. Two useful co-monomers are 1-octene and styrene. This invention offers the possibility of higher incorporation of co-monomers such as 1-octene and styrene.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_4$–$C_{10}$ alkanes, chlorobenzene, and aromatic and alkyl substituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

In some embodiments, a solution process is specified for crystalline polypropylene production. The solution process to prepare isotactic polypropylene comprises adding a catalyst and propylene monomer to a reactor and subjecting the contents to polymerization conditions.

In addition to polymerization of olefinic monomers, the ligands, compositions, and complexes according to the invnention can be incorporated in catalysts for the selective dimerization, trimerization or oligomerization of olefinic monomers, such as the selective dimerization of propylene to 4-methyl-1-pentene, or the selective trimerization of ethylene to 1-hexene. See, for example, Forni and Invernizzi, *Ind. Eng. Chem. Process Des. Develop.* 1973, 12, 455–459; Svejda and Brookhart, *Organometallics* 1999, 18, 65–75; Agapie et al., *J. Am. Chem. Soc.* 2004, 126, 1304–1305; Carter et al., *Chem. Comm.* 2002, 858–859; Deckers et al., *Organometallics* 2002, 21, 5122–5135; McGuinness et al., *Chem. Comm.* 2003, 334–335; McGuinness et al., *J. Am. Chem. Soc.* 2003, 125, 5272–5273; EP 1,110,930; WO 02/083306; and WO 01/48028.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may be take the form of an array comprising a plurality of compounds wherein each compound can be characterized by any of the above general formulas (i.e., I, II, III, etc.). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. Pat. Nos. 6,306,658, 6,508,984 and WO 01/98371, each of which is herein incorporated by reference.

EXAMPLES

General: All air sensitive reactions were performed under a purified argon or nitrogen atmosphere in a Vacuum Atmospheres or MBraun glove box. All solvents used were anhydrous, de-oxygenated and purified according to known techniques. All ligands and metal precursors were prepared according to procedures known to those of skill in the art, e.g., under inert atmosphere conditions, etc. Ethylene/1-octene copolymerizations and propylene polymerizations were carried out in a parallel pressure reactor, which is described in U.S. Pat. Nos. 6,306,658, 6,455,316 and 6,489,168, and in U.S. application Ser. No. 09/177,170, filed Oct. 22, 1998, and WO 00/09255, each of which is incorporated herein by reference.

High temperature Size Exclusion Chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388 each of which is incorporated herein by reference. In the current apparatus, a series of two 30 cm×7.5 mm linear columns in used, with both columns containing PLgel 10 um, MixB (available from Polymer Labs). The GPC system was calibrated using narrow polystyrene standards. The system was operated at an eluent flow rate of 1.5 mL/min and an oven temperature of 160° C. o-dichlorobenzene was used as the eluent. The polymer samples were dissolved 1,2,4-trichlorobenzene at a concentration of about 5 mg/mL. 200 µL of a polymer solution were injected into the system. The concentration of the polymer in the eluent was monitored using an evaporative light scattering detector. All of the molecular weight results obtained are relative to linear polystyrene standards.

The ratio of 1-octene to ethylene incorporated in the ethylene-octene copolymer products was determined by Raman spectroscopy. All spectra were obtained using a Jobin Yvon Spectrometer LABRAM 3/203IM, 1×50 objective, YAG Laser with an acquisition from 100 cm−1 to 3450 cm−1, 1 second exposure, 5 repeat scans. Analysis was performed using LabSpec Spectral Software package by taking the absorbance of the peaks at 2955, 2956, and 2957 cm-1 (for the asymmetric CH3 stretch) and the peak maximum between 2844 and 2854 cm-1 (for the symmetric CH2 stretch). The absorbance of the baseline at 3200 cm-1 was then subtracted from these values and the peaks were ratioed. Mol % 1-octene values determined from x=A2956/A2848 ratio where Mol %=1068.7×2−35.711×+1.6825. This method was calibrated using a set of ethylene/1-octene copolymers with a range of known mol% 1-octene content.

Crystallinity in polypropylene was determined by FTIR spectroscopy. FTIR spectra of thin films deposited from solution onto gold coated Si wafers are acquired at 4 cm$^{-1}$ resolution and with 16 scans in reflection-absorption mode on a Bruker Equinox 55 FTIR spectrometer equipped with a Pike MappIR accessory. The height ratio of two bands at 997 cm$^{-1}$ (C—H bending and CH$_3$ rocking mode from regular crystalline isotactic helices) and 973 cm$^{-1}$ (coupled C—C stretching and CH$_3$ rocking mode, independent of crystallinity) is determined as a measure of isotacticity (as known in the art, see, e.g., J. P. Luongo, *J. Appl. Polym. Sci* 3 (1960) 302–309, and T. Sundell, H. Fagerholm, H. Crozier, *Polymer* 37 (1996) 3227–3231, each of which is incorporated herein by reference). For blends of atactic and isotactic polypropylene (PP) with 0–70% isotactic PP, the IR ratio is proportional to the percentage of isotactic PP. For greater than 98% isotactic PP the ratio is greater than 0.95, for amorphous PP the ratio is 0.2.

Differential Scanning Calorimetry (DSC) measurements were performed on a TA instrument DSC 2920 to determine the melting point of polymers. 3–5 mg of polymer were despoited as a 40 mg/mL solution in dichlorobenzene into an Aluminium substrate and dried. The sample was equilibrated at 200° C. and held for 10 minutes. The sample was then cooled with a rate of 10° C. per minute to −50° C. and data were collected during the cooling period. The sample was held at −50° C. for 4 minutes. Then, the sample was heated to 200° C. at a rate of 110° C./min and data were collected during that heating period. Reported are the peak maxima of the melting transition. In case of multiple peaks in the transition, multiple melting temperatures are reported, ("#/#").

I. Ligand Synthesis

As used in this section, R is substitution at the position ortho to the phenol in the upper-ring building blocks. R' an R"are substitutions on the upper- and lower aryl rings, respectively. X=S or O. Hal=Cl, Br, I or trifluoromethanesulfonyl (OTf). DIEA=diisopropylethylamine. MOMCl= chloromethyl methyl ether. MEMCl=chloromethyl ethyl ether. OMOM=OCH$_2$OCH$_3$. OMEM=OCH$_2$OCH$_2$CH$_3$. NMP=1-methyl-2-pyrrolidinone. MsCl=methanesulfonyl chloride; OMs=methanesulfonate. KHMDS=potassium bis (trimethylsilyl)amide. The symbol ∽B∼ represents a bridging moiety as defined elsewhere in this document.

The ligands in these examples are prepared according to the general schemes described above and shown below, where "building blocks" are first prepared and then coupled together.

Part A: General Synthesis Methods

General Method A: MOM Protected Bromophenol

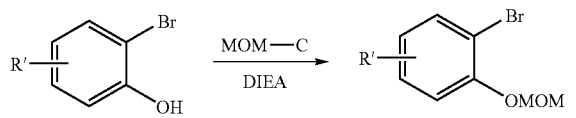

In a typical procedure, the appropriate bromophenol (11 mmol, 1.0 eq) was taken up in dry THF (20 mL) under N$_2$ and cooled to 0° C. DIEA (2.8 mL, 16 mmol, 1.5 eq) was added followed by dropwise addition of MOMCl (1.2 mL, 16 mmol, 1.5 eq). The reaction was allowed to stir and warm to RT over 18 h. The THF was removed and the crude material was redissolved in EtOAc and washed with 2 M NaOH and water. The organic layer was dried over Na$_2$SO$_4$ and the crude material was purified by flash chromatography.

General Method B: MOM-Protected Cbz-Substituted Upper Ring Building Block

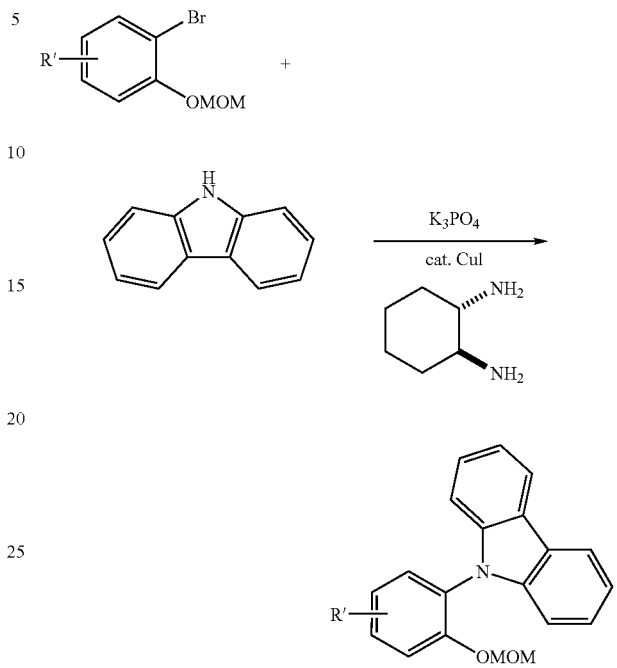

The MOM-protected bromophenol (1.4 mmol, 1.0 eq) was dissolved in dry dioxane (1.4 mL) under N$_2$. Carbazole or substituted carbazole (1.7 mmol, 1.2 eq), CuI (27 μg, 0.14 mmol, 10 mol %), racemic trans-1,2-diaminocyclohexane (33 mg, 0.29 mmol, 20 mol %), and K$_3$PO$_4$ (0.64 g, 3.0 mmol, 2.1 eq) were added and the reaction was heated to 110° C. for 22 h. The reaction was diluted with CH$_2$Cl$_2$ and filtered. The crude material was purified by flash chromatography.

General Method C: MOM-Protected H$_8$An-Substituted Upper Ring Building Block

Step C1: Anthracene coupling

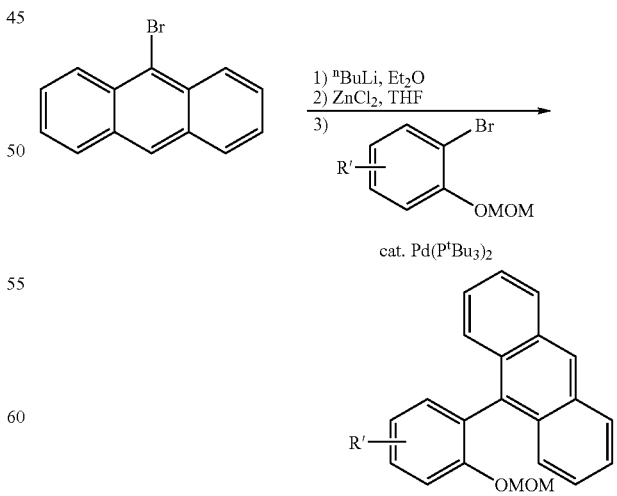

A solution of 9-bromoanthracene (0.67 g, 2.6 mmol, 1.2 eq) in dry Et$_2$O (13 mL) under N$_2$ was cooled to −30° C. and $^n$Buli (1.6 M in hexane, 1.6 mL, 2.6 mmol, 1.2 eq) was added dropwise. The solution was stirred for 20 min. at −30° C. followed by dropwise addition of ZnCl$_2$ (0.50 M in THF, 5.2 mL, 2.6 mmol, 1.2 eq). The reaction was stirred and warmed to RT over 30 min. The volatiles were removed under N$_2$ purge and the residue was redissolved in 3:1 THF/NMP (11 mL). The MOM-protected bromophenol (2.2 mmol, 1.0 eq) and Pd(P$^t$Bu$_3$)$_2$ (22 mg, 44 μmol, 4 mol %) were added and the reaction was heated to 100° C. for 2 h. The reaction was cooled to RT and the THF was removed. The residue was diluted with CH$_2$Cl$_2$, washed with 1 M HCl, and dried over Na$_2$SO$_4$. The crude material was purified by flash chromatography.

Step C2: Anthracene Reduction

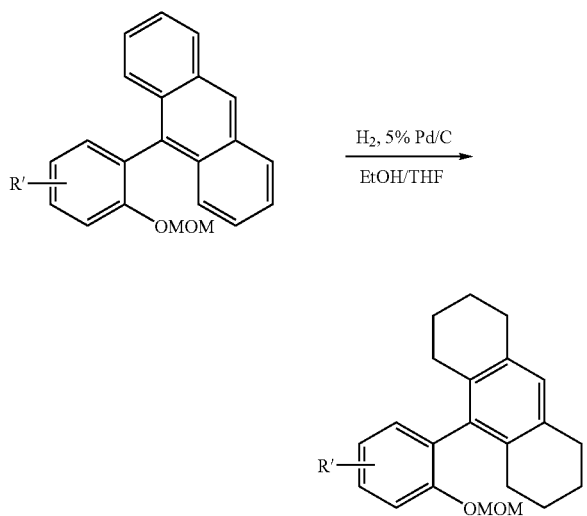

To a solution of the MOM-protected anthracene-substituted upper ring building block (1.2 mmol) in THF (6 mL) was added EtOH (6 mL) and 5% Pd/C (0.20 g, Johnson Matthey, 57.45% H$_2$O). The reaction was placed under 50 psi H$_2$ and was heated to 50° C. for 18 h. The reaction was filtered through a plug of Celite and concentrated to a viscous clear liquid. The crude material was purified by flash chromatography.

General Method D1: MEM-Protected 6-substituted 2-Bromophenol

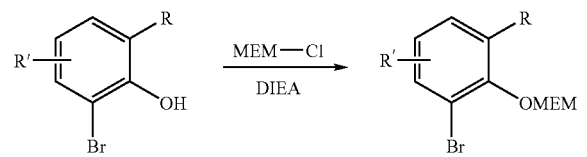

In a typical procedure, the appropriate 6-substituted-2-bromophenol (11 mmol, 1.0 eq) was taken up in dry THF (20 mL) under N$_2$ and cooled to 0° C. DIEA (2.8 mL, 16 mmol, 1.5 eq) was added followed by dropwise addition of MEMCl (1.2 mL, 16 mmol, 1.5 eq). The reaction was allowed to stir and warm to RT over 18 h. The THF was removed and the crude material was redissolved in EtOAc and washed with 2 M NaOH and water. The organic layer was dried over Na$_2$SO$_4$ and the crude material was purified by flash chromatography.

General Method D2: MOM-Protected 6-substituted 2-Bromophenol

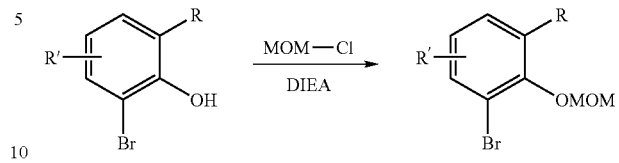

In a typical procedure, the appropriate 6-substituted-2-bromophenol (11 mmol, 1.0 eq) was taken up in dry THF (20 mL) under N$_2$ and cooled to 0° C. DIEA (2.8 mL, 16 mmol, 1.5 eq) was added followed by dropwise addition of MOMCl (1.2 mL, 16 mmol, 1.5 eq). The reaction was allowed to stir and warm to RT over 18 h. The THF was removed and the crude material was redissolved in EtOAc and washed with 2 M NaOH and water. The organic layer was dried over Na$_2$SO$_4$ and the crude material was purified by flash chromatography.

General Method E: Bridged Lower Ring Dibromide Building Block

Step E1: Synthesis of Bridge Bis-mesylate

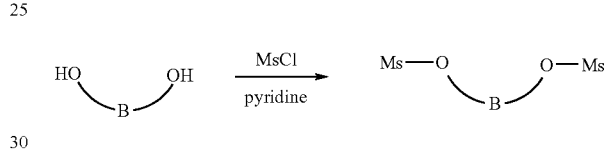

Pyridine (6 mL) was cooled to 0° C. and methanesulfonyl chloride (0.94 mL, 12 mmol, 2.2 eq) was added. A solution of diol (5.6 mmol, 1.0 eq) in pyridine (3 mL) was added dropwise and the reaction was allowed to stir at 0° C. After 2 h, the reaction was diluted with CH$_2$Cl$_2$ and the solution was washed with cold water, 1 M HCl, and saturated NaHCO$_3$. The organic extracts were dried over Na$_2$SO$_4$, filtered and concentrated to a viscous orange liquid. After further drying, the crude material solidified and was washed with ethanol.

Step E2: Synthesis of sodium phenoxide

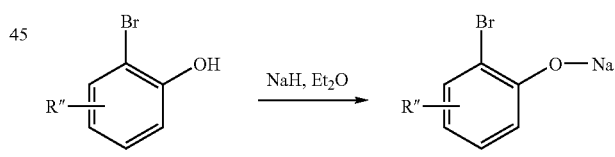

NaH (60% dispersion in mineral oil, 0.46 g, 12 mmol, 1.0 eq) was suspended in dry Et$_2$O (10 mL) and cooled to 0° C. in an ice/water bath. The appropriate bromophenol (12 mmol, 1.0 eq) in Et$_2$O (10 mL) was added dropwise to the solution with vigorous stirring. After H$_2$ evolution ceased, the solid ppt. was collected by vacuum filtration, washed with 2×50 mL hexanes, and dried under vacuum.

Step E3: Double Displacement of Bridge bis-mesylate

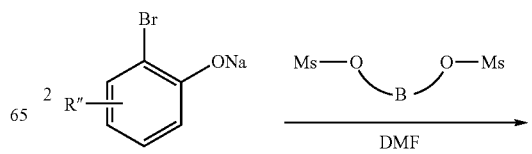

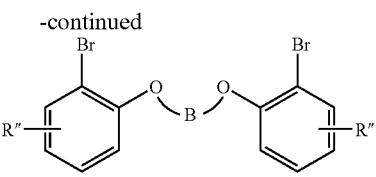

The bridge dimesylate (0.99 mmol, 1.0 eq) and the appropriate sodium phenoxide (2.2 mmol, 2.2 eq) were combined in DMF (3 mL) and heated to 80° C. for 18 h. After cooling to room temperature, the reaction was diluted with $CH_2Cl_2$, washed with $H_2O$, 1 M HCl and 2 M NaOH. The organic extracts were dried over $Na_2SO_4$, filtered, and concentrated. The crude material was purified by flash chromatography.

General Method F: Bridged Lower Ring Dibromide Building Block

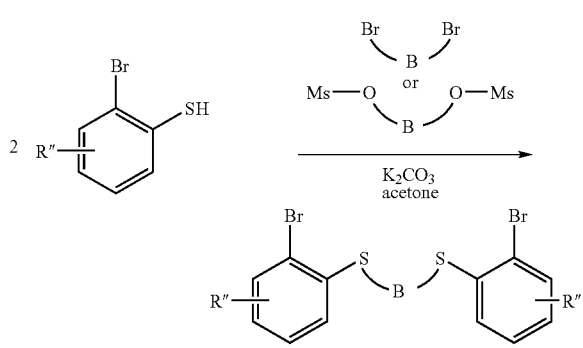

To a solution of thiophenol (1.8 mmol, 2.1 eq) in acetone (2 mL) under an atmosphere of argon was added $K_2CO_3$ (5.0 mmol, 3.0 eq) and dibromide or dimesylate (0.85 mmol, 1.0 eq). The reaction was heated to 60° C. for 18 h. The acetone was evaporated and the residue was redissolved in $CH_2Cl_2$ and washed with 2 M NaOH. The organic extracts were dried over $Na_2SO_4$ and concentrated to yield the desired material.

General Method G: Bridged Lower Ring Diiodo Building Block

Step G1: Synthesis of Bridged Dinitro Intermediate

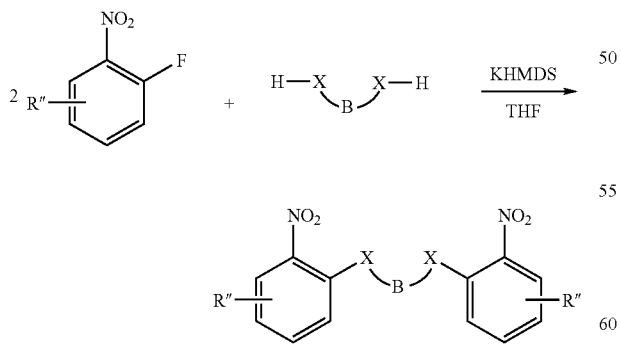

A solution of nitrofluorobenzene (14.4 mmol, 3.0 eq) and diol or dithiol (4.8 mmol, 1.0 eq) in THF (9.6 mL) was cooled to 0° C. and KHMDS (0.5 M in toluene, 21.1 mL, 10.6 mmol, 2.2 eq) was added dropwise. The reaction was allowed to stir and warm slowly to RT. After 18 h, the sodium salt of mercaptoacetic acid (0.82 g, 7.2 mmol, 1.5 eq) was added to the solution. The reaction was cooled to 0° C. and KHMDS (0.5 M in toluene, 14.4 mL, 7.2 mmol, 1.5 eq) was added dropwise. The reaction was allowed to stir and warm to RT over 2 h. Once the excess nitrofluorobenzene was consumed by the mercaptoacetic acid, the solvent was removed and the residue redissolved in $CH_2Cl_2$. The crude material was washed (2×) with saturated $NaHCO_3$. The organic layer was dried over $Na_2SO_4$, filtered, and concentrated to a dark brown oil. The crude material was purified by flash chromatography to yield the desired product.

Step G2: Reduction of Bridged Dinitro Intermediate

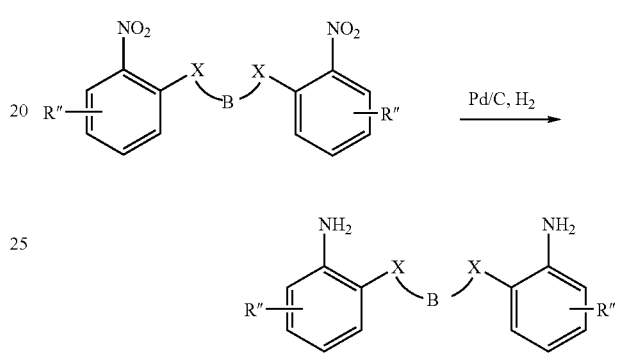

To a solution of bridged dinitro intermediate (2.89 mmol, 1.0 eq) in 1:1 EtOAc/EtOH (14 mL) was added 10% Pd/C (50 wt% $H_2O$, 0.25 g). The reaction was placed under an atmosphere of $H_2$ and allowed to stir at RT for 18 h. The material was filtered through a plug of Celite, concentrated, and used immediately without further purification.

Step G3: Diazonium Salt Displacement

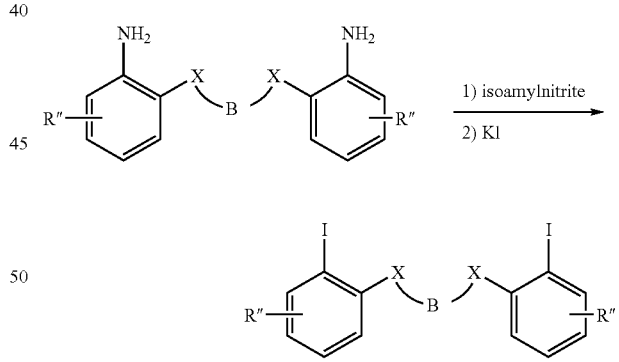

The bridged diamine intermediate (1.2 mmol, 1.0 eq) was taken up in 2:1 $CH_2Cl_2/CH_3CN$ (4.5 mL) and cooled to −20° C. TFA (0.38 mL, 5.9 mmol, 4.2 eq) was added followed by dropwise addition of isoamylnitrite (0.34 mL, 3.1 mmol, 2.2 eq). The solution was maintained at −20° C. for 2 h. A solution of KI (1.63 g, 11.7 mmol, 8.4 eq) in DMF (6 mL) was added and the solution was allowed to stir and slowly warm to RT. After 18 h, the dark red solution was diluted with $CH_2Cl_2$ and washed with 10% aq. $Na_2S_2O_3$. The organic layer was dried over $Na_2SO_4$, filtered, and concentrated. The crude material was purified by flash chromatography.

General Method H: Double Negishi Synthesis of MOM Protected Ligand

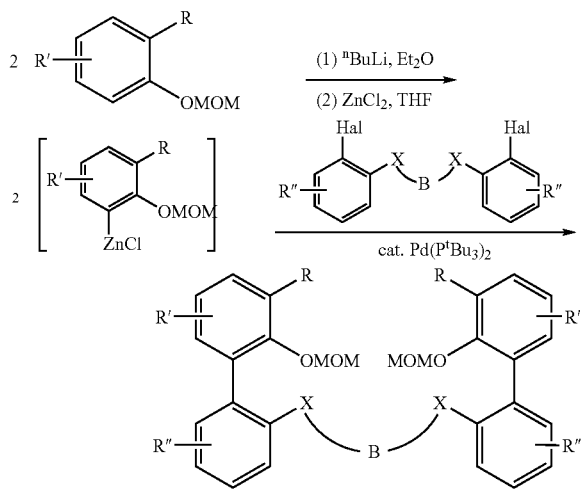

The MOM-protected upper-ring building block (0.18 mmol, 2.2 eq) was dissolved in dry Et₂O (2 mL) under N₂ and "Buli (1.6 M solution in hexane, 0.12 mL, 0.18 mmol, 2.2 eq) was added dropwise at RT. After stirring at RT for 18 h, a solution of ZnCl₂ (0.5 M in THF, 0.37 mL, 0.18 mmol, 2.2 eq) was added dropwise and stirring was continued for 30 min. Volatiles were removed under N₂ purge and the residue was redissolved in 3:1 THF/NMP (2 mL). The bridged lower-ring dihalide building block (83 μmol, 1.0 eq) and Pd(P'Bu₃)₂ (1.7 mg, 3.0 μmol, 4 mol%) were added and the reaction was heated to 80° C. for 2 h. The reaction was cooled to RT and the THF was removed. The residue was diluted with CH₂Cl₂, washed with 1 M HCl, and dried over Na₂SO₄. The crude material was purified by flash chromatography.

General Method I: Deprotection of MOM Protected Ligand

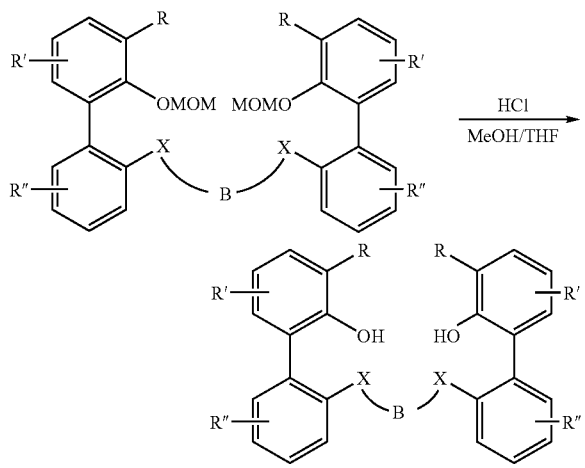

In a typical procedure, the MOM-protected ligand (0.14 mmol) dissolved in THF (1.8 mL) was treated with a solution of MeOH (0.9 mL) containing ten drops of conc. HCl. Additional THF was added if the solution became cloudy. The reaction was stirred at RT and was monitored by TLC (alumina plates, typically 1:1 Et₂O/hexane) until reaction completion. After ca. 18 h, the solvent was removed and the residue was dissolved in CH₂Cl₂ and washed with H₂0. The organic extracts were dried over Na₂SO₄, filtered, and concentrated. The crude material was purified by flash chromatography.

General Method J: Double Negishi Synthesis of MEM Protected Ligand

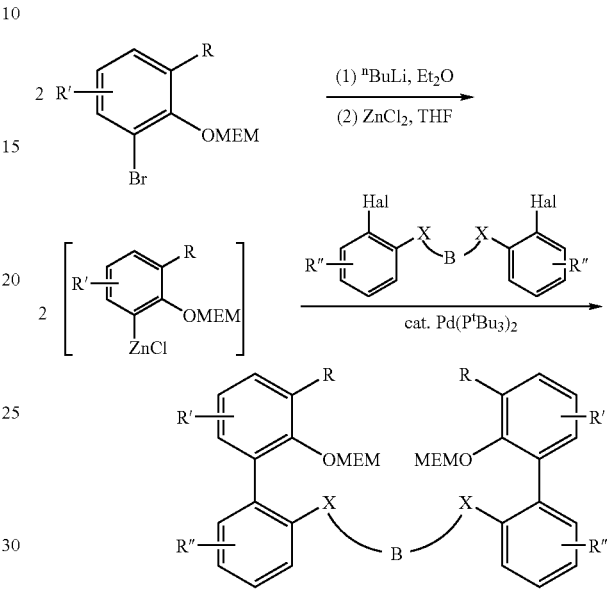

The MEM-protected 2-bromo upper-ring building block (0.18 mmol, 2.2 eq) in dry Et₂O (2 mL) under N₂ was cooled to −30° C. and "Buli (1.6 M solution in hexane, 0.12 mL, 0.18 mmol, 2.2 eq) was added dropwise. The solution was stirred at 20° C. for 20 min. after which a solution of ZnCl₂ (0.5 M in THF, 0.37 mL, 0.18 mmol, 2.2 eq) was added dropwise and the solution was stirred and warmed to room temperature over 30 min. The volatiles were removed under N₂ purge and the residue was redissolved in 3:1 THF/NMP (2 mL). The bridged lower-ring dihalide building block (83 μmol, 1.0 eq) and Pd(P'Bu₃)₂ (1.7 mg, 3.0 μmol, 4 mol%) were added and the reaction was heated to 80° C. for 2 h. The reaction was cooled to RT and the THF was removed. The residue was diluted with CH₂Cl₂, washed with 1 M HCl, and dried over Na₂SO₄. The crude material was purified by flash chromatography.

General Method K: Double Negishi Synthesis of MOM Protected Ligand

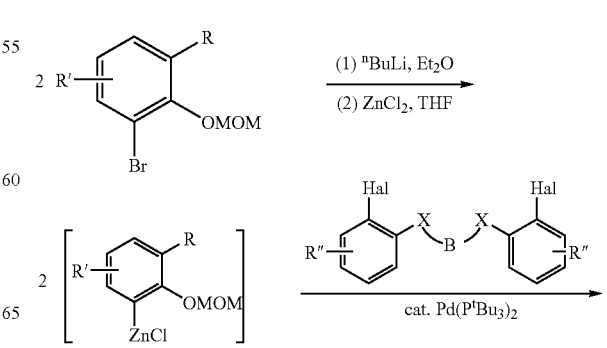

-continued

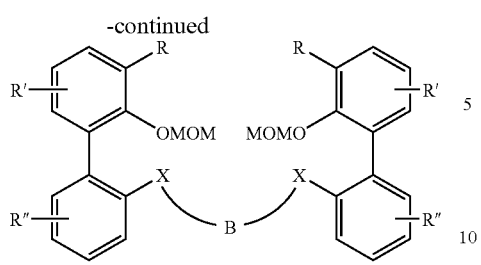

The MOM-protected 2-bromo upper-ring building block (0.18 mmol, 2.2 eq) in dry Et$_2$O (2 mL) under N$_2$ was cooled to −30° C. and "BuLi (1.6 M solution in hexane, 0.12 mL, 0.18 mmol, 2.2 eq) was added dropwise. The solution was stirred at −20° C. for 20 min. after which a solution of ZnCl$_2$ (0.5 M in THF, 0.37 mL, 0.18 mmol, 2.2 eq) was added dropwise and the solution was stirred and warmed to room temperature over 30 min. The volatiles were removed under N$_2$ purge and the residue was redissolved in 3:1 THF/NMP (2 mL). The bridged lower-ring dihalide building block (83 μmol, 1.0 eq) and Pd(P$^t$Bu$_3$)$_2$ (1.7 mg, 3.0 μmol, 4 mol%) were added and the reaction was heated to 80° C. for 2 h. The reaction was cooled to RT and the THF was removed. The residue was diluted with CH$_2$Cl$_2$, washed with 1 M HCl, and dried over Na$_2$SO$_4$. The crude material was purified by flash chromatography.

General Method L: Deprotection of MEM Protected Ligand

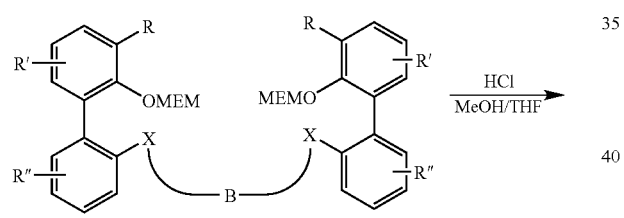

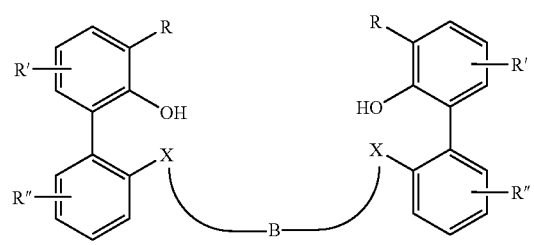

In a typical procedure, the MEM-protected ligand (0.14 mmol) dissolved in THF (1.8 mL) was treated with a solution of MeOH (0.9 mL) containing ten drops of conc. HCl. Additional THF was added if the solution became cloudy. The reaction was stirred at RT and was monitored by TLC (alumina plates, typically 1:1 Et$_2$O/hexane) until reaction completion. After ca. 18 h, the solvent was removed and the residue was dissolved in CH$_2$Cl$_2$ and washed with H$_2$O. The organic extracts were dried over Na$_2$SO$_4$, filtered, and concentrated. The crude material was purified by flash chromatography.

Part B: Specific Ligand Syntheses

Example 1

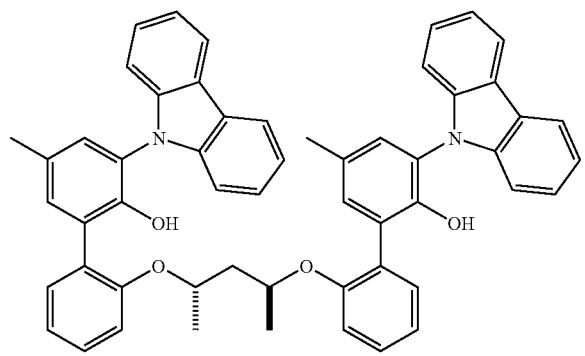

Step 1: Synthesis of Upper Ring Building Block

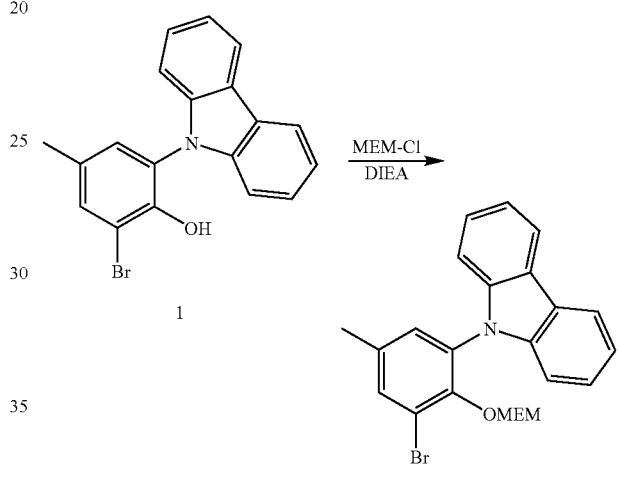

Step 2: Synthesis of Bridged Dibromo Lower-ring Building Block

2a: Synthesis of Bridge Bis-mesylate

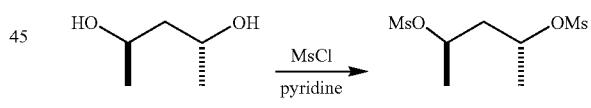

2b: Synthesis of Bridged Dibromo Lower-ring Building Block

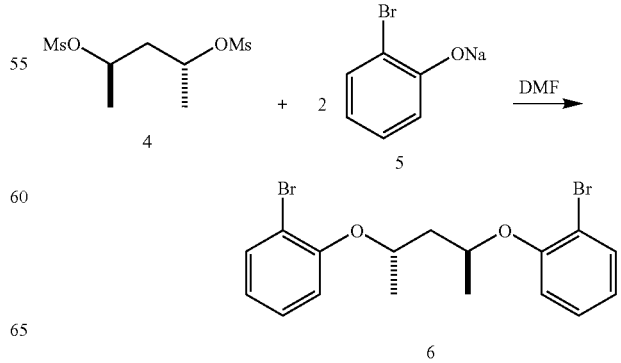

Step 3: Double Negishi Coupling of Upper and Lower Ring Building Blocks
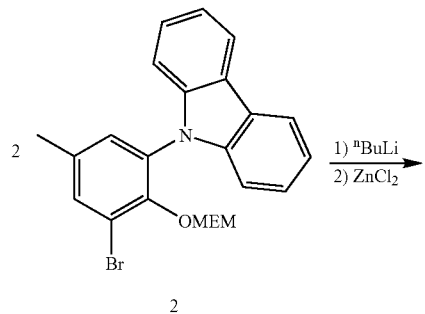
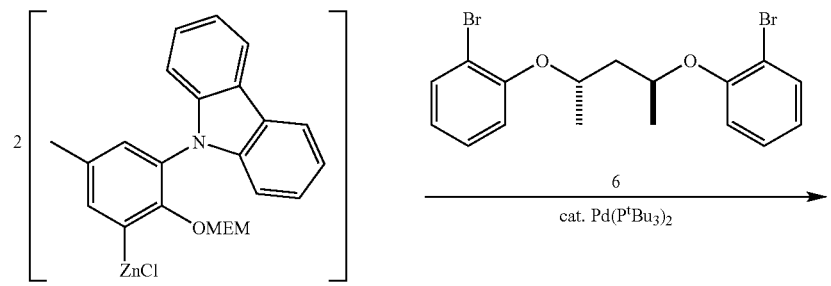
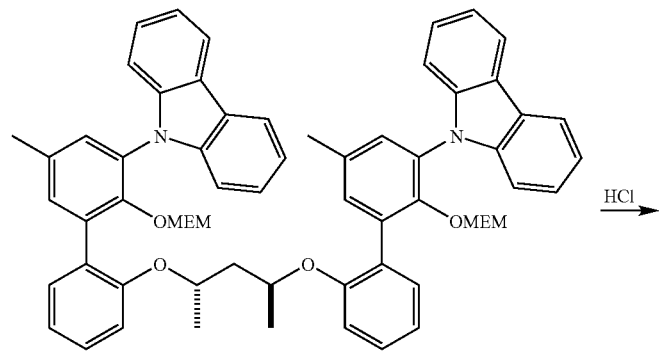
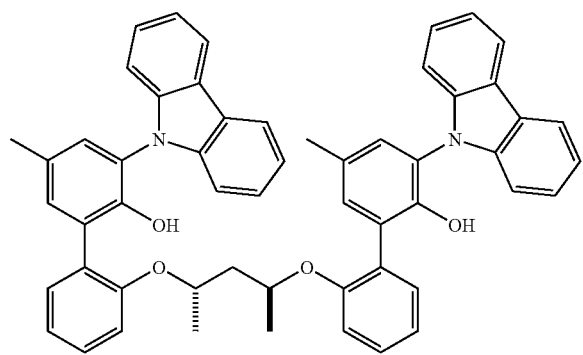

Experimental Details

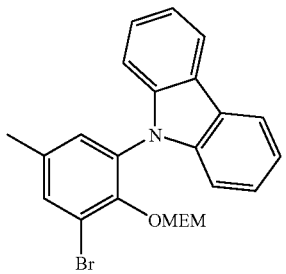
2

Synthesized by General Method D1. The synthesis of the precursor 1 is described in U.S. Application No. 10/421,212, U.S. Application No. 10/421,219, and U.S. Application No. 10/421,235, all filed on Apr. 23, 2003. The crude reaction mixture was filtered, concentrated, and diluted with MeOH to precipitate product. The product was collected by filtration, washed (2X) with MeOH, and dried to yield 2.9 g (70%) of 2 as a white solid. $^1$H NMR (CDCl$_3$, 300 MHz): 8.12 (d, J=7.8 Hz, 2H), 7.56 (d, J=1.8 Hz, 1H), 7.42 (dt, J=7.7 Hz, J=1.2 Hz, 2H), 7.32–7.22 (m, 5H), 4.56 (s, 2H), 2.91 (m, J=7.2 Hz, 2H), 2.38 (s, 3H), 0.59 (t, J=7.2 Hz, 3H).

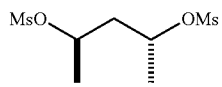
4

Synthesized by General Method E, Step E, Compound 4 (2.2 g, 62%) was isolated as a viscous clear oil. $^1$H NMR (CDCl$_3$, 300 MHz): 4.94 (m, 2H), 3.08 (s, 6H), 1.91 (m, 2H), 1.49 (d, J=6.0Hz, 6H).

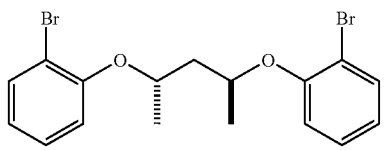
6

Synthesized by General Method E, Steps E2/E3. Purified by flash chromatography (Biotage FLASH 12M KP-Sil silica, 2% Et$_2$O/hexane) to yield 0.36 g (37%) of 6 as a clear oil. $^1$HNMR(CDCl$_3$, 300MHz): 7.44 (dd, J=7.8 Hz, J=1.5Hz, 2H), 7.12–7.03 (m, 2H), 6.78 (dd, J=8.7 Hz, J=1.2 Hz, 2H), 6.74 (dt, J=7.8 Hz, J=1.2 Hz), 4.76 (m, 2H), 2.08 (m, 2H), 1.37 (d, J=6.0 Hz, 6H).

7

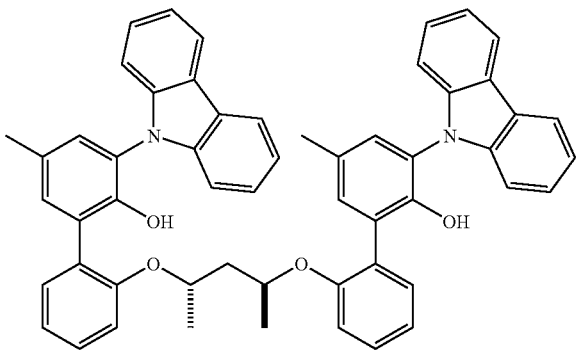

Synthesized by General Method J. Purified by flash chromatography (Biotage FLASH 40S KP-Sil silica, 10–30% Et$_2$O/hexane) to yield 81 mg (74%) of 7 as a white solid. $^1$H NMR (CDCl$_3$, 300 MHz): 8.14 (d, J=7.5 Hz, 4H), 7.50–7.05 (m, 18H), 7.13 (t, J=6.9, 2H), 6.93 (t, J=7.2 Hz, 2H), 6.81 (d, J=8.1 Hz, 2H), 4.70 (m, 2H), 4.17 (m, 4H), 2.44 (s, 6H), 2.37 (m, J=7.2 Hz, 4H), 2.12 (t, J=6.3 Hz, 2H), 1.29 (d, J=6.0Hz, 6H), 0.37 (t, J=7.2 Hz, 6H).

8

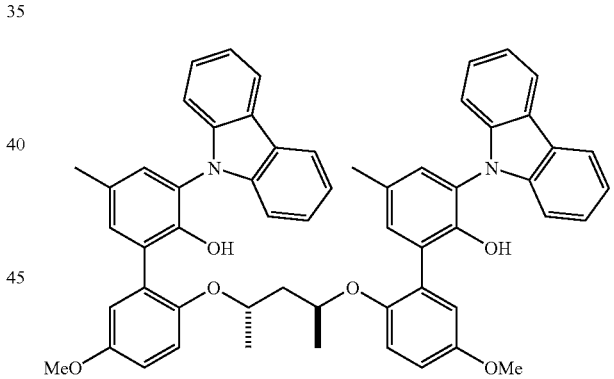

Synthesized by General Method L. Purified by flash chromatography (Biotage FLASH 40S KP-Sil silica, 5–7% EtOAc/hexane) to yield 0.13 g (74%) of 8 as a white solid. $^1$H NMR (CDCl$_3$, 300 MHz): 8.16 (dd, J=7.2 Hz, J=2.7 Hz, 4H), 7.40–7.10 (m, 18H), 7.02 (m, 4H), 6.53 (m, 2H), 6.09 (s, 2H), 4.47 (m, 2H), 2.40 (s, 6H), 1.81 (t, J 6.6 Hz, 2H), 1.04 (d, J=6.0 Hz, 6H).

Example 2

Step 1: Synthesis of Bridged Lower Ring Dibromide Building Block

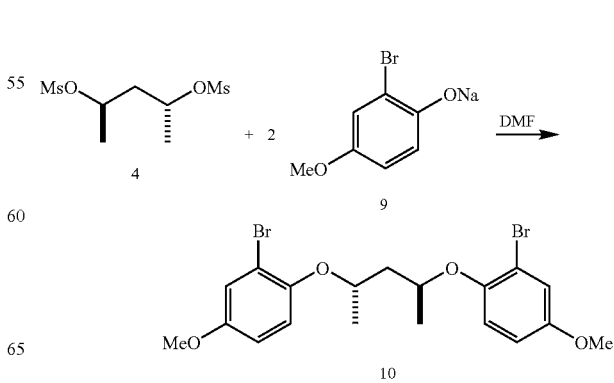

Step 2: Double Negishi Coupling of Upper and Lower Ring Building Blocks
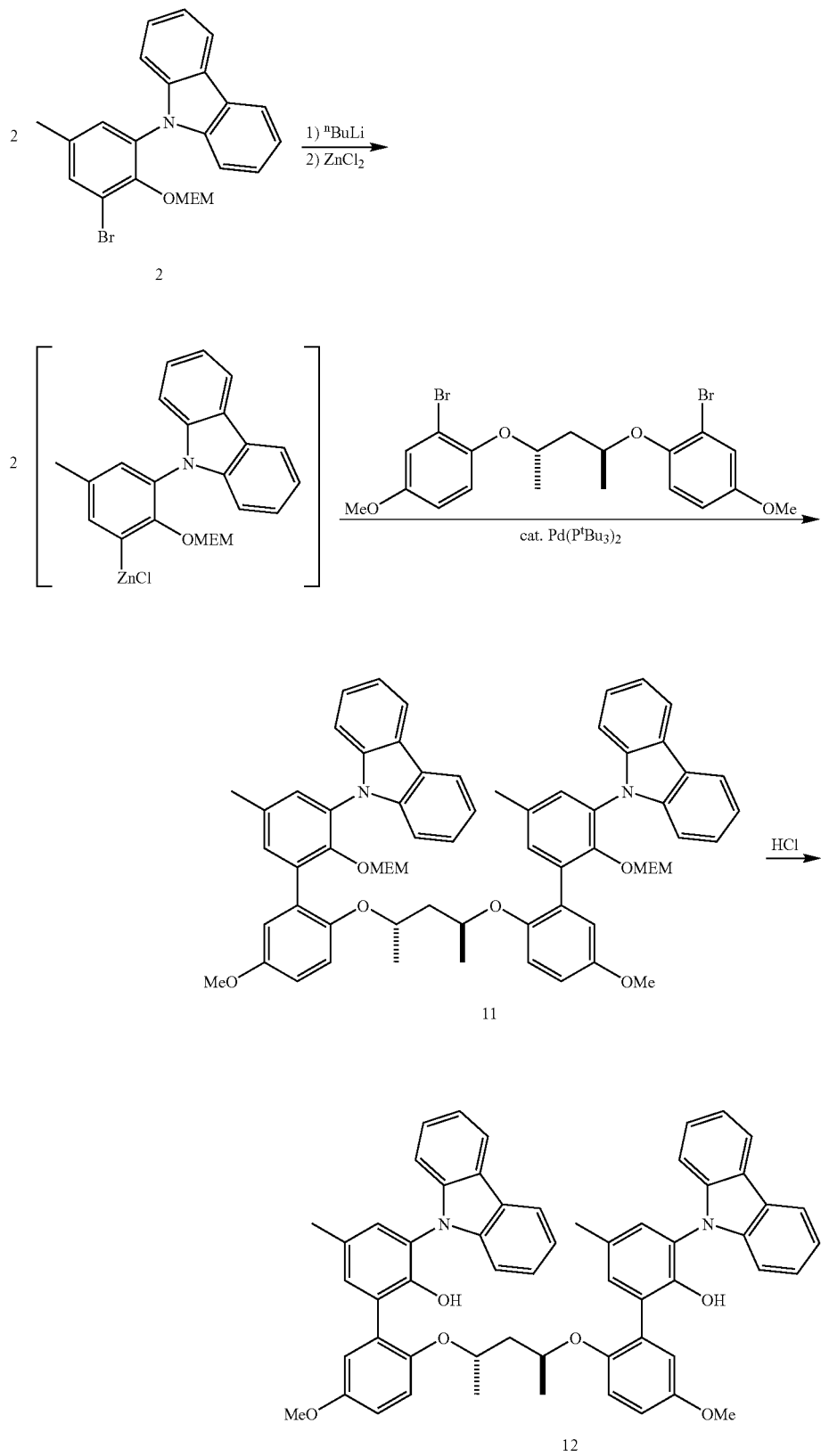

Experimental Details

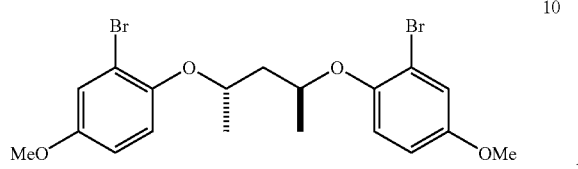

Synthesized by General Method E, Steps E2/E3. Purified by flash chromatography (Biotage FLASH 12M KP-Sil, 10% EtOAc/hexane) to yield 0.15 g (27%) of 10. ¹H NMR (CDCl₃, 300 MHz): 7.03 (d, J=3.0 Hz, 2H), 6.74 (d, J=9.0 Hz, 2H), 6.65 (dd, J=9.0 Hz, J=2.7 Hz, 2H), 4.64 (m, 2H), 3.72 (s, 6H), 2.02 (m, 2H), 1.32 (d, J=6.0 Hz, 6H).

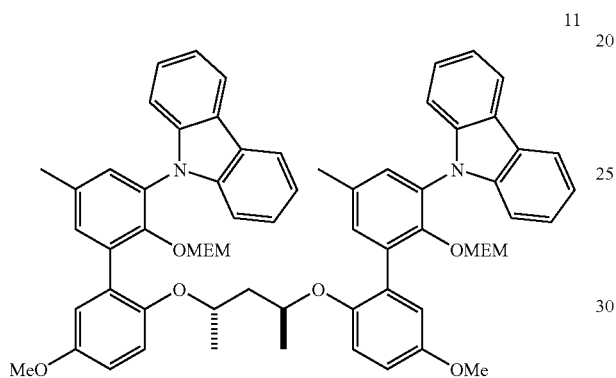

Synthesized by General Method J. Purified by flash chromatography (Biotage FLASH 12M KP-Sil silica, 10–15% EtOAc/hexane) to yield 67 mg (62%) of 11 as a white solid. ¹H NMR (CDCl₃, 300 MHz): 8.12 (d, J=7.8 Hz, 4H), 7.39 (t, J=3.6 Hz, 8H), 7.30–7.18 (m, 8H), 6.93 (d, J=3.0 Hz, 2H), 6.77 (d, J=9.0 Hz, 2H), 6.68 (dd, J=9.0 Hz, J=3.0 Hz, 2H), 4.54 (m, 2H), 4.19 (m, 4H), 3.77 (s, 6H), 2.41 (m, 10H), 2.03 (t, J=6.0 Hz, 2H), 1.21 (d, J=6.0 Hz, 6H), 0.38 (t, J=7.2 Hz, 6H).

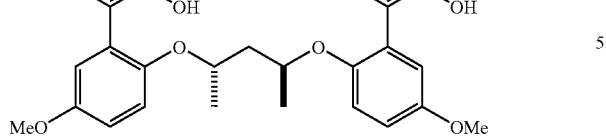

Synthesized by General Method L. Purified by flash chromatography (Biotage FLASH 12M KP-Sil silica, 10% EtOAc/hexane) to yield 0.17 g (93%) of 12 as white solid. ¹H NMR (CDCl₃, 300 MHz): 8.16 (d, J=7.8 Hz, 4H), 7.40–7.10 (m, 14H), 6.93 (d, J=3.0 Hz, 2H), 6.61 (dd, J=9.0 Hz, J=3.0 Hz, 2H), 6.51 (d, J=9.0 Hz, 2H), 6.48 (s, 2H), 4.34 (m, 2H), 3.78 (s, 6H), 2.41 (s, 6H), 1.75 (t, J=6.3 Hz, 2H), 0.96 (d, J=6.0 Hz, 6H).

Example 3

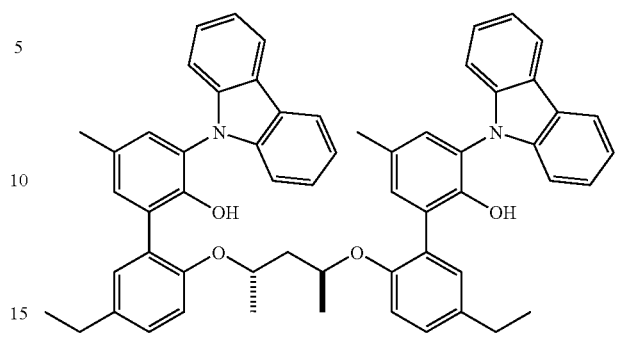

Step 1: Synthesis of Upper Ring Building Block

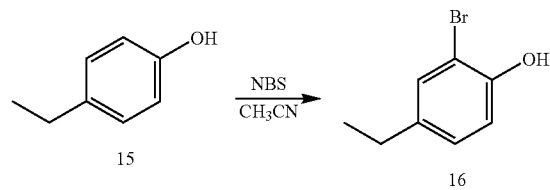

Step 2: Synthesis of Bridged Lower Ring Dibromide Building Block

2a: Synthesis of 2-bromo-4-ethylphenol

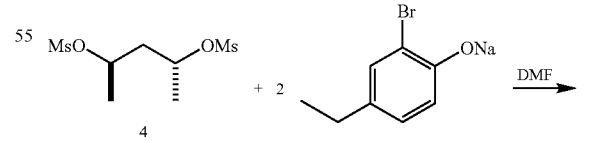

2b: Synthesis of Bridged Lower Ring Building Block

Step 3: Double Negishi Coupling of Upper and Lower Ring Building Blocks
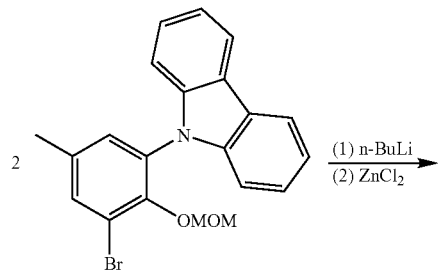
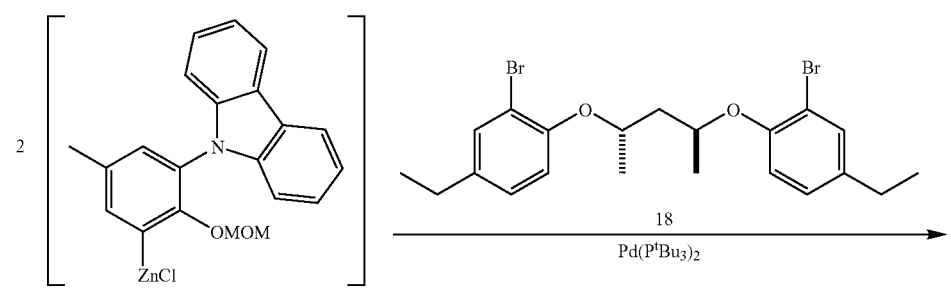
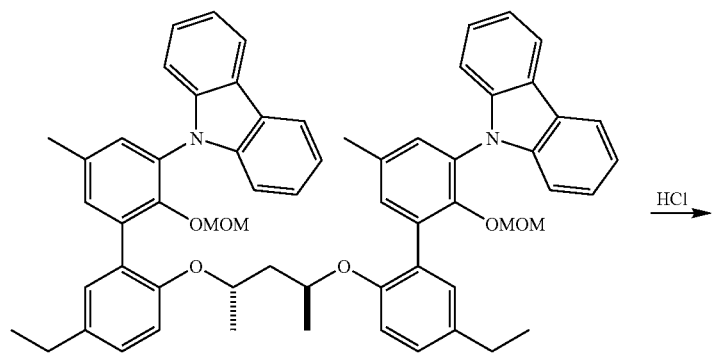
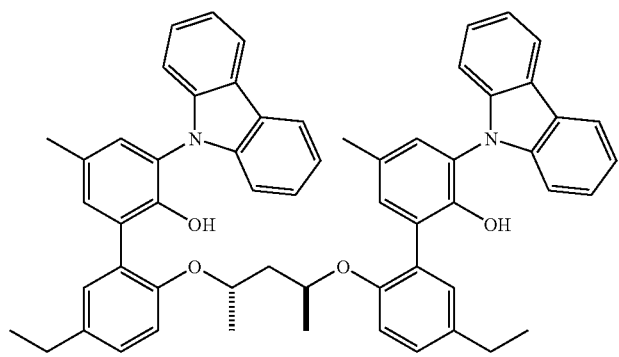

Experimental Details

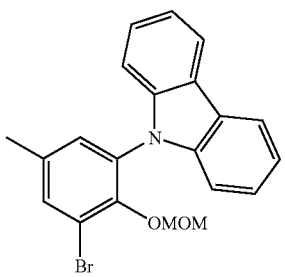

14

Synthesized by General Method D1. The synthesis of the precursor 1 is described in U.S. application Ser. No. 10/421,212, U.S. application Ser. No. 10/421,219, and U.S. Application No. 10/421,235, all filed on Apr. 23, 2003. Purified by flash chromatography (Biotage 40M KP-Sil silica, 10% Et$_2$O/hexanes) to yield 2.1 g (91%) of 14 as a white solid. $^1$H NMR (CDCl$_3$, 300 MHz): 8.09 (d, J=7.8 Hz, 2H), 7.54 (d, J=1.8 Hz, 1H), 7.40 (dt, J=7.7 Hz, J=1.2 Hz, 2H), 7.30–7.20 (m, 5H), 4.49 (s, 2H), 2.64 (s, 3H), 2.36 (s, 3H).

16

To a solution of 4-ethylphenol (1.0 g, 8.2 mmol, 1.0 eq) in dry acetonitrile (40 mL) was added NBS (1.46 g, 8.2 mmol, 1.0 eq). The mixture was allowed to stir at RT for 2 h followed by removal of acetonitrile. The residue was redissolved in Et$_2$O and washed with H$_2$0. The organic extracts were dried over Na$_2$SO$_4$, filtered, and concentrated. The crude material was purified by flash chromatography (Biotage FLASH 40S KP-Sil silica, 5% Et$_2$O/hexanes) to yield 1.0 g (52%) of 16 as a clear oil. $^1$H NMR (CD$_2$Cl$_2$, 300 MHz): 7.33 (s, 1H), 7.07 (d, J=8.1 Hz, 1H), 6.93 (d, J=8.1 Hz, 1H), 2.58 (m, J=7.5 Hz, 2H), 1.20 (t, J=7.5 Hz, 3H).

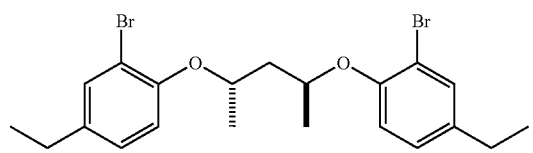

18

Synthesized by General Method E, Steps E2/E3. Purified by flash chromatography (Biotage FLASH 40S KP-Sil silica, 2–4% Et$_2$O/hexanes) to yield 0.18 g (56%) of 18. $^1$H NMR (CDCl$_3$, 300 MHz): 7.36 (d, J=2.1 Hz, 2H), 6.89 (dd, J=8.4 Hz, J=2.1 Hz, 2H), 6.70 (d, J=8.4 Hz, 2H), 4.68 (m, 2H), 2.50 (m. J=7.5 Hz, 4H), 2.05 (m, 2H), 1.34 (d, J=6.0 Hz, 6H), 1.16 (t, J=7.5 Hz, 6H).

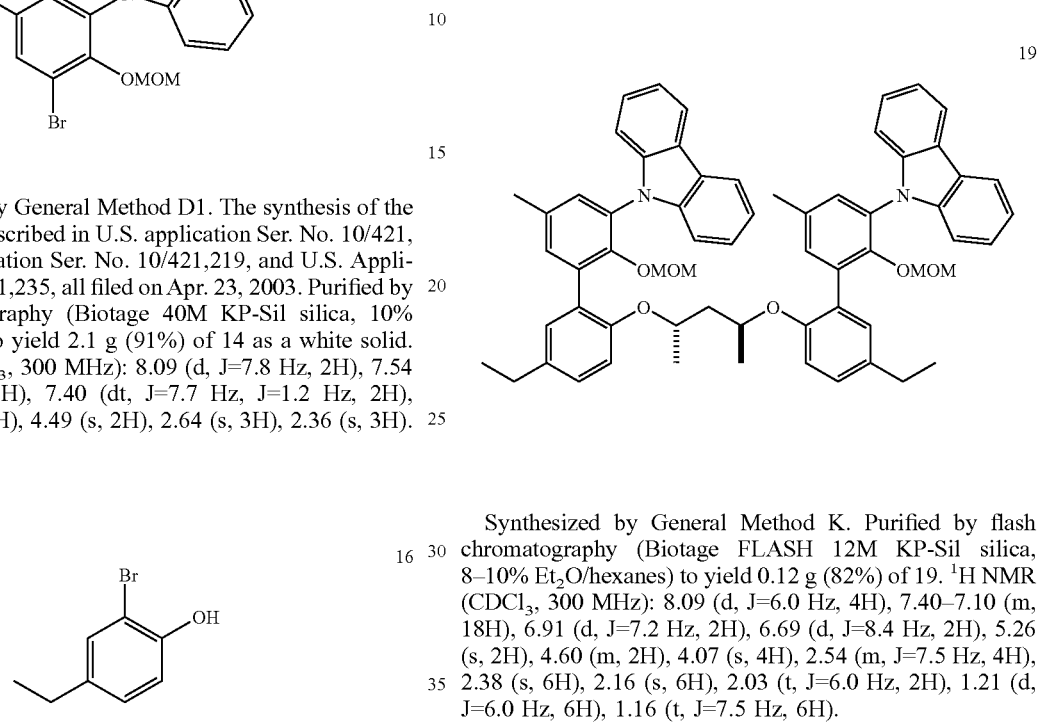

19

Synthesized by General Method K. Purified by flash chromatography (Biotage FLASH 12M KP-Sil silica, 8–10% Et$_2$O/hexanes) to yield 0.12 g (82%) of 19. $^1$H NMR (CDCl$_3$, 300 MHz): 8.09 (d, J=6.0 Hz, 4H), 7.40–7.10 (m, 18H), 6.91 (d, J=7.2 Hz, 2H), 6.69 (d, J=8.4 Hz, 2H), 5.26 (s, 2H), 4.60 (m, 2H), 4.07 (s, 4H), 2.54 (m, J=7.5 Hz, 4H), 2.38 (s, 6H), 2.16 (s, 6H), 2.03 (t, J=6.0 Hz, 2H), 1.21 (d, J=6.0 Hz, 6H), 1.16 (t, J=7.5 Hz, 6H).

20

Synthesized by General Method I. Purified by flash chromatography (Biotage FLASH 12M KP-Sil silica, 5% Et$_2$O/hexanes) to yield 69 mg (62%) of 20. $^1$H NMR (CDCl$_3$, 300 MHz): 8.16 (d, J=7.8 Hz, 4H), 7.40–7.10 (m, 18H), 6.94 (dd, J=8.4 Hz, J=2.1 Hz, 2H), 6.54 (d, J=8.7 hz, 2H), 6.28 (s, 2H), 4.42 (m, 2H), 2.61 (m, J=7.5 Hz, 4H), 2.42 (s, 6H), 1.83 (t, J=6.9 Hz, 2H), 1.22 (t, J=7.5 Hz, 6H), 1.07 (d, J=6.0 Hz, 6H).

Example 4
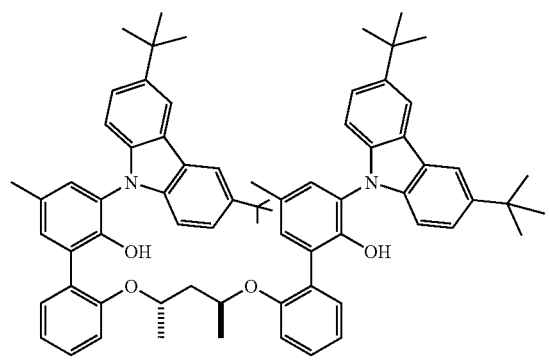
Step 1: Synthesis of MOM-Protected Upper-Ring Building Block
1a: MOM-protection of Bromophenol
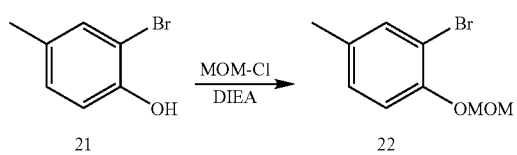
1b: Substituted Carbazole Cross-Coupling
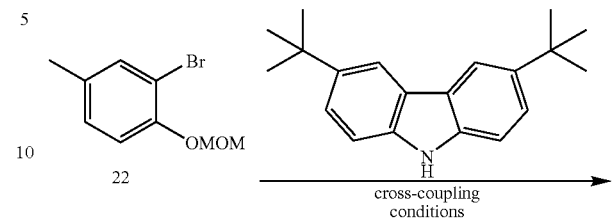
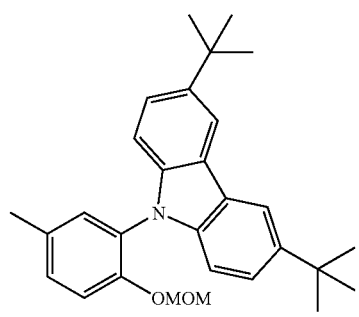
Step 2: Double Negishi Coupling of Upper and Lower Ring Building Blocks
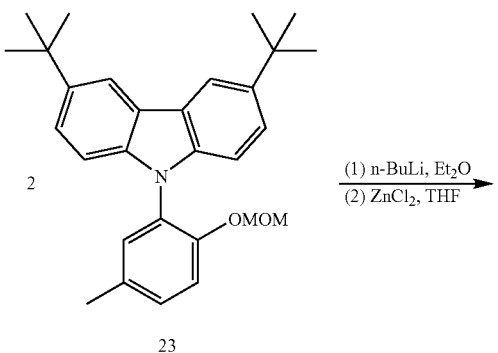
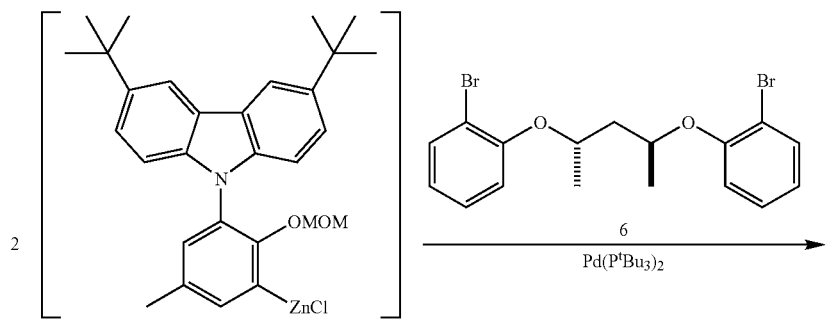

-continued
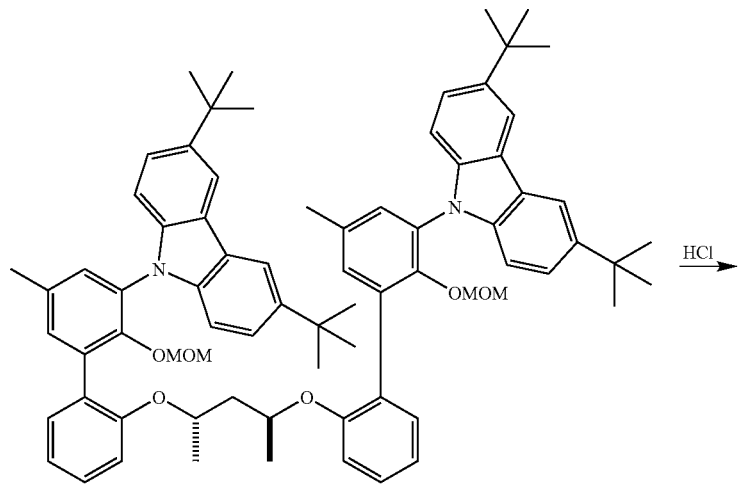
24
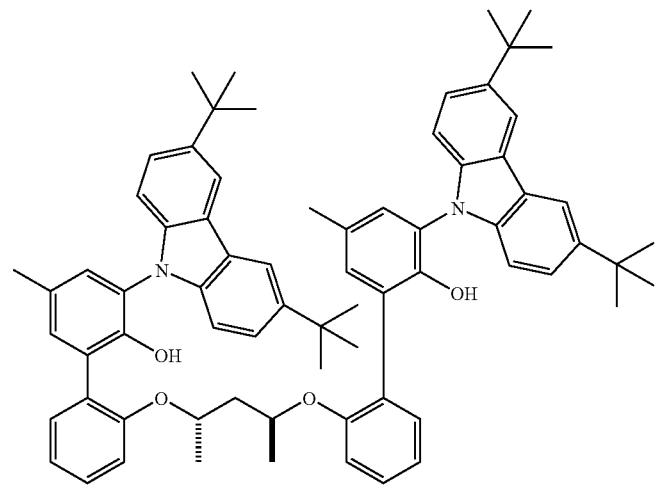
25
Experimental Details
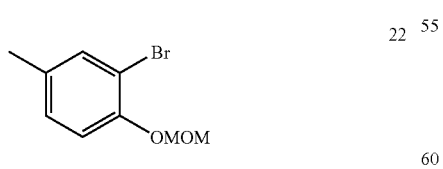
22
Synthesized by General Method A. Purified by flash chromatography (Biotage FLASH 40M KP-Sil silica, 4% Et$_2$O/hexane) to yield 2.12 g (86%) of 22 as clear viscous oil. $^1$H NMR (CD$_2$Cl$_2$, 300 MHz): 7.36 (d, J=1.4 Hz, 1H), 7.10–6.97 (m, 2H), 5.18 (s, 2H), 3.49 (s, 3H), 2.27 (s, 3H).
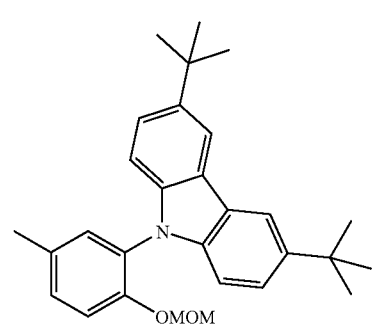
23

Synthesized by General Method B, using 3,6-di-tert-butylcarbazole synthesized according to literature procedures (Neugebauer, Fischer *Chem. Ber.* 1972, 105, 2686; Neugebauer, Fischer *Angew. Chem.* 1971, 83, 756). Purified by flash chromatography (Biotage FLASH 40S KP-Sil silica, 3% Et$_2$O/hexanes). The compound was then further purified by recrystallization from MeOH to yield 0.39 g (50%) of 23 as a white solid. $^1$H NMR (CDCl$_3$, 300 MHz): 8.13 (d, J=1.8 Hz, 2H), 7.42 (dd, J=8.7 Hz, J=1.8 Hz, 2H), 7.32–7.20 (m, 3H), 7.10 (d, J=8.4 Hz, 2H), 4.90 (s, 2H), 3.18 (s, 3H), 2.35 (s, 3H), 1.46 (s, 18H).

24

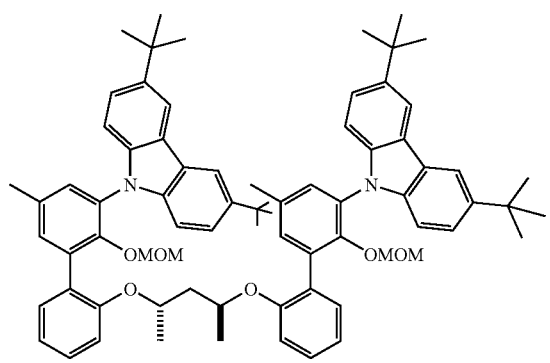

Synthesized by General Method H. Purified by flash chromatography (Biotage FLASH 12M KP-Sil silica, 8% Et$_2$O/hexanes) to yield an inseparable mixture of the desired product 24 and starting material 23. The material was carried on without further purification. $^1$H NMR (CDCl$_3$, 300 MHz): 8.12 (d, J=1.2 Hz, 4H), 7.51–7.42 (m, 4H), 7.35–7.15 (m, 12H), 7.09 (dt, J=9.0 Hz, J=3.0 Hz, 2H), 6.90 (t, J=7.2 Hz, 2H), 6.79 (d, J=8.1 Hz, 2H), 4.72 (m, J=6.0 Hz, 2H), 4.11 (s, 4H), 2.40 (s, 6H), 2.25 (s, 6H), 2.09 (t, J=6.0 Hz, 2H), 1.47 (s, 18H), 1.46 (s, 18H), 1.27 (d, J=6.0 Hz, 6H).

25

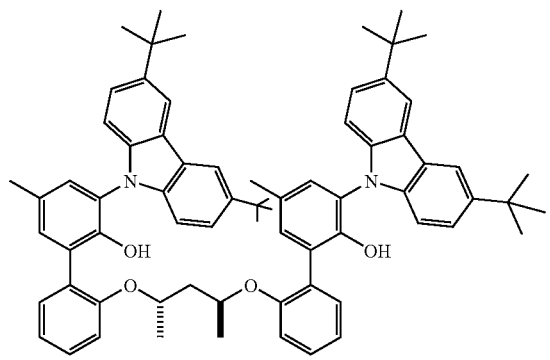

Synthesized by General Method I from a mixture of 23 and 24. Purified by flash chromatography (Biotage FLASH 12M KP-Sil silica, 2–10% Et$_2$O/hexanes) to yield 22 mg (18% over 2 steps) of 25 as a white solid. $^1$H NMR (CD$_2$Cl$_2$, 300 MHz): 8.18 (m, 4H), 7.50–7.40 (m, 4H), 7.38–7.32 (m, 2H), 7.24 (d, J=1.8 Hz, 2H), 7.16–6.97 (m, 12H), 6.55–6.50 (m, 2H), 5.98 (s, 2H), 4.46 (m, J=6.3 Hz, J=6.0 Hz, 2H), 2.40 (s, 6H), 1.85 (t, J=6.0 Hz, 2H), 1.46 (s, 18H), 1.44 (s, 18H), 1.05 (d, J=6.0 Hz, 6H).

Example 5

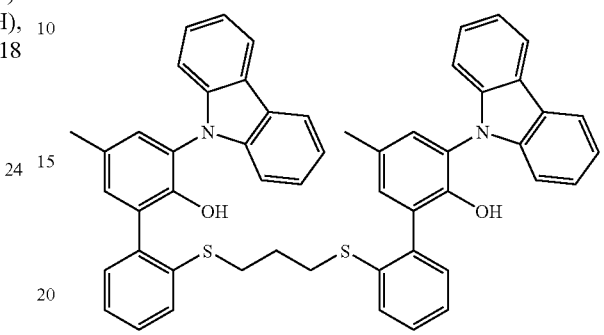

Step 1: Synthesis of MOM-Protected Upper-Ring Building Block:

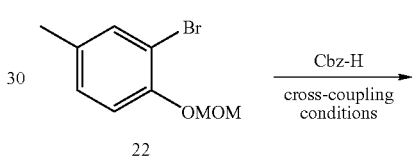

22

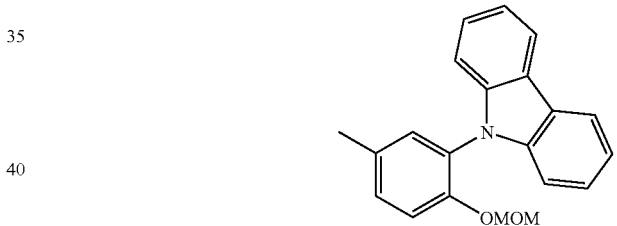

26

Step 2: Synthesis of Lower Ring Dibromide Building Block

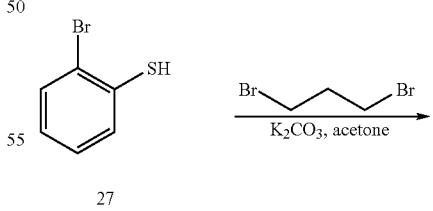

27

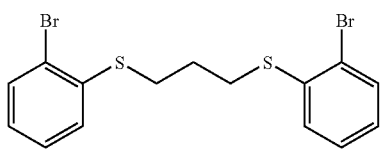

28

Step 3: Double Negishi Coupling of Upper and Lower Ring Building Blocks
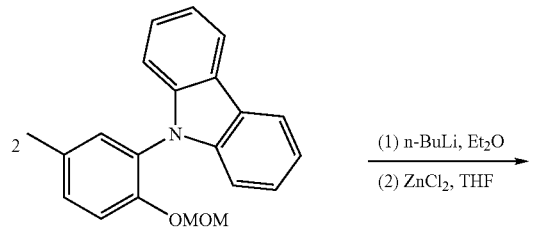
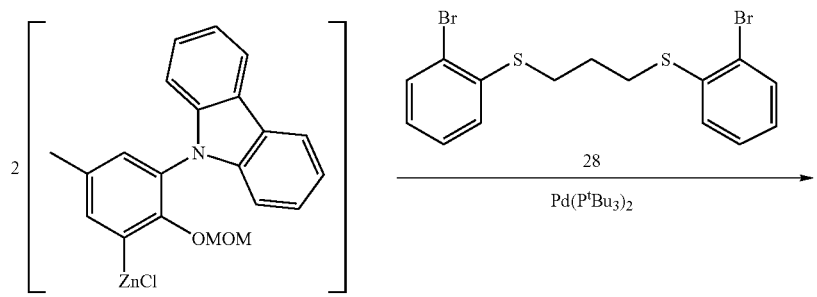
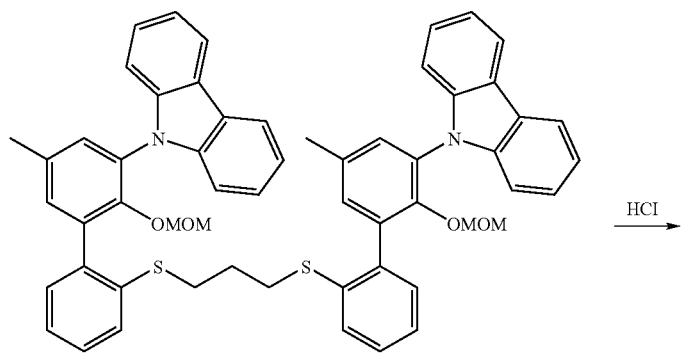
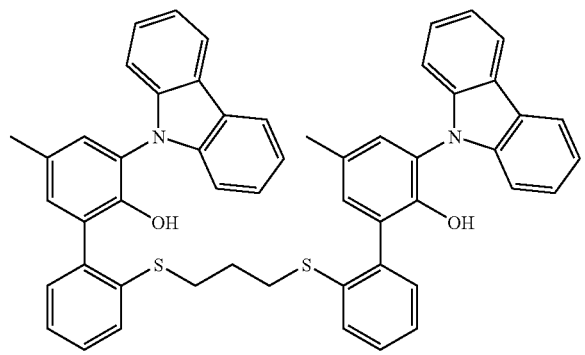

Experimental Details

26

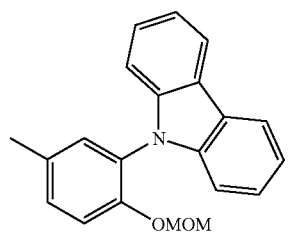

Synthesized by General Method B. Purified by flash chromatography (Biotage FLASH 40S KP-Sil silica, 5% Et$_2$O/hexane) to yield 0.24 g (53%) of 26 as an off-white solid. $^1$H NMR (CD$_2$Cl$_2$, 300 MHz): 8.14 (d, J=6.9 Hz, 2H), 7.39 (dt, J=5.4 Hz, J=0.9 Hz, 2H), 7.32–7.23 (m, 4H), 7.17 (d, J=8.1 Hz, 2H), 4.94 (s, 2H), 3.15 (s, 3H), 2.39 (s, 3H).

28

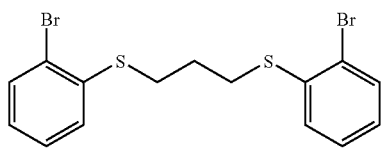

Synthesized by General Method F. $^1$H NMR (CDCl$_3$, 300 MHz): 7.54 (d, J=7.8 Hz, 2H), 7.28–7.22 (m, 4H), 7.07–6.98 (m, 2H), 3.11 (t, J=6.9 Hz, 4H), 2.05 (m, J=6.9 Hz, 2H).

29

Synthesized by General Method H. Purified by flash chromatography (Biotage FLASH 12M KP-Sil silica, 8%–12% Et$_2$O/hexanes) to yield 25 mg (20%) of 29. $^1$H NMR (CDCl$_3$, 300 MHz): 8.11 (t, J=6.9 Hz, 4H), 7.51–7.10 (m, 24H), 4.06 (m, 4H), 3.04 (m, 4H), 2.38 (s, 6H), 2.20 (s, 3H), 2.19 9s, 3H), 1.99 (m, 2H).

30

Synthesized by General Method I. Purified by flash chromatography (Biotage FLASH 12M KP-Sil silica, 7%–10% EtOAc/hexanes) to yield 18 mg (80%) of 30. $^1$H NMR (CD$_2$Cl$_2$, 300 MHz): 8.16 (d, J=7.5 Hz, 4H), 7.45–7.20 (m, 22H), 7.07 (d, J=8.1 Hz, 2H), 2.99 (t, J=7.2 Hz, 4H), 2.37 (s, 6H), 1.93 (m, J=7.2 Hz, 2H).

Example 6

Step 1: Upper-ring Anthracene Coupling

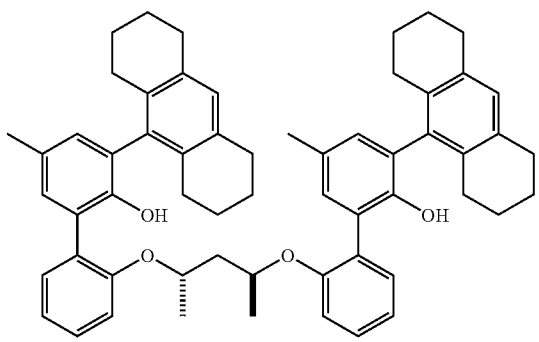

31

Step 2: Anthracene Reduction to Form Upper-Ring Building Block

31

-continued

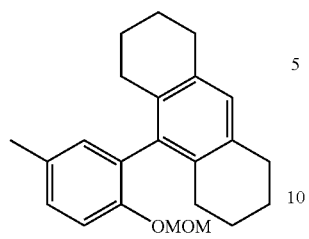

5

32

Step 3: Double Negishi Coupling of Upper and Lower Ring Building Blocks

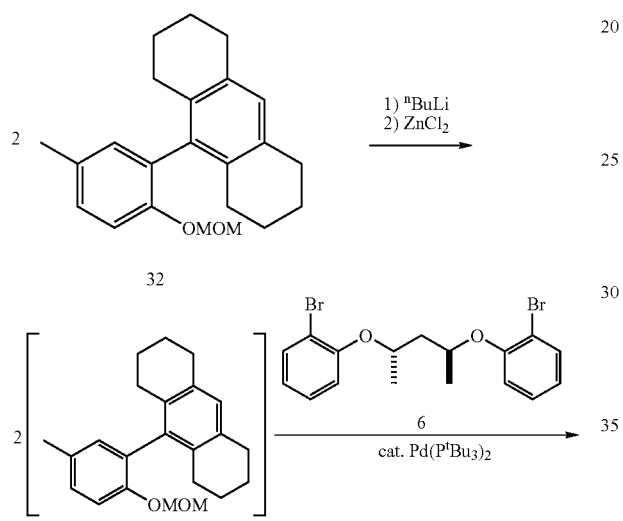

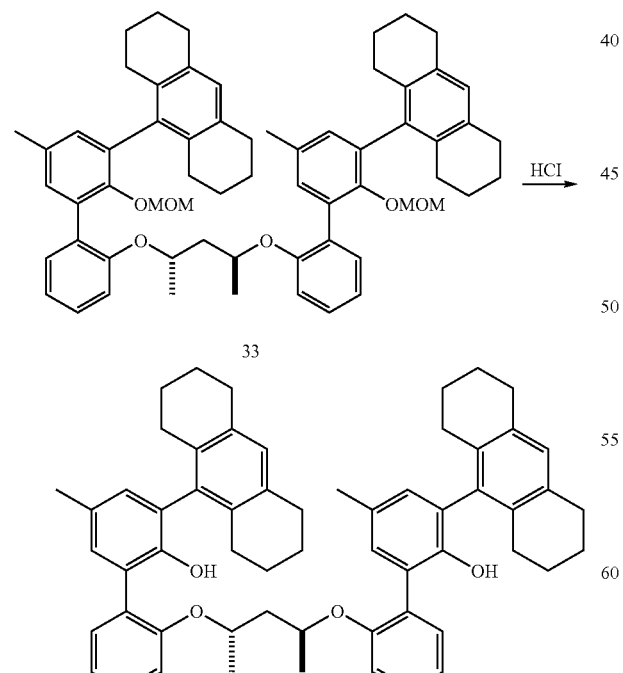

Experimental Details

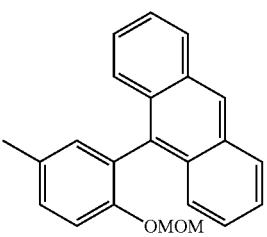

31

Synthesized by General Method C 1. Purified by flash chromatography (Biotage FLASH 40S KP-Sil silica, 0–5% Et$_2$O/hexanes) to yield 0.59 g (84%) of 31 as a white solid. $^1$H NMR (CDCl$_3$, 300 MHz): 8.48 (s, 1H), 8.03 (d, J=8.7 Hz, 2H), 7.65 (dd, J=8.7 Hz, J=0.6 Hz, 2H), 7.50–7.20 (m, 6H), 7.09 (d, J=1.8 Hz, 1H), 4.84 (s, 2H), 3.00 (s, 3H), 2.38 (s, 3H).

32

Synthesized by General Method C2. Purified by flash chromatography (Biotage FLASH 40S KP-Sil silica, 5% Et$_2$O/hexanes) to yield 0.39 g (95%) of 32 as a white solid. $^1$H NMR (CDCl$_3$, 300 MHz): 7.10 (s, 2H), 6.85 (s, 1H), 6.80 (s, 1H), 5.03 (s, 2H), 3.31 (s, 3H), 2.77 (m, 4H), 2.30 (s, 3H), 2.40–2.15 (m, 4H), 1.80–1.60 (m, 8H).

33

Synthesized by General Method H. Purified by flash chromatography (Biotage FLASH 12M KP-Sil silica, 5% Et$_2$O/hexanes) to yield 0.11 g (80%) of 33 as a white solid. $^1$H NMR (CDCl$_3$, 300 MHz): 7.25 (dd, J=7.5 Hz, J=1.5 Hz, 2H), 7.17–7.09 (m, 2H), 6.99 (d, J=1.8 Hz, 2H), 6.93–6.74 (m, 8H), 4.45 (m, 2H), 4.23 (dd, J=11.0 Hz, J=5.7 Hz, 4H), 2.75 (m, 8H), 2.60–2.25 (m, 8H), 2.50 (s, 6H), 2.34 (s, 6H), 1.66 (m, 18H), 1.11 (d, J=5.7 Hz, 6H).

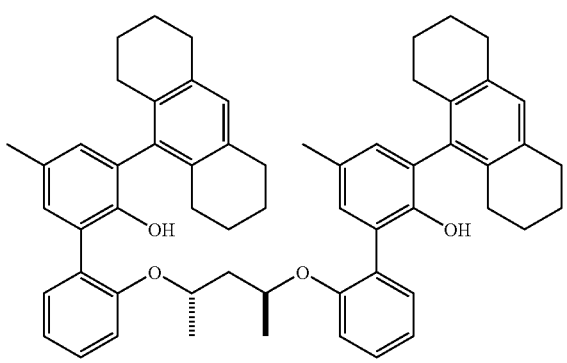
Synthesized by General Method I. Purified by flash chromatography (Biotage FLASH 12M KP-Sil silica, 3–5% EtOAc/hexane) to yield 47 mg (48%) of 34 as a white solid. $^1$H NMR (CDCl$_3$, 300 MHz): 7.34 (dd, J=7.5 Hz, J=1.8 Hz, 2H), 7.20–7.14 (m, 2H), 7.04 (t, J=7.5 Hz, 2H), 6.95 (d, J=1.8 Hz), 6.86 (s, 2H), 6.81 (d, J=1.8 Hz, 2H), 6.70 (d, J=8.1 Hz), 5.96 (s, 2H), 4.43 (m, 2H), 2.77 (m, 8H), 2.45–2.20 (m, 8H), 2.34 (s, 6H), 1.80–1.55 (m, 18H), 1.08 (d, J=6.0 Hz).
Example 7
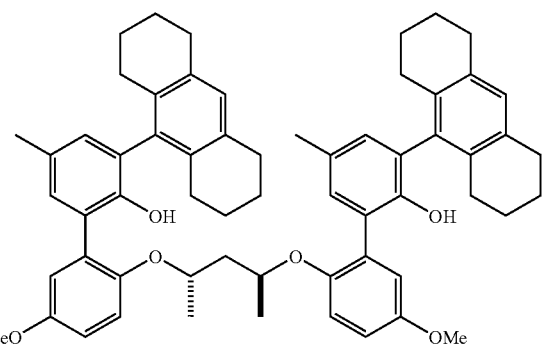
Step 1: Double Negishi Coupling of Upper and Lower Ring
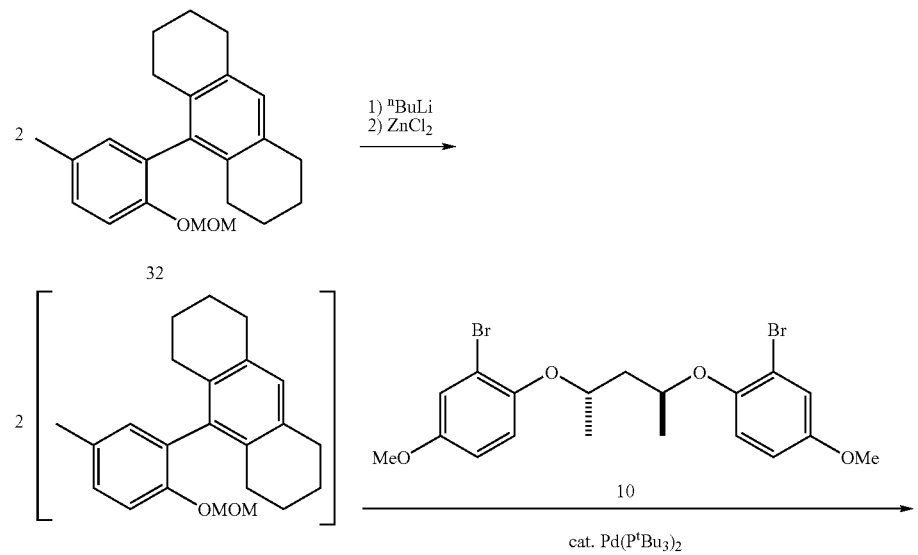
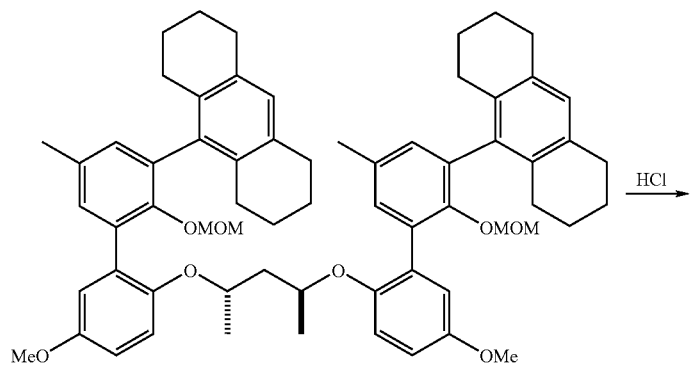

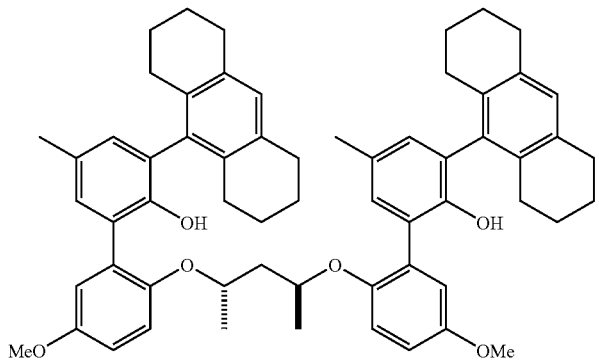

36

Experimental Details

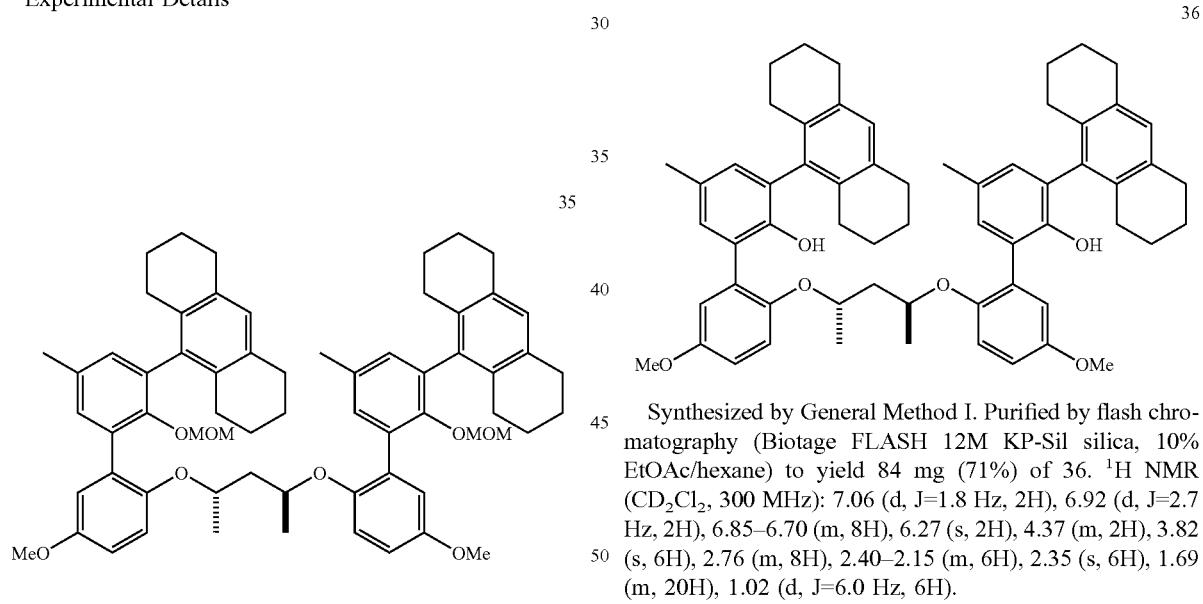

Synthesized by General Method H. Purified by flash chromatography (Biotage FLASH 12M KP-Sil silica, 5–7% EtOAc/hexane) to yield 0.13 g (75%) of the desired product. $^1$H NMR (CDCl$_3$, 300 MHz): 7.00 (d, J=2.1 Hz, 2H), 6.85 (dd, J=7.8 Hz, J=2.7 Hz, 4H), 6.81 (s, 2H), 6.75–6.65 (m, 4H), 4.28 (m, 6H), 3.76 (s, 6H), 2.75 (m, 8H), 2.55 (s, 6H), 2.50–2.30 (m, 6H), 2.33 (s, 6H), 1.64 (m, 20H), 1.02 (d, J=6.0 Hz, 6H).

Synthesized by General Method I. Purified by flash chromatography (Biotage FLASH 12M KP-Sil silica, 10% EtOAc/hexane) to yield 84 mg (71%) of 36. $^1$H NMR (CD$_2$Cl$_2$, 300 MHz): 7.06 (d, J=1.8 Hz, 2H), 6.92 (d, J=2.7 Hz, 2H), 6.85–6.70 (m, 8H), 6.27 (s, 2H), 4.37 (m, 2H), 3.82 (s, 6H), 2.76 (m, 8H), 2.40–2.15 (m, 6H), 2.35 (s, 6H), 1.69 (m, 20H), 1.02 (d, J=6.0 Hz, 6H).

Example 8

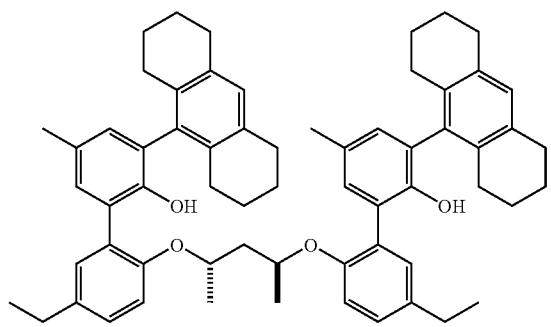

Step 1: Double Negishi Coupling of Upper and Lower Ring Building Blocks
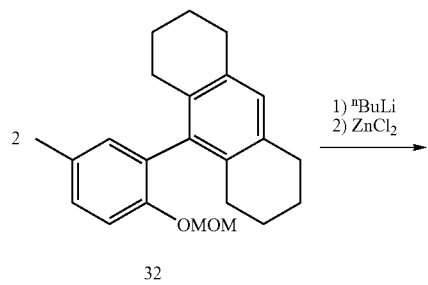
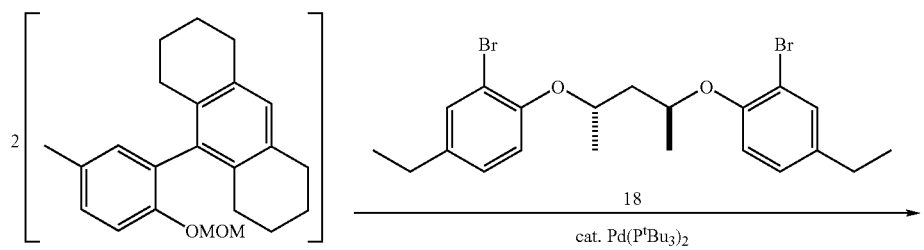
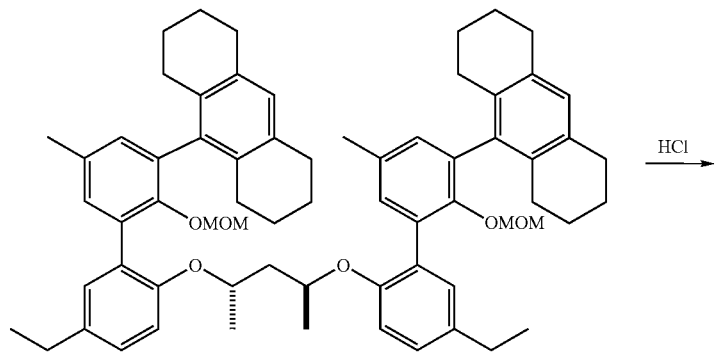
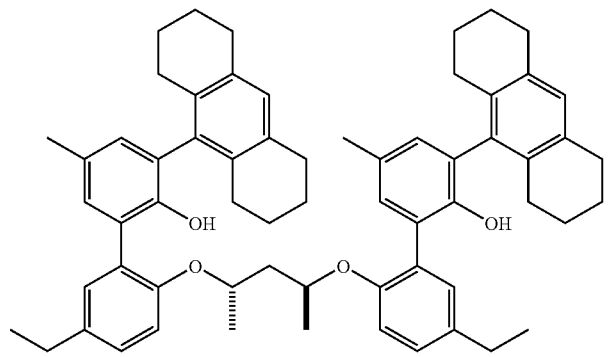

Experimental Details

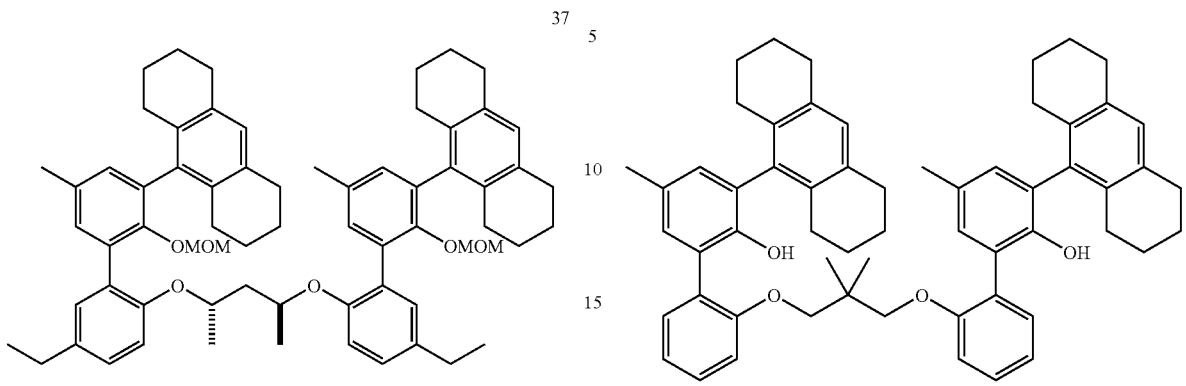

37

Synthesized by General Method H. Purified by flash chromatography (Biotage FLASH 12M KP-Sil silica, 5% Et$_2$O/hexane) to yield 0.12 g of a mixture of the desired product 37, monocoupled material and starting material 32. The material was carried on for deprotection without further attempts at purification. $^1$H NMR (CDCl$_3$, 300 MHz): 7.09 (d, J=2.4 Hz, 2H), 6.99 (d, J=1.8 Hz, 2H), 6.95 (dd, J=8.4 Hz, J=2.4 Hz, 2H), 6.83 (d, J=2.1 Hz, 2H), 6.81 (s, 2H), 6.69 (d, J=8.4 Hz, 2H), 4.39 (m, 2H), 4.26 (m, 4H), 2.60–2.40 (m, 6H), 2.75 (m, 8H), 2.57 (m, J=7.8 Hz, 4H), 2.51 (s, 6H), 2.34 (s, 6H), 1.68 (m, 20H), 1.20 (t, J=7.8 Hz, 6H), 1.07 (d, J=6.0 Hz, 6H).

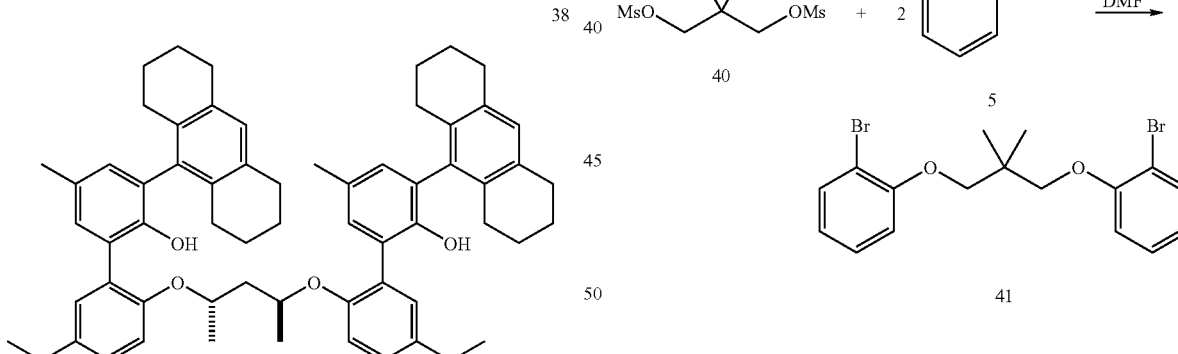

38

Synthesized by General Method I from the mixture of products from the synthesis of 37. Purified by flash chromatography (Biotage FLASH 12M KP-Sil silica, 3–5% EtOAc/hexane) to yield 53 mg (47% over two steps) of the desired product. 7.16 (d, J=2.1 Hz, 2H), 7.03 (dd, J=8.4 Hz, 2.4 Hz, 2H), 7.00 (d, J=1.8 Hz, 2H), 6.82 (s, 2H), 6.77 (d, J=2.1 Hz, 2H), 6.66 (d, J=8.4 Hz, 2H), 6.07 (s, 2H), 4.42 (m, 2H), 2.74 (m, 8H), 2.63 (m, J=7.5Hz, 4H), 2.40–2.15 (m, 6H), 2.34 (s, 6H), 1.70 (m, 20H), 1.24 (t, J=7.5 Hz, 6H), 1.08 (d, J=6.0 Hz, 6H).

Example 9

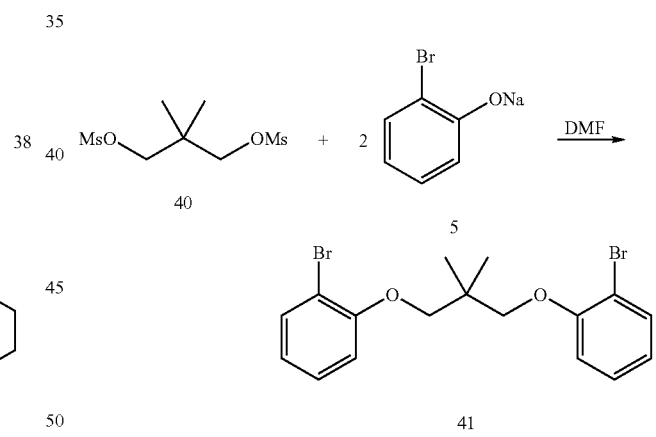

5

Step 1: Synthesis of Bridged Dibromo Lower-ring Building Block

1a: Synthesis of Bridge Bis-mesylate

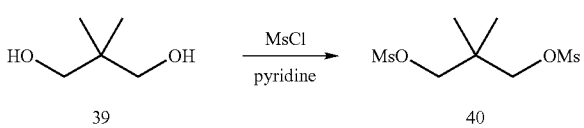

1b: Synthesis of Bridged Dibromo Lower-ring Building Block

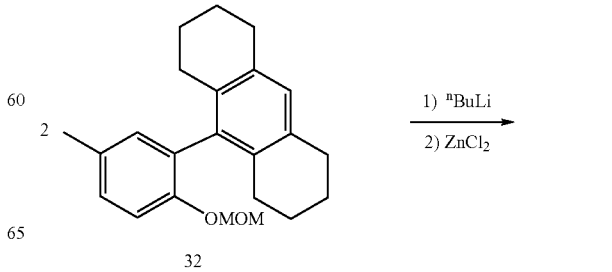

Step 2: Double Negishi Coupling of Upper and Lower Ring Building Blocks

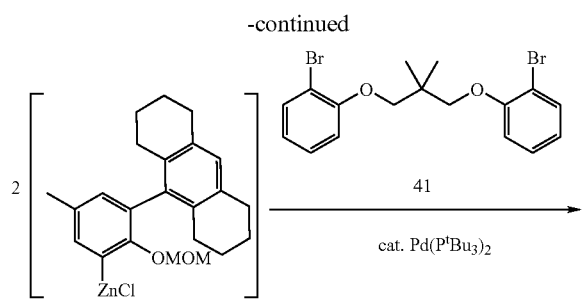

Synthesized by General Method E, Steps E2/E3. Purified by flash chromatography (Biotage FLASH 40S KP-Sil silica, 3% Et$_2$O/hexanes) to yield 0.39 g (82%) of the desired product as a viscous clear oil. $^1$H NMR (CD$_2$Cl$_2$, 300 MHz): 7.50 (dd, J=7.8 Hz, J=1.5 Hz, 2H), 7.26 (dt, J=8.1 Hz, J=1.5 Hz, 2H), 6.95 (dd, J=8.1 Hz, J=1.2 Hz, 2H), 6.82 (dt, J=7.8 Hz, J=1.2 Hz, 2H), 3.98 (s, 4H), 1.25 (s, 6H).

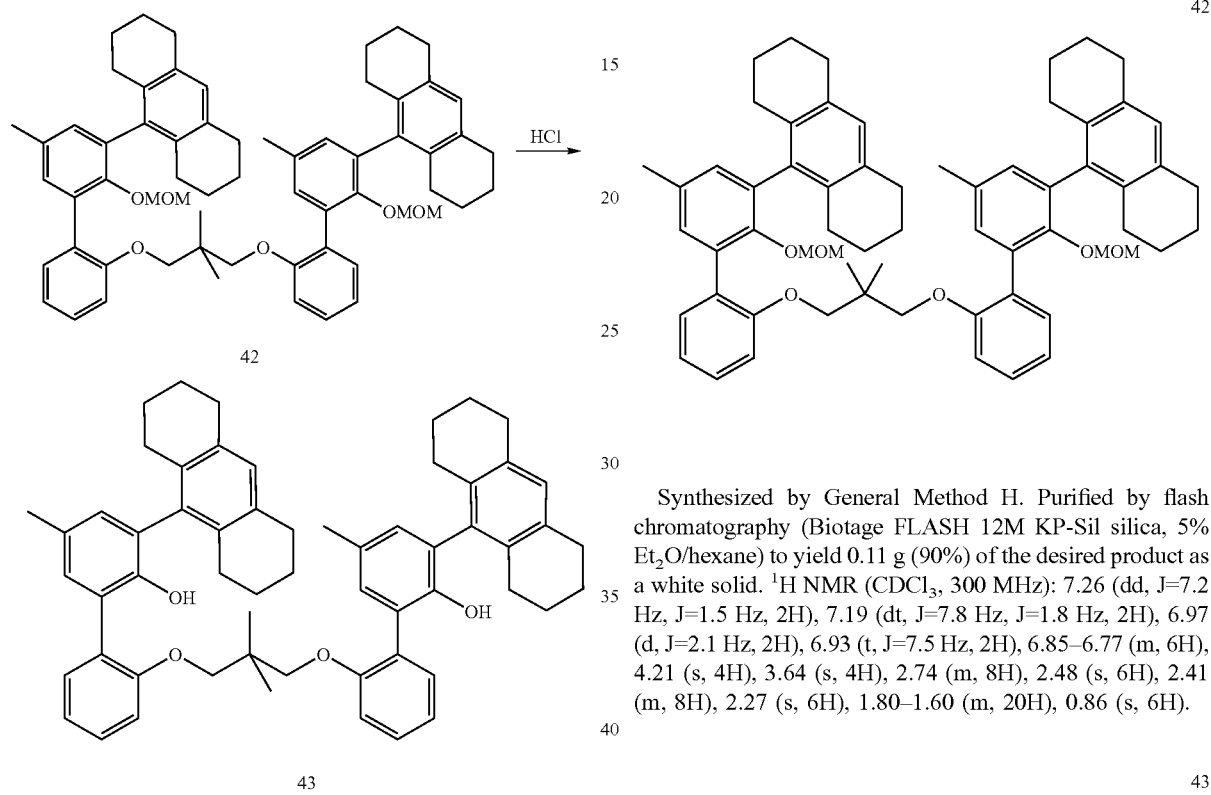

Synthesized by General Method H. Purified by flash chromatography (Biotage FLASH 12M KP-Sil silica, 5% Et$_2$O/hexane) to yield 0.11 g (90%) of the desired product as a white solid. $^1$H NMR (CDCl$_3$, 300 MHz): 7.26 (dd, J=7.2 Hz, J=1.5 Hz, 2H), 7.19 (dt, J=7.8 Hz, J=1.8 Hz, 2H), 6.97 (d, J=2.1 Hz, 2H), 6.93 (t, J=7.5 Hz, 2H), 6.85–6.77 (m, 6H), 4.21 (s, 4H), 3.64 (s, 4H), 2.74 (m, 8H), 2.48 (s, 6H), 2.41 (m, 8H), 2.27 (s, 6H), 1.80–1.60 (m, 20H), 0.86 (s, 6H).

Experimental Details

Synthesized by General Method E, Step E1. Compound 38 (3.3 g, 63%) was isolated as a white solid. $^1$H NMR (CD$_2$Cl$_2$, 300 MHz): 4.01 (s, 4H), 3.04 (s, 6H), 1.07 (s, 6H).

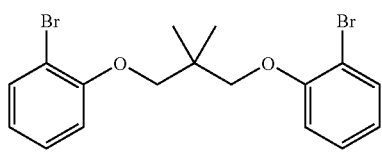

Synthesized by General Method I. Purified by flash chromatography (Biotage FLASH 12M KP-Sil silica, 3% EtOAc/hexane) to yield 63 mg (63%) of the desired product as a white solid. $^1$H NMR (CDCl$_3$, 300 MHz): 7.26 (dd, J=7.2Hz, J=1.8Hz, 2H), 7.09 (dt, J=7.5 Hz, J=1.8 Hz, 2H), 6.97 (t, J=6.6 Hz, 2H), 6.90 (bs, 4H), 6.79 (d, 2.1 Hz, 2H), 6.61 (d, J=7.8 Hz, 2H), 5.08 (s, 2H), 3.69 (s, 4H), 2.78 (m, 8H), 2.40–2.22 (m, 8H), 2.29 (s, 6H), 1.80–1.50 (m, 20H), 0.88 (s, 6H).

Example 10
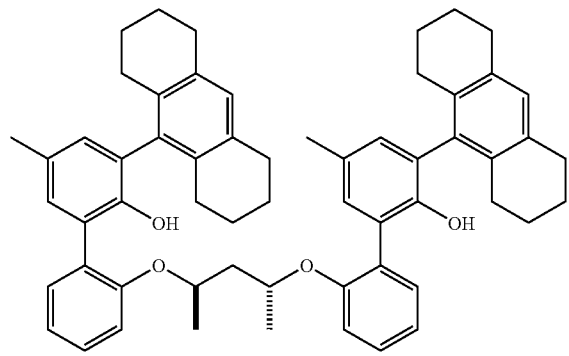
Step 1: Synthesis of Bridged Diiodo Lower-ring Building Block
1a: Synthesis of Bridged Dinito Intermediate
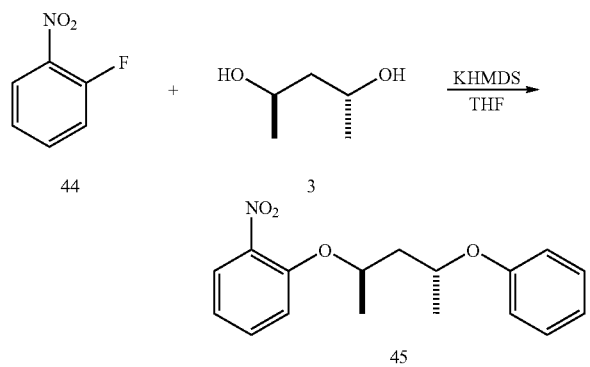
1b: Reduction of Bridge Dinitro Intermediate
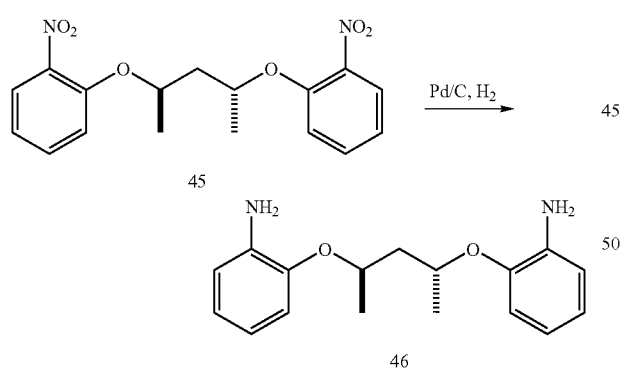
1c: Diazonium Salt Displacement to Form Lower-ring Building Block
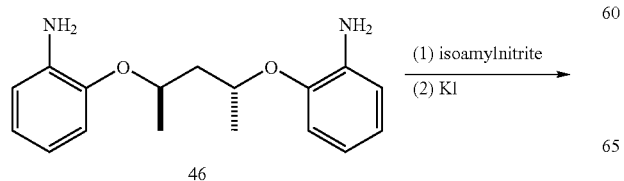
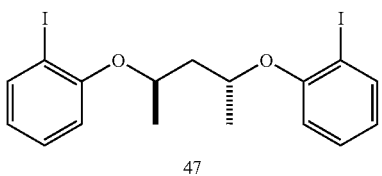
Step 2: Double Negishi Coupling of Upper and Lower Ring Building Blocks
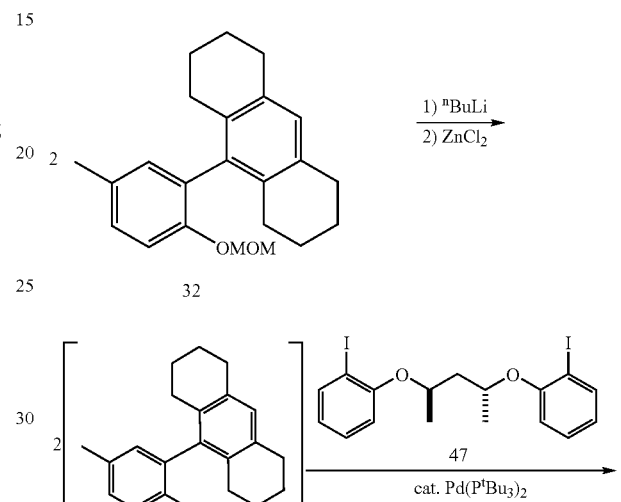
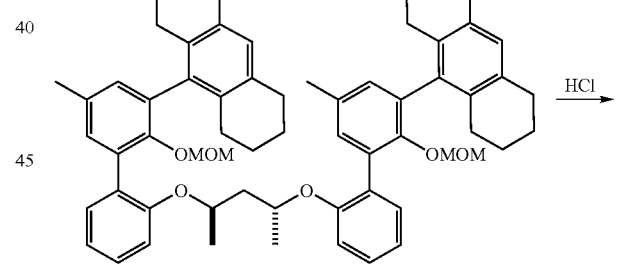
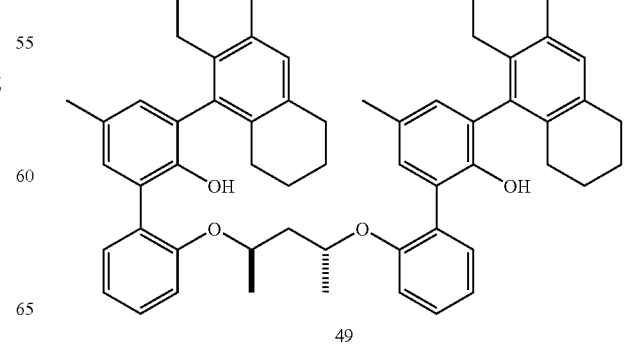

Experimental Details

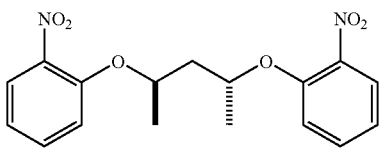

45

Synthesized by General Method G, Step G1. Purified by flash chromatography (Biotage FLASH 40S KP-Sil silica, 12% EtOAc/hexane) to yield 1.4 g (86%) of 9 as a waxy yellow solid. $^1$H NMR (CD$_2$Cl$_2$, 300 MHz): 7.64 (dd, J=8.1 Hz, J=1.8 Hz, 2H), 7.32 (m, 2H), 6.99 (d, J=8.4 Hz, 2H), 6.87 (t, J=7.5 Hz, 2H), 4.91 (m, 2H), 2.07 (m, 2H), 1.37 (d, J=6.0 Hz, 6H).

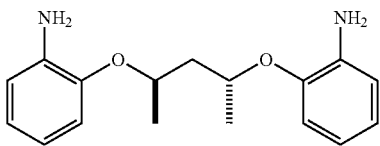

46

Synthesized by General Method G, Step G2. Filtered and concentrated to yield 0.71 g (87%) of 10 as a viscous yellow oil that rapidly turned brown when exposed to air. $^1$H NMR (CD$_2$Cl$_2$, 300 MHz): 6.80–6.68 (m, 6H), 6.67–6.58 (m, 2H), 4.68 (m, 2H), 2.04 (m, 2H), 1.32 (d, J=6.3 Hz, 6H).

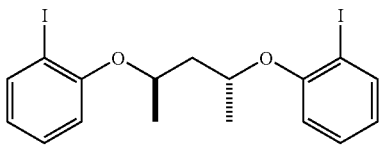

47

Synthesized by General Method G, Step G3. Purified by flash chromatography (Biotage FLASH 40S KP-Sil silica, 3% Et$_2$O/hexane) to yield 0.41 g (69%) of the desired product as a viscous yellow oil. $^1$H NMR (CD$_2$Cl$_2$, 300 MHz): 7.14 (m, 2H), 6.73 (dd, J=8.1 Hz, J=0.9 Hz, 2H), 6.61 (dt, J=7.8 Hz, J=1.5 Hz, 2H), 4.78 (m, 2H), 2.10 (m, 2H), 1.39 (d, J=6.0 Hz, 6H).

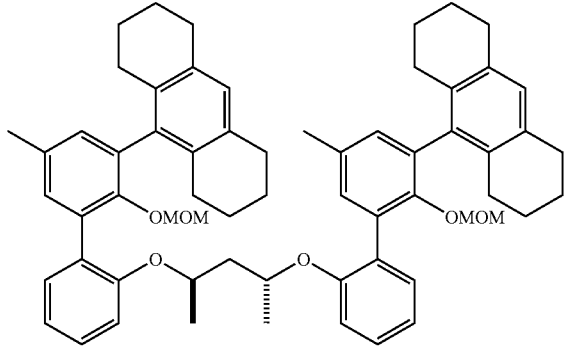

48

Synthesized by General Method H. Purified by flash chromatography (Biotage FLASH 12M KP-Sil silica, 5% Et$_2$O in hexanes) to yield 0.18 g (64%) of the desired product as a white solid. $^1$H NMR (CDCl$_3$, 300 MHz): 7.25 (dd, J=7.5 Hz, J=1.5 Hz, 2H), 7.17–7.09 (m, 2H), 6.99 (d, J=1.8 Hz, 2H), 6.93–6.74 (m, 8H), 4.45 (m, 2H), 4.23 (dd, J=11.0 Hz, J=5.7 Hz, 4H), 2.75 (m, 8H), 2.60–2.25 (m, 8H), 2.50 (s, 6H), 2.34 (s, 6H), 1.66 (m, 18H), 1.11 (d, J=5.7 Hz, 6H).

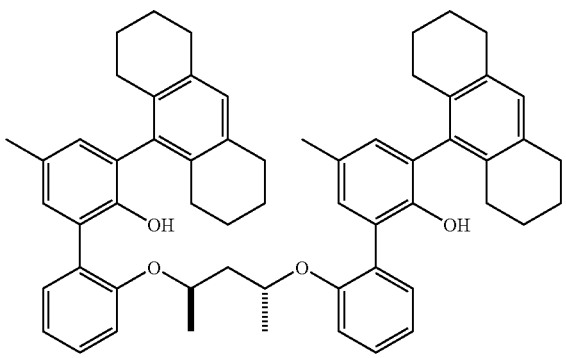

49

Synthesized by General Method I. Purified by flash chromatography (Biotage FLASH 12M KP-Sil silica, 3–5% EtOAc in hexane) to yield 0.14 g (88%) of the desired product as a white solid. $^1$H NMR (CDCl$_3$, 300 MHz): 7.34 (dd, J=7.5 Hz, J=1.8 Hz, 2H), 7.20–7.14 (m, 2H), 7.04 (t, J=7.5 Hz, 2H), 6.95 (d, J=1.8 Hz), 6.86 (s, 2H), 6.81 (d, J=1.8 Hz, 2H), 6.70 (d, J=8.1 Hz), 5.96 (s, 2H), 4.43 (m, 2H), 2.77 (m, 8H), 2.45–2.20 (m, 8H), 2.34 (s, 6H), 1.80–1.55 (m, 18H), 1.08 (d, J=6.0 Hz).

II. Polymerization Reactions

In the following sections, "Me" refers to methyl, "Et" refers to ethyl, and "Bz" refers to benzyl. The examples described below were performed under a purified argon or nitrogen atmosphere in a Vacuum Atmospheres or MBraun glove box at ambient (room) temperature, except where otherwise stated. MBz$_4$ (M=Hf, Zr) was purchased from StremChemicals, Inc. in Newburyport, Mass., U.S.A. [MBz$_3$][BzB(C$_6$F$_5$)$_3$] (M=Hf, Zr) were synthesized as described in Pellecchia et al., *Organometallics* 1994, 13, 298–302; Pellecchia et al., *J. Am. Chem. Soc.* 1993, 115, 1160–1162; Pellecchia et al., *Organometallics* 1993, 13, 3773–3775 and Bochmann et al., *Organometallics* 1993, 12, 633–640, each of which is incorporated herein by reference. HfCl$_2$Bz$_2$(Et$_2$O) was synthesized by reacting HfBz$_4$ and HfCl$_4$ in a mole ratio of 1.04:1.00 in diethyl ether (0.133 M solution in Hafnium) for 4–5 hours at room temperature. The solution was concentrated to aproximately 20 vol% and placed in freezer at −30° C. The yellow solid product was isolated from the supernatant solution and dried in vacuum to constant weight. The number of coordinating diethyl ether moieties was determined by proton NMR. $^1$H NMR (C$_6$D$_6$, 300 MHz): 7.40 (d), 7.08 (t), 6.82 (t), 3.06 (q), 2.77 (s), 0.77 (t). ZrCl$_2$BZ$_2$(Et$_2$O) was synthesized analogous to HfCl$_2$Bz$_2$(Et$_2$O) outlined above. $^1$H NMR (C$_6$D$_6$, 300 MHz): 7.32 (d), 7.09 (t), 6.90 (t), 3.24 (q), 2.65 (s), 0.81 (t). Complexes used in some of the examples are shown below:

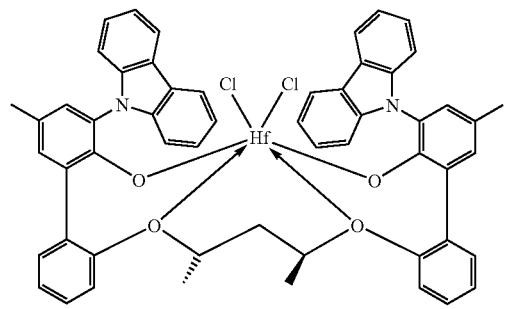
C10
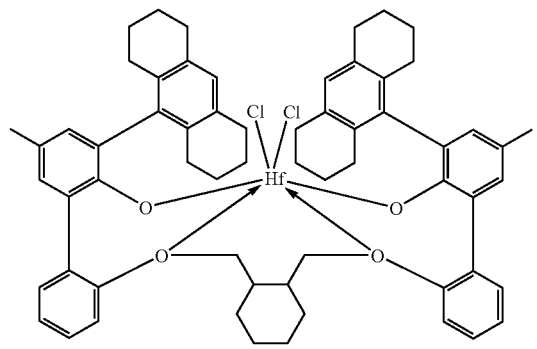
C11
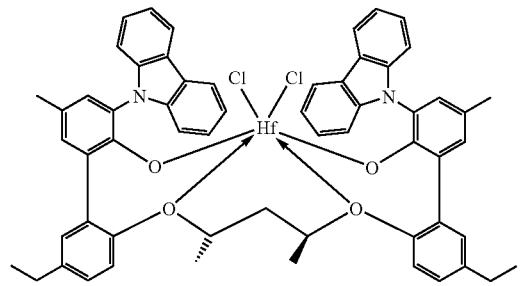
C12
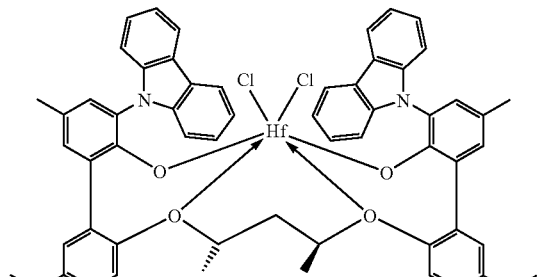
C13
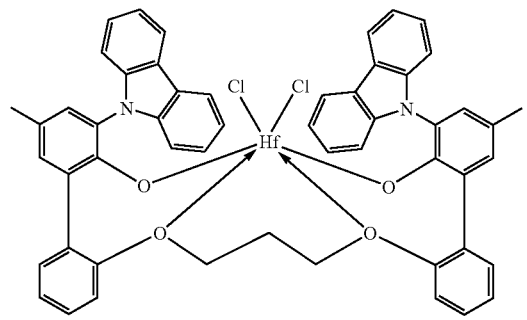
C14
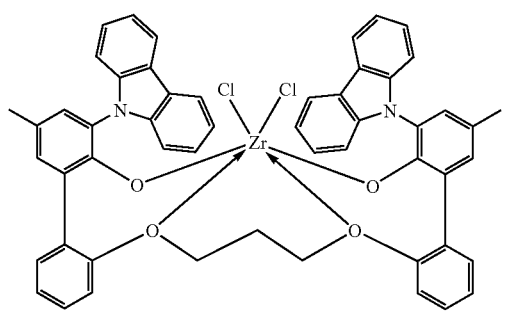
C15
C16
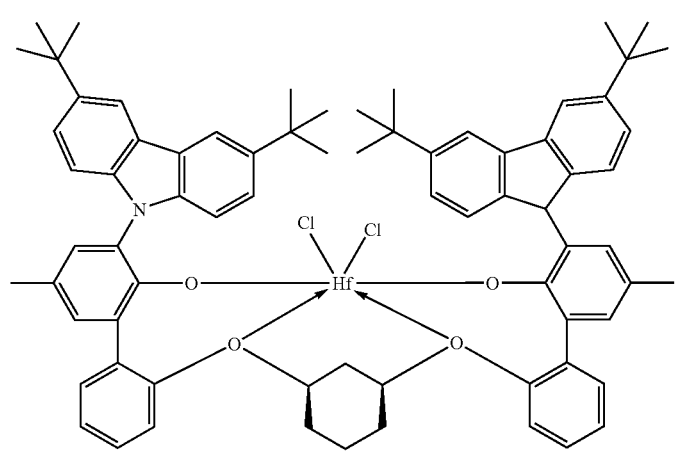

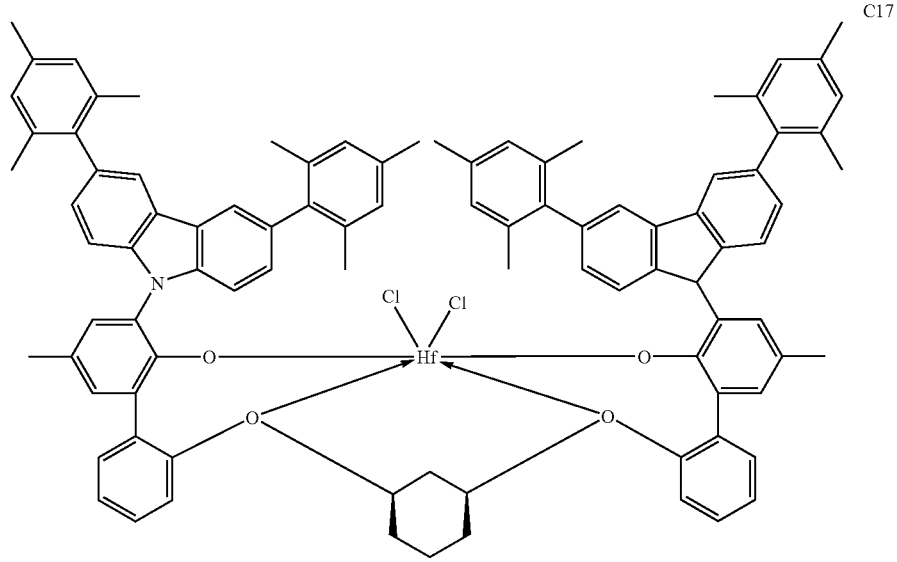

C17

Example 11

Synthesis of C10

30.6 mg (38.3 μmol) of the ligand LL129 was dissolved in 1.8 mL toluene. 1.910 mL of a 20 mM solution of HfCl$_2$BZ$_2$(Et$_2$O) in toluene was added. The reaction mixture was placed on a hotplate (80° C.) for 1.5 hours. The reaction mixture was concentrated and placed in freezer (−30° C.) over night. Crystalline material was obtained. A part of the crystalline material was set aside for x-ray analysis and another part was recrystallized from toluene. Single crystal x-ray diffraction analysis confirmed the molecular structure, and also confirmed the approximate C2 symmetry of the complex excluding the bridge. Total yield 22 mg (55%) 1H-NMR in C$_6$D$_6$/CD$_2$Cl$_2$ (80:20 by volume, ref. to C$_6$D$_5$H=7.15 ppm): δ (ppm)=8.26 (d), 8.10 (d), 7.6–6.6 (m), 5.15 (d), 4.81 (d), 4.22 (m, broad), 3.70 (m, broad). 2.15 (s), 1.20 (m), 1.01 (m), 0.75 (m), 0.66 (m), 0.29 (d), 0.17 (d).

Example 12

Synthesis of C11

36.3 mg (41.4 μmol) of the a racemic mixture of LL137 and LL 179 was dissolved in 1.0 mL toluene. 20.9 mg (41.4 μmol) of HfCl$_2$Bz$_2$(Et$_2$O) was dissolved in 1.0 mL toluene. The metal solution was added to the ligand solution. The reaction mixture was placed on a hotplate (80° C.) for 1 hour. The reaction mixture was concentrated and placed in freezer (−30° C.) over night. No crystalline material was formed. The reaction mixture was dried. A part of the crystalline material was set aside and another part was recrystallized from ca. 600 μl toluene. 1H-NMR in C$_6$D$_6$/CD$_2$Cl$_2$ (80:20 by volume, ref to C$_6$D$_5$H=7.15 ppm): δ (ppm)=7.5–7.0 (m), 6.36 (d), 6.30 (d), 4.87 (m), 4.27 (d), 3.30 (m), 3.1–0.2 (m), 2.23 (s), 2.20 (s).

Example 13

Synthesis of C12

34.8 mg (40.7 μmol) of the ligand LL147 was dissolved in 9 mL toluene. 20.6 mg of HfCl$_2$Bz$_2$(Et$_2$O) in 5 mL toluene was added. The reaction mixture was placed in a sandbath (80° C.) for 2 hours. The reaction mixture was concentrated to 2 mL and placed in freezer (−30° C.) over night. Crystalline material was obtained. Yield: 25 mg (56%). NMR in CD$_2$Cl$_2$ ref to C$_2$HDCl$_2$=5.32 ppm): δ (ppm)=8.33 (m), 8.15 (m), 7.8–7.0 (m), 6.55 (m), 4.84 (d), 4.51 (d), 4.41 (m), 4.10 (m), 2.61 (q), 2.41 (s), 2.39 (s), 1.71 (m), 1.38 (m), 1.23 (t), 0.97 (m), 0.68 (d), 0.55 (d).

Example 14

Synthesis of C13

61.5 mg (71.6 μmol) of the ligand LL132 was dissolved in 12 mL toluene. 37.9 mg of HfCl$_2$Bz$_2$(Et$_2$O) in 5 mL toluene was added. The reaction mixture was placed into a sandbath (80° C.) for 1 hour. The reaction mixture was concentrated and placed in freezer (−30° C.) over night. Crystalline material was obtained. Yield: 32 mg (40%). NMR in CD$_2$Cl$_2$ ref to C$_2$HDCl$_2$=5.33 ppm): δ (ppm)=8.32 (m), 8.14 (m), 7.6–6.7 (m), 6.23 (m), 4.86 (d), 4.50 (d), 4.34 (m), 4.05 (m), 3.79 (s), 2.41 (s), 2.39 (s), 1.69 (m), 1.30 (m), 0.90 (m), 0.66 (d), 0.53 (d).

Example 15

Synthesis of C14

158.5 mg (206 μmol) of the ligand LL5 (prepared as described in WO 03/091262) was dissolved in 5 mL toluene. 118 mg (217 μmol) of HfBz$_2$Cl$_2$(Et$_2$O)$_{1.5}$ were dissolved in 15 mL toluene, filtered and added to the ligand solution. The reaction mixture was heated to 90° C. and stirred for 1 hour. The reaction mixture was allowed to cool to room temperature and was concentrated to 50% of initial volume. A white precipitate formed from the yellow solution. The reaction mixture is centrifuged and the supernatant solution is removed. The white precipitate is dried under vacuum. Yield 144 mg. A second crop of white precipitate formed from the supernatant solution in the freezer, yielding another 23 mg. Total yield: 78%. NMR in CD$_2$Cl$_2$ ref to C$_2$HDCl$_2$=5.32 ppm): δ (ppm)=8.36 (d) 8.12 (d), 7.7–7.0 (m), 6.75 (t), 4.61 (d), 4.20 (m), 3.70 (m), 2.40 (s), 1.71 (m).

Example 16

Synthesis of C15

70.5 mg (91.56 µmol) of the ligand LL5 was dissolved in 5 mL toluene. 38.4 mg (91.6 µmol) of ZrBz$_2$Cl$_2$(Et$_2$O) were dissolved in 4 mL toluene and added to the ligand solution. The reaction mixture was heated to 80° C. and stirred for 45 min. The reaction mixture was allowed to cool to room temperature and was concentrated to 50% of initial volume. A white precipitate formed from the yellow solution. The reaction mixture is centrifuged and the supernatant solution is removed. The white precipitate is washed with 4 mL toluene and is dried under vacuum. Yield: 53 mg. A second crop of white precipitate formed from the combined supernatant and wash solution in the freezer, yielding another 18 mg. Total yield: 78%. NMR in CD$_2$Cl$_2$ ref to C$_2$HDCl$_2$=5.32 ppm: δ (ppm)=8.36 (d), 8.12 (d), 7.7–7.0 (m), 6.75 (t), 4.61 (d), 4.17 (m), 3.68 (m), 2.40 (s), 1.69 (m).

Example 17

Synthesis of C16

26 mg (25.1 µmol) of the ligand LL193 was dissolved in 3 mL toluene. 13 mg (25.2 µmol) of HfBz$_2$Cl$_2$(Et$_2$O) were dissolved in 3 mL toluene and added to the ligand allowed to cool to room temperature and was concentrated to ca. 1 mL. 1 mL pentane was added and the reaction mixture was cooled to −30° C. over night. The supernatant solution was removed and the white precipitate was dried under vacuum. Yield: 25 mg (78%). NMR in CD$_2$Cl$_2$ ref to C$_2$HDCl$_2$=5.32 ppm: δ (ppm)=8.36 (d), 8.12 (d), 7.6–6.9 (m), 6.5 (t), 5.03 (d), 4.90 (d), 3.9 (m), 2.58 (m), 2.40 (d), 1.75 (m), 1.51 (s), 1.50 (s), 1.40 (s), 1.36 (s), 1.10 (m).

Example 18

Synthesis of C17

31 mg (24.1 µmol) of the ligand LL194 was dissolved in 3 mL toluene. 12.5 mg (24.3 µmol) of HfBz$_2$Cl$_2$(Et$_2$O) were dissolved in 3 mL toluene and added to the ligand solution. The reaction mixture was heated to 95° C. for 1 h. The reaction mixture was allowed to cool to room temperature and was concentrated to ca. 0.20 mL. 1 mL pentane was added and the reaction mixture was cooled to −30° C. over night. The supernatant solution was removed and the pale brown precipitate was dried under vacuum. Yield: 30 mg (81%). NMR in CD$_2$Cl$_2$ ref to C$_2$HDCl$_2$=5.32 ppm: δ (ppm)=8.09 (d), 7.82 (d), 7.6–6.8 (m), 6.7 (t), 5.48 (d), 5.20 (d), 3.96 (m), 2.68 (m), 2.43 (m), 2.28 (s), 2.12 (d), 2.04 (s), 1.99 (s), 1.95 (s), 1.85 (s), 1.78 (s), 1.7–1.5 (m), 1.3–1.0 (m).

Example 19

Propylene Polymerizations Using Metal-Ligand Compositions

A total of 41 separate polymerization reactions were performed as follows.

Preparation of the polymerization reactor prior to injection of catalyst composition: A pre-weighed glass vial insert and disposable stirring paddle were fitted to each reaction vessel of the reactor. The reactor was then closed, 0.200 mL of a 0.05 M solution of Modified Methylaluminoxane 3A (from Azko Chemical Inc., Chicago, Ill.) ("MMAO") in toluene and 3.8 mL of toluene were injected into each pressure reaction vessel through a valve. The temperature was then set to the appropriate setting (with specific temperatures for each polymerization being listed in Table 3, below), and the stirring speed was set to 800 rpm, and the mixture was exposed to propylene at 100 psi pressure. A propylene pressure of 100 psi in the pressure cell and the temperature setting were maintained, using computer control, until the end of the polymerization experiment.

In situ preparation of metal-ligand compositions: The following methods were employed to prepare the metal-ligand compositions as indicated in the Table 3. Method A: 50 µl of the ligand solution (10 mM in toluene) was dispensed in a 1 mL glass vial. To the 1 mL glass vial containing the ligand solution was added an equimolar amount of metal precursor solution (10 mM in toluene) to form the metal-ligand composition solution. The reaction mixture was heated to 60° C. for 1 hour. Method B: 100 µL of a ligand solution (5mM in toluene/1,2-dichloroethane 50:50 vol%) was dispensed in a 1 mL glass vial at a scale of 0.5 mmol. The solvent was removed. To the 1 mL glass vial containing the ligand was added 50 µl toluene and an equimolar amount of metal precursor solution (5 mM in toluene) to form the metal-ligand composition solution. The reaction mixture was heated to 60° C. for 1 hour. Method C: Similar to Method A except that the metal-ligand composition solution was heated to 80° C. for 1 hour. Method D: Similar to Method A except the metal precursor solution was 5 mM. Method E: Similar to Method B except the metal precursor solution was 10 mM and the reaction mixture was heated to 80° C. for 1 hour. Method F: Similar to Method B except the concentration of the metal precursor solution was 10 mM. Method G: 80 µl of the ligand solution (5 mM in toluene) was dispensed in a 1 mL glass vial. To the 1 mL glass vial containing the ligand solution was added an equimolar amount of metal precursor solution (5 mM in toluene) to form the metal-ligand composition solution. The reaction mixture was heated to 60° C. for 1 hour. Method H: 60 µL of the ligand solution (5 mM in toluene) was dispensed in a 1 mL glass vial. To the 1 mL glass vial containing the ligand solution was added an equimolar amount of metal precursor solution (10 mM in toluene) to form the metal-ligand composition solution. The reaction mixture was heated to 60° C. for 1 hour. Method I: Similar to Method H except the concentration of the metal precursor solution was 5 mM and the reaction mixture was heated to 80° C. Method K: 80 µL of the ligand solution (5 mM in toluene) was dispensed in a 1 mL glass vial. To the 1 mL glass vial containing the ligand solution was added an equimolar amount of metal precursor solution (10 mM in toluene) to form the metal-ligand composition solution. The reaction mixture was heated to 70° C. for 1 hour. Method L: Similar to Method K except the metal precursor solution was 5 mM.

Preparation of the group 13 reagent and activator stock solutions: The "activator solution" is a solution of N,N'-dimethylanilinium tetrakis (pentafluorophenyl) borate ("ABF$_{20}$") in toluene. The molarity of this solution is indicated in the "activation method" of the individual example described below. The solution is heated to approximately 85° C. to dissolve the reagent. The "group 13 reagent" solution is either a solution of triisobutyl aluminium ("TIBA") or a solution of diisobutyl aluminium hydride ("DIBAL") or a solution of Modified Methylaluminoxane 3A (from Azko Chemical Inc., Chicago, Ill.) ("MMAO"), all "group 13 reagent" solutions were solutions in toluene. The molarity of the solutions used is indicated in the "activation method" of the individual example described below.

Activation methods and Injection of solutions into the pressure reactor vessel: The following methods were employed to activate and inject the metal-ligand compositions for the examples in the Table 3. Method AA: To the metal-ligand composition, the appropriate amount of the group 13 reagent solution as a 50 mM solution, containing the indicated equivalents group 13 reagent (per metal precursor) in the specific example, was added to the 1 mL vial. After 45 sec, 1.1 mol equivalents (per metal precursor) of the "activator solution" (2.5 mM) was added to the 1 mL vial and the reaction mixture was mixed. About another 30 seconds later, a fraction of the 1 mL vial contents corresponding to the indicated "catalyst amount injected", based on nanomoles (nmol) of metal precursor, was injected into the prepressurized reaction vessel and was followed immediately by injection of toluene to bring the total volume injected to 0.500 mL. Method BB: To the metal-ligand composition, the appropriate amount of the group 13 reagent solution as a 200 mM solution, containing the indicated equivalents group 13 reagent (per metal precursor) in the specific example, was added to the 1 mL vial. After about 11 min, 220 μL of the activator solution in toluene (2.5 mM) was added to the 1 mL vial followed by 500 μL toluene and the reaction mixture was mixed. About another 90 seconds later a fraction of the total 1 mL vial contents containing the indicated "catalyst amount injected", based on nanomoles (nmol) of metal precursor, was injected into the pre-pressurized reaction vessel and was followed immediately by injection of toluene to increase the total volume injected of 0.500 mL. Method CC: To the metal-ligand composition, the appropriate amount of the group 13 reagent solution as a 50 mM solution, containing the indicated equivalents group 13 reagent (per metal precursor) in the specific example, was added to the 1 mL vial followed by 300 μL toluene. After about 45 sec, 1.1 mol equivalents (per metal precursor) of the "activator solution" (2.5 mM) was added to the 1 mL vial followed by 300 μL toluene and the reaction mixture was mixed. About another 30 seconds later, a fraction of the 1 mL vial contents corresponding to the indicated "catalyst amount injected", based on nanomoles (nmol) of metal precursor, was injected into the prepressurized reaction vessel and was followed immediately by injection of toluene to bring the total volume injected to 0.500 mL. Method DD: Similar to method CC except 150 μL toluene (instead of 300 μL toluene) were added after each the group 13 reagent and the activator additon. Method EE: 75 μL of a 0.200M solution of the group 13 reagent was added to a 1 mL vial containing the ligand-metal composition solution. After about 11 min, 220 μL of the activator solution in toluene (2.5 mM) was added to the 1 mL and the reaction mixture was mixed. About another 90 seconds later a fraction of the total 1 mL vial contents containing the indicated "catalyst amount injected", based on nanomoles (nmol) of metal precursor, was injected into the pre-pressurized reaction vessel and was followed immediately by injection of toluene to increase the total volume injected of 0.500 mL. Method FF: Similar to method CC except 100 μL toluene (instead of 300 μL toluene) were added after each the group 13 reagent and the activator additon. Method GG: Similar to method CC except 50 μL toluene (instead of 300 μL toluene) were added after each the group 13 reagent and the activator additon. Method HH: Similar to method BB except 700 μL toluene (instead of 500 μL toluene) were added after the activator additon. Method II: Similar to method CC except 400 μL toluene (instead of 300 μL toluene) were added after each the group 13 reagent and the activator additon. Method KK: Similar to method BB except 600 μL toluene (instead of 500 μL toluene) was added after the activator additon. Method LL: Similar to method BB except 800 μL toluene (instead of 500 μL toluene) was added after the activator additon.

Polymerization: The polymerization reaction was allowed to continue for 60–900 seconds, during which time the temperature and pressure were maintained at their pre-set levels by computer control. The specific polymerization times for each polymerization are shown in Table 3. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Product work up: Propylene Polymerizations: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and by FTIR spectroscopy to determine the crystallinity index. The melting point of selected samples was measured by DSC, as described above.

TABLE 3

| Example | Ligand | Metal precursor | complexation method | Group 13 reagent and mole equiv. | Activator and mol equiv. | activation method | catalyst amount injected (nmol) | Polym. temp. (Celsius) | Polym. time (sec) | Activity (g polymer/ (min* mmol) | FTIR index | Mp DSC data (Celsius) | Mw (/1000) | PDI (Mw/Mn) |
|---|---|---|---|---|---|---|---|---|---|---|---|---|---|---|
| 19.1 | LL109 | HfBz$_4$ | A | 6 MMAO | 1.1 ABF$_{20}$ | AA | 60 | 110 | 60 | 3592 | 0.78 | | 2 | 1.2[a] |
| 19.2 | LL109 | ZrBz$_4$ | A | 6 MMAO | 1.1 ABF$_{20}$ | AA | 100 | 110 | 726 | 54 | 0.30 | | 1 | 1.1[b] |
| 19.3 | LL111 | [HfBz$_3$] [BzB(C$_6$F$_5$)$_3$] | B | 6 MMAO | 1.1 ABF$_{20}$ | AA | 100 | 110 | 329 | 160 | 0.41 | | 1 | 1.1[c] |
| 19.4 | LL118 | HfCl$_2$Bz$_2$ (Et$_2$O) | C | 30 DIBAL | 1.1 ABF$_{20}$ | BB | 20 | 110 | 133 | 3764 | 0.90 | 134 | 117 | 1.7 |

TABLE 3-continued

| Example | Ligand | Metal precursor | complexation method | Group 13 reagent and mole equiv. | Activator and mol equiv. | activation method | catalyst amount injected (nmol) | Polym. temp. (Celsius) | Polym. time (sec) | Activity (g polymer/ (min* mmol) | FTIR index | Mp DSC data (Celsius) | Mw (/1000) | PDI (Mw/Mn) |
|---|---|---|---|---|---|---|---|---|---|---|---|---|---|---|
| 19.5 | LL118 | HfCl$_2$Bz$_2$(Et$_2$O) | C | 30 TIBA | 1.1 ABF$_{20}$ | BB | 20 | 110 | 62 | 9853 | 0.90 | 133 | 104 | 1.7 |
| 19.6 | LL119 | [HfBz$_3$][BzB(C$_6$F$_5$)$_3$] | B | 6 DIBAL | 1.1 ABF$_{20}$ | CC | 20 | 110 | 175 | 4557 | 0.93 | 131 | 62 | 1.5 |
| 19.7 | LL119 | HfCl$_2$Bz$_2$(Et$_2$O) | E | 30 TIBA | 1.1 ABF$_{20}$ | BB | 20 | 110 | 65 | 8963 | 0.89 | | 57 | 1.7 |
| 19.8 | LL121 + LL170 | HfBz$_4$ | A | 6 DIBAL | 1.1 ABF$_{20}$ | AA | 60 | 110 | 200 | 1251 | 0.90 | 143 | 690 | 2.2) |
| 19.9 | LL121 + LL170 | [HfBz$_3$][BzB(C$_6$F$_5$)$_3$] | B | 6 MMAO | 1.1 ABF$_{20}$ | EE | 60 | 110 | 81 | 3612 | 0.90 | | 500 | 2.5 |
| 19.10 | LL117 | HfCl$_2$Bz$_2$(Et$_2$O) | C | 6 TIBA | 1.1 ABF$_{20}$ | BB | 20 | 110 | 171 | 3586 | 0.93 | 122 | 440 | 1.9 |
| 19.11 | LL117 | [HfBz$_3$][BzB(C$_6$F$_5$)$_3$] | D | 6 MMAO | 1.1 ABF$_{20}$ | CC | 20 | 110 | 500 | 794 | 0.83 | 115 | 658 | 1.7 |
| 19.12 | LL116 | HfCl$_2$Bz$_2$(Et$_2$O) | E | 30 TIBA | 1.1 ABF$_{20}$ | EE | 60 | 110 | 254 | 1500 | 0.91 | | 605 | 1.9 |
| 19.13 | LL116 | HfBz$_4$ | F | 6 MMAO | 1.1 ABF$_{20}$ | AA | 60 | 110 | 351 | 520 | 0.93 | 144 | 920 | 1.6 |
| 19.14 | LL138 | HfCl$_2$Bz$_2$(Et$_2$O) | C | 30 TIBA | 1.1 ABF$_{20}$ | BB | 20 | 110 | 352 | 1180 | 0.92 | 153 | 59 | 2.1 |
| 19.15 | LL138 | ZrCl$_2$Bz$_2$(Et$_2$O) | C | 30 TIBA | 1.1 ABF$_{20}$ | BB | 20 | 110 | 172 | 2620 | 0.95 | 140 | 10 | 2.3 |
| 19.16 | LL129 | HfBz$_4$ | A | 6 MMAO | 1.1 ABF$_{20}$ | AA | 60 | 110 | 235 | 1007 | 0.94 | 152 | 518 | 4.1 |
| 19.17 | LL129 | [HfBz$_3$][BzB(C$_6$F$_5$)$_3$] | D | 6 MMAO | 1.1 ABF$_{20}$ | FF | 40 | 110 | 199 | 1590 | 0.92 | 149 | 384 | 4.3 |
| 19.18 | LL129 | [ZrBz$_3$][BzB(C$_6$F$_5$)$_3$] | D | 6 MMAO | 1.1 ABF$_{20}$ | FF | 40 | 110 | 234 | 1440 | 0.85 | 129 | 287 | 2.1 |
| 19.19 | LL139 | [HfBz$_3$][BzB(C$_6$F$_5$)$_3$] | D | 6 MMAO | 1.1 ABF$_{20}$ | CC | 40 | 110 | 901 | 72 | 0.93 | 155 | 131 | 2.8 |
| 19.20 | LL139 | [ZrBz$_3$][BzB(C$_6$F$_5$)$_3$] | D | 6 MMAO | 1.1 ABF$_{20}$ | DD | 20 | 110 | 540 | 1118 | 0.91 | 147 | 156 | 3.4 |
| 19.21 | LL142 | [HfBz$_3$][BzB(C$_6$F$_5$)$_3$] | D | 6 MMAO | 1.1 ABF$_{20}$ | CC | 20 | 110 | 65 | 11720 | 0.85 | 133 | 183 | 5.8 |
| 19.22 | LL142 | ZrCl$_2$Bz$_2$(Et$_2$O) | C | 30 TIBA | 1.1 ABF$_{20}$ | CC | 20 | 110 | 99 | 6263 | 0.75 | | 50 | 2.2) |
| 19.23 | LL132 | HfBz$_4$ | A | 6 DIBAL | 1.1 ABF$_{20}$ | CC | 30 | 110 | 262 | 1340 | 0.95 | 155 | 1260 | 3.6 |
| 19.24 | LL132 | HfCl$_2$Bz$_2$(Et$_2$O) | C | 30 TIBA | 1.1 ABF$_{20}$ | BB | 15 | 110 | 135 | 6200 | 0.95 | 153 | 871 | 3.6 |
| 19.25 | LL132 | ZrBz$_4$ | A | 6 DIBAL | 1.1 ABF$_{20}$ | CC | 30 | 110 | 582 | 535 | 0.88 | 139 | 1210 | 2.3 |
| 19.26 | LL132 | ZrCl$_2$Bz$_2$(Et$_2$O) | C | 30 TIBA | 1.1 ABF$_{20}$ | BB | 15 | 110 | 166 | 5405 | 0.91 | 136 | 770 | 2.1 |
| 19.27 | LL152 | [HfBz$_3$][BzB(C$_6$F$_5$)$_3$] | G | 6 MMAO | 1.1 ABF$_{20}$ | GG | 60 | 110 | 900 | 59 | 0.89 | 156 | 74 | 1.8 |
| 19.28 | LL147 | [HfBz$_3$][BzB(C$_6$F$_5$)$_3$] | D | 6 MMAO | 1.1 ABF$_{20}$ | II | 15 | 110 | 1111 | 7385 | 0.90 | 152 | 194 | 6.2) |
| 19.29 | LL147 | [ZrBz$_3$][BzB(C$_6$F$_5$)$_3$] | D | 6 MMAO | 1.1 ABF$_{20}$ | II | 15 | 110 | 164 | 4945 | 0.80 | 134 | 187 | 2.7 |
| 19.30 | LL151 | [HfBz$_3$][BzB(C$_6$F$_5$)$_3$] | G | 6 MMAO | 1.1 ABF$_{20}$ | GG | 60 | 110 | 900 | 59 | 0.90 | 151/157 | 66 | 2.4 |
| 19.31 | LL146 | HfBz$_4$ | H | 6 MMAO | 1.1 ABF$_{20}$ | GG | 45 | 110 | 609 | 350 | 0.85 | 153 | 553 | 2.5) |
| 19.32 | LL146 | HfCl$_2$Bz$_2$(Et$_2$O) | I | 30 TIBA | 1.1 ABF$_{20}$ | HH | 15 | 110 | 166 | 5020 | 087 | 141/151 | 500 | 2.3 |
| 19.33 | LL158 | HfCl$_2$Bz$_2$(Et$_2$O) | K | 30 TIBA | 1.1 ABF$_{20}$ | KK | 15 | 110 | 132 | 7195 | 0.90 | 143 | 322 | 1.8 |
| 19.34 | LL158 | [HfBz$_3$][BzB(C$_6$F$_5$)$_3$] | L | 6 MMAO | 1.1 ABF$_{20}$ | II | 15 | 110 | 290 | 2070 | 0.91 | 145 | 599 | 1.6 |
| 19.35 | LL158 | ZrCl$_2$Bz$_2$(Et$_2$O) | K | 30 TIBA | 1.1 ABF$_{20}$ | KK | 15 | 110 | 231 | 3040 | 0.74 | 110 | 346 | 2.0 |
| 19.36 | LL154 | HfCl$_2$Bz$_2$(Et$_2$O) | K | 30 TIBA | 1.1 ABF$_{20}$ | LL | 20 | 110 | 233 | 1910 | 0.97 | 152 | 620 | 2.4 |
| 19.37 | LL154 | ZrCl$_2$Bz$_2$(Et$_2$O) | K | 30 TIBA | 1.1 ABF$_{20}$ | KK | 15 | 110 | 202 | 3555 | 0.86 | 109/124 | 237 | 2.0 |
| 19.38 | LL155 | [HfBz$_3$][BzB(C$_6$F$_5$)$_3$] | L | 6 MMAO | 1.1 ABF$_{20}$ | II | 15 | 110 | 298 | 1710 | 0.71 | | 179 | 1.6 |
| 19.39 | LL155 | ZrCl$_2$Bz$_2$(Et$_2$O) | K | 30 TIBA | 1.1 ABF$_{20}$ | KK | 15 | 110 | 131 | 5570 | 0.53 | 33 | | 1.5 |

TABLE 3-continued

| Example | Ligand | Metal precursor | complexation method | Group 13 reagent and mole equiv. | Activator and mol equiv. | activation method | catalyst amount injected (nmol) | Polym. temp. (Celsius) | Polym. time (sec) | Activity (g polymer/ (min* mmol) | FTIR index | Mp DSC data (Celsius) | Mw (/1000) | PDI (Mw/Mn) |
|---|---|---|---|---|---|---|---|---|---|---|---|---|---|---|
| 19.40 | LL156 | HfBz$_4$ | K | 6 MMAO | 1.1 ABF$_{20}$ | BB | 20 | 110 | 205 | 2085 | 0.91 | 125 | 6 | 1.5 |
| 19.41 | LL156 | ZrCl$_2$Bz$_2$ (Et$_2$O) | K | 30 TIBA | 1.1 ABF$_{20}$ | KK | 15 | 110 | 900 | 193 | 0.56 | | 3 | 2.0 |

[a]Mn = 1300 by NMR;
[b]Mn = 480 by NMR;
[c]Mn = 500 by NMR

Example 20

Propylene Polymerizations Using Isolated Complexes.

A total of 18 separate polymerization reactions were performed as follows.

Preparation of the polymerization reactor prior to injection of catalyst composition: The polymerization reactor was prepared in the manner described in Example 19.

Preparation of the group 13 reagent and activator stock solutions: The "activator solution" is either a solution of N,N'-dimethylanilinium tetrakis (pentafluorophenyl) borate ("ABF$_{20}$") in toluene or a solution of trityl tetrakis (pentafluorophenyl) borate ("TBF$_{20}$") in toluene. The "ABF$_{20}$" solution is heated to approximately 85° C. to dissolve the reagent. The molarity is indicated in the "activation method" of the individual example described below. The "group 13 reagent" solution is either a solution of triisobutyl aluminium ("TIBA") or a solution of trimethylaluminium ("TMA") or a solution of diisobuthylaluminium hydride ("DIBAL"), all "group 13 reagent" solutions were solutions in toluene. The molarity of the solutions used is indicated in the "activation method" of the individual example described below.

Activation method and Injection of solutions into the pressure reactor vessel: The following methods were employed to activate and inject the isolated complexes as indicated in the Table 4. Method AA: 60 µL of a 0.200M solution of the group 13 reagent is dispensed into a 1mL vial. 80 µL complex solution (5 mM in toluene/1,2-dichloroethane 50:50 vol%) containing 0.4 µmol metal complex is added. After about 12 min, 176 µL of the activator solution in toluene (2.5 mM) was added to the 1 mL vial followed by 500 µL toluene and the content of the 1 mL vial was mixed. About another 70 seconds later a fraction of the total 1 mL vial contents containing the indicated "catalyst amount injected" in Table 4, based on nanomoles (nmol) of metal complex, was injected into the pre-pressurized reaction vessel and was followed immediately by injection of toluene to increase the total volume injected of 0.500 mL. Method BB: 90 µL of a 0.200M solution of the group 13 reagent is dispensed into a 1 mL vial. 120 µL complex solution (5 mM in toluene/1,2-dichloroethane 50:50 vol%) containing 0.6 µmol metal complex is added. After about 12 min, 264 µL of the activator solution in toluene (2.5 mM) was added to the 1 mL vial followed by 500 µL toluene and the content of the 1 mL vial was mixed. About another 70 seconds later a fraction of the total 1 mL vial contents containing the indicated "catalyst amount injected" in Table 4, based on nanomoles (nmol) of metal complex, was injected into the pre-pressurized reaction vessel and was followed immediately by injection of toluene to increase the total volume injected of 0.500 mL. Method CC: Similar to Method AA but the complex was dissolved in 1,2-dichloroethane instead. The additional solvent after activator additon was 600 µL. Method DD: 180 µL of the 0.020 M solution of the group 13 reagent is dispensed into a 1 mL vial. 75 µL of a 0.004 M complex solution in chlorobenzene is added into a 1 mL vial. After about 12 min, 132 µL of the activator solution in toluene (2.5 mM) was added to the 1 mL vial followed by 700 µL toluene and the content of the 1 mL vial was mixed. About another 70 sec later, a fraction of the total 1 mL vial contents containing the indicated "catalyst amount injected" in Table 4, based on nanomoles (nmol) of metal complex, was injected into the prepressurized reaction vessel and was followed immediately by injection of toluene to increase the total volume injected of 0.500 mL. Method EE: 75 µL of a of a 0.004 M complex solution in 1,2-dichloroethane is dispensed into a 1 mL vial. The solvent was removed by a stream of N$_2$. 75 µL of toluene was added to the dry complex in the 1 mL vial. 180 µL of a 0.050 M solution of the group 13 reagent was then added into a 1 mL vial. After about 12 min, 132 µL of the activator solution in toluene (2.5 mM) was added to the 1 mL vial followed by 900 µL toluene and the contents of the 1 mL vial were mixed. About another 70 sec later, a fraction of the total 1 mL vial contents containing the indicated "catalyst amount injected" in Table 4, based on nanomoles (nmol) of metal complex, was injected into the prepressurized reaction vessel and was followed immediately by injection of toluene to increase the total volume injected of 0.500 mL. Method FF: 50 µL of a 0.200M solution of the group 13 reagent is dispensed into a 1.5 mL vial. 100 µL complex solution (2 mM in toluene) containing 0.2 µmol metal complex is added. After about 12 min, 100 µL of the activator solution in toluene (400 mM) was added to the 1.5 mL vial followed by 900 µL toluene and the content of the 1.5 mL vial was mixed. About another 70 seconds later a fraction of the total 1.5 mL vial contents containing the indicated "catalyst amount injected" in Table 4, based on nanomoles (nmol) of metal complex, was injected into the pre-pressurized reaction vessel and was followed immediately by injection of toluene to increase the total volume injected of 0.500 mL. Method GG: same as method FF except that 750 µl toluene was added to the 1.5 mL vial. Method HH: similar to method FF except 60 µL of a 0.020M solution of the group 13 reagent was used and 88 µL of a 0.0025 M solution of the activator solution was used. 1000 µL toluene was added to the 1.5 mL vial.

Polymerization and Product work up: The polymerization reaction and product work up were preformed in the manner described in Example 19.

ing 0.25 μmol metal complex is added. After about 12 min, an appropriate amount of the activator solution in toluene containing the indicated equivalents activator (per metal

TABLE 4

| Example | Complex | Group 13 reagent and mole equiv. | Activator and mol equiv. | Activation method | catalyst amount injected (nmol) | Polym. temp. (Celsius) | Polym. time (sec) | Activity (g polymer/ (min* mmol) | Crystal-linity index | Mw (/1000) | PDI (Mw/Mn) | Melting point by DSC |
|---|---|---|---|---|---|---|---|---|---|---|---|---|
| 20.1 | C10 | 30 TIBA | 1.1 $ABF_{20}$ | AA | 20 | 110 | 135 | 4764 | 0.93 | 290 | 2.9 | 151 |
| 20.2 | C10 | 30 DIBAL | 1.1 $ABF_{20}$ | AA | 20 | 110 | 100 | 7650 | 0.93 | 226 | 3.1 | 151 |
| 20.3 | C10 | 30 TIBA | 1.1 $ABF_{20}$ | AA | 20 | 130 | 420 | 1505 | 0.90 | 215 | 3.0 | 149 |
| 20.4 | C11 | 30 TIBA | 1.1 $ABF_{20}$ | BB | 20 | 110 | 459 | 794 | 0.89 | 343 | 2.1 | 149 |
| 20.5 | C11 | 30 DIBAL | 1.1 $ABF_{20}$ | BB | 20 | 110 | 399 | 742 | 0.89 | 342 | 2.0 | 151 |
| 20.6 | C11 | 30 TIBA | 1.1 $ABF_{20}$ | BB | 20 | 130 | 601 | 490 | 0.91 | 134 | 2.0 | 146 |
| 20.7 | C13 | 30 TIBA | 1.1 $ABF_{20}$ | CC | 20 | 110 | 136 | 4868 | 0.95 | 559 | 7.7 | 139/145 |
| 20.8 | C13 | 30 DIBAL | 1.1 $ABF_{20}$ | CC | 20 | 110 | 138 | 4986 | 0.96 | 344 | 7.3 | 152 |
| 20.9 | C13 | 30 DIBAL | 1.1 $TBF_{20}$ | CC | 20 | 110 | 129 | 4968 | 0.96 | 358 | 6.3 | 153 |
| 20.10 | C13 | 30 DIBAL | 1.1 $ABF_{20}$ | CC | 20 | 130 | 242 | 2023 | 0.98 | 308 | 6.2 | 151 |
| 20.11 | C12 | 12 TIBA | 1.1 $ABF_{20}$ | DD | 10 | 110 | 170 | 8051 | 0.95 | 89 | 3.5 | 146/152 |
| 20.12 | C12 | 12 DIBAL | 1.1 $ABF_{20}$ | DD | 10 | 110 | 154 | 7765 | 0.98 | 81 | 3.3 | 144/152 |
| 20.13 | C12 | 30 TIBA | 1.1 $ABF_{20}$ | EE | 06 | 110 | 405 | 4686 | 0.95 | 94 | 3.9 | 145/152 |
| 20.14 | C12 | 30 DIBAL | 1.1 $ABF_{20}$ | EE | 06 | 110 | 378 | 5548 | 0.97 | 72 | 3.9 | nd |
| 20.15 | C16 | 50 MMAO | 200 MMAO | FF | 7 | 110 | 284 | 3486 | nd | 564 | 2.3 | 156 |
| 20.16 | C16 | 50 MMAO | 200 MMAO | GG | 25 | 130 | 600 | 373 | nd | 143 | 2.2 | 154/157 |
| 20.17 | C17 | 15 TIBA | 1.1 $ABF_{20}$ | HH | 5 | 110 | 151 | 17280 | nd | 1050 | 2.7 | 151 |
| 20.18 | C17 | 50 MMAO | 200 MMAO | GG | 13 | 130 | 600 | 910 | nd | 429 | 1.9 | 151 |

Example 21

Ethylene-1-Octene Copolymerizations Using Isolated Complexes

A total of 9 separate ethylene-1-octene polymerization reactions were performed as follows.

Preparation of the polymerization reactor prior to injection of catalyst composition: A pre-weighed glass vial insert and disposable stirring paddle were fitted to each reaction vessel of the reactor. The reactor was then closed, 0.200 mL of a 0.05 M MMAO solution in toluene followed by 2.3 mL of toluene and 0.400 mL 1-octene followed with 2.1 mL toluene were injected into each pressure reaction vessel through a valve. The temperature was then set to 110° C., and the stirring speed was set to 800 rpm, and the mixture was exposed to ethylene at 100 psi pressure. An ethylene pressure of 100 psi in the pressure cell and the temperature setting were maintained, using computer control, until the end of the polymerization experiment.

Preparation of the group 13 reagent and activator stock solutions: The "activator solution" is either a 2.5 mM solution of N,N'-dimethylanilinium tetrakis (pentafluorophenyl) borate ("$ABF_{20}$") in toluene or a 400 mM solution of Modified Methylaluminoxane—3A (Azko) ("MMAO") in toluene. The "$ABF_{20}$" solution is heated to approximately 85° C. to dissolve the reagent. The group 13 reagent solution is either a solution of triisobutyl aluminium ("TIBA") (50 mM) or a solution of diisobuthylaluminium hydride ("DIBAL") (50 mM) in toluene.

Activation methods and Injection of solutions into the pressure reactor vessel: 50 μL of a 0.050M solution of the group 13 reagent is dispensed into a 1 mL vial. 83 μL complex solution (0.003 M in 1,2-dichloroethane) contain-precursor) in the specific examples in Table 5 was added to the 1 mL vial and the content of the 1 mL vial was mixed. About another 70 seconds later a fraction of the total 1 mL vial contents corresponding to the indicated "catalyst amount injected" in Table 5, based on nanomoles (nmol) of metal complex, was injected into the pre-pressurized reaction vessel and was followed immediately by injection of toluene to increase the total volume injected of 0.500 mL.

Polymerization: The polymerization reaction was allowed to continue for 60–900 seconds, during which time the temperature and pressure were maintained at their pre-set levels by computer control. The specific times for each polymerization are shown in Table 5. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Product work up: ethylene/1-octene copolymerizations After the polymerization reaction, the glass vial insert, containing the polymer product and solvent, was removed from the pressure cell and removed from the inert atmosphere dry box, and the volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and Raman spectroscopy to determine the comonomer incorporation. Results are presented in the Table 5.

TABLE 5

| Example | Complex | Metal | Group 13 reagent and mole equiv. | Activator and mol equiv. | activation method | catalyst amount injected (nmol) | Polym. temp. (Celsius) | Polym. time (sec) | Activity (g polymer/ (min*mmol) | Mol % Octene by Raman | Mw (/1000) | PDI (Mw/Mn) |
|---|---|---|---|---|---|---|---|---|---|---|---|---|
| 21.1 | C10 | Hf | 10 TIBA | 1.1 $ABF_{20}$ | EE | 10 | 100 | 587 | 2769 | 21 | 492 | 3.0 |
| 21.2 | C10 | Hf | 10 TIBA | 200 MMAO | EE | 10 | 100 | 312 | 5029 | 20 | 379 | 2.3 |
| 21.3 | C10 | Hf | 10 TIBA | 200 MMAO | EE | 10 | 130 | 901 | 968 | 15 | 906 | 2.6 |
| 21.4 | C14 | Hf | 10 TIBA | 1.1 $ABF_{20}$ | EE | 10 | 100 | 222 | 4068 | 13 | 333 | 3.4 |
| 21.5 | C14 | Hf | 10 TIBA | 200 MMAO | EE | 10 | 100 | 138 | 8078 | 16 | 250 | 2.3 |
| 21.6 | C14 | Hf | 10 TIBA | 200 MMAO | EE | 10 | 130 | 900 | 984 | 15 | 289 | 2.5 |
| 21.7 | C15 | Zr | 10 TIBA | 1.1 $ABF_{20}$ | EE | 2 | 100 | 61 | 115160 | 19 | 57 | 1.7 |
| 21.8 | C15 | Zr | 10 TIBA | 200 MMAO | EE | 2 | 100 | 61 | 118160 | 17 | 60 | 1.8 |
| 21.9 | C15 | Zr | 10 TIBA | 200 MMAO | EE | 4 | 130 | 104 | 36890 | 17 | 52 | 1.7 |

A number of embodiments of the invention have been described. Nevertheless, it will be understood that various modifications may be made without departing from the spirit and scope of the invention. Accordingly, other embodiments are within the scope of the following claims.

The invention claimed is:

1. A metal complex characterized by the general formula:

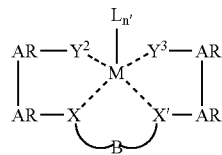

wherein at least two of the bonds from $Y^2$, $Y^3$, X and X' to M are covalent, with the other bonds being dative; AR is an aromatic group that can be the same or different from the other AR groups with each AR being independently selected from the group consisting of optionally substituted aryl and heteroaryl; B is a bridging group having from two to 50 atoms not counting hydrogen atoms and is selected from the group consisting of substituted divalent hydrocarbyl and divalent heteroatom-containing hydrocarbyl; X and X' are independently selected from the group consisting of oxygen, sulfur, $—P(R^{30})_r—$, and optionally substituted alkoxy, aryloxy, alkylthio, arylthio; $Y^2$ and $Y^3$ are independently selected from the group consisting of oxygen, sulfur, $—N(R^{30})_r—$, $—P(R^{30})_r—$, and optionally substituted alkoxy, aryloxy, alkylthio, or arylthio, where $R^{30}$ is selected from the group consisting of hydrogen, halogen, and optionally substituted hydrocarbyl, heteroatom-containing hydrocarbyl, silyl, boryl, alkoxy, or aryloxy and r is 0 or 1;

M is a metal selected from groups 3–6 and lanthanide elements of the periodic table of elements;

each L is independently a moiety that forms a covalent dative or ionic bond with M; and n' is 1, 2, 3 or 4.

2. The complex of claim 1, wherein B is selected from the group consisting of substituted divalent alkyl, alkenyl, alkynyl, heteroalkyl, heteroalkenyl, heteroalkynyl, aryl, heteroaryl and silyl.

3. The complex of claim 1, wherein the bridging group B is substituted with one or more optionally substituted hyrocarbyl or heteroatom-containing hydrocarbyl groups, not counting AR—X and AR—X'.

4. The complex of claim 1, wherein the bridging group B is substituted with two or more hydrocarbyl or heteroatom-containing hydrocarbyl groups, not counting AR—X and AR—X', wherein two or more of the hydrocarbyl or heteroatom-containing hydrocarbyl groups are optionally joined into a ring structure having from 3 to 50 atoms in the ring structure not counting hydrogen atoms.

5. The complex of claim 1, wherein:

the bridging group B includes a bridge of one or more atoms extending from X to X', the bridge including one or more atoms adjacent to the X and/or the X'; and one or more of the bridge atoms adjacent to one or more of the X and/or the X' is bonded to one or more substituents, not counting bonds to X and/or X' or neighboring atoms along the bridge, the one or more substitutents being independently selected from the group consisting of optionally substituted alkyl, heteroalkyl, aryl and heteroaryl.

6. The complex of claim 1, wherein the bridging group B is substituted with a plurality of substitutents independently selected from the group consisting of optionally substituted alky, heteroalkyl, aryl and heteroaryl, each of the bridge atoms adjacent to the X and/or the X' being bonded to at least one of the plurality of substituents, not counting bonds to X and/or X' or neighboring atoms along the bridge, wherein two or more of the substituents are optionally joined into a ring structure having from 3 to 50 atoms in the ring structure not counting hydrogen atoms.

7. The complex of claim 6, wherein each of the bridge atoms adjacent to the X and/or the X' is bonded to two of the plurality of substituents.

8. The complex of claim 1, wherein the group X—B—X' is selected from the group consisting of

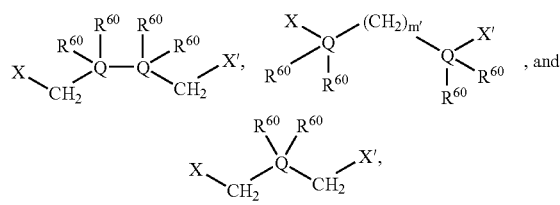

wherein each Q is independently selected from the group consisting of carbon and silicon, each $R^{60}$ is independently selected from the group consisting of hydrogen and optionally substituted hydrocarbyl and heteroatom containing hydrocarbyl, provided that at least one $R^{60}$ substituent is not hydrogen, wherein the $R^{60}$ substituents are optionally joined into a ring structure having from 3 to 50 atoms in the ring structure not counting hydrogen atoms, and m' is 0, 1, or 2.

9. The complex of claim 8, wherein the group X—B—X' is selected from the group consisting of X—CH(CH$_3$)—CH(CH$_3$)—X', X—CH$_2$—CH(CH$_3$)—CH$_2$—X', X—CH$_2$—C(CH$_3$)$_2$—CH$_2$—X', X—CH$_2$—CH(C$_6$H$_5$)—CH$_2$—X', X—CH(CH$_3$)—CH$_2$—CH(CH$_3$)—X', X—CH(CH$_2$H$_5$)—CH$_2$—CH(C$_2$H$_5$)—X', X—CH(CH$_3$)CH$_2$CH$_2$CH(CH$_3$)—X', X—CH(C$_6$H$_5$)CH$_2$CH(C$_6$C$_5$)—X',

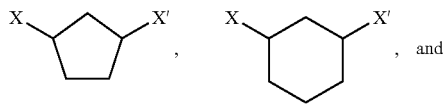, and

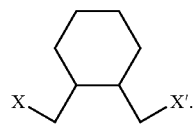.

10. The complex of claim 1, wherein B is represented by the general formula (Q"R$^{40}_{z-z"}$)$_{z'}$— wherein each Q" is independently either carbon or silicon and wherein each R$^{40}$ substituent is independently selected from the group consisting of hydrogen and optionally substituted hydrocarbyl or heteroatom containing hydrocarbyl, provided that at least one R$^{40}$ substituent is not hydrogen, wherein two or more R$^{40}$ substituents are optionally joined into a ring structure having from 3 to 50 atoms in the ring structure not counting hydrogen atoms; z' is an integer from 1 to 10; and z" is 0, 1 or 2.

11. The complex of claim 9, wherein z' is an integer greater than 1, and two or more R$^{40}$ substituents are independently selected from the group consisting of optionally substituted hydrocarbyl and heteroatom-containing hydrocarbyl.

12. The complex of claim 9, wherein z' is an integer greater than 1, and the bridging group B is substituted such that one or more of the R$^{40}$ substituents bonded to a Q" adjacent to one or more of X and X' is independently selected from the group consisting of optionally substituted alkyl, heteroalkyl, aryl and heteroaryl.

13. The complex of claim 9, wherein the bridging group B is substituted such that a plurality of R$^{40}$ substitutents are independently selected from the group consisting of optionally substituted alkyl, heteroalkyl, alkyl and heteroaryl, each Q" adjacent to the X and or the X' being bonded to at least one of the plurality of R$^{40}$ substituents.

14. The complex of claim 9, wherein each Q"adjacent to the X and/or the X'is bonded to two of the plurality of R$^{40}$ substituents.

15. The complex of claim 1, wherein the metal complex includes one or more chiral centers.

16. The complex of claim 15, wherein the bridging group B includes at least one chiral center.

17. The complex of claim 15, wherein the metal complex can be formed into enantiomeric or diasteremeric forms.

18. A metal complex characterized by the general formula:

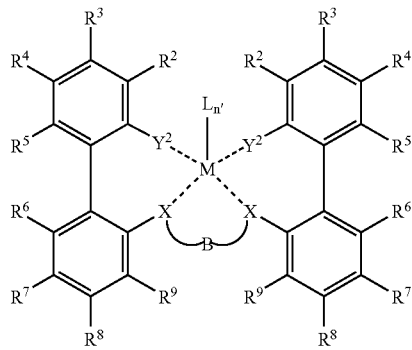

wherein each of $R^2$, $R^3$, $R^4$, $R^5$, $R^6$, $R^7$, $R^8$ and $R^9$ is independently selected from the group consisting of hydrogen, halogen, nitro, and optionally substituted alkyl, alkenyl, alkynyl, heteroalkyl, heteroalkenyl, heteroalkynyl, aryl, heteroaryl, alkoxyl, aryloxyl, silyl, boryl phosphino, amino, alkylthio, or arylthio; and wherein at least two of the bonds from $Y^2$, $Y^3$, X and X' to M are covalent, with the other bonds being dative; B is a bridging group having from two to 50 atoms not counting hydrogen atoms and is selected from the group consisting of substituted divalent hydrocarbyl and divalent heteroatom-containing hydrocarbyl; X and X' are independently selected from the group consisting of oxygen, sulfur, —P(R$^{30}$)$_r$—, and optionally substituted alkoxy, aryloxy, alkylthio, arylthio; $Y^2$ and $Y^3$ are independently selected from the group consisting of oxygen, sulfur, —N(R$^{30}$)$_r$—, —P(R$^{30}$)$_r$—, and optionally substituted alkoxy, aryloxy, alkylthio, or arylthio, where R$^{30}$ is selected from the group consisting of hydrogen, halogen, and optionally substituted hydrocarbyl, heteroatom-containing hydrocarbyl, silyl, boryl, alkoxy, or aryloxy, and r is 0 or 1;

M is a metal selected from groups 3–6 and lanthanide elements of the periodic table of elements;

each L is independently a moiety that forms a covalent, dative or ionic bond with M; and n' is 1, 2, 3 or 4.

19. The complex of claim 18, wherein B is selected from the group consisting of substituted divalent alkyl, alkenyl, alkynyl, heteroalkyl, heteroalkenyl, heteroalkynyl, aryl, heteroaryl and silyl.

20. The complex of claim 18, wherein:

the bridging group B includes a bridge of one or more atoms extending from X to X', the bridge including one or more atoms adjacent to the X and/or the X'; and one or more of the bridge atoms adjacent to one or more of the X and/or the X' is bonded to one or more substituents, not counting bonds to X and/or X' or neighboring atoms along the bridge, the one or more substitutents being independently selected from the group consisting of optionally substituted alkyl, heteroalkyl, aryl and heteroaryl.

21. The complex of claim 18, wherein the bridging group B is substituted with a plurality of substitutents independently selected from the group consisting of optionally substituted alkyl, heteroalkyl, aryl and heteroaryl, each of the bridge atoms adjacent to the X and/or the X' being bonded to at least one of the plurality of substituents, not counting bonds to X and/or X' or neighboring atoms along the bridge, wherein two or more of the substituents are optionally joined into a ring structure having from 3 to 50 atoms in the ring structure not counting hydrogen atoms.

22. The complex of claim 18, wherein the group X—B—X' is selected from the group consisting of

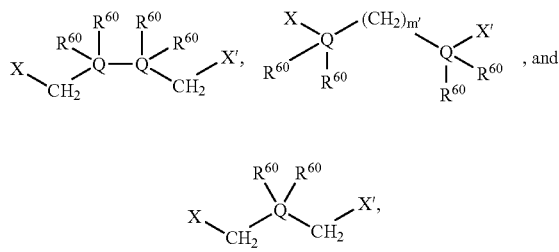

wherein each Q is independently selected from the group consisting of carbon and silicon, each $R^{60}$ is independently selected from the group consisting of hydrogen and optionally substituted hydrocarbyl or heteroatom containing hydrocarbyl, provided that at least one $R^{60}$ substituent is not hydrogen, wherein the $R^{60}$ substituents are optionally joined into a ring structure having from 3 to 50 atoms in the ring structure not counting hydrogen atoms, and m' is 0, 1, or 2.

23. The complex of claim 18, wherein the bridging group B includes one or more chiral centers.

24. The complex of claim 18, wherein X—B—X' is characterized by the formula

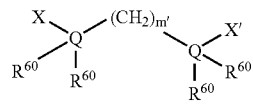

and at least one $R^{60}$ group is not hydrogen or at least one $R^{60}$ group on each Q is not hydrogen.

25. The complex of claim 18, wherein the group X—B—X' is selected from the group consisting of X—CH(CH$_3$)—CH(CH$_3$)—X', X—CH$_2$—CH(CH$_3$)—CH$_2$—X', X—CH$_2$—C(CH$_3$)$_2$—CH$_2$—X', X—CH$_2$—CH(C$_6$H$_5$)—CH$_2$—X', X—CH(CH$_3$)—CH$_2$—CH(CH$_3$)—X', X—CH$_2$—(C$_2$H$_5$)—CH$_2$—CH(C$_2$H$_5$)—X', X—CH(CH$_3$)CH$_2$CH$_2$CH(CH$_3$X', X—CH(C$_6$H$_5$)CH$_2$CH(C$_6$H$_5$)—X',

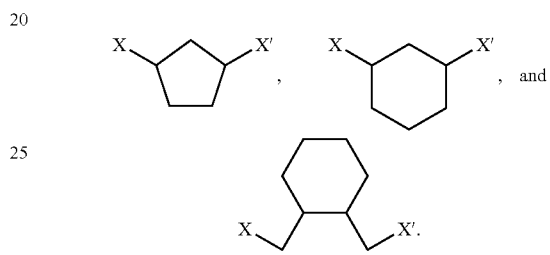

* * * * *

UNITED STATES PATENT AND TRADEMARK OFFICE
CERTIFICATE OF CORRECTION

PATENT NO. : 7,060,848 B2 Page 1 of 2
APPLICATION NO. : 11/117006
DATED : June 13, 2006
INVENTOR(S) : Boussie et al.

It is certified that error appears in the above-identified patent and that said Letters Patent is hereby corrected as shown below:

TITLE PAGE, ITEM (56) References Cited, OTHER PUBLICATIONS:

*Forni et al.*, replace "vol.:23" with --vol.: 12--

*Zhang et al.*, replace "vol.: 22" with --vol.: 122--

*LaPointe*, replace "vol.: 22" with --vol.: 122--

On page 3 of the coversheet of the patent, (56) References Cited, OTHER PUBLICATIONS:

*Vathauer et al.*, replace "Tera(pentafluorophenyl)-borate" with --Tetra (pentafluorophenyl)-borate--

Col. 241, Line 46, insert -- or -- between "alkylthio" and "arylthio"

Col. 243, Line 9, replace "X-CH(CH$_2$H$_5$)-." " with X-CH(C$_2$H$_5$)-

Col. 243, Line 11, replace "X-CH(C$_6$H$_5$)CH$_2$CH(C$_6$C$_5$)-X'," with X-CH(C$_6$H$_5$)CH$_2$CH(C$_6$H$_5$)-X'

Col. 243, Line 25, replace "(Q"R$^{40}$z-z")$_{z'}$-" with (Q"R$^{40}$$_{2-z''}$)$_{z'}$-

Col. 243, Line 31, insert -- R -- after "more" and before "$^{40}$"

Col. 243, Line 53, replace "alkyl" with -- aryl --

Col. 243, Line 54, insert -- / -- between "and" and "or"

Col. 243, Line 58, insert a space between -- X' -- and -- is --

Col. 244, Line 33, insert -- or -- between "alkylthio" and "arylthio"

UNITED STATES PATENT AND TRADEMARK OFFICE
CERTIFICATE OF CORRECTION

PATENT NO. : 7,060,848 B2
APPLICATION NO. : 11/117006
DATED : June 13, 2006
INVENTOR(S) : Boussie et al.

It is certified that error appears in the above-identified patent and that said Letters Patent is hereby corrected as shown below:

Col. 246, Line 15, replace
"X-CH$_2$-(C$_2$H$_5$)-CH$_2$-CH(C$_2$H$_5$)-X'," with X-CH-(C$_2$H$_5$)-CH$_2$-CH(C$_2$H$_5$)-X'

Col. 246, Line 16, replace "CH$_2$CH$_2$CH(CH$_3$X'," with CH$_2$CH$_2$CH(CH$_3$)-X',

Signed and Sealed this

Fifth Day of September, 2006

JON W. DUDAS
*Director of the United States Patent and Trademark Office*